United States Patent
Xu et al.

(10) Patent No.: US 10,053,507 B2
(45) Date of Patent: *Aug. 21, 2018

(54) HUMAN PAC1 ANTIBODIES

(71) Applicant: AMGEN INC., Thousand Oaks, CA (US)

(72) Inventors: Cen Xu, Newbury Park, CA (US); Agnes Eva Hamburger, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/592,115

(22) Filed: May 10, 2017

(65) Prior Publication Data

US 2017/0247451 A1    Aug. 31, 2017

Related U.S. Application Data

(63) Continuation of application No. 14/775,995, filed as application No. PCT/US2014/029128 on Mar. 14, 2014, now Pat. No. 9,676,851.

(60) Provisional application No. 61/792,678, filed on Mar. 15, 2013.

(51) Int. Cl.
 *A61K 35/12*    (2015.01)
 *A61K 39/00*    (2006.01)
 *C07K 16/28*    (2006.01)

(52) U.S. Cl.
 CPC .......... *C07K 16/28* (2013.01); *C07K 16/2869* (2013.01); *C07K 2317/21* (2013.01); *C07K 2317/41* (2013.01); *C07K 2317/76* (2013.01); *C07K 2317/92* (2013.01)

(58) Field of Classification Search
 None
 See application file for complete search history.

(56) References Cited

U.S. PATENT DOCUMENTS

| 5,486,472 | A | 1/1996 | Suzuki et al. |
| 5,858,787 | A | 1/1999 | Onda et al. |
| 5,892,004 | A | 4/1999 | Ohtaki et al. |
| 5,973,117 | A | 10/1999 | Onda et al. |

(Continued)

FOREIGN PATENT DOCUMENTS

| EP | 0 522 159 B1 | 12/2001 |
| EP | 2 048 162 A1 | 4/2009 |

(Continued)

OTHER PUBLICATIONS

Bendig, Mary M. (1995), "Humanization of rodent oclonal antibodies by CDR grafting", Methods: A Companion to Methods in Enzymology, 9:83-93.

(Continued)

*Primary Examiner* — Jeffrey Stucker
*Assistant Examiner* — Aurora M Fontainhas
(74) *Attorney, Agent, or Firm* — Angela L. Purcell

(57) ABSTRACT

Antibodies and antigen-binding fragments thereof that bind to human PAC1 are provided. Nucleic acids encoding the antibodies and antigen-binding fragments thereof, vectors, and cells encoding the same are also provided. The antibodies and antigen-binding fragments thereof can inhibit binding of PAC1 to PACAP, and are useful in a number of PAC1 related disorders, including the treatment and/or prevention of headache disorders, including migraine and cluster headache.

19 Claims, 2 Drawing Sheets

(56) References Cited

U.S. PATENT DOCUMENTS

| | | | |
|---|---|---|---|
| 6,017,533 | A | 1/2000 | Moro et al. |
| 6,242,563 | B1 | 6/2001 | Dong |
| 6,399,316 | B1 | 6/2002 | Onda et al. |
| 6,462,016 | B1 | 10/2002 | Wakita et al. |
| 2002/0155533 | A1 | 10/2002 | Onda et al. |
| 2002/0182729 | A1 | 12/2002 | DiCicco-Bloom et al. |
| 2005/0129687 | A1 | 6/2005 | Vizzard et al. |
| 2005/0142133 | A1 | 6/2005 | Lazar et al. |
| 2006/0062785 | A1 | 3/2006 | Freson et al. |
| 2006/0160996 | A9 | 7/2006 | Lazar et al. |
| 2007/0054843 | A1 | 3/2007 | Yeomans et al. |
| 2009/0215895 | A1 | 8/2009 | Ferrante et al. |
| 2009/0291900 | A1 | 11/2009 | Yeomans et al. |
| 2010/0112601 | A1 | 5/2010 | Shirakawa et al. |
| 2011/0021426 | A1 | 1/2011 | Toll et al. |
| 2013/0196908 | A1 | 8/2013 | Toll et al. |

FOREIGN PATENT DOCUMENTS

| | | |
|---|---|---|
| EP | 1 098 906 B1 | 11/2009 |
| EP | 1 928 484 B1 | 2/2010 |
| EP | 2 161 282 A1 | 3/2010 |
| WO | 00/05260 A1 | 2/2000 |
| WO | 2004/062684 A | 7/2004 |
| WO | 2004/099249 A2 | 11/2004 |
| WO | 2005/073164 A1 | 8/2005 |
| WO | 2007/025249 A2 | 3/2007 |
| WO | 2009/003489 A2 | 3/2009 |
| WO | 2010/066125 A1 | 6/2010 |
| WO | 2011/017122 A1 | 2/2011 |
| WO | 2013/177062 A2 | 11/2013 |

OTHER PUBLICATIONS

Bourgault et al. (2009), "Molecular and conformational determinants of pituitary adenylate cyclase-activating polypeptide (PACAP) for activation of the PAC1 receptor", J. Med. Chem., 52:3308-3316.

Colman, P.M. (1994), "Effects of amino acid sequence changes antibody-antigen interactions", Research in Immunology, 145:33-36.

Goetzl et al., "PAC1 and VIP receptors", pp. 2249-2253, DOI:10.1006/rwcy.2000.23009.

Guirland et al.(2003), "Direct cAMP signaling through G-protein-coupled receptors mediates growth cone attraction induced by pituitary adenylate cyclase-activating polypeptide", J. Neurosci., 23(6):2274-2283.

Inooka, Hiroshi et al. (2001), "Conformation of a peptide ligand bound to its G-protein coupled receptor", Nature Struct. Biol., 8(2):161-165.

Laburthe, Marc et al. (2007), "Class II G protein-coupled receptors for VIP and PACAP: structure, models of activation and pharmacology", Peptides, 28:1631-1639.

Lerner et al. 007), "Maxadilan, a PAC1 receptor agonist from sand flies", Peptides, 28(9):1651-1654, NIH-Public Access.

Moretti, C. (2006), "PACAP and type I PACAP receptors in human prostate cancer tissue", Annals NYAS, 1070(I):440-449.

Moro et al. (1999), "Functional characterization of structural alterations in the sequence of the vasodilatory peptide maxadilan yields a pituitary adenylate cyclase-activating peptide type 1 receptor-specific antagonist", J. Biol. Chem., 274(33):23103-23110.

Paul, William E. (1993), "Fv structure and diversity in three dimensions", Fundamental Immunology, 3$^{rd}$ ed., pp. 292-295.

Rudikoff et al. (1982), "Single amino acid substitution altering antigen-binding specificity", 79:1979-1983.

Sazinsky, S.L. (2008), "Aglycosylated immunoglobulin G1 variants productively engage activating Fc receptors", PNAS, 105(51):20167-20172.

Schulz et al. (2004), "Immunocytochemical identification of VPACI, VPAC2, and PAC1 receptors in normal and neoplastic human tissues with subtype-specific antibodies", Clin. Cancer Res., 10:8235.

Schytz. H.W. et al, (2010), "The PACAP receptor: a novel target for migraine treatment", Neurotherap., 7(2):191-196.

Schytz, et al. (2008),"PACAP38 induces migraine-like attacks in patients with migraine without aura", Brain, 132:16-2:5.

Shirakawa et al.(2001), "Conformation of a peptide ligand hound to its G-protein coupled receptor", Nature Struct. Biol., 8(2)161-165.

Vaudry, David et al. (2009), "Pituitary adenylate cyclase-actiyating polypeptide and its receptors: 20 years after the discovery", Pharmacol. Rev., 61(3):283-357.

Vaudry et al. (2000), "Pituitary adenylate cyclase-activating polypeptide and its receptors: from structure to functions", Pharmtacol. Rev., 52(2):269-324.

Zvirbliene et al, (1999), "Production and characterization of monoclonal antibodies to pituitary adenylate cyclase activating polypeptide type i receptor", Hybridoma, 18(4):335-342.

ISR and Written Opinion for PCT/US2014/029128 dated Oct. 8, 2014.

| Seq Group | Sequence | SEQ ID NO: |
|---|---|---|
| CDRL1-1 | R A S Q S I G R - S L H | 196 |
| CDRL1-2 | R A S Q S V G R - S L H | 197 |
| CDRL1-3 | R A S Q S I S R - Y L N | 198 |
| CDRL1-4 | R A S Q S V S S S Y L A | 199 |
| CDRL1-5 | R A S Q T V S R S Y L A | 200 |
| CDRL1-13 | R A S Q S I G S - S L H | 208 |
| CDRL1-C1 | R A S Q S V S R S Y L A<br>        T I G S - S   H<br>                          N | 251 |

| Seq Group | Sequence | SEQ ID NO: |
|---|---|---|
| CDRL1-7 | K S S Q N V L Y S S N N K N F L T | 202 |
| CDRL1-8 | K S S Q S V L Y R S N N N N F L A | 203 |
| CDRL1-9 | K S S Q S V L Y S S N N K H Y L A | 204 |
| CDRL1-10 | K S S Q S V L Y S S N N K N F L T | 205 |
| CDRL1-11 | K S S Q S V L Y S S N N K N Y L A | 206 |
| CDRL1-12 | K S S Q S V L Y S S N N R N F L S | 207 |
| CDRL1-C2 | K S S Q S V L Y S S N N K N F L T<br>        N       R         N H Y   A<br>                          R         S | 252 |

| Seq Group | Sequence | SEQ ID NO: |
|---|---|---|
| CDRL2-1 | Y A S Q S L S | 209 |
| CDRL2-2 | A A S S L Q S | 210 |
| CDRL2-C1 | Y A S Q S L S<br>A     S L Q | 253 |

| Seq Group | Sequence | SEQ ID NO: |
|---|---|---|
| CDRL2-3 | G A S S R A T | 211 |
| CDRL2-4 | L G S N R A S | 212 |
| CDRL2-C2 | G A S S R A T<br>L G   N     S | 254 |

| Seq Group | Sequence | SEQ ID NO: |
|---|---|---|
| CDRL2-5 | R A S T R E S | 213 |
| CDRL2-6 | W A S T R E S | 214 |
| CDRL2-C3 | R A S T R E S<br>W | 255 |

| Seq Group | Sequence | SEQ ID NO: |
|---|---|---|
| CDRL3-1 | H Q S S R L P F T | 215 |
| CDRL3-2 | Q Q S Y S P P F T | 216 |
| CDRL3-4 | Q Q F G S S P W T | 218 |
| CDRL3-6 | Q Q Y Y S A P F T | 220 |
| CDRL3-7 | Q Q Y Y I S P L T | 221 |
| CDRL3-8 | Q Q Y Y S S P F T | 222 |
| CDRL3-C1 | Q Q S Y S P P F T<br>H   Y S R S   L<br>      F G I A   W<br>              L | 256 |

Fig. 1

| Seq Group | Sequence | SEQ ID NO: |
|---|---|---|
| CDRH1-1 | R F A M H | 223 |
| CDRH1-3 | R Y A M H | 225 |
| CDRH1-4 | R Y G V S | 226 |
| CDRH1-9 | S Y G I S | 231 |
| CDRH1-10 | S Y Y W S | 232 |
| CDRH1-11 | Y Y A I H | 233 |
| CDRH1-C1 | R Y A M H<br>S F G V S<br>Y    Y I<br>        W | 257 |

| Seq Group | Sequence | SEQ ID NO: |
|---|---|---|
| CDRH1-2 | R G G Y Y W S | 224 |
| CDRH1-5 | S G G F Y W S | 227 |
| CDRH1-6 | S G G Y Y W S | 228 |
| CDRH1-7 | S N S A A W N | 229 |
| CDRH1-8 | S N S A T W N | 230 |
| CDRH1-C2 | R G G Y Y W S<br>S N S F A    N<br>        A T | 258 |

| Seq Group | Sequence | SEQ ID NO: |
|---|---|---|
| CDRH2-8 | Y I Y Y – S – G N T Y Y N P S L K S | 241 |
| CDRH2-1 | R I Y T – S – G S T N Y N P S L K S | 234 |
| CDRH2-2 | R T Y Y R S K W S N H Y A V S V K S | 235 |
| CDRH2-3 | R T Y Y R S R W Y N D Y A V S V K S | 236 |
| CDRH2-C1 | R T Y Y R S K W S N H Y A V S V K S<br>Y I    T –      R G N T N    N P    L<br>                –         Y        Y<br>                               D | 259 |

| Seq Group | Sequence | SEQ ID NO: |
|---|---|---|
| CDRH2-4 | V I S Y D G G N K Y Y A E S V K G | 237 |
| CDRH2-5 | V I S Y D G S N K Y Y A D S V K G | 238 |
| CDRH2-C2 | V I S Y D G G N K Y Y A E S V K G<br>              S                    D | 260 |

| Seq Group | Sequence | SEQ ID NO: |
|---|---|---|
| CDRH2-6 | W I N A Y N G H T N Y A Q T F Q G | 239 |
| CDRH2-7 | W I T T Y N G N T N Y A Q K L Q G | 240 |
| CDRH2-C3 | W I N A Y N G H T N Y A Q T F Q G<br>     T T           N           K L | 261 |

| Seq Group | Sequence | SEQ ID NO: |
|---|---|---|
| CDRH3-3 | G T W K Q L W F L D H | 236 |
| CDRH3-4 | G V F Y S K G A F D I | 245 |
| CDRH3-5 | G Y D I L T G Y P D Y | 246 |
| CDRH3-6 | G Y D V L T G Y P D Y | 247 |
| CDRH3-9 | G Y D L L T G Y P D Y | 250 |
| CDRH3-C1 | G Y D V L T G Y P D Y<br>   T W K Q L W F L    H<br>   V F Y S K    A F    I<br>      L | 262 |

Fig. 2

SEQUENCE LISTING

<160> NUMBER OF SEQ ID NOS: 262

<210> SEQ ID NO 1
<211> LENGTH: 642
<212> TYPE: DNA
<213> ORGANISM: Artificial Sequence
<220> FEATURE:
<223> OTHER INFORMATION: Synthetic LC-01 polynucleotide

<400> SEQUENCE: 1

| | | | | | |
|---|---|---|---|---|---|
| gacatccaga | tgacccagtc | tccatcctcc | ctgtctgcat | ctgtaggaga | cagaatcacc | 60 |
| atcacttgcc | gggcaagtca | gagcattagc | aggtatttaa | attggtatca | acagaaacca | 120 |
| gggaaagccc | ctaaactcct | gatctatgct | gcatccagtt | tgcaaagtgg | gatcccatca | 180 |
| aggttcagcg | gcagtggatc | tgggacagat | ttcactctca | ccatcaacag | tctgcaacct | 240 |
| gaagattttg | caacttactt | ctgtcaacag | agttacagtc | ccccattcac | tttcggccct | 300 |
| gggaccaaag | tggatatcaa | acgtacggtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gt | | 642 |

<210> SEQ ID NO 2
<211> LENGTH: 642
<212> TYPE: DNA
<213> ORGANISM: Artificial Sequence
<220> FEATURE:
<223> OTHER INFORMATION: Synthetic LC-02 polynucleotide

<400> SEQUENCE: 2

| | | | | | |
|---|---|---|---|---|---|
| gaaattgtgc | tgactcagtc | tccagacttt | cagtctgtga | ctccaaagga | aaagtcacc | 60 |
| atcacctgcc | gggccagtca | gagcattggt | agtagcttac | actggtacca | gcagaaacca | 120 |
| gatcagtctc | caaagctcct | catcaagtat | gcttcccagt | ccttgtcagg | gatcccctcg | 180 |
| aggtttagtg | gcagtggatc | tgggacagat | ttcaccctca | ccatcaatag | cctggaagct | 240 |
| gaagatgctg | caacgtatta | ctgtcatcag | agtagtcgtt | taccattcac | tttcggccct | 300 |
| gggaccaaag | tggatatcaa | acgaacggtg | gctgcaccat | ctgtcttcat | cttcccgcca | 360 |
| tctgatgagc | agttgaaatc | tggaactgct | agcgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gt | | 642 |

<210> SEQ ID NO 3
<211> LENGTH: 642
<212> TYPE: DNA
<213> ORGANISM: Artificial Sequence
<220> FEATURE:
<223> OTHER INFORMATION: Synthetic LC-03 polynucleotide

<400> SEQUENCE: 3

| | | | | | |
|---|---|---|---|---|---|
| gatatccagc | tcactcaatc | gccatcattt | ctctccgctt | cggtaggcga | ccgggtcacg | 60 |
| atcacatgca | gggcgtcgca | aagcattggg | aggtcgttgc | attggtatca | gcagaaaccc | 120 |

```
ggaaaggccc cgaaacttct gatcaaatac gcatcacaaa gcttgagcgg tgtgccgtcg      180
cgcttctccg gttccggaag cggaacggaa ttcacgctta caatctcctc actgcagccc      240
gaggatttcg cgacctatta ctgtcaccag tcatccagac tcccgtttac ttttggccct      300
gggaccaagg tggacattaa gcgtacggtg gctgcaccat ctgtcttcat cttcccgcca      360
tctgatgagc agttgaaatc tggaactgcc tctgttgtgt gcctgctgaa taacttctat      420
cccagagagc ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642

<210> SEQ ID NO 4
<211> LENGTH: 642
<212> TYPE: DNA
<213> ORGANISM: Artificial Sequence
<220> FEATURE:
<223> OTHER INFORMATION: Synthetic LC-04 polynucleotide

<400> SEQUENCE: 4
gaaattgtgc tgactcagtc tccagacttt cagtctgtga ctccaaagga gaaagtcacc      60
atcacctgcc gggccagtca gagcgttggt cgtagtttac actggtacca tcagaaacca     120
gatcagtctc caaagctcct catcaagtat gcttcccagt ccttatcagg ggtcccctcg     180
aggttcagtg gcagtggatc tgggacagat ttcaccctca ttatcaatag cctggaagct     240
gaagatgctg caacgtatta ctgtcatcag agtagtcgtt accattcac tttcggccct       300 gggaccaaag tggatatcaa acgaacggtg gctgcaccat ctgtcttcat cttcccgcca      360
tctgatgagc agttgaaatc tggaactgct agcgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642

<210> SEQ ID NO 5
<211> LENGTH: 642
<212> TYPE: DNA
<213> ORGANISM: Artificial Sequence
<220> FEATURE:
<223> OTHER INFORMATION: Synthetic LC-05 polynucleotide

<400> SEQUENCE: 5
gatatccagc tcactcaatc gccatcattt ctctccgctt cggtaggcga ccgggtcacg      60
atcacatgca gggcgtcgca aagcattggg aggtcgttgc attggtatca gcagaaaccc     120
ggaaaggccc cgaaacttct gatcaaatac gcatcacaaa gcttgagcgg tgtgccgtcg     180
cgcttctccg gttccggaag cggaacggaa ttcacgctta caatctcctc actgcagccc     240
gaggatttcg cgacctatta ctgtcaccag tcatccagac tcccgtttac ttttggccct     300
gggaccaagg tggacattaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
```

| | | |
|---|---|---|
| ctgagcaaag cagactacga gaaacacaaa gtctacgcct gcgaagtcac ccatcagggc | | 600 |
| ctgagctcgc ccgtcacaaa gagcttcaac aggggagagt gt | | 642 |

<210> SEQ ID NO 6
<211> LENGTH: 642
<212> TYPE: DNA
<213> ORGANISM: Artificial Sequence
<220> FEATURE:
<223> OTHER INFORMATION: Synthetic LC-06 polynucleotide

<400> SEQUENCE: 6

| | | |
|---|---|---|
| gatatccagc tcactcaatc gccatcattt ctctccgctt cggtaggcga ccgggtcacg | | 60 |
| atcacatgca gggcgtcgca aagcattggg aggtcgttgc attggtatca ccagaaaccc | | 120 |
| ggaaaggccc cgaaacttct gatcaaatac gcatcacaaa gcttgagcgg tgtgccgtcg | | 180 |
| cgcttctccg gttccggaag cggaacggaa ttcacgctta tcatctcctc actgcagccc | | 240 |
| gaggatttcg cgacctatta ctgtcaccag tcatccagac tcccgtttac ttttggccct | | 300 |
| gggaccaagg tggacattaa gcgtacggtg gctgcaccat ctgtcttcat cttcccgcca | | 360 |
| tctgatgagc agttgaaatc tggaactgcc tctgttgtgt gcctgctgaa taacttctat | | 420 |
| cccagagagg ccaaagtaca gtggaaggtg gataacgccc tccaatcggg taactcccag | | 480 |
| gagagtgtca cagagcagga cagcaaggac agcacctaca gcctcagcag caccctgacg | | 540 |
| ctgagcaaag cagactacga gaaacacaaa gtctacgcct gcgaagtcac ccatcagggc | | 600 |
| ctgagctcgc ccgtcacaaa gagcttcaac aggggagagt gt | | 642 |

<210> SEQ ID NO 7
<211> LENGTH: 642
<212> TYPE: DNA
<213> ORGANISM: Artificial Sequence
<220> FEATURE:
<223> OTHER INFORMATION: Synthetic LC-07 polynucleotide

<400> SEQUENCE: 7

| | | |
|---|---|---|
| gaaattgtgc tgactcagtc tccagacttt cagtctgtga ctccaaagga gaaagtcacc | | 60 |
| atcacctgcc gggccagtca gagcgttggt cgtagtttac actggtacca gcagaaacca | | 120 |
| gatcagtctc caaagctcct catcaagtat gcttcccagt ccttatcagg ggtcccctcg | | 180 |
| aggttcagtg gcagtggatc tgggacagat ttcaccctca ctatcaatag cctggaagct | | 240 |
| gaagatgctg caacgtatta ctgtcatcag agtagtcgtt taccattcac tttcggccct | | 300 |
| gggaccaaag tggatatcaa acgaacggtg gctgcaccat ctgtcttcat cttcccgcca | | 360 |
| tctgatgagc agttgaaatc tggaactgct agcgttgtgt gcctgctgaa taacttctat | | 420 |
| cccagagagg ccaaagtaca gtggaaggtg gataacgccc tccaatcggg taactcccag | | 480 |
| gagagtgtca cagagcagga cagcaaggac agcacctaca gcctcagcag caccctgacg | | 540 |
| ctgagcaaag cagactacga gaaacacaaa gtctacgcct gcgaagtcac ccatcagggc | | 600 |
| ctgagctcgc ccgtcacaaa gagcttcaac aggggagagt gt | | 642 |

<210> SEQ ID NO 8
<211> LENGTH: 642
<212> TYPE: DNA
<213> ORGANISM: Artificial Sequence
<220> FEATURE:
<223> OTHER INFORMATION: Synthetic LC-08 polynucleotide

<400> SEQUENCE: 8

| | | |
|---|---|---|
| gagatcgtac ttactcagtc acccgccaca ttgtccctga gcccgggtga acgggcgacc | | 60 | ctcagctgcc gagcatccca gtccgtcgga cgatcattgc actggtacca acaaaaaccg    120 ggccaggccc ccagacttct gatcaagtat gcgtcacaga gcttgtcggg tattcccgct    180 cgcttttcgg ggtcgggatc cgggacagat ttcacgctca caatctcctc gctggaaccc    240 gaggacttcg cggtctacta ttgtcatcag tcatcgaggt tgcctttcac gtttggacca    300 gggaccaagg tggacattaa gcgtacggtg gctgcaccat ctgtcttcat cttcccgcca    360 tctgatgagc agttgaaatc tggaactgcc tctgttgtgt gcctgctgaa taacttctat    420 cccagagagg ccaaagtaca gtggaaggtg gataacgccc tccaatcggg taactcccag    480 gagagtgtca cagagcagga cagcaaggac agcacctaca gcctcagcag cacccctgacg    540 ctgagcaaag cagactacga gaaacacaaa gtctacgcct gcgaagtcac ccatcagggc    600 ctgagctcgc ccgtcacaaa gagcttcaac aggggagagt gt    642

<210> SEQ ID NO 9
<211> LENGTH: 642
<212> TYPE: DNA
<213> ORGANISM: Artificial Sequence
<220> FEATURE:
<223> OTHER INFORMATION: Synthetic LC-09 polynucleotide

<400> SEQUENCE: 9
gagatcgtac ttactcagtc acccggcaca ttgtccctga gcccgggtga acgggcgacc     60
ctcagctgcc gagcatccca gtccgtcgga cgatcattgc actggtacca acaaaaaccg    120
ggccaggccc ccagacttct gatcaagtat gcgtcacaga gcttgtcggg tattcccgat    180
cgcttttcgg ggtcgggatc cgggacagat ttcacgctca caatctcccg actggaaccc    240
gaggacttcg cgacctacta ttgtcatcag tcatcgaggt tgcctttcac gtttggacag    300
gggaccaagg tggagattaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt    642

<210> SEQ ID NO 10
<211> LENGTH: 642
<212> TYPE: DNA
<213> ORGANISM: Artificial Sequence
<220> FEATURE:
<223> OTHER INFORMATION: Synthetic LC-10 polynucleotide

<400> SEQUENCE: 10
gaaattgtgc tgactcagtc tccagacttt cagtctgtga ctccaaagga aaagtcacc     60 atcacctgcc gggccagtca gagcattggt cgtagtttac actggtacca gcagaaacca    120
gatcagtctc caaagctcct cttcaagtat gcttcccagt ccttatcagg ggtcccctcg    180
aggttcagtg gcagtggatc tgggacagat ttcaccctca caatcaatag cctggaagct    240
gaagatgctg caacgtatta ctgtcatcag agtagtcgtt taccattcac tttcggccct    300
gggaccaaag tggatatcaa acgaacggtg gctgcaccat ctgtcttcat cttcccgcca    360
tctgatgagc agttgaaatc tggaactgct agcgttgtgt gcctgctgaa taacttctat    420
cccagagagg ccaaagtaca gtggaaggtg gataacgccc tccaatcggg taactcccag    480

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 11
<211> LENGTH: 642
<212> TYPE: DNA
<213> ORGANISM: Artificial Sequence
<220> FEATURE:
<223> OTHER INFORMATION: Synthetic LC-11 polynucleotide

<400> SEQUENCE: 11
gatatccagc tcactcaatc gccatcattt ctctccgctt cggtaggcga ccgggtcacg     60
atcacatgca gggcgtcgca aagcattggg aggtcgttgc attggtatca gcagaaaccc    120
ggaaaggccc cgaaacttct gttcaaatac gcatcacaaa gcttgagcgg tgtgccgtcg    180
cgcttctccg gttccggaag cggaacggaa ttcacgctta caatctcctc actgcagccc    240
gaggatttcg cgacctatta ctgtcaccag tcatccagac tcccgtttac ttttggccct    300
gggaccaagg tggacattaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 12
<211> LENGTH: 642
<212> TYPE: DNA
<213> ORGANISM: Artificial Sequence
<220> FEATURE:
<223> OTHER INFORMATION: Synthetic LC-12 polynucleotide

<400> SEQUENCE: 12
gaaattgtgt tgacgcagtc gccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtaacagtgg gtctgggaca gacttcactc tcaccatcag cagactggag    240
cctgaagatt ttgcagtgta ttactgtcag aggtatggta gctcacggac gttcggccaa    300
gggaccaagg tggaaatcaa acgaactgtg gctgcaccat ctgtcttcat cttcccgcca    360
tctgatgagc agttgaaatc tggtaccgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 13
<211> LENGTH: 657
<212> TYPE: DNA
<213> ORGANISM: Artificial Sequence
<220> FEATURE:
<223> OTHER INFORMATION: Synthetic LC-13 polynucleotide

<400> SEQUENCE: 13
```

```
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgctct atttgggttc taatcgggcc     180
tccggggtcc ctgacaggtt cagtggcagt ggatcaggca cagattttac actgcaaatc     240
agcagagtgg aggctgagga tgttggggtt tattactgca tgcaaactct acaaactcca     300
ttcactttcg gccctgggac caaagtggat atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt      657
```

<210> SEQ ID NO 14
<211> LENGTH: 657
<212> TYPE: DNA
<213> ORGANISM: Artificial Sequence
<220> FEATURE:
<223> OTHER INFORMATION: Synthetic LC-14 polynucleotide

<400> SEQUENCE: 14

```
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgctct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaaactct acaaactcca     300
ttcactttcg gccctgggac caaagtggat atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt      657
```

<210> SEQ ID NO 15
<211> LENGTH: 645
<212> TYPE: DNA
<213> ORGANISM: Artificial Sequence
<220> FEATURE:
<223> OTHER INFORMATION: Synthetic LC-15 polynucleotide

<400> SEQUENCE: 15

```
gaaattgtgt tgacgcagtc tccaggcacc ctgtctttgt ctccagggga aagagccacc      60
ctctcctgca gggccagtca gactgttagc aggagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgccgtgtt ttactgtcag cagtttggta gctcaccgtg acgttcggc     300 caagggacca aggtggaaat caaacgtacg gtggctgcac catctgtctt catcttcccg     360
ccatctgatg agcagttgaa atctggaact gcctctgttg tgtgcctgct gaataacttc     420
```

```
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                     645

<210> SEQ ID NO 16
<211> LENGTH: 660
<212> TYPE: DNA
<213> ORGANISM: Artificial Sequence
<220> FEATURE:
<223> OTHER INFORMATION: Synthetic LC-16 polynucleotide

<400> SEQUENCE: 16
gacatcgtga tgacccagtc tccagactcc ctggctgtgt ctctgggcga gagggccacc     60
atccattgca agtccagcca gaatgtttta tacagctcca acaataagaa cttcttaact    120
tggtaccagc agaaaccagg acagccccct aaactgctca tttaccgggc atctacccgg    180
gaatccgggg tccctgaccg attcagtggc agcgggtctg ggacggattt cactctcact    240
atcagcagtc tgcaggctga agatgtggca gtttatttct gtcagcaata ttatagtgct    300
ccattcactt tcggccctgg gaccaaagtg gatatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660

<210> SEQ ID NO 17
<211> LENGTH: 660
<212> TYPE: DNA
<213> ORGANISM: Artificial Sequence
<220> FEATURE:
<223> OTHER INFORMATION: Synthetic LC-17 polynucleotide

<400> SEQUENCE: 17
gacatcgtga tgacccagtc tccagactcc ctggctgtgt ctctgggcga gaggaccacc     60
atcaagtgca agtccagcca gagtgtttta tacagatcca acaataacaa cttcttagct    120
tggtaccagc agaaaccagg acagcctcct aagctgctca tttattgggc atctacccgg    180
gaatccgggg tccctgaccg attcagtggc agcgggtctg ggacagattt cactctcacc    240
atcagcagcc tgcaggctga agatgtggct gtttatttct gtcagcaata ttatatattct    300 ccgctcactt tcggcggagg gaccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660

<210> SEQ ID NO 18
<211> LENGTH: 660
<212> TYPE: DNA
<213> ORGANISM: Artificial Sequence
<220> FEATURE:
<223> OTHER INFORMATION: Synthetic LC-18 polynucleotide
```

<400> SEQUENCE: 18

```
gacatcgtga tgacccagtc tccagactcc ctggctgtgt ctctgggcga gagggccacc    60
atcaactgca agtccagcca gagtgtttta tacagttcca acaataagca ctacttagct   120
tggtaccggc agaaaccagg acagcctcct aaactgctca tttacagggc atctacccgg   180
gaatccgggg tccctgaccg attcagtggc agcgggtctg ggacagattt cactctcacc   240
atcagcagcc tgcagcctga agatgtggca gtgtattact gtcagcaata ttatagttct   300
ccattcactt tcggccctgg gaccaaagtg gatatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc    600
gaagtcaccc atcagggcct gagctcgccc gtcacaaaga gcttcaacag gggagagtgt   660
```

<210> SEQ ID NO 19
<211> LENGTH: 660
<212> TYPE: DNA
<213> ORGANISM: Artificial Sequence
<220> FEATURE:
<223> OTHER INFORMATION: Synthetic LC-19 polynucleotide

<400> SEQUENCE: 19

```
gacatcgtga tgacccagtc tccagactcc ctggctgtgt ctctgggcga gagggccacc    60
atccactgca agtccagcca gagtgtttta tacagctcca acaataagaa cttcttaact   120
tggtaccagc agaaaccagg acagcctcct aaacttctca tttaccgggc atctacccgg   180
gaatccgggg ttcctgaccg attcagtggc agcgggtctg ggacagattt cactctcacc   240
atcagcagcc tgcaggctga agatgtggca gtttatttct gtcagcaata ttatagtgct   300
ccattcactt tcggccctgg gaccagagtg gatatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc    600
gaagtcaccc atcagggcct gagctcgccc gtcacaaaga gcttcaacag gggagagtgt   660
```

<210> SEQ ID NO 20
<211> LENGTH: 660
<212> TYPE: DNA
<213> ORGANISM: Artificial Sequence
<220> FEATURE:
<223> OTHER INFORMATION: Synthetic LC-20 polynucleotide

<400> SEQUENCE: 20

```
gacatcgtga tgactcagtc tccagactcc ctggctgtgt ctctgggcga gagggccacc    60
atccactgca agtccagcca gagtgtttta tacagctcca acaataggaa cttcttaagt   120
tggtaccagc agaaaccagg acagcctcct aaactgctca tttaccgggc atctacccgg   180
gaatccgggg tccctgaccg attcagtggc agcgggtctg ggacagattt cactctcacc   240
atcagcagcc tgcaggctga agatgtggca gtttatttct gtcagcaata ttatagtgct   300
ccattcactt tcggccctgg gaccacagtg gatatcaaac gtacggtggc tgcaccatct   360
```

```
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
```

<210> SEQ ID NO 21
<211> LENGTH: 660
<212> TYPE: DNA
<213> ORGANISM: Artificial Sequence
<220> FEATURE:
<223> OTHER INFORMATION: Synthetic LC-21 polynucleotide

<400> SEQUENCE: 21

```
gacatcgtga tgacccagtc tccagactcc ctggctgtgt ctctgggcga gagggccacc     60
atcaactgca gtccagcca gagtgtttta tacagttcca acaataagaa ctacttagct    120
tggtaccggc agaaaccagg acagcctcct aagctgctca tttacagggc atctacccgg    180
gaatccgggg tccctgaccg attcagtggc agcgggtctg ggacagattt cactctcacc    240
atcagcagcc tgcaggctga agatgtggca gtgtatcact gtcagcaata ttatagttct    300
ccattcactt tcggccctgg gaccaaagtg gatatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
```

<210> SEQ ID NO 22
<211> LENGTH: 1347
<212> TYPE: DNA
<213> ORGANISM: Artificial Sequence
<220> FEATURE:
<223> OTHER INFORMATION: Synthetic HC-01 polynucleotide

<400> SEQUENCE: 22

```
caggtacagc tgcagcagtc aggtccagga ctggtgaagc cctcgcagac cctctcactc     60
acctgtgcca tctccgggga cagtgtctct agcaacagtg ctacttggaa ctggatcagg    120
cagtccccat cgagaggcct tgagtggctg gaaggacat attacaggtc caagtggtct     180
aatcattatg cagtatctgt gaaaagtcga ataaccatca ccccgacac gtccaagagc     240 cagttctccc tgcagctgaa ctctgtgact cccgaggaca cggctgtgta ttactgtgca    300
agaggaacgt ggaaacagct atggttcctt gaccactggg gccagggaac cctggtcacc    360
gtctctagtg cctccaccaa gggcccatcg gtcttccccc tggcgccctg ctccaggagc    420
acctccgaga gcacagcggc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca caccaaggt ggacaagaca    660 gttgagcgca aatgttgtgt cgagtgccca ccgtgcccag caccacctgt ggcaggaccg    720
tcagtcttcc tcttcccccc aaaacccaag gacaccctca tgatctcccg gacccctgag    780
gtcacgtgcg tggtggtgga cgtgagccac gaagaccccg aggtccagtt caactggtac    840
```

```
gtggacggcg tggaggtgca taatgccaag acaaagccac gggaggagca gttcaacagc      900
acgttccgtg tggtcagcgt cctcaccgtt gtgcaccagg actggctgaa cggcaaggag      960
tacaagtgca aggtctccaa caaaggcctc ccagccccca tcgagaaaac catctccaaa     1020
accaaagggc agccccgaga accacaggtg tacaccctgc ccccatcccg ggaggagatg     1080
accaagaacc aggtcagcct gacctgcctg gtcaaaggct tctacccag  cgacatcgcc     1140 gtggagtggg agagcaatgg gcagccggag aacaactaca agaccacacc tcccatgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaa                                         1347
```

<210> SEQ ID NO 23
<211> LENGTH: 1359
<212> TYPE: DNA
<213> ORGANISM: Artificial Sequence
<220> FEATURE:
<223> OTHER INFORMATION: Synthetic HC-02 polynucleotide

<400> SEQUENCE: 23

```
caggtacagc tgcagcagtc aggtccagga ctggtgaagc cctcgcagac cctctcactc       60
acctgtgcca tctccgggga cagtgtctct agcaacagtg ctacttggaa ctggatcagg      120
cagtccccat cgagaggcct tgagtggctg ggaaggacat attacaggtc caagtggtct      180
aatcattatg cagtatctgt gaaaagtcga ataaccatca accccgacac gtccaagagc      240
cagttctccc tgcagctgaa ctctgtgact cccgaggaca cggctgtgta ttactgtgca      300
agaggaacgt ggaaacagct atggttcctt gaccactggg gccagggaac cctggtcacc      360
gtctctagtg cctccaccaa gggcccatcg gtcttccccc tggcaccctc ctccaagagc      420
acctctgggg gcacagcggc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca caccaaggt ggacaagaaa       660 gttgagccca aatcttgtga caaaactcac acatgcccac cgtgcccagc acctgaactc      720
ctggggggac cgtcagtctt cctcttcccc ccaaaaccca aggacaccct catgatctcc      780
cggacccctg aggtcacatg cgtggtggtg gacgtgagcc acgaagaccc tgaggtcaag      840
ttcaactggt acgtggacgg cgtggaggtg cataatgcca agacaaagcc gcgggaggag      900
cagtacggca gcacgtaccg tgtggtcagc gtcctcaccg tcctgcacca ggactggctg      960
aatggcaagg agtacaagtg caaggtctcc aacaaagccc tcccagcccc catcgagaaa     1020
accatctcca aagccaaagg gcagccccga gaaccacagg tgtacaccct gcccccatcc     1080
cgggaggaga tgaccaagaa ccaggtcagc ctgacctgcc tggtcaaagg cttctatccc     1140
agcgacatcg ccgtggagtg ggagagcaat gggcagccgg agaacaacta caagaccacg     1200
cctcccgtgc tggactccga cggctccttc ttcctctata gcaagctcac cgtggacaag     1260
agcaggtggc agcaggggaa cgtcttctca tgctccgtga tgcatgaggc tctgcacaac     1320
cactacacgc agaagagcct ccctgtctc cgggtaaa                              1359
```

<210> SEQ ID NO 24
<211> LENGTH: 1338
<212> TYPE: DNA

<213> ORGANISM: Artificial Sequence
<220> FEATURE:
<223> OTHER INFORMATION: Synthetic HC-03 polynucleotide

<400> SEQUENCE: 24

```
caggtgcagt tggtggagtc tgggggaggc gtggtccagc ctgggaggtc cctgagactc      60
tcctgtgcag cctctggatt caccttcagt tactatgcca tacactgggt ccgccaggct     120
ccaggcaagg ggctagagtg ggtggcagtt atctcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gagaggatac     300
gatcttttga ctggttaccc cgactactgg ggccagggaa ccctggtcac cgtctcctca     360
gctagcacca agggcccatc ggtcttcccc ctggcgccct gctccaggag cacctccgag     420
agcacagcgg ccctgggctg cctggtcaag gactacttcc ccgaaccggt gacggtgtcg     480
tggaactcag gcgctctgac cagcggcgtg cacaccttcc cagctgtcct acagtcctca     540
ggactctact ccctcagcag cgtggtgacc gtgccctcca gcaacttcgg cacccagacc     600
tacacctgca acgtagatca caagcccagc aacaccaagg tggacaagac agttgagcgc     660
aaatgttgtg tcgagtgccc accgtgccca gcaccacctg tggcaggacc gtcagtcttc     720
ctcttccccc caaaacccaa ggacaccctc atgatctccc ggaccctga ggtcacgtgc      780
gtggtggtgg acgtgagcca cgaagacccc gaggtccagt tcaactggta cgtggacggc     840
gtggaggtgc ataatgccaa gacaaagcca cgggaggagc agttcaacag cacgttccgt     900
gtggtcagcg tcctcaccgt tgtgcaccag gactggctga acggcaagga gtacaagtgc     960
aaggtctcca acaaaggcct cccagccccc atcgagaaaa ccatctccaa aaccaaaggg    1020
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacac ctcccatgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 25
<211> LENGTH: 1350
<212> TYPE: DNA
<213> ORGANISM: Artificial Sequence
<220> FEATURE:
<223> OTHER INFORMATION: Synthetic HC-04 polynucleotide

<400> SEQUENCE: 25

```
caggtgcagt tggtggagtc tgggggaggc gtggtccagc ctgggaggtc cctgagactc      60
tcctgtgcag cctctggatt caccttcagt tactatgcca tacactgggt ccgccaggct     120
ccaggcaagg ggctagagtg ggtggcagtt atctcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gagaggatac     300
gatcttttga ctggttaccc cgactactgg ggccagggaa ccctggtcac cgtctcctca     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
```

```
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacggc    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggaggag    1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                   1350

<210> SEQ ID NO 26
<211> LENGTH: 1350
<212> TYPE: DNA
<213> ORGANISM: Artificial Sequence
<220> FEATURE:
<223> OTHER INFORMATION: Synthetic HC-05 polynucleotide

<400> SEQUENCE: 26
caggtgcagt tggtggagtc tgggggaggc gtggtccagc ctgggaggtc cctgagactc     60
tcctgtgcag cctctggatt caccttcagt tactatgcca tacactgggt ccgccaggct    120
ccaggcaagg ggctagagtg ggtggcagtt atctcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gagaggatac    300
gatcttttga ctggttaccc cgactactgg ggccagggaa ccctggtcac cgtctcctca    360
gcctcgacga gggggccgtc cgtatttccg cttgcgccct cgtcgaagtc aacttcggga    420
gggaccgcgg cacttggctg tcttgtcaaa gattacttcc ctgagccagt gacagtcagc    480
tggaattccg gtgccctcac gtcaggagta catacattcc ctgcggtatt gcagtcctcc    540
ggactctact ccctgtcgtc ggtggtaacg gtgcccagct ccagcttggg gacccagacg    600
tacatttgta acgtgaatca caaaccaagc aatactaagg tagataagaa agtagaaccg    660
aagagctgcg acaagaccca cacatgtcct ccgtgccccg cacccgagct gttgggagga    720
ccctcggtgt ttttgtttcc tcccaagcca aggacacgt tgatgatttc gcgcactcca    780
gaggtcacgt gtgtagtcgt ggacgtgtca catgaggacc ccgaggtaaa gttcaattgg    840
tatgtggacg gagtcgaggt ccataacgcc aaaacaaagc cgtgcgaaga acagtacggg    900
tcaacgtata ggtgcgtcag cgtcctcact gtgctgcacc aagactggct caatggtaaa    960
gaatacaagt gcaaggtgtc gaacaaggcc ctccctgccc ctatcgagaa aaccatctcc   1020
aaagcgaagg gcagccgcg agaaccccaa gtctacacgc tgccgccctc gcgggaggaa    1080
atgaccaaaa accaggtgtc gcttacgtgt cttgtgaaag gcttctatcc atcagatatc   1140
gcggtcgagt gggagtcgaa cggccagccc gaaaacaatt acaaaacaac acctccggtc   1200
```

| | |
|---|---|
| ctcgattcag atggaagctt cttcttgtat tcgaagctga ccgtcgataa gtcaaggtgg | 1260 |
| caacagggaa atgtgttctc gtgctcagtg atgcacgagg ctctgcataa ccactatacg | 1320 |
| cagaaatcat tgtcgctcag ccccggtaaa | 1350 |

<210> SEQ ID NO 27
<211> LENGTH: 1338
<212> TYPE: DNA
<213> ORGANISM: Artificial Sequence
<220> FEATURE:
<223> OTHER INFORMATION: Synthetic HC-06 polynucleotide

<400> SEQUENCE: 27

| | |
|---|---|
| caggtgcagc tggtggagtc tgggggaggc gtggtccagc ctggggaggtc cctgcgactc | 60 |
| tcctgtgcag cctctggatt caccttcagt agatttgcca tgcactgggt ccgccgggct | 120 |
| ccaggcaagg ggctggagtg ggtggcagtt atatcatatg atggaggaaa taaatactat | 180 |
| gcagagtccg tgaagggccg gttcaccatc tccagagaca attccaagaa caccctgaat | 240 |
| ctgctaatga acagcctgag agctgaggac acggctctgt tttactgtgc gagaggatac | 300 |
| gatgttttga ctggttaccc cgactactgg ggccagggaa ccctggtcac cgtctcctca | 360 |
| gcttccacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgctctgac cagcggcgtg cacaccttcc cagctgtcct acagtcctca | 540 |
| ggactctact ccctcagcag cgtggtgacc gtgccctcca gcaacttcgg cacccagacc | 600 |
| tacacctgca acgtagatca caagcccagc aacaccaagg tggacaagac agttgagcgc | 660 |
| aaatgttgtg tcgagtgccc accgtgccca gcaccacctg tggcaggacc gtcagtcttc | 720 |
| ctcttccccc caaaacccaa ggacaccctc atgatctccc ggacccctga ggtcacgtgc | 780 |
| gtggtggtgg acgtgagcca cgaagacccc gaggtccagt tcaactggta cgtggacggc | 840 |
| gtggaggtgc ataatgccaa gacaaagcca cgggaggagc agttcaacag cacgttccgt | 900 |
| gtggtcagcg tcctcaccgt tgtgcaccag gactggctga acggcaagga gtacaagtgc | 960 |
| aaggtctcca acaaaggcct cccagccccc atcgagaaaa ccatctccaa aaccaaaggg | 1020 |
| cagccccgag aaccacaggt gtacaccctg cccccatccc gggaggagat gaccaagaac | 1080 |
| caggtcagcc tgacctgcct ggtcaaaggc ttctacccca gcgacatcgc cgtggagtgg | 1140 |
| gagagcaatg ggcagccgga gaacaactac aagaccacac ctcccatgct ggactccgac | 1200 |
| ggctccttct tcctctacag caagctcacc gtggacaaga gcaggtggca gcaggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 28
<211> LENGTH: 1350
<212> TYPE: DNA
<213> ORGANISM: Artificial Sequence
<220> FEATURE:
<223> OTHER INFORMATION: Synthetic HC-07 polynucleotide

<400> SEQUENCE: 28

| | |
|---|---|
| caggtgcagc tggtggagtc tgggggaggc gtggtccagc ctggggaggtc cctgcgactc | 60 |
| tcctgtgcag cctctggatt caccttcagt agatttgcca tgcactgggt ccgccgggct | 120 |
| ccaggcaagg ggctggagtg ggtggcagtt atatcatatg atggaggaaa taaatactat | 180 |
| gcagagtccg tgaagggccg gttcaccatc tccagagaca attccaagaa caccctgaat | 240 |

```
ctgctaatga acagcctgag agctgaggac acggctctgt tttactgtgc gagaggatac      300
gatgttttga ctggttaccc cgactactgg ggccagggaa ccctggtcac cgtctcctca      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacggc      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag gcagccccg agaaccacag gtgtacaccc tgcccccatc ccgggaggag      1080
atgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctat agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa                                      1350

<210> SEQ ID NO 29
<211> LENGTH: 1350
<212> TYPE: DNA
<213> ORGANISM: Artificial Sequence
<220> FEATURE:
<223> OTHER INFORMATION: Synthetic HC-08 polynucleotide

<400> SEQUENCE: 29
caggtgcagc tggtggagtc tgggggaggc gtggtccagc ctgggaggtc cctgcgactc       60
tcctgtgcag cctctggatt caccttcagt agatttgcca tgcactgggt ccgccgggct      120
ccaggcaagg ggctggagtg ggtggcagtt atatcatatg atggaggaaa taaatactat      180
gcagagtccg tgaagggccg gttcaccatc tccagagaca attccaagaa caccctgaat      240
ctgctaatga acagcctgag agctgaggac acggctctgt tttactgtgc gagaggatac      300
gatgttttga ctggttaccc cgactactgg ggccagggaa ccctggtcac cgtctcctca      360
gcctcgacga aggggccgtc cgtatttccg cttcgcgccct cgtcgaagtc aacttcggga      420
gggaccgcgg cacttggctg tcttgtcaaa gattacttcc ctgagccagt gacagtcagc      480
tggaattccg gtgccctcac gtcaggagta catacattcc ctgcggtatt gcagtcctcc      540
ggactctact ccctgtcgtc ggtggtaacg gtgcccagct ccagcttggg gacccagacg      600
tacatttgta acgtgaatca caaaccaagc aatactaagg tagataagaa agtgagaaccg      660
aagagctgcg acaagaccca cacatgtcct ccgtgccccg cacccgagct gttgggagga      720
ccctcggtgt ttttgtttcc tcccaagcca aggacacgt tgatgatttc gcgcactcca      780
gaggtcacgt gtgtagtcgt ggacgtgtca catgaggacc ccgaggtaaa gttcaattgg      840
tatgtggacg gagtcgaggt ccataacgcc aaaacaaagc cgtgcgaaga acagtacggg      900
```

| | |
|---|---|
| tcaacgtata ggtgcgtcag cgtcctcact gtgctgcacc aagactggct caatggtaaa | 960 |
| gaatacaagt gcaaggtgtc gaacaaggcc ctccctgccc ctatcgagaa aaccatctcc | 1020 |
| aaagcgaagg ggcagccgcg agaaccccaa gtctacacgc tgccgccctc gcgggaggaa | 1080 |
| atgaccaaaa accaggtgtc gcttacgtgt cttgtgaaag ggttctatcc atcagatatc | 1140 |
| gcggtcgagt gggagtcgaa cggccagccc gaaaacaatt acaaaacaac acctccggtc | 1200 |
| ctcgattcag atggaagctt cttcttgtat tcgaagctga ccgtcgataa gtcaaggtgg | 1260 |
| caacagggaa atgtgttctc gtgctcagtg atgcacgagg ctctgcataa ccactatacg | 1320 |
| cagaaatcat tgtcgctcag ccccggtaaa | 1350 |

<210> SEQ ID NO 30
<211> LENGTH: 1338
<212> TYPE: DNA
<213> ORGANISM: Artificial Sequence
<220> FEATURE:
<223> OTHER INFORMATION: Synthetic HC-09 polynucleotide

<400> SEQUENCE: 30

| | |
|---|---|
| caggtgcagc tggtggagtc tgggggaggc gtggtccagc ctggagggtc cctgcgactc | 60 |
| tcctgtgcag cctctggatt caccttcagt agatttgcca tgcactgggt ccgccaggct | 120 |
| ccaggcaagg ggctggagtg ggtggcagtt atatcatatg atggagaaa taaatactat | 180 |
| gcagagtccg tgaagggccg gttcaccatc tccagagaca attccaagaa caccctgaat | 240 |
| ctgctaatga acagcctgag agctgaggac acggctctgt tttactgtgc gagaggatac | 300 |
| gatgttttga ctggttaccc cgactactgg ggccagggaa ccctggtcac cgtctcctca | 360 |
| gcttccacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgctctgac cagcggcgtg cacaccttcc cagctgtcct acagtcctca | 540 |
| ggactctact ccctcagcag cgtggtgacc gtgccctcca gcaacttcgg cacccagacc | 600 |
| tacacctgca acgtagatca caagcccagc aacaccaagg tggacaagac agttgagcgc | 660 |
| aaatgttgtg tcgagtgccc accgtgccca gcaccacctg tgcaggacc gtcagtcttc | 720 |
| ctcttccccc caaaacccaa ggacaccctc atgatctccc ggacccctga ggtcacgtgc | 780 |
| gtggtggtgg acgtgagcca cgaagacccc gaggtccagt tcaactggta cgtggacggc | 840 |
| gtggaggtgc ataatgccaa gacaaagcca cgggaggagc agttcaacag cacgttccgt | 900 |
| gtggtcagcg tcctcaccgt tgtgcaccag gactggctga acggcaagga gtacaagtgc | 960 |
| aaggtctcca acaaaggcct cccagccccc atcgagaaaa ccatctccaa aaccaaaggg | 1020 |
| cagccccgag aaccacaggt gtacaccctg cccccatccc gggaggagat gaccaagaac | 1080 |
| caggtcagcc tgacctgcct ggtcaaaggc ttctacccca gcgacatcgc cgtggagtgg | 1140 |
| gagagcaatg ggcagccgga gaacaactac aagaccacac tcccatgct ggactccgac | 1200 |
| ggctccttct tcctctacag caagctcacc gtggacaaga gcaggtggca gcaggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 31
<211> LENGTH: 1350
<212> TYPE: DNA
<213> ORGANISM: Artificial Sequence
<220> FEATURE:
<223> OTHER INFORMATION: Synthetic HC-10 polynucleotide

<400> SEQUENCE: 31

| | | |
|---|---|---|
| caggtgcagc tggtggagtc tgggggaggc gtggtccagc ctgggaggtc cctgcgactc | 60 |
| tcctgtgcag cctctggatt caccttcagt agatttgcca tgcactgggt ccgccaggct | 120 |
| ccaggcaagg ggctggagtg ggtggcagtt atatcatatg atggaggaaa taaatactat | 180 |
| gcagagtccg tgaagggccg gttcaccatc tccagagaca attccaagaa caccctgaat | 240 |
| ctgctaatga acagcctgag agctgaggac acggctctgt tttactgtgc gagaggatac | 300 |
| gatgttttga ctggttaccc cgactactgg ggccagggaa ccctggtcac cgtctcctca | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacggc | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 32
<211> LENGTH: 1350
<212> TYPE: DNA
<213> ORGANISM: Artificial Sequence
<220> FEATURE:
<223> OTHER INFORMATION: Synthetic HC-11 polynucleotide

<400> SEQUENCE: 32

| | | |
|---|---|---|
| caggtgcagc tggtggagtc tgggggaggc gtggtccagc ctgggaggtc cctgcgactc | 60 |
| tcctgtgcag cctctggatt caccttcagt agatttgcca tgcactgggt ccgccaggct | 120 |
| ccaggcaagg ggctggagtg ggtggcagtt atatcatatg atggaggaaa taaatactat | 180 |
| gcagagtccg tgaagggccg gttcaccatc tccagagaca attccaagaa caccctgaat | 240 |
| ctgctaatga acagcctgag agctgaggac acggctctgt tttactgtgc gagaggatac | 300 |
| gatgttttga ctggttaccc cgactactgg ggccagggaa ccctggtcac cgtctcctca | 360 |
| gcctcgacga aggggccgtc cgtatttccg cttgcgccct cgtcgaagtc aacttcggga | 420 |
| gggaccgcgg cacttggctg tcttgtcaaa gattacttcc ctgagccagt gacagtcagc | 480 |
| tggaattccg gtgccctcac gtcaggagta catacattcc ctgcggtatt gcagtcctcc | 540 |
| ggactctact ccctgtcgtc ggtggtaacg gtgcccagct ccagcttggg gacccagacg | 600 |

-continued

| | |
|---|---|
| tacatttgta acgtgaatca caaaccaagc aatactaagg tagataagaa agtagaaccg | 660 |
| aagagctgcg acaagaccca cacatgtcct ccgtgccccg cacccgagct gttgggagga | 720 |
| ccctcggtgt ttttgtttcc tcccaagcca aaggacacgt tgatgatttc gcgcactcca | 780 |
| gaggtcacgt gtgtagtcgt ggacgtgtca catgaggacc ccgaggtaaa gttcaattgg | 840 |
| tatgtggacg gagtcgaggt ccataacgcc aaaacaaagc cgtgcgaaga acagtacggg | 900 |
| tcaacgtata ggtgcgtcag cgtcctcact gtgctgcacc aagactggct caatggtaaa | 960 |
| gaatacaagt gcaaggtgtc gaacaaggcc ctccctgccc ctatcgagaa aaccatctcc | 1020 |
| aaagcgaagg ggcagccgcg agaacccaa gtctacacgc tgccgccctc gcggaggaa | 1080 |
| atgaccaaaa accaggtgtc gcttacgtgt cttgtgaaag ggttctatcc atcagatatc | 1140 |
| gcggtcgagt gggagtcgaa cggccagccc gaaaacaatt acaaaacaac acctccggtc | 1200 |
| ctcgattcag atggaagctt cttcttgtat tcgaagctga ccgtcgataa gtcaaggtgg | 1260 |
| caacagggaa atgtgttctc gtgctcagtg atgcacgagg ctctgcataa ccactatacg | 1320 |
| cagaaatcat tgtcgctcag ccccggtaaa | 1350 |

<210> SEQ ID NO 33
<211> LENGTH: 1338
<212> TYPE: DNA
<213> ORGANISM: Artificial Sequence
<220> FEATURE:
<223> OTHER INFORMATION: Synthetic HC-12 polynucleotide

<400> SEQUENCE: 33

| | |
|---|---|
| caggtgcagc tggtggagtc tgggggaggc gtggtccagc ctgggaggtc cctgcgactc | 60 |
| tcctgtgcag cctctggatt caccttcagt agatttgcca tgcactgggt ccgccaggct | 120 |
| ccaggcaagg ggctggagtg gtggcagtt atatcatatg atggaggaaa taaatactat | 180 |
| gcagagtccg tgaagggccg gttcaccatc tccagagaca attccaagaa caccctgtat | 240 |
| ctgcaaatga acagcctgag agctgaggac acggctctgt tttactgtgc gagaggatac | 300 |
| gatgttttga ctggttaccc cgactactgg ggccagggaa ccctggtcac cgtctcctca | 360 |
| gcttccacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgctctgac cagcggcgtg cacaccttcc cagctgtcct acagtcctca | 540 |
| ggactctact ccctcagcag cgtggtgacc gtgccctcca gcaacttcgg cacccagacc | 600 |
| tacacctgca acgtagatca caagcccagc aacaccaagg tggacaagac agttgagcgc | 660 |
| aaatgttgtg tcgagtgccc accgtgccca gcaccacctg tggcaggacc gtcagtcttc | 720 |
| ctcttccccc caaaacccaa ggacaccctc atgatctccc ggacccctga ggtcacgtgc | 780 |
| gtggtggtgg acgtgagcca cgaagacccc gaggtccagt tcaactggta cgtggacggc | 840 |
| gtggaggtgc ataatgccaa gacaaagcca cgggaggagc agttcaacag cacgttccgt | 900 |
| gtggtcagcg tcctcaccgt tgtgcaccag gactggctga acggcaagga gtacaagtgc | 960 |
| aaggtctcca acaaaggcct cccagccccc atcgagaaaa ccatctccaa accaaaggg | 1020 |
| cagccccgag aaccacaggt gtacaccctg cccccatccc gggaggagat gaccaagaac | 1080 |
| caggtcagcc tgacctgcct ggtcaaaggc ttctacccca gcgacatcgc cgtggagtgg | 1140 |
| gagagcaatg ggcagccgga gaacaactac aagaccacac ctcccatgct ggactccgac | 1200 |
| ggctccttct tcctctacag caagctcacc gtggacaaga gcaggtggca gcagggaac | 1260 |
| gtcttctcat gctccgtgat gcatgaggct ctgcacaacc actacacgca gaagagcctc | 1320 |

```
tccctgtctc cgggtaaa                                           1338

<210> SEQ ID NO 34
<211> LENGTH: 1350
<212> TYPE: DNA
<213> ORGANISM: Artificial Sequence
<220> FEATURE:
<223> OTHER INFORMATION: Synthetic HC-13 polynucleotide

<400> SEQUENCE: 34
caggtgcagc tggtggagtc tgggggaggc gtggtccagc ctggaggtc  cctgcgactc     60 tcctgtgcag cctctggatt caccttcagt agatttgcca tgcactgggt ccgccaggct    120
ccaggcaagg ggctggagtg ggtggcagtt atatcatatg atggaggaaa taaatactat    180
gcagagtccg tgaagggccg gttcaccatc tccagagaca attccaagaa caccctgtat    240
ctgcaaatga acagcctgag agctgaggac acggctctgt tttactgtgc gagaggatac    300
gatgttttga ctggttaccc cgactactgg ggccagggaa ccctggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggggga     720 ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacggc    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg  agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                   1350

<210> SEQ ID NO 35
<211> LENGTH: 1350
<212> TYPE: DNA
<213> ORGANISM: Artificial Sequence
<220> FEATURE:
<223> OTHER INFORMATION: Synthetic HC-14 polynucleotide

<400> SEQUENCE: 35
caggtgcagc tggtggagtc tgggggaggc gtggtccagc ctggaggtc  cctgcgactc     60 tcctgtgcag cctctggatt caccttcagt agatttgcca tgcactgggt ccgccaggct    120
ccaggcaagg ggctggagtg ggtggcagtt atatcatatg atggaggaaa taaatactat    180
gcagagtccg tgaagggccg gttcaccatc tccagagaca attccaagaa caccctgtat    240
ctgcaaatga acagcctgag agctgaggac acggctctgt tttactgtgc gagaggatac    300
```

| | |
|---|---|
| gatgttttga ctggttaccc cgactactgg ggccagggaa ccctggtcac cgtctcctca | 360 |
| gcctcgacga aggggccgtc cgtatttccg cttgcgccct cgtcgaagtc aacttcggga | 420 |
| gggaccgcgg cacttggctg tcttgtcaaa gattacttcc ctgagccagt gacagtcagc | 480 |
| tggaattccg gtgccctcac gtcaggagta catacattcc ctgcggtatt gcagtcctcc | 540 |
| ggactctact ccctgtcgtc ggtggtaacg gtgcccagct ccagcttggg gacccagacg | 600 |
| tacatttgta acgtgaatca caaaccaagc aatactaagg tagataagaa agtagaaccg | 660 |
| aagagctgcg acaagaccca cacatgtcct ccgtgccccg cacccgagct gttgggagga | 720 |
| ccctcggtgt ttttgtttcc tcccaagcca aggacacgt tgatgatttc gcgcactcca | 780 |
| gaggtcacgt gtgtagtcgt ggacgtgtca catgaggacc ccgaggtaaa gttcaattgg | 840 |
| tatgtggacg gagtcgaggt ccataacgcc aaaacaaagc cgtgcgaaga acagtacggg | 900 |
| tcaacgtata ggtgcgtcag cgtcctcact gtgctgcacc aagactggct caatggtaaa | 960 |
| gaatacaagt gcaaggtgtc gaacaaggcc ctccctgccc ctatcgagaa aaccatctcc | 1020 |
| aaagcgaagg ggcagccgcg agaacccaa gtctacacgt tgccgccctc gcgggaggaa | 1080 |
| atgaccaaaa accaggtgtc gcttacgtgt cttgtgaaag ggttctatcc atcagatatc | 1140 |
| gcggtcgagt gggagtcgaa cggccagccc gaaacaatt acaaacaac acctccggtc | 1200 |
| ctcgattcag atggaagctt cttcttgtat tcgaagctga ccgtcgataa gtcaaggtgg | 1260 |
| caacagggaa atgtgttctc gtgctcagtg atgcacgagg ctctgcataa ccactatacg | 1320 |
| cagaaatcat tgtcgctcag ccccggtaaa | 1350 |

<210> SEQ ID NO 36
<211> LENGTH: 1338
<212> TYPE: DNA
<213> ORGANISM: Artificial Sequence
<220> FEATURE:
<223> OTHER INFORMATION: Synthetic HC-15 polynucleotide

<400> SEQUENCE: 36

| | |
|---|---|
| caggtgcagc tggtggagtc tgggggaggc gtggtccagc ctggaggtc cctgcgactc | 60 |
| tcctgtgcag cctctggatt caccttcagt agatttgcca tgcactgggt ccgccgggct | 120 |
| ccaggcaagg ggctggagtg ggtggcagtt atatcatatg atggaggaaa taaatactat | 180 |
| gcagagtccg tgaagggccg gttcaccatc tccagagaca attccaagaa caccctgaat | 240 |
| ctgctaatgg acagcctgag agctgaggac acggctctgt tttactgtgc gagaggatac | 300 |
| gatgttttga ctggttaccc cgactactgg ggccagggaa ccctggtcac cgtctcctca | 360 |
| gcttccacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgctctgac cagcggcgtg cacaccttcc cagctgtcct acagtcctca | 540 |
| ggactctact ccctcagcag cgtggtgacc gtgcccctca gcaacttcgg cacccagacc | 600 |
| tacacctgca acgtagatca caagcccagc aacaccaagg tggacaagac agttgagcgc | 660 |
| aaatgttgtg tcgagtgccc accgtgccca gcaccacctg tggcaggacc gtcagtcttc | 720 |
| ctcttccccc caaaacccaa ggacaccctc atgatctccc ggacccctga ggtcacgtgc | 780 |
| gtggtggtgg acgtgagcca cgaagacccc gaggtccagt tcaactggta cgtggacggc | 840 |
| gtggaggtgc ataatgccaa gacaaagcca cgggaggagc agttcaacag cacgttccgt | 900 |
| gtggtcagcg tcctcaccgt tgtgcaccag gactggctga acggcaagga gtacaagtgc | 960 |
| aaggtctcca acaaaggcct cccagccccc atcgagaaaa ccatctccaa aaccaaaggg | 1020 |

```
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacac ctcccatgct ggactccgac    1200
ggctccttct tcctctacag caagctcacc gtggacaaga gcaggtggca gcagggaac     1260 gtcttctcat gctccgtgat gcatgaggct ctgcacaacc actacacgca gaagagcctc    1320
tccctgtctc cgggtaaa                                                  1338
```

<210> SEQ ID NO 37
<211> LENGTH: 1350
<212> TYPE: DNA
<213> ORGANISM: Artificial Sequence
<220> FEATURE:
<223> OTHER INFORMATION: Synthetic HC-16 polynucleotide

<400> SEQUENCE: 37

```
caggtgcagc tggtggagtc tgggggaggc gtggtccagc ctgggaggtc cctgcgactc      60
tcctgtgcag cctctggatt caccttcagt agatttgcca tgcactgggt ccgccgggct    120
ccaggcaagg ggctggagtg ggtggcagtt atatcatatg atggaggaaa taaatactat    180
gcagagtccg tgaagggccg gttcaccatc tccagagaca attccaagaa caccctgaat    240
ctgctaatgg acagcctgag agctgaggac acggctctgt tttactgtgc gagaggatac    300
gatgttttga ctggttaccc cgactactgg ggccagggaa ccctggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag cgcccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggggagga gcagtacggc    900 agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag gcagccccg agaaccacag gtgtacaccc tgcccccatc ccggaggag     1080 atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                     1350
```

<210> SEQ ID NO 38
<211> LENGTH: 1350
<212> TYPE: DNA
<213> ORGANISM: Artificial Sequence
<220> FEATURE:
<223> OTHER INFORMATION: Synthetic HC-17 polynucleotide

<400> SEQUENCE: 38

```
caggtgcagc tggtggagtc tgggggaggc gtggtccagc ctggggaggtc cctgcgactc    60 tcctgtgcag cctctggatt caccttcagt agatttgcca tgcactgggt ccgccgggct   120
ccaggcaagg ggctggagtg ggtggcagtt atatcatatg atggaggaaa taaatactat   180
gcagagtccg tgaagggccg gttcaccatc tccagagaca attccaagaa cacccctgaat  240 ctgctaatgg acagcctgag agctgaggac acggctctgt tttactgtgc gagaggatac   300
gatgttttga ctggttaccc cgactactgg ggccagggaa ccctggtcac cgtctcctca   360
gcctcgacga aggggccgtc cgtatttccg cttgcgccct cgtcgaagtc aacttcggga   420
gggaccgcgg cacttggctg tcttgtcaaa gattacttcc ctgagccagt gacagtcagc   480
tggaattccg gtgccctcac gtcaggagta catacattcc ctgcggtatt gcagtcctcc   540
ggactctact ccctgtcgtc ggtggtaacg gtgcccagct ccagcttggg gacccagacg   600
tacatttgta acgtgaatca caaaccaagc aatactaagg tagataagaa agtagaaccg   660
aagagctgcg acaagaccca cacatgtcct ccgtgccccg cacccgagct gttgggagga   720
ccctcggtgt ttttgtttcc tcccaagcca aaggacacgt tgatgatttc gcgcactcca   780
gaggtcacgt gtgtagtcgt ggacgtgtca catgaggacc ccgaggtaaa gttcaattgg   840
tatgtggacg gagtcgaggt ccataacgcc aaaacaaagc cgtgcgaaga acagtacggg   900
tcaacgtata ggtgcgtcag cgtcctcact gtgctgcacc aagactggct caatggtaaa   960
gaatacaagt gcaaggtgtc gaacaaggcc ctccctgccc ctatcgagaa aaccatctcc  1020
aaagcgaagg ggcagccgcg agaaccccaa gtctacacgc tgccgccctc gcgggaggaa  1080
atgaccaaaa accaggtgtc gcttacgtgt cttgtgaaag ggttctatcc atcagatatc  1140
gcggtcgagt gggagtcgaa cggccagccc gaaaacaatt acaaaacaac acctccggtc  1200
ctcgattcag atggaagctt cttcttgtat tcgaagctga ccgtcgataa gtcaaggtgg  1260
caacagggaa atgtgttctc gtgctcagtg atgcacgagg ctctgcataa ccactatacg  1320
cagaaatcat tgtcgctcag ccccggtaaa                                    1350

<210> SEQ ID NO 39
<211> LENGTH: 1338
<212> TYPE: DNA
<213> ORGANISM: Artificial Sequence
<220> FEATURE:
<223> OTHER INFORMATION: Synthetic HC-18 polynucleotide

<400> SEQUENCE: 39
caagttcagt tggtgcaatc tggagccgaa gtaaagaagc caggagcttc agtgaaagtc    60
tcttgtaaag caagtggatt cacgtttagc cgctttgcca tgcattgggt gcggcaagct   120
cccggtcagg ggttggagtg gatgggagtt attagctatg acgggggcaa taagtactac   180
gccgagtctg ttaagggtcg ggtcacaatg acacgggaca cctcaaccag tacagcctat   240
atggaactgt ctagcctgag atccgaggac accgctgtgt attattgcgc tagggggtac   300
gatgtattga cgggttatcc tgattactgg ggcaggggaa cactcgtaac cgtctctagt   360
gcctccacca agggcccatc ggtcttcccc ctggcgccct gctccaggag cacctccgag   420
agcacagcgg ccctgggctg cctggtcaag gactacttcc ccgaaccggt gacggtgtcg   480
tggaactcag gcgctctgac cagcggcgtg cacaccttcc cagctgtcct acagtcctca   540
ggactctact ccctcagcag cgtggtgacc gtgccctcca gcaacttcgg cacccagacc   600
tacacctgca acgtagatca caagcccagc aacaccaagg tggacaagac agttgagcgc   660
aaatgttgtg tcgagtgccc accgtgccca gcaccacctg tggcaggacc gtcagtcttc   720
```

```
ctcttccccc caaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcaacag cacgttccgt    900
gtggtcagcg tcctcaccgt tgtgcaccag gactggctga acggcaagga gtacaagtgc    960
aaggtctcca acaaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac ctcccatgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 40
<211> LENGTH: 1350
<212> TYPE: DNA
<213> ORGANISM: Artificial Sequence
<220> FEATURE:
<223> OTHER INFORMATION: Synthetic HC-19 polynucleotide

<400> SEQUENCE: 40

```
caagttcagt tggtgcaatc tggagccgaa gtaaagaagc caggagcttc agtgaaagtc     60
tcttgtaaag caagtggatt cacgtttagc cgctttgcca tgcattgggt gcggcaagct    120
cccggtcagg ggttggagtg gatgggagtt attagctatg acggggggcaa taagtactac    180 gccgagtctg ttaagggtcg ggtcacaatg acacgggaca cctcaaccag tacagcctat    240
atggaactgt ctagcctgag atccgaggac accgctgtgt attattgcgc taggggggtac    300 gatgtattga cggggttatcc tgattactgg gggcagggga cactcgtaac cgtctctagt    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggaccccct    780 gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacggc    900
agcacgtacc gtgtggtcag cgtcctcacc gtcctgcacc aggactggct gaatggcaag    960
gagtacaagt gcaaggtctc caacaaagcc ctcccagccc catcgagaa aaccatctcc    1020 aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                   1350
```

<210> SEQ ID NO 41
<211> LENGTH: 1350
<212> TYPE: DNA
<213> ORGANISM: Artificial Sequence
<220> FEATURE:
<223> OTHER INFORMATION: Synthetic HC-20 polynucleotide

<400> SEQUENCE: 41

| | | | | | |
|---|---|---|---|---|---|
| caagttcagt | tggtgcaatc | tggagccgaa | gtaaagaagc | caggagcttc agtgaaagtc | 60 |
| tcttgtaaag | caagtggatt | cacgtttagc | cgctttgcca | tgcattgggt gcggcaagct | 120 |
| cccggtcagg | ggttggagtg | gatgggagtt | attagctatg | acgggggcaa taagtactac | 180 |
| gccgagtctg | ttaagggtcg | ggtcacaatg | acacgggaca | cctcaaccag tacagcctat | 240 |
| atggaactgt | ctagcctgag | atccgaggac | accgctgtgt | attattgcgc taggggtac | 300 |
| gatgtattga | cgggttatcc | tgattactgg | gggcagggga | cactcgtaac cgtctctagt | 360 |
| gcctcgacga | gggggccgtc | cgtatttccg | cttgcgccct | cgtcgaagtc aacttcggga | 420 |
| gggaccgcgg | cacttggctg | tcttgtcaaa | gattacttcc | ctgagccagt gacagtcagc | 480 |
| tggaattccg | gtgccctcac | gtcaggagta | catacattcc | ctgcggtatt gcagtcctcc | 540 |
| ggactctact | ccctgtcgtc | ggtggtaacg | gtgcccagct | ccagcttggg gacccagacg | 600 |
| tacatttgta | acgtgaatca | caaaccaagc | aatactaagg | tagataagaa agtagaaccg | 660 |
| aagagctgcg | acaagaccca | cacatgtcct | ccgtgccccg | cacccgagct gttgggagga | 720 |
| ccctcggtgt | ttttgtttcc | tcccaagcca | aaggacacgt | tgatgatttc gcgcactcca | 780 |
| gaggtcacgt | gtgtagtcgt | ggacgtgtca | catgaggacc | ccgaggtaaa gttcaattgg | 840 |
| tatgtggacg | gagtcgaggt | ccataacgcc | aaaacaaagc | cgtgcgaaga acagtacggg | 900 |
| tcaacgtata | ggtgcgtcag | cgtcctcact | gtgctgcacc | aagactggct caatggtaaa | 960 |
| gaatacaagt | gcaaggtgtc | gaacaaggcc | ctccctgccc | ctatcgagaa aaccatctcc | 1020 |
| aaagcgaagg | ggcagccgcg | agaacccaa | gtctacacgc | tgccgccctc gcgggaggaa | 1080 |
| atgaccaaaa | accaggtgtc | gcttacgtgt | cttgtgaaag ggttctatcc atcagatatc | 1140 |
| gcggtcgagt | gggagtcgaa | cggccagccc | gaaaacaatt | acaaaacaac acctcccggtc | 1200 |
| ctcgattcag | atggaagctt | cttcttgtat | tcgaagctga | ccgtcgataa gtcaaggtgg | 1260 |
| caacagggaa | atgtgttctc | gtgctcagtg | atgcacgagg | ctctgcataa ccactatacg | 1320 |
| cagaaatcat | tgtcgctcag | ccccggtaaa | | | 1350 |

<210> SEQ ID NO 42
<211> LENGTH: 1338
<212> TYPE: DNA
<213> ORGANISM: Artificial Sequence
<220> FEATURE:
<223> OTHER INFORMATION: Synthetic HC-21 polynucleotide

<400> SEQUENCE: 42

| | | | | | |
|---|---|---|---|---|---|
| caagttcagt | tggtgcaatc | tggagccgaa | gtaaagaagc | caggagcttc agtgaaagtc | 60 |
| tcttgtgccg | caagtggatt | cacgtttagc | cgctttgcca | tgcattgggt gcggcaagct | 120 |
| cccggtcagg | ggttggagtg | gatgggagtt | attagctatg | acgggggcaa taagtactac | 180 |
| gccgagtctg | ttaagggtcg | ggtcacaatg | acacgggaca | actcaaaaaa tacagcctat | 240 |
| atggaactgt | ctagcctgag | atccgaggac | accgctgtgt | attattgcgc taggggtac | 300 |
| gatgtattga | cgggttatcc | tgattactgg | gggcagggga | cactcgtaac cgtctctagt | 360 |
| gcctccacca | agggcccatc | ggtcttcccc | ctggcgccct | gctccaggag cacctccgag | 420 |

```
agcacagcgg ccctgggctg cctggtcaag gactacttcc ccgaaccggt gacggtgtcg      480
tggaactcag gcgctctgac cagcggcgtg cacaccttcc cagctgtcct acagtcctca      540
ggactctact ccctcagcag cgtggtgacc gtgccctcca gcaacttcgg cacccagacc      600
tacacctgca acgtagatca caagcccagc aacaccaagg tggacaagac agttgagcgc      660
aaatgttgtg tcgagtgccc accgtgccca gcaccacctg tggcaggacc gtcagtcttc      720
ctcttccccc caaaacccaa ggacaccctc atgatctccc ggacccctga ggtcacgtgc      780
gtggtggtgg acgtgagcca cgaagacccc gaggtccagt tcaactggta cgtggacggc      840
gtggaggtgc ataatgccaa gacaaagcca cgggaggagc agttcaacag cacgttccgt      900
gtggtcagcg tcctcaccgt tgtgcaccag gactggctga acggcaagga gtacaagtgc      960
aaggtctcca acaaaggcct cccagccccc atcgagaaaa ccatctccaa aaccaaaggg     1020
cagccccgag aaccacaggt gtacaccctg cccccatccc gggaggagat gaccaagaac     1080
caggtcagcc tgacctgcct ggtcaaaggc ttctacccca gcgacatcgc cgtggagtgg     1140
gagagcaatg ggcagccgga gaacaactac aagaccacac ctcccatgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtctc cgggtaaa                                                   1338

<210> SEQ ID NO 43
<211> LENGTH: 1350
<212> TYPE: DNA
<213> ORGANISM: Artificial Sequence
<220> FEATURE:
<223> OTHER INFORMATION: Synthetic HC-22 polynucleotide

<400> SEQUENCE: 43
caagttcagt tggtgcaatc tggagccgaa gtaaagaagc caggagcttc agtgaaagtc       60
tcttgtgccg caagtggatt cacgtttagc cgctttgcca tgcattgggt gcggcaagct      120
cccggtcagg ggttggagtg gatgggagtt attagctatg acggggggcaa taagtactac      180 gccgagtctg ttaagggtcg ggtcacaatg acacgggaca actcaaaaaa tacagcctat      240
atggaactgt ctagcctgag atccgaggac accgctgtgt attattgcgc taggggggtac      300 gatgtattga cgggttatcc tgattactgg ggcaggggga cactcgtaac cgtctctagt      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctggggggga      720 ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacggc      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggaggag     1080
```

```
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                     1350

<210> SEQ ID NO 44
<211> LENGTH: 1350
<212> TYPE: DNA
<213> ORGANISM: Artificial Sequence
<220> FEATURE:
<223> OTHER INFORMATION: Synthetic HC-23 polynucleotide

<400> SEQUENCE: 44
caagttcagt tggtgcaatc tggagccgaa gtaaagaagc caggagcttc agtgaaagtc      60
tcttgtgccg caagtggatt cacgtttagc cgctttgcca tgcattgggt gcggcaagct    120
cccggtcagg ggttggagtg gatggagtt attagctatg acggggggcaa taagtactac    180 gccgagtctg ttaagggtcg ggtcacaatg acacgggaca actcaaaaaa tacagcctat    240
atggaactgt ctagcctgag atccgaggac accgctgtgt attattgcgc tagggggtac    300
gatgtattga cgggttatcc tgattactgg ggcagggga cactcgtaac cgtctctagt     360
gcctcgacga aggggccgtc cgtatttccg cttgcgccct cgtcgaagtc aacttcggga    420
gggaccgcgg cacttggctg tcttgtcaaa gattacttcc ctgagccagt gacagtcagc    480
tggaattccg gtgccctcac gtcaggagta catacattcc ctgcggtatt gcagtcctcc    540
ggactctact ccctgtcgtc ggtggtaacg gtgcccagct ccagcttggg gacccagacg    600
tacatttgta acgtgaatca caaaccaagc aatactaagg tagataagaa agtagaaccg    660
aagagctgcg acaagaccca cacatgtcct ccgtgccccg cacccgagct gttgggagga    720
ccctcggtgt ttttgtttcc tcccaagcca aggacacgt tgatgatttc gcgcactcca     780
gaggtcacgt gtgtagtcgt ggacgtgtca catgaggacc ccgaggtaaa gttcaattgg    840
tatgtggacg gagtcgaggt ccataacgcc aaaacaaagc cgtgcgaaga acagtacggg    900
tcaacgtata ggtgcgtcag cgtcctcact gtgctgcacc aagactggct caatggtaaa    960
gaatacaagt gcaaggtgtc gaacaaggcc ctccctgccc ctatcgagaa aaccatctcc   1020
aaagcgaagg ggcagccgcg agaaccccaa gtctacacgc tgccgccctc gcgggaggaa   1080
atgaccaaaa accaggtgtc gcttacgtgt cttgtgaaag gttctatccc atcagatatc    1140
gcggtcgagt gggagtcgaa cggccagccc gaaaacaatt acaaaacaac acctccggtc   1200
ctcgattcag atggaagctt cttcttgtat tcgaagctga ccgtcgataa gtcaaggtgg    1260
caacagggaa atgtgttctc gtgctcagtg atgcacgagg ctctgcataa ccactatacg    1320
cagaaatcat tgtcgctcag ccccggtaaa                                    1350

<210> SEQ ID NO 45
<211> LENGTH: 1338
<212> TYPE: DNA
<213> ORGANISM: Artificial Sequence
<220> FEATURE:
<223> OTHER INFORMATION: Synthetic HC-24 polynucleotide

<400> SEQUENCE: 45
gaggtgcagc tgctggagtc tggggggaggc ctggtccagc ctggggggtc cctgcgactc       60
tcctgtgcag cctctggatt caccttcagt agatttgcca tgcactgggt ccgccaggct    120
```

```
ccaggcaagg ggctggagtg ggtggcagtt atatcatatg atggaggaaa taaatactat      180
gcagagtccg tgaagggccg gttcaccatc tccagagaca attccaagaa cacctgtat       240 ctgcaaatga acagcctgag agctgaggac acggctgtgt attactgtgc gagaggatac      300
gatgttttga ctggttaccc cgactactgg ggccagggaa ccctggtcac cgtctcctca      360
gcttccacca agggcccatc cgtcttcccc ctggcgccct gctccaggag cacctccgag      420
agcacagccg ccctgggctg cctggtcaag gactacttcc ccgaaccggt gacggtgtcg      480
tggaactcag gcgctctgac cagcggcgtg cacaccttcc cagctgtcct acagtcctca      540
ggactctact ccctcagcag cgtggtgacc gtgccctcca gcaacttcgg cacccagacc      600
tacacctgca acgtagatca caagcccagc aacaccaagg tggacaagac agttgagcgc      660
aaatgttgtg tcgagtgccc accgtgccca gcaccacctg tggcaggacc gtcagtcttc      720
ctcttccccc caaaacccaa ggacaccctc atgatctccc ggacccctga ggtcacgtgc      780
gtggtggtgg acgtgagcca cgaagacccc gaggtccagt tcaactggta cgtggacggc      840
gtggaggtgc ataatgccaa gacaaagcca cgggaggagc agttcaacag cacgttccgt      900
gtggtcagcg tcctcaccgt tgtgcaccag gactggctga acggcaagga gtacaagtgc      960
aaggtctcca acaaaggcct cccagccccc atcgagaaaa ccatctccaa aaccaaaggg     1020
cagccccgag aaccacaggt gtacaccctg cccccatccc gggaggagat gaccaagaac     1080
caggtcagcc tgacctgcct ggtcaaaggc ttctacccca gcgacatcgc cgtggagtgg     1140
gagagcaatg ggcagccgga gaacaactac aagaccacac ctcccatgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtctc cgggtaaa                                                   1338
```

<210> SEQ ID NO 46
<211> LENGTH: 1350
<212> TYPE: DNA
<213> ORGANISM: Artificial Sequence
<220> FEATURE:
<223> OTHER INFORMATION: Synthetic HC-25 polynucleotide

<400> SEQUENCE: 46

```
gaggtgcagc tgctggagtc tgggggaggc ctggtccagc ctggggggtc cctgcgactc       60
tcctgtgcag cctctggatt caccttcagt agatttgcca tgcactgggt ccgccaggct      120
ccaggcaagg ggctggagtg ggtggcagtt atatcatatg atggaggaaa taaatactat      180
gcagagtccg tgaagggccg gttcaccatc tccagagaca attccaagaa cacctgtat      240 ctgcaaatga acagcctgag agctgaggac acggctgtgt attactgtgc gagaggatac      300
gatgttttga ctggttaccc cgactactgg ggccagggaa ccctggtcac cgtctcctca      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
```

| | |
|---|---|
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacggc | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 47
<211> LENGTH: 1350
<212> TYPE: DNA
<213> ORGANISM: Artificial Sequence
<220> FEATURE:
<223> OTHER INFORMATION: Synthetic HC-26 polynucleotide

<400> SEQUENCE: 47

| | |
|---|---|
| gaggtgcagc tgctggagtc tgggggaggc ctggtccagc ctgggggtc cctgcgactc | 60 |
| tcctgtgcag cctctggatt caccttcagt agatttgcca tgcactgggt ccgccaggct | 120 |
| ccaggcaagg ggctggagtg ggtggcagtt atatcatatg atggaggaaa taaatactat | 180 |
| gcagagtccg tgaagggccg gttcaccatc tccagagaca attccaagaa caccctgtat | 240 |
| ctgcaaatga acagcctgag agctgaggac acggctgtgt attactgtgc gagaggatac | 300 |
| gatgttttga ctggttaccc cgactactgg ggccagggaa ccctggtcac cgtctcctca | 360 |
| gcctcgacga aggggccgtc cgtatttccg cttgcgccct cgtcgaagtc aacttcggga | 420 |
| gggaccgcgg cacttggctg tcttgtcaaa gattacttcc ctgagccagt gacagtcagc | 480 |
| tggaattccg gtgccctcac gtcaggagta catacattcc ctgcggtatt gcagtcctcc | 540 |
| ggactctact ccctgtcgtc ggtggtaacg gtgcccagct ccagcttggg gacccagacg | 600 |
| tacatttgta acgtgaatca caaaccaagc aatactaagg tagataagaa agtagaaccg | 660 |
| aagagctgcg acaagaccca cacatgtcct ccgtgccccg cacccgagct gttgggagga | 720 |
| ccctcggtgt tttgtttcc tcccaagcca aaggacacgt tgatgatttc gcgcactcca | 780 |
| gaggtcacgt gtgtagtcgt ggacgtgtca catgaggacc ccgaggtaaa gttcaattgg | 840 |
| tatgtggacg gagtcgaggt ccataacgcc aaaacaaagc cgtgcgaaga acagtacggg | 900 |
| tcaacgtata ggtgcgtcag cgtcctcact gtgctgcacc aagactggct caatggtaaa | 960 |
| gaatacaagt gcaaggtgtc gaacaaggcc ctccctgccc ctatcgagaa aaccatctcc | 1020 |
| aaagcgaagg ggcagccgcg agaacccaa gtctacacgc tgccgccctc gcgggaggaa | 1080 |
| atgaccaaaa accaggtgtc gcttacgtgt cttgtgaaag ggttctatcc atcagatatc | 1140 |
| gcggtcgagt gggagtcgaa cggccagccc gaaaacaatt acaaaacaac cctccggtc | 1200 |
| ctcgattcag atggaagctt cttcttgtat tcgaagctga ccgtcgataa gtcaaggtgg | 1260 |
| caacagggaa atgtgttctc gtgctcagtg atgcacgagg ctctgcataa ccactatacg | 1320 |
| cagaaatcat tgtcgctcag ccccggtaaa | 1350 |

<210> SEQ ID NO 48
<211> LENGTH: 1338

```
<212> TYPE: DNA
<213> ORGANISM: Artificial Sequence
<220> FEATURE:
<223> OTHER INFORMATION: Synthetic HC-27 polynucleotide

<400> SEQUENCE: 48
caggtgcagc tgctggagtc tgggggaggc ctggtccagc ctgggggtc cctgcgactc      60
tcctgtgcag cctctggatt caccttcagt agatttgcca tgcactgggt ccgccaggct    120
ccaggcaagg ggctggagtg ggtggcagtt atatcatatg atggaggaaa taaatactat    180
gcagagtccg tgaagggccg gttcaccatc tccagagaca attccaagaa caccctgtat    240
ctgcaaatga acagcctgag agctgaggac acggctgtgt attactgtgc gagaggatac    300
gatgttttga ctggttaccc cgactactgg ggccagggaa ccctggtcac cgtctcctca    360
gcttccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgctctgac cagcggcgtg cacaccttcc cagctgtcct acagtcctca    540
ggactctact ccctcagcag cgtggtgacc gtgccctcca gcaacttcgg cacccagacc    600
tacacctgca acgtagatca caagcccagc aacaccaagg tggacaagac agttgagcgc    660
aaatgttgtg tcgagtgccc accgtgccca gcaccacctg tggcaggacc gtcagtcttc    720
ctcttccccc caaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcaacag cacgttccgt    900
gtggtcagcg tcctcaccgt tgtgcaccag gactggctga acggcaagga gtacaagtgc    960
aaggtctcca acaaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac ctcccatgct ggactccgac   1200
ggctccttct cctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338

<210> SEQ ID NO 49
<211> LENGTH: 1350
<212> TYPE: DNA
<213> ORGANISM: Artificial Sequence
<220> FEATURE:
<223> OTHER INFORMATION: Synthetic HC-28 polynucleotide

<400> SEQUENCE: 49
caggtgcagc tgctggagtc tgggggaggc ctggtccagc ctgggggtc cctgcgactc      60
tcctgtgcag cctctggatt caccttcagt agatttgcca tgcactgggt ccgccaggct    120
ccaggcaagg ggctggagtg ggtggcagtt atatcatatg atggaggaaa taaatactat    180
gcagagtccg tgaagggccg gttcaccatc tccagagaca attccaagaa caccctgtat    240
ctgcaaatga acagcctgag agctgaggac acggctgtgt attactgtgc gagaggatac    300
gatgttttga ctggttaccc cgactactgg ggccagggaa ccctggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
```

| | |
|---|---|
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacggc | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag gcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 50
<211> LENGTH: 1350
<212> TYPE: DNA
<213> ORGANISM: Artificial Sequence
<220> FEATURE:
<223> OTHER INFORMATION: Synthetic HC-29 polynucleotide

<400> SEQUENCE: 50

| | |
|---|---|
| caggtgcagc tgctggagtc tgggggaggc ctggtccagc ctggggggtc cctgcgactc | 60 |
| tcctgtgcag cctctggatt caccttcagt agatttgcca tgcactgggt ccgccaggct | 120 |
| ccaggcaagg gctggagtg gtggcagtt atatcatatg atggaggaaa taaatactat | 180 |
| gcagagtccg tgaagggccg gttcaccatc tccagagaca attccaagaa caccctgtat | 240 |
| ctgcaaatga acagcctgag agctgaggac acggctgtgt attactgtgc gagaggatac | 300 |
| gatgttttga ctggttaccc cgactactgg ggccagggaa ccctggtcac cgtctcctca | 360 |
| gcctcgacga gggggccgtc cgtatttccg cttgcgccct cgtcgaagtc aacttcggga | 420 |
| gggaccgcgg cacttggctg tcttgtcaaa gattacttcc ctgagccagt gacagtcagc | 480 |
| tggaattccg gtgccctcac gtcaggagta catacattcc ctgcggtatt gcagtcctcc | 540 |
| ggactctact ccctgtcgtc ggtggtaacg gtgcccagct ccagcttggg gacccagacg | 600 |
| tacatttgta acgtgaatca caaaccaagc aatactaagg tagataagaa agtagaaccg | 660 |
| aagagctgcg acaagaccca cacatgtcct ccgtgccccg cacccgagct gttgggagga | 720 |
| ccctcggtgt ttttgtttcc tcccaagcca aggacacgt tgatgatttc gcgcactcca | 780 |
| gaggtcacgt gtgtagtcgt ggacgtgtca catgaggacc ccgaggtaaa gttcaattgg | 840 |
| tatgtggacg gagtcgaggt ccataacgcc aaaacaaagc cgtgcgaaga acagtacggg | 900 |
| tcaacgtata ggtgcgtcag cgtcctcact gtgctgcacc aagactggct caatggtaaa | 960 |
| gaatacaagt gcaaggtgtc gaacaaggcc ctccctgccc ctatcgagaa aaccatctcc | 1020 |
| aaagccaagg gcagccgcgc agaacccaa gtctacacgc tgccgccctc gcgggaggaa | 1080 |
| atgaccaaaa accaggtgtc gcttacgtgt cttgtgaaag gcttctatcc atcagatatc | 1140 |
| gcggtcgagt gggagtcgaa cggccagccc gaaaacaatt acaaaacaac acctccggtc | 1200 |

```
ctcgattcag atggaagctt cttcttgtat tcgaagctga ccgtcgataa gtcaaggtgg    1260
caacagggaa atgtgttctc gtgctcagtg atgcacgagg ctctgcataa ccactatacg    1320
cagaaatcat tgtcgctcag ccccggtaaa                                    1350
```

<210> SEQ ID NO 51
<211> LENGTH: 1338
<212> TYPE: DNA
<213> ORGANISM: Artificial Sequence
<220> FEATURE:
<223> OTHER INFORMATION: Synthetic HC-30 polynucleotide

<400> SEQUENCE: 51

```
caagttcagt tggtgcaatc tggagccgaa gtaaagaagc caggagcttc agtgaaagtc      60
tcttgtaaag caagtggatt cacgtttagc cgctttgcca tgcattgggt gcggcaagct     120
cccggtcagg ggttggagtg gatgggagtt attagctatg acggggggcaa taagtactac    180 gccgagtctg ttaagggtcg ggtcacaatg acacgggaca cctcaaccag tacactctat    240
atggaactgt ctagcctgag atccgaggac accgctgtgt attattgcgc taggggggtac    300 gatgtattga cggggttatcc tgattactgg gggcagggga cactcgtaac cgtctctagt    360
gcctccacca agggcccatc ggtcttcccc ctggcgccct gctccaggag cacctccgag    420
agcacagcgg ccctgggctg cctggtcaag gactacttcc ccgaaccggt gacggtgtcg    480
tggaactcag gcgctctgac cagcggcgtg cacaccttcc cagctgtcct acagtcctca    540
ggactctact ccctcagcag cgtggtgacc gtgccctcca gcaacttcgg cacccagacc    600
tacacctgca acgtagatca caagcccagc aacaccaagg tggacaagac agttgagcgc    660
aaatgttgtg tcgagtgccc accgtgccca gcaccacctg tggcaggacc gtcagtcttc    720 ctcttcccccc aaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcaacag cacgttccgt    900
gtggtcagcg tcctcaccgt tgtgcaccag gactggctga acggcaagga gtacaagtgc    960
aaggtctcca acaaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac ctcccatgct ggactccgac   1200
ggctccttct cctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                1338
```

<210> SEQ ID NO 52
<211> LENGTH: 1350
<212> TYPE: DNA
<213> ORGANISM: Artificial Sequence
<220> FEATURE:
<223> OTHER INFORMATION: Synthetic HC-31 polynucleotide

<400> SEQUENCE: 52

```
caagttcagt tggtgcaatc tggagccgaa gtaaagaagc caggagcttc agtgaaagtc      60
tcttgtaaag caagtggatt cacgtttagc cgctttgcca tgcattgggt gcggcaagct     120
cccggtcagg ggttggagtg gatgggagtt attagctatg acggggggcaa taagtactac    180
```

```
gccgagtctg ttaagggtcg ggtcacaatg acacgggaca cctcaaccag tacactctat      240
atggaactgt ctagcctgag atccgaggac accgctgtgt attattgcgc tagggggtac      300
gatgtattga cgggttatcc tgattactgg gggcagggga cactcgtaac cgtctctagt      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag cgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacggc      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggaggag     1080
atgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctat agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa                                      1350
```

<210> SEQ ID NO 53
<211> LENGTH: 1350
<212> TYPE: DNA
<213> ORGANISM: Artificial Sequence
<220> FEATURE:
<223> OTHER INFORMATION: Synthetic HC-32 polynucleotide

<400> SEQUENCE: 53

```
caagttcagt tggtgcaatc tggagccgaa gtaaagaagc caggagcttc agtgaaagtc       60
tcttgtaaag caagtggatt cacgtttagc cgctttgcca tgcattgggt gcggcaagct      120
cccggtcagg ggttggagtg gatgggagtt attagctatg acgggggcaa taagtactac      180
gccgagtctg ttaagggtcg ggtcacaatg acacgggaca cctcaaccag tacactctat      240
atggaactgt ctagcctgag atccgaggac accgctgtgt attattgcgc tagggggtac      300
gatgtattga cgggttatcc tgattactgg gggcagggga cactcgtaac cgtctctagt      360
gcctcgacga aggggccgtc cgtatttccg cttgcgccct cgtcgaagtc aacttcggga      420
gggaccgcgg cacttggctg tcttgtcaaa gattacttcc ctgagccagt gacagtcagc      480
tggaattccg gtgccctcac gtcaggagta catacattcc ctgcgtatt gcagtcctcc      540 ggactctact ccctgtcgtc ggtggtaacg gtgcccagct ccagcttggg acccagacg      600 tacatttgta acgtgaatca caaaccaagc aatactaagg tagataagaa agtagaaccg      660
aagagctgcg acaagaccca cacatgtcct ccgtgccccg cacccgagct gttgggagga      720
ccctcggtgt tttgtgtttcc tcccaagcca aggacacgt tgatgatttc gcgcactcca      780
gaggtcacgt gtgtagtcgt ggacgtgtca catgaggacc ccgaggtaaa gttcaattgg      840
tatgtggacg gagtcgaggt ccataacgcc aaaacaaagc cgtgcgaaga acagtacggg      900
```

```
tcaacgtata ggtgcgtcag cgtcctcact gtgctgcacc aagactggct caatggtaaa    960
gaatacaagt gcaaggtgtc gaacaaggcc ctccctgccc ctatcgagaa aaccatctcc   1020
aaagcgaagg ggcagccgcg agaaccccaa gtctacacgc tgccgccctc gcgggaggaa   1080
atgaccaaaa accaggtgtc gcttacgtgt cttgtgaaag ggttctatcc atcagatatc   1140
gcggtcgagt gggagtcgaa cggccagccc gaaaacaatt acaaaacaac acctccggtc   1200
ctcgattcag atggaagctt cttcttgtat tcgaagctga ccgtcgataa gtcaaggtgg   1260
caacagggaa atgtgttctc gtgctcagtg atgcacgagg ctctgcataa ccactatacg   1320
cagaaatcat tgtcgctcag ccccggtaaa                                    1350
```

<210> SEQ ID NO 54
<211> LENGTH: 1338
<212> TYPE: DNA
<213> ORGANISM: Artificial Sequence
<220> FEATURE:
<223> OTHER INFORMATION: Synthetic HC-33 polynucleotide

<400> SEQUENCE: 54

```
caagttcagt tggtgcaatc tggagccgaa gtaaagaagc caggagcttc agtgaaagtc     60
tcttgtaaag caagtggatt cacgtttagc cgctttgcca tgcattgggt gcggcaagct    120
cccggtcagg ggttggagtg gatgggagtt attagctatg acgggggcaa taagtactac    180
gccgagtctg ttaagggtcg ggtcacaatg acacgggaca cctcaaagag tacagcctat    240
atggaactgt ctagcctgag atccgaggac accgctgtgt attattgcgc tagggggtac    300
gatgtattga cgggttatcc tgattactgg gggcagggga cactcgtaac cgtctctagt    360
gcctccacca agggcccatc ggtcttcccc ctggcgccct gctccaggag cacctccgag    420
agcacagcgg ccctgggctg cctggtcaag gactacttcc ccgaaccggt gacggtgtcg    480
tggaactcag gcgctctgac cagcggcgtg cacaccttcc cagctgtcct acagtcctca    540
ggactctact ccctcagcag cgtggtgacc gtgccctcca gcaacttcgg cacccagacc    600
tacacctgca acgtagatca caagcccagc aacaccaagg tggacaagac agttgagcgc    660
aaatgttgtg tcgagtgccc accgtgccca gcaccacctg tggcaggacc gtcagtcttc    720
ctcttccccc caaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcaacag cacgttccgt    900
gtggtcagcg tcctcaccgt tgtgcaccag gactggctga acggcaagga gtacaagtgc    960
aaggtctcca acaaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac tcccatgct ggactccgac   1200 ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 55
<211> LENGTH: 1350
<212> TYPE: DNA
<213> ORGANISM: Artificial Sequence
<220> FEATURE:

<223> OTHER INFORMATION: Synthetic HC-34 polynucleotide

<400> SEQUENCE: 55

| | | | | | |
|---|---|---|---|---|---|
| caagttcagt | tggtgcaatc | tggagccgaa | gtaaagaagc | caggagcttc | agtgaaagtc | 60 |
| tcttgtaaag | caagtggatt | cacgtttagc | cgctttgcca | tgcattgggt | gcggcaagct | 120 |
| cccggtcagg | ggttggagtg | gatgggagtt | attagctatg | acggggggcaa | taagtactac | 180 |
| gccgagtctg | ttaagggtcg | ggtcacaatg | acacgggaca | cctcaaagag | tacagcctat | 240 |
| atggaactgt | ctagcctgag | atccgaggac | accgctgtgt | attattgcgc | taggggggtac | 300 |
| gatgtattga | cggggttatcc | tgattactgg | gggcagggga | cactcgtaac | cgtctctagt | 360 |
| gcctccacca | agggcccatc | ggtcttcccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | gcgccctgac | cagcggcgtg | cacaccttcc | cggctgtcct | acagtcctca | 540 |
| ggactctact | ccctcagcag | cgtggtgacc | gtgccctcca | gcagcttggg | cacccagacc | 600 |
| tacatctgca | acgtgaatca | caagcccagc | aacaccaagg | tggacaagaa | agttgagccc | 660 |
| aaatcttgtg | acaaaactca | cacatgccca | ccgtgcccag | cacctgaact | cctggggggga | 720 |
| ccgtcagtct | tcctcttccc | cccaaaaccc | aaggacaccc | tcatgatctc | ccggacccct | 780 |
| gaggtcacat | gcgtggtggt | ggacgtgagc | cacgaagacc | ctgaggtcaa | gttcaactgg | 840 |
| tacgtggacg | gcgtggaggt | gcataatgcc | aagacaaagc | cgcggggagga | gcagtacggc | 900 |
| agcacgtacc | gtgtggtcag | cgtcctcacc | gtcctgcacc | aggactggct | gaatggcaag | 960 |
| gagtacaagt | gcaaggtctc | caacaaagcc | ctcccagccc | ccatcgagaa | aaccatctcc | 1020 |
| aaagccaaag | ggcagccccg | agaaccacag | gtgtacaccc | tgcccccatc | ccgggaggag | 1080 |
| atgaccaaga | accaggtcag | cctgacctgc | ctggtcaaag | gcttctatcc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctat | agcaagctca | ccgtggacaa | gagcaggtgg | 1260 |
| cagcagggga | acgtcttctc | atgctccgtg | atgcatgagg | ctctgcacaa | ccactacacg | 1320 |
| cagaagagcc | tctccctgtc | tccgggtaaa | | | | 1350 |

<210> SEQ ID NO 56
<211> LENGTH: 1350
<212> TYPE: DNA
<213> ORGANISM: Artificial Sequence
<220> FEATURE:
<223> OTHER INFORMATION: Synthetic HC-35 polynucleotide

<400> SEQUENCE: 56

| | | | | | |
|---|---|---|---|---|---|
| caagttcagt | tggtgcaatc | tggagccgaa | gtaaagaagc | caggagcttc | agtgaaagtc | 60 |
| tcttgtaaag | caagtggatt | cacgtttagc | cgctttgcca | tgcattgggt | gcggcaagct | 120 |
| cccggtcagg | ggttggagtg | gatgggagtt | attagctatg | acggggggcaa | taagtactac | 180 |
| gccgagtctg | ttaagggtcg | ggtcacaatg | acacgggaca | cctcaaagag | tacagcctat | 240 |
| atggaactgt | ctagcctgag | atccgaggac | accgctgtgt | attattgcgc | taggggggtac | 300 |
| gatgtattga | cggggttatcc | tgattactgg | gggcagggga | cactcgtaac | cgtctctagt | 360 |
| gcctcgacga | agggccgtc | cgtatttccg | cttgcgccct | cgtcgaagtc | aacttcggga | 420 |
| gggaccgcgg | cacttggctg | tcttgtcaaa | gattacttcc | ctgagccagt | gacagtcagc | 480 |
| tggaattccg | gtgccctcac | gtcaggagta | catacattcc | ctgcgtgtatt | gcagtcctcc | 540 |
| ggactctact | ccctgtcgtc | ggtggtaacg | gtgcccagct | ccagcttggg | gacccagacg | 600 |

| | | |
|---|---|---|
| tacatttgta acgtgaatca caaaccaagc aatactaagg tagataagaa agtagaaccg | 660 |
| aagagctgcg acaagaccca cacatgtcct ccgtgccccg cacccgagct gttgggagga | 720 |
| ccctcggtgt ttttgtttcc tcccaagcca aaggacacgt tgatgatttc gcgcactcca | 780 |
| gaggtcacgt gtgtagtcgt ggacgtgtca catgaggacc ccgaggtaaa gttcaattgg | 840 |
| tatgtggacg gagtcgaggt ccataacgcc aaaacaaagc cgtgcgaaga acagtacggg | 900 |
| tcaacgtata ggtgcgtcag cgtcctcact gtgctgcacc aagactggct caatggtaaa | 960 |
| gaatacaagt gcaaggtgtc gaacaaggcc ctccctgccc ctatcgagaa aaccatctcc | 1020 |
| aaagcgaagg ggcagccgcg agaacccaa gtctacacgc tgccgccctc gcgggaggaa | 1080 |
| atgaccaaaa accaggtgtc gcttacgtgt cttgtgaaag ggttctatcc atcagatatc | 1140 |
| gcggtcgagt gggagtcgaa cggccagccc gaaaacaatt acaaaacaac acctccggtc | 1200 |
| ctcgattcag atggaagctt cttcttgtat tcgaagctga ccgtcgataa gtcaaggtgg | 1260 |
| caacagggaa atgtgttctc gtgctcagtg atgcacgagg ctctgcataa ccactatacg | 1320 |
| cagaaatcat tgtcgctcag ccccggtaaa | 1350 |

<210> SEQ ID NO 57
<211> LENGTH: 1338
<212> TYPE: DNA
<213> ORGANISM: Artificial Sequence
<220> FEATURE:
<223> OTHER INFORMATION: Synthetic HC-36 polynucleotide

<400> SEQUENCE: 57

| | | |
|---|---|---|
| caagttcagt tggtggagtc tggagccgaa gtagtaaagc caggagcttc agtgaaagtc | 60 |
| tcttgtaaag caagtggatt cacgtttagc cgctttgcca tgcattgggt gcggcaagct | 120 |
| cccggtcagg ggttggagtg gatgggagtt attagctatg acggggggcaa taagtactac | 180 |
| gccgagtctg ttaagggtcg ggtcacaatg acacgggaca cctcaaccag tacactctat | 240 |
| atggaactgt ctagcctgag atccgaggac accgctgtgt attattgcgc taggggggtac | 300 |
| gatgtattga cgggttatcc tgattactgg gggcagggga cactcgtaac cgtctctagt | 360 |
| gcctccacca agggcccatc ggtcttcccc ctggcgccct gctccaggag cacctccgag | 420 |
| agcacagcgg ccctgggctg cctggtcaag gactacttcc ccgaaccggt gacggtgtcg | 480 |
| tggaactcag gcgctctgac cagcggcgtg cacaccttcc cagctgtcct acagtcctca | 540 |
| ggactctact ccctcagcag cgtggtgacc gtgccctcca gcaacttcgg cacccagacc | 600 |
| tacacctgca acgtagatca caagcccagc aacaccaagg tggacaagac agttgagcgc | 660 |
| aaatgttgtg tcgagtgccc accgtgccca gcaccacctg tggcaggacc gtcagtcttc | 720 |
| ctcttccccc caaaacccaa ggacaccctc atgatctccc ggacccctga ggtcacgtgc | 780 |
| gtggtggtgg acgtgagcca cgaagacccc gaggtccagt tcaactggta cgtggacggc | 840 |
| gtggaggtgc ataatgccaa gacaaagcca cgggaggagc agttcaacag cacgttccgt | 900 |
| gtggtcagcg tcctcaccgt tgtgcaccag gactggctga acggcaagga gtacaagtgc | 960 |
| aaggtctcca acaaaggcct cccagccccc atcgagaaaa ccatctccaa aaccaagggg | 1020 |
| cagccccgag aaccacaggt gtacaccctg cccccatccc gggaggagat gaccaagaac | 1080 |
| caggtcagcc tgacctgcct ggtcaaaggc ttctacccca gcgacatcgc cgtggagtgg | 1140 |
| gagagcaatg ggcagccgga gaacaactac aagaccacac tcccatgct ggactccgac | 1200 |
| ggctccttct tcctctacag caagctcacc gtggacaaga gcaggtggca gcaggggaac | 1260 |

```
gtcttctcat gctccgtgat gcatgaggct ctgcacaacc actacacgca gaagagcctc    1320
tccctgtctc cgggtaaa                                                  1338

<210> SEQ ID NO 58
<211> LENGTH: 1350
<212> TYPE: DNA
<213> ORGANISM: Artificial Sequence
<220> FEATURE:
<223> OTHER INFORMATION: Synthetic HC-37 polynucleotide

<400> SEQUENCE: 58
caagttcagt tggtggagtc tggagccgaa gtagtaaagc caggagcttc agtgaaagtc     60
tcttgtaaag caagtggatt cacgtttagc cgctttgcca tgcattgggt gcggcaagct    120
cccggtcagg ggttggagtg gatgggagtt attagctatg acgggggcaa taagtactac    180
gccgagtctg ttaagggtcg ggtcacaatg acacgggaca cctcaaccag tacactctat    240
atggaactgt ctagcctgag atccgaggac accgctgtgt attattgcgc taggggtac    300 gatgtattga cgggttatcc tgattactgg ggcagggga cactcgtaac cgtctctagt    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag cgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacggc    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350

<210> SEQ ID NO 59
<211> LENGTH: 1350
<212> TYPE: DNA
<213> ORGANISM: Artificial Sequence
<220> FEATURE:
<223> OTHER INFORMATION: Synthetic HC-38 polynucleotide

<400> SEQUENCE: 59
caagttcagt tggtggagtc tggagccgaa gtagtaaagc caggagcttc agtgaaagtc     60
tcttgtaaag caagtggatt cacgtttagc cgctttgcca tgcattgggt gcggcaagct    120
cccggtcagg ggttggagtg gatgggagtt attagctatg acgggggcaa taagtactac    180
gccgagtctg ttaagggtcg ggtcacaatg acacgggaca cctcaaccag tacactctat    240
atggaactgt ctagcctgag atccgaggac accgctgtgt attattgcgc taggggtac    300
```

| | |
|---|---|
| gatgtattga cgggttatcc tgattactgg gggcagggga cactcgtaac cgtctctagt | 360 |
| gcctcgacga aggggccgtc cgtatttccg cttgcgccct cgtcgaagtc aacttcggga | 420 |
| gggaccgcgg cacttggctg tcttgtcaaa gattacttcc ctgagccagt gacagtcagc | 480 |
| tggaattccg gtgccctcac gtcaggagta catacattcc ctgcggtatt gcagtcctcc | 540 |
| ggactctact ccctgtcgtc ggtggtaacg gtgcccagct ccagcttggg acccagacg | 600 |
| tacatttgta acgtgaatca caaaccaagc aatactaagg tagataagaa agtagaaccg | 660 |
| aagagctgcg acaagaccca cacatgtcct ccgtgccccg cacccgagct gttgggagga | 720 |
| ccctcggtgt ttttgtttcc tcccaagcca aggacacgt tgatgatttc gcgcactcca | 780 |
| gaggtcacgt gtgtagtcgt ggacgtgtca catgaggacc ccgaggtaaa gttcaattgg | 840 |
| tatgtggacg gagtcgaggt ccataacgcc aaaacaaagc cgtgcgaaga acagtacggg | 900 |
| tcaacgtata ggtgcgtcag cgtcctcact gtgctgcacc aagactggct caatggtaaa | 960 |
| gaatacaagt gcaaggtgtc gaacaaggcc ctccctgccc ctatcgagaa aaccatctcc | 1020 |
| aaagcgaagg ggcagccgcg agaaccccaa gtctacacgc tgccgccctc gcgggaggaa | 1080 |
| atgaccaaaa accaggtgtc gcttacgtgt cttgtgaaag ggttctatcc atcagatatc | 1140 |
| gcggtcgagt gggagtcgaa cggccagccc gaaaacaatt acaaaacaac acctccggtc | 1200 |
| ctcgattcag atggaagctt cttcttgtat tcgaagctga ccgtcgataa gtcaaggtgg | 1260 |
| caacagggaa atgtgttctc gtgctcagtg atgcacgagg ctctgcataa ccactatacg | 1320 |
| cagaaatcat tgtcgctcag ccccggtaaa | 1350 |

<210> SEQ ID NO 60
<211> LENGTH: 1338
<212> TYPE: DNA
<213> ORGANISM: Artificial Sequence
<220> FEATURE:
<223> OTHER INFORMATION: Synthetic HC-39 polynucleotide

<400> SEQUENCE: 60

| | |
|---|---|
| caggtgcagc tggtggagtc tgggggaggc gtggtccagc ctggagtc cctgcgactc | 60 |
| tcctgtgcag cctctggatt caccttcagt cgctatgcca tgcactgggt ccgccaggct | 120 |
| tcaggcaagg gctggagtg ggtggcagtt atatcatatg atggaagtaa taaatactat | 180 |
| gcagactccg tgaagggccg attcaccatc tccagagaca attccaagaa caccctgtat | 240 |
| ctgctaatga gcagcctgag agctgaggac acggctgtgt tttactgtgc gagaggatac | 300 |
| gatatttga ctggttaccc cgactactgg ggccaggaa ccctggtcac cgtctcctca | 360 |
| gctagcacca agggcccatc ggtcttcccc ctggcgccct gctccaggag cacctccgag | 420 |
| agcacagcgg ccctgggctg cctggtcaag gactacttcc ccgaaccggt gacggtgtcg | 480 |
| tggaactcag gcgctctgac cagcggcgtg cacaccttcc cagctgtcct acagtcctca | 540 |
| ggactctact ccctcagcag cgtggtgacc gtgcccctca gcaacttcgg cacccagacc | 600 |
| tacacctgca acgtagatca caagcccagc aacaccaagg tggacaagac agttgagcgc | 660 |
| aaatgttgtg tcgagtgccc accgtgccca gcaccacctg tggcaggacc gtcagtcttc | 720 |
| ctcttccccc caaaacccaa ggacaccctc atgatctccc ggacccctga ggtcacgtgc | 780 |
| gtggtggtgg acgtgagcca cgaagaccc gaggtccagt tcaactggta cgtggacggc | 840 |
| gtggaggtgc ataatgccaa gacaaagcca cgggaggagc agttcaacag cacgttccgt | 900 |
| gtggtcagcg tcctcaccgt tgtgcaccag gactggctga acggcaagga gtacaagtgc | 960 |

```
aaggtctcca acaaaggcct cccagccccc atcgagaaaa ccatctccaa aaccaaaggg    1020
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacac ctcccatgct ggactccgac    1200
ggctccttct tcctctacag caagctcacc gtggacaaga gcaggtggca gcagggaac    1260 gtcttctcat gctccgtgat gcatgaggct ctgcacaacc actacacgca gaagagcctc    1320
tccctgtctc cgggtaaa                                                  1338
```

<210> SEQ ID NO 61
<211> LENGTH: 1350
<212> TYPE: DNA
<213> ORGANISM: Artificial Sequence
<220> FEATURE:
<223> OTHER INFORMATION: Synthetic HC-40 polynucleotide

<400> SEQUENCE: 61

```
caggtgcagc tggtggagtc tgggggaggc gtggtccagc ctgggaggtc cctgcgactc      60
tcctgtgcag cctctggatt caccttcagt cgctatgcca tgcactgggt ccgccaggct    120
tcaggcaagg ggctggagtg ggtggcagtt atatcatatg atggaagtaa taaatactat    180
gcagactccg tgaagggccg attcaccatc tccagagaca attccaagaa caccctgtat    240
ctgctaatga gcagcctgag agctgaggac acggctgtgt tttactgtgc gagaggatac    300
gatattttga ctggttaccc cgactactgg ggccagggaa ccctggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggaggga gcagtacggc    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag ggcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                    1350
```

<210> SEQ ID NO 62
<211> LENGTH: 1350
<212> TYPE: DNA
<213> ORGANISM: Artificial Sequence
<220> FEATURE:
<223> OTHER INFORMATION: Synthetic HC-41 polynucleotide

<400> SEQUENCE: 62

```
caggtgcagc tggtggagtc tgggggaggc gtggtccagc ctggggaggtc cctgcgactc     60 tcctgtgcag cctctggatt caccttcagt cgctatgcca tgcactgggt ccgccaggct    120
tcaggcaagg ggctggagtg ggtggcagtt atatcatatg atggaagtaa taaatactat    180
gcagactccg tgaagggccg attcaccatc tccagagaca attccaagaa cacccctgtat   240 ctgctaatga gcagcctgag agctgaggac acggctgtgt tttactgtgc gagaggatac    300
gatattttga ctggttaccc cgactactgg ggccagggaa ccctggtcac cgtctcctca    360
gcctcgacga aggggccgtc cgtatttccg cttgcgccct cgtcgaagtc aacttcggga    420
gggaccgcgg cacttggctg tcttgtcaaa gattacttcc ctgagccagt gacagtcagc    480
tggaattccg gtgccctcac gtcaggagta catacattcc ctgcggtatt gcagtcctcc    540
ggactctact ccctgtcgtc ggtggtaacg gtgcccagct ccagcttggg gacccagacg    600
tacatttgta acgtgaatca caaaccaagc aatactaagg tagataagaa agtagaaccg    660
aagagctgcg acaagaccca cacatgtcct ccgtgccccg cacccgagct gttgggagga    720
ccctcggtgt ttttgtttcc tcccaagcca aggacacgt gatgatttc gcgcactcca     780 gaggtcacgt gtgtagtcgt ggacgtgtca catgaggacc ccgaggtaaa gttcaattgg    840
tatgtggacg gagtcgaggt ccataacgcc aaaacaaagc cgtgcgaaga acagtacggg    900
tcaacgtata ggtgcgtcag cgtcctcact gtgctgcacc aagactggct caatggtaaa    960
gaatacaagt gcaaggtgtc gaacaaggcc ctccctgccc ctatcgagaa aaccatctcc   1020
aaagcgaagg ggcagccgcg agaaccccaa gtctacacgc tgccgccctc gcgggaggaa   1080
atgaccaaaa accaggtgtc gcttacgtgt cttgtgaaag ggttctatcc atcagatatc   1140
gcggtcgagt gggagtcgaa cggccagccc gaaacaatt acaaaacaac acctccggtc    1200
ctcgattcag atggaagctt cttcttgtat tcgaagctga ccgtcgataa gtcaaggtgg   1260
caacagggaa atgtgttctc gtgctcagtg atgcacgagg ctctgcataa ccactatacg   1320
cagaaatcat tgtcgctcag ccccggtaaa                                    1350
```

<210> SEQ ID NO 63
<211> LENGTH: 1347
<212> TYPE: DNA
<213> ORGANISM: Artificial Sequence
<220> FEATURE:
<223> OTHER INFORMATION: Synthetic HC-42 polynucleotide

<400> SEQUENCE: 63

```
caggttcagc tggtgcagtc tggagctgag gtgaagaagc ctgggcctc agtgaaggtc      60 tcctgcaagg cttctggtta cacctttacc agctatggta tcagctgggt gcgacaggcc   120
cctggacaag ggcttgagtg gatgggatgg atcaacgctt acaatggtca cacaaactat   180
gcacagacgt tccagggcag agtcaccatg accacagaca catccacgag cacagcctac   240
atggagctga ggagcctgag atctgacgac acggccgtgt attactgtgc gagggaactg    300
gaactacgct ccttctatta cttcggtatg gacgtctggg gccaagggac cacggtcccc    360
gtctctagtg cctccaccaa gggcccatcg gtcttcccc tggcgccctg ctccaggagc    420
acctccgaga gcacagcggc cctgggctgc ctggtcaagg actacttccc cgaaccggtg   480
acggtgtcgt ggaactcagg cgctctgacc agcggcgtgc acaccttccc agctgtccta   540
cagtcctcag gactctactc cctcagcagc gtggtgaccg tgccctccag caacttcggc    600
acccagacct acacctgcaa cgtagatcac aagcccagca acaccaaggt ggacaagaca    660
```

```
gttgagcgca aatgttgtgt cgagtgccca ccgtgcccag caccacctgt ggcaggaccg    720
tcagtcttcc tcttcccccc aaaacccaag gacaccctca tgatctcccg gacccctgag    780
gtcacgtgcg tggtggtgga cgtgagccac gaagaccccg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagcccca tcgagaaaac catctccaaa    1020
accaaagggc agccccgaga accacaggtg tacaccctgc ccccatcccg ggaggagatg    1080
accaagaacc aggtcagcct gacctgcctg gtcaaaggct tctacccag cgacatcgcc    1140 gtggagtggg agagcaatgg gcagccggag aacaactaca agaccacacc tcccatgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 64
<211> LENGTH: 1347
<212> TYPE: DNA
<213> ORGANISM: Artificial Sequence
<220> FEATURE:
<223> OTHER INFORMATION: Synthetic HC-43 polynucleotide

<400> SEQUENCE: 64

```
caggttcagc tggtgcagtc tggagctgaa gtgaagaagc ctggggcctc agtgaaggtc    60
tcctgcaagg cttctggtta caccttacc agctatggta tcagctgggt gcgacaggcc   120
cctggacaag gcttgagtg gatgggatgg atcaacgctt acaatggtca cacaaactat   180
gcacagacgt tccagggcag agtcaccatg accacagaca catccacgag cacagcctac   240
atggaactga ggagcctgag atctgacgac acggccgtgt attactgtgc gagggaactg   300
gaactacgct ccttctatta cttcggtatg gacgtctggg gccaagggac cacggtcacc   360
gtctctagtg cctccaccaa gggcccatcg gtcttccccc tggcgccctg ctccaggagc   420
acctccgaga gcacagcggc cctgggctgc ctggtcaagg actacttccc cgaaccggtg   480
acggtgtcgt ggaactcagg cgctctgacc agcggcgtgc acaccttccc agctgtccta   540
cagtcctcag gactctactc cctcagcagc gtggtgaccg tgccctccag caacttcggc   600
acccagacct acacctgcaa cgtagatcac aagcccagca caccaaggt ggacaagaca   660 gttgagcgca aatgttgtgt cgagtgccca ccgtgcccag caccacctgt ggcaggaccg    720
tcagtcttcc tcttcccccc aaaacccaag gacaccctca tgatctcccg gacccctgag    780
gtcacgtgcg tggtggtgga cgtgagccac gaagaccccg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagcccca tcgagaaaac catctccaaa    1020
accaaagggc agccccgaga accacaggtg tacaccctgc ccccatcccg ggaggagatg    1080
accaagaacc aggtcagcct gacctgcctg gtcaaaggct tctacccag cgacatcgcc    1140 gtggagtggg agagcaatgg gcagccggag aacaactaca agaccacacc tcccatgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 65
<211> LENGTH: 1341
<212> TYPE: DNA
<213> ORGANISM: Artificial Sequence
<220> FEATURE:
<223> OTHER INFORMATION: Synthetic HC-44 polynucleotide

<400> SEQUENCE: 65

| | |
|---|---|
| caggttcagc tggtgcagtc tggagctgag gtgaagaagt ctggggcctc tttgaaggtc | 60 |
| tcctgcaagg cttctggtta cattttttacc cgctatggtg tcagctgggt gcgacaggcc | 120 |
| cctggacaag gcttgagtg gatgggatgg atcaccactt acaatggtaa cacaaactat | 180 |
| gcacagaagc tccagggcag agtcaccatg accatagaca catccacgag cacagcctac | 240 |
| atggaactga aagcctcag atctgacgac acggccgtgt attactgtgc gagaagagtg | 300 |
| cggtatagtg ggggctactc gtttgacaac tggggccagg gaaccctggt caccgtctct | 360 |
| agtgcctcca ccaagggccc atcggtcttc cccctggcgc cctgctccag gagcacctcc | 420 |
| gagagcacag cggccctggg ctgcctggtc aaggactact tccccgaacc ggtgacggtg | 480 |
| tcgtggaact caggcgctct gaccagcggc gtgcacacct tcccagctgt cctacagtcc | 540 |
| tcaggactct actccctcag cagcgtggtg accgtgccct ccagcaactt cggcacccag | 600 |
| acctacacct gcaacgtaga tcacaagccc agcaacacca aggtggacaa gacagttgag | 660 |
| cgcaaatgtt gtgtcgagtg cccaccgtgc ccagcaccac ctgtggcagg accgtcagtc | 720 |
| ttcctcttcc ccccaaaacc caaggacacc ctcatgatct cccggacccc tgaggtcacg | 780 |
| tgcgtggtgg tggacgtgag ccacgaagac cccgaggtcc agttcaactg gtacgtggac | 840 |
| ggcgtggagg tgcataatgc caagacaaag ccacgggagg agcagttcaa cagcacgttc | 900 |
| cgtgtggtca gcgtcctcac cgttgtgcac caggactggc tgaacggcaa ggagtacaag | 960 |
| tgcaaggtct ccaacaaagg cctcccagcc cccatcgaga aaaccatctc caaaaccaaa | 1020 |
| gggcagcccc gagaaccaca ggtgtacacc ctgcccccat cccgggagga gatgaccaag | 1080 |
| aaccaggtca gcctgacctg cctggtcaaa ggcttctacc ccagcgacat cgccgtggag | 1140 |
| tgggagagca atgggcagcc ggagaacaac tacaagacca cacctcccat gctggactcc | 1200 |
| gacggctcct tcttcctcta cagcaagctc accgtggaca gagcaggtg gcagcagggg | 1260 |
| aacgtcttct catgctccgt gatgcatgag gctctgcaca accactacac gcagaagagc | 1320 |
| ctctccctgt ctccgggtaa a | 1341 |

<210> SEQ ID NO 66
<211> LENGTH: 1341
<212> TYPE: DNA
<213> ORGANISM: Artificial Sequence
<220> FEATURE:
<223> OTHER INFORMATION: Synthetic HC-45 polynucleotide

<400> SEQUENCE: 66

| | |
|---|---|
| caggttcagc tggtgcagtc tggagctgag gtgaagaagt ctggggcctc tttgaaggtc | 60 |
| tcctgcaagg cttctggtta cattttttacc cgctatggtg tcagctgggt gcgacaggcc | 120 |
| cctggacaag gcttgagtg gatgggatgg atcaccactt acaatggtaa tacaaactat | 180 |
| gcacagaagc tccagggcag agtcaccatg accacagaca catccacgag cacagcctac | 240 |
| atggaactga ggagcctcag atctgacgac acggccgtgt attactgtgc gagaagagtg | 300 |
| cggtacagtg ggggctactc gtttgacaac tggggccagg gaaccctggt caccgtctct | 360 |

```
agtgcctcca ccaagggccc atcggtcttc ccctggcgc cctgctccag gagcacctcc    420
gagagcacag cggccctggg ctgcctggtc aaggactact tccccgaacc ggtgacggtg    480
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgtggcagg accgtcagtc    720
ttcctcttcc ccccaaaacc caaggacacc ctcatgatct cccggacccc tgaggtcacg    780
tgcgtggtgg tggacgtgag ccacgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttgtgcac caggactggc tgaacggcaa ggagtacaag    960
tgcaaggtct ccaacaaagg cctcccagcc cccatcgaga aaaccatctc caaaaccaaa   1020
gggcagcccc gagaaccaca ggtgtacacc ctgcccccat cccgggagga gatgaccaag   1080
aaccaggtca gcctgacctg cctggtcaaa ggcttctacc ccagcgacat cgccgtggag   1140
tgggagagca atgggcagcc ggagaacaac tacaagacca cacctcccat gctggactcc   1200
gacggctcct tcttcctcta cagcaagctc accgtggaca gagcaggtg gcagcagggg    1260 aacgtcttct catgctccgt gatgcatgag gctctgcaca accactacac gcagaagagc   1320 ctctcccctgt ctccgggtaa a                                            1341

<210> SEQ ID NO 67
<211> LENGTH: 1341
<212> TYPE: DNA
<213> ORGANISM: Artificial Sequence
<220> FEATURE:
<223> OTHER INFORMATION: Synthetic HC-46 polynucleotide

<400> SEQUENCE: 67
caggttcagc tggtgcagtc tggagctgag gtgaagaagt ctggggcctc tttgaaggtc      60
tcctgcaagg cttctggtta cattttttacc cgctatggtg tcagctgggt gcgacaggcc    120
cctggacaag gccttgagtg gatgggatgg atcaccactt acaatggtaa tacaaactat    180
gcacagaaac tccagggcag agtcaccatg accacagaca catccacgaa cacagcctac    240
atggaactga ggagcctcag atctgacgac acggccgtgt attactgtgc gagaagagtg    300
cggtatagtg ggggctactc gtttgacaac tgggggccagg gaaccctggt caccgtctct    360
agtgcctcca ccaagggccc atcggtcttc ccctggcgc cctgctccag gagcacctcc    420
gagagcacag cggccctggg ctgcctggtc aaggactact tccccgaacc ggtgacggtg    480
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgtggcagg accgtcagtc    720
ttcctcttcc ccccaaaacc caaggacacc ctcatgatct cccggacccc tgaggtcacg    780
tgcgtggtgg tggacgtgag ccacgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttgtgcac caggactggc tgaacggcaa ggagtacaag    960
tgcaaggtct ccaacaaagg cctcccagcc cccatcgaga aaaccatctc caaaaccaaa   1020
gggcagcccc gagaaccaca ggtgtacacc ctgcccccat cccgggagga gatgaccaag   1080
```

```
aaccaggtca gcctgacctg cctggtcaaa ggcttctacc ccagcgacat cgccgtggag    1140
tgggagagca atgggcagcc ggagaacaac tacaagacca cacctcccat gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                               1341

<210> SEQ ID NO 68
<211> LENGTH: 1332
<212> TYPE: DNA
<213> ORGANISM: Artificial Sequence
<220> FEATURE:
<223> OTHER INFORMATION: Synthetic HC-47 polynucleotide

<400> SEQUENCE: 68
caggtgcagc tgcaggagtc gggcccagga ctggtgaagc cttcggagac cctgtccctc      60
acctgcactg tctctggtgg ctccatcagt agttactact ggagctggat ccggcagccc     120
gccgggaagg gactggaatg gattgggcgt atctatacca gtgggagcac caactacaac     180
ccctccctca gagtcgagt caccatgtca ataggcacgt ccaagaacca gttctccctg     240
aagctgagct ctgtgaccgc cgcggacacg gccgtgtatt actgtgcgat tattgcatct     300
cgtggctggt acttcgatct ctggggccgt ggcaccctgg tcaccgtctc tagtgcctcc     360
accaagggcc catcggtctt ccccctggcg ccctgctcca ggagcacctc cgagagcaca     420
gcggccctgg gctgcctggt caaggactac ttccccgaac cggtgacggt gtcgtggaac     480
tcaggcgctc tgaccagcgg cgtgcacacc ttcccagctg tcctacagtc ctcaggactc     540
tactccctca gcagcgtggt gaccgtgccc tccagcaact tcggcaccca gacctacacc     600
tgcaacgtag atcacaagcc cagcaacacc aaggtggaca agacagttga gcgcaaatgt     660
tgtgtcgagt gcccaccgtg cccagcacca cctgtggcag gaccgtcagt cttcctcttc     720
cccccaaaac ccaaggacac cctcatgatc tcccggaccc ctgaggtcac gtgcgtggtg     780
gtggacgtga gccacgaaga cccgaggtc cagttcaact ggtacgtgga cggcgtggag     840
gtgcataatg ccaagacaaa gccacgggag gagcagttca acagcacgtt ccgtgtggtc     900
agcgtcctca ccgttgtgca ccaggactgg ctgaacggca aggagtacaa gtgcaaggtc     960
tccaacaaag gcctcccagc ccccatcgag aaaaccatct ccaaaaccaa agggcagccc    1020
cgagaaccac aggtgtacac cctgccccca tcccgggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acacctccca tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aa                                                         1332

<210> SEQ ID NO 69
<211> LENGTH: 1335
<212> TYPE: DNA
<213> ORGANISM: Artificial Sequence
<220> FEATURE:
<223> OTHER INFORMATION: Synthetic HC-48 polynucleotide

<400> SEQUENCE: 69
caggtgcagc tgcaggagtc gggcccagga ctggtgaagc cttcacagac cctgtccctc      60
```

```
acctgcactg tctctggtgg ctccatcagc agtggtggtt actactggag ctggatccgc    120
cagcacccag ggaagggcct ggagtggatt gggtacatct attacagtgg gaacacctac    180
tacaacccgt ccctcaagag tcgagttacc atatcaggag acacgtctaa gaaccagttc    240
tccctgaagc tgaggtctgt gactgccgcg gacacggccg tgtattactg tgcgagagga    300
ggagcagctc gcggtatgga cgtctggggc caagggacca cggtcaccgt ctctagtgcc    360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca cttcggcac ccagacctac     600 acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                    1335
```

<210> SEQ ID NO 70
<211> LENGTH: 1347
<212> TYPE: DNA
<213> ORGANISM: Artificial Sequence
<220> FEATURE:
<223> OTHER INFORMATION: Synthetic HC-49 polynucleotide

<400> SEQUENCE: 70

```
caggtacagc tgcagcagtc aggtccagga ctggtgaagc cctcgcagac cctctcactc     60
acctgtgcca tctccgggga cagtgtctct agcaacagtg ctgcttggaa ctggatcagg    120
cagtccccat cgagaggcct tgagtggctg ggaaggacat actacaggtc caggtggtat    180
aatgattatg cagtatctgt gaaaagtcga ataaccatca cccagacac atccaagaac     240 cagttctccc tgcagctgaa ctctgtgact cccgaggaca cggctgtgta ttactgtgca    300
agaggggtct tttatagcaa aggtgctttt gatatctggg gccaaggac aatggtcacc     360 gtctctagtg cctccaccaa gggcccatcg gtcttccccc tggcgccctg ctccaggagc    420
acctccgaga gcacagcggc cctgggctgc ctggtcaagg actacttccc cgaaccggtg    480
acggtgtcgt ggaactcagg cgctctgacc agcggcgtgc acacctccc agctgtccta    540 cagtcctcag gactctactc cctcagcagc gtggtgaccg tgccctccag caacttcggc    600
acccagacct acacctgcaa cgtagatcac aagcccagca acaccaaggt ggacaagaca    660
gttgagcgca aatgttgtgt cgagtgccca ccgtgcccag caccacctgt ggcaggaccg    720
tcagtcttcc tcttcccccc aaaacccaag gacaccctca tgatctcccg gacccctgag    780
```

```
gtcacgtgcg tggtggtgga cgtgagccac gaagacccg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagcccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctacccag cgacatcgcc   1140
gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                      1347
```

<210> SEQ ID NO 71
<211> LENGTH: 1335
<212> TYPE: DNA
<213> ORGANISM: Artificial Sequence
<220> FEATURE:
<223> OTHER INFORMATION: Synthetic HC-50 polynucleotide

<400> SEQUENCE: 71

```
caggtgcagc tgcaggagtc gggcccagga ctggtgaagc cttcacagac cctgtccctc     60
acctgcactg tctctggtgg ctccatcagc cgtggtggtt actactggag ctggatccgc    120
cagcacccag ggaagggcct ggagtggatt gggtacatat attacagtgg gaatacctac    180
tacaacccgt ccctcaagag tcgagttatc atatcaggag acacgtctaa gaaccagctc    240
tccctgaagc tgaggtctgt gactgccgcg gacacggccg tgtattattg tgcgagagga    300
ggagcagctc gcggtatgga cgtctgggc caagggacca cggtcaccgt ctctagtgcc    360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca cttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gccaggac tggctgaacg gcaaggagta caagtgcaag    960
gtctccaaca aaggcctccc agcccccatc gagaaaacca tctccaaaac caaagggcag   1020
ccccgagaac acaggtgta caccctgccc catcccggg aggagatgac caagaaccag   1080
gtcagcctga cctgcctggt caaaggcttc tacccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                   1335
```

<210> SEQ ID NO 72

<211> LENGTH: 1335
<212> TYPE: DNA
<213> ORGANISM: Artificial Sequence
<220> FEATURE:
<223> OTHER INFORMATION: Synthetic HC-51 polynucleotide

<400> SEQUENCE: 72

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gaacacctac     180
tacaacccgt ccctcaagag tcgagttacc atatcaggag acacgtctaa gaaccagttc     240
tccctgaagc tgaggtctgt gactgccgcg gacacggccg tgtattactg tacgagagga     300
ggagcagctc gcggtatgga cgtctggggc caagggacca cggtcaccgt ctctagtgcc     360
tccaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttcccag ctgtcctaca gtcctcagga     540
ctctactccc tcagcagcgt ggtgaccgtg ccctccagca acttcggcac ccagacctac     600
acctgcaacg tagatcacaa gcccagcaac accaaggtgg acaagacagt tgagcgcaaa     660
tgttgtgtcg agtgcccacc gtgcccagca ccacctgtgg caggaccgtc agtcttcctc     720
ttccccccaa aacccaagga caccctcatg atctcccgga cccctgaggt cacgtgcgtg     780
gtggtggacg tgagccacga agaccccgag gtccagttca actggtacgt ggacggcgtg     840
gaggtgcata atgccaagac aaagccacgg gaggagcagt tcaacagcac gttccgtgtg     900
gtcagcgtcc tcaccgttgt gcaccaggac tggctgaacg gcaaggagta caagtgcaag     960
gtctccaaca aaggcctccc agcccccatc gagaaaacca tctccaaaac caaagggcag    1020
ccccgagaac acaggtgta ccctgcccc catcccggg aggagatgac caagaaccag    1080
gtcagcctga cctgcctggt caaaggcttc taccccagcg acatcgccgt ggagtgggag    1140
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                      1335
```

<210> SEQ ID NO 73
<211> LENGTH: 1347
<212> TYPE: DNA
<213> ORGANISM: Artificial Sequence
<220> FEATURE:
<223> OTHER INFORMATION: Synthetic HC-52 polynucleotide

<400> SEQUENCE: 73

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gaacacctac     180
tacaacccgt ccctcaagag tcgagttacc atatcaggag acacgtctaa gaaccagttc     240
tccctgaagc tgaggtctgt gactgccgcg gacacggccg tgtattactg tacgagagga     300
ggagcagctc gcggtatgga cgtctggggc caagggacca cggtcaccgt ctctagtgcc     360
tccaccaagg gcccatcggt cttccccctg gcacctcct ccaagagcac ctctgggggc     420
acagcggccc tgggctgcct ggtcaaggac tacttccccg aaccggtgac ggtgtcgtgg     480
```

```
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacggcagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                       1347

<210> SEQ ID NO 74
<211> LENGTH: 1335
<212> TYPE: DNA
<213> ORGANISM: Artificial Sequence
<220> FEATURE:
<223> OTHER INFORMATION: Synthetic HC-53 polynucleotide

<400> SEQUENCE: 74
caggtgcagc tgcaggagtc gggcccagga ctggtgaagc cttcacagac cctgtccctc     60
acctgcactg tctctggtgg ctccatcagc agtggtggtt ctactggag ctggatccgc    120 cagcacccag ggaagggcct ggagtggatt gggtacatct attacagtgg aataccta    180 tacaacccgt ccctcaagag tcgagttatc atatcaggag acacgtctaa gaaccagttc    240
tccctgaagc tgagctctgt gacggccgcg gacacggccg tgtattactg tgcgagagga    300
ggagcagctc gcggtatgga cgtctggggc caagggacca cggtcaccgt ctctagtgcc    360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca ctggtacgt ggacggcgtg    840 gaggtgcata tgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag    1020
ccccgagaac acaggtgta cccctgccc ccatcccggg aggagatgac caagaaccag    1080
gtcagcctga cctgcctggt caaaggcttc taccccagcg acatcgccgt ggagtgggag    1140
```

```
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                     1335
```

<210> SEQ ID NO 75
<211> LENGTH: 214
<212> TYPE: PRT
<213> ORGANISM: Artificial Sequence
<220> FEATURE:
<223> OTHER INFORMATION: Synthetic LC-01 polypeptide

<400> SEQUENCE: 75

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Ile Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Phe Cys Gln Gln Ser Tyr Ser Pro Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 214
<212> TYPE: PRT
<213> ORGANISM: Artificial Sequence
<220> FEATURE:
<223> OTHER INFORMATION: Synthetic LC-02 polypeptide

<400> SEQUENCE: 76

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Leu Ser Gly Ile Pro Ser Arg Phe Ser Gly
 50                  55                  60

Ser Gly Ser Gly Thr His Phe Thr Leu Thr Ile Asn Ser Leu Glu Ala
 65                  70                  75                  80

Glu Asp Ala Ala Thr Tyr Tyr Cys His Gln Ser Ser Arg Leu Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 77
<211> LENGTH: 214
<212> TYPE: PRT
<213> ORGANISM: Artificial Sequence
<220> FEATURE:
<223> OTHER INFORMATION: Synthetic LC-03 polypeptide

<400> SEQUENCE: 77

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Ser Ile Gly Arg Ser
             20                  25                  30

Leu His Trp Tyr Gln Gln Lys Pro Gly Lys Ala Pro Lys Leu Leu Ile
         35                  40                  45

Lys Tyr Ala Ser Gln Ser Leu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys His Gln Ser Ser Arg Leu Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 78
<211> LENGTH: 214
<212> TYPE: PRT
<213> ORGANISM: Artificial Sequence
<220> FEATURE:
<223> OTHER INFORMATION: Synthetic LC-04 polypeptide

<400> SEQUENCE: 78

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Val Gly Arg Ser
            20                  25                  30

Leu His Trp Tyr His Gln Lys Pro Asp Gln Ser Pro Lys Leu Leu Ile
        35                  40                  45

Lys Tyr Ala Ser Gln Ser Leu Ser Gly Val Pro Ser Arg Phe Ser Gly
    50                  55                  60

Ser Gly Ser Gly Thr Asp Phe Thr Leu Ile Ile Asn Ser Leu Glu Ala
65                  70                  75                  80

Glu Asp Ala Ala Thr Tyr Tyr Cys His Gln Ser Ser Arg Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 79
<211> LENGTH: 214
<212> TYPE: PRT
<213> ORGANISM: Artificial Sequence
<220> FEATURE:
<223> OTHER INFORMATION: Synthetic LC-05 polypeptide

<400> SEQUENCE: 79

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Arg Ser
            20                  25                  30

Leu His Trp Tyr Gln Gln Lys Pro Gly Lys Ala Pro Lys Leu Leu Ile
        35                  40                  45

Lys Tyr Ala Ser Gln Ser Leu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys His Gln Ser Ser Arg Leu Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 80
<211> LENGTH: 214
<212> TYPE: PRT
<213> ORGANISM: Artificial Sequence
<220> FEATURE:
<223> OTHER INFORMATION: Synthetic LC-06 polypeptide

<400> SEQUENCE: 80

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Ser Ile Gly Arg Ser
             20                  25                  30

Leu His Trp Tyr His Gln Lys Pro Gly Lys Ala Pro Lys Leu Leu Ile
         35                  40                  45

Lys Tyr Ala Ser Gln Ser Leu Ser Gly Val Pro Ser Arg Phe Ser Gly
     50                  55                  60

Ser Gly Ser Gly Thr Glu Phe Thr Leu Ile Ile Ser Ser Leu Gln Pro
 65                  70                  75                  80

Glu Asp Phe Ala Thr Tyr Tyr Cys His Gln Ser Ser Arg Leu Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
                Phe Asn Arg Gly Glu Cys
                    210

<210> SEQ ID NO 81
<211> LENGTH: 214
<212> TYPE: PRT
<213> ORGANISM: Artificial Sequence
<220> FEATURE:
<223> OTHER INFORMATION: Synthetic LC-07 polypeptide

<400> SEQUENCE: 81

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Val Gly Arg Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Leu Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Arg Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 214
<212> TYPE: PRT
<213> ORGANISM: Artificial Sequence
<220> FEATURE:
<223> OTHER INFORMATION: Synthetic LC-08 polypeptide

<400> SEQUENCE: 82

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Ser
            20                  25                  30

Leu His Trp Tyr Gln Gln Lys Pro Gly Gln Ala Pro Arg Leu Leu Ile
        35                  40                  45

Lys Tyr Ala Ser Gln Ser Leu Ser Gly Ile Pro Ala Arg Phe Ser Gly
    50                  55                  60

Ser Gly Ser Gly Thr Asp Phe Thr Leu Thr Ile Ser Ser Leu Glu Pro
```

```
              65                  70                  75                  80
Glu Asp Phe Ala Val Tyr Tyr Cys His Gln Ser Ser Arg Leu Pro Phe
                    85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 83
<211> LENGTH: 214
<212> TYPE: PRT
<213> ORGANISM: Artificial Sequence
<220> FEATURE:
<223> OTHER INFORMATION: Synthetic LC-09 polypeptide

<400> SEQUENCE: 83

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Arg Ser
                20                  25                  30

Leu His Trp Tyr Gln Gln Lys Pro Gly Gln Ala Pro Arg Leu Leu Ile
                35                  40                  45

Lys Tyr Ala Ser Gln Ser Leu Ser Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Thr Tyr Tyr Cys His Gln Ser Ser Arg Leu Pro Phe
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

```
<210> SEQ ID NO 84
<211> LENGTH: 214
<212> TYPE: PRT
<213> ORGANISM: Artificial Sequence
<220> FEATURE:
<223> OTHER INFORMATION: Synthetic LC-10 polypeptide

<400> SEQUENCE: 84

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Arg Ser
            20                  25                  30

Leu His Trp Tyr Gln Gln Lys Pro Asp Gln Ser Pro Lys Leu Leu Phe
        35                  40                  45

Lys Tyr Ala Ser Gln Ser Leu Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Arg Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 214
<212> TYPE: PRT
<213> ORGANISM: Artificial Sequence
<220> FEATURE:
<223> OTHER INFORMATION: Synthetic LC-11 polypeptide

<400> SEQUENCE: 85

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Arg Ser
            20                  25                  30

Leu His Trp Tyr Gln Gln Lys Pro Gly Lys Ala Pro Lys Leu Leu Phe
        35                  40                  45

Lys Tyr Ala Ser Gln Ser Leu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Glu Asp Phe Ala Thr Tyr Tyr Cys His Gln Ser Ser Arg Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 86
<211> LENGTH: 214
<212> TYPE: PRT
<213> ORGANISM: Artificial Sequence
<220> FEATURE:
<223> OTHER INFORMATION: Synthetic LC-12 polypeptide

<400> SEQUENCE: 86

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Asn Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 87
<211> LENGTH: 219
<212> TYPE: PRT
<213> ORGANISM: Artificial Sequence
<220> FEATURE:
<223> OTHER INFORMATION: Synthetic LC-13 polypeptide

<400> SEQUENCE: 87

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Leu Tyr Leu Gly Ser Asn Arg Ala Ser Gly Val Pro
    50                  55                  60

Asp Arg Phe Ser Gly Ser Gly Ser Gly Thr Asp Phe Thr Leu Gln Ile
65                  70                  75                  80

Ser Arg Val Glu Ala Glu Asp Val Gly Val Tyr Tyr Cys Met Gln Thr
                85                  90                  95

Leu Gln Thr Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 88
<211> LENGTH: 219
<212> TYPE: PRT
<213> ORGANISM: Artificial Sequence
<220> FEATURE:
<223> OTHER INFORMATION: Synthetic LC-14 polypeptide

<400> SEQUENCE: 88

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Leu Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

```
Leu Gln Thr Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 89
<211> LENGTH: 215
<212> TYPE: PRT
<213> ORGANISM: Artificial Sequence
<220> FEATURE:
<223> OTHER INFORMATION: Synthetic LC-15 polypeptide

<400> SEQUENCE: 89

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Phe Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215
```

<210> SEQ ID NO 90

<211> LENGTH: 220
<212> TYPE: PRT
<213> ORGANISM: Artificial Sequence
<220> FEATURE:
<223> OTHER INFORMATION: Synthetic LC-16 polypeptide

<400> SEQUENCE: 90

Asp Ile Val Met Thr Gln Ser Pro Asp Ser Leu Ala Val Ser Leu Gly
1               5                   10                  15

Glu Arg Ala Thr Ile His Cys Lys Ser Ser Gln Asn Val Leu Tyr Ser
            20                  25                  30

Ser Asn Asn Lys Asn Phe Leu Thr Trp Tyr Gln Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Ala Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 91
<211> LENGTH: 220
<212> TYPE: PRT
<213> ORGANISM: Artificial Sequence
<220> FEATURE:
<223> OTHER INFORMATION: Synthetic LC-17 polypeptide

<400> SEQUENCE: 91

Asp Ile Val Met Thr Gln Ser Pro Asp Ser Leu Ala Val Ser Leu Gly
1               5                   10                  15

Glu Arg Thr Thr Ile Lys Cys Lys Ser Ser Gln Ser Val Leu Tyr Arg
            20                  25                  30

Ser Asn Asn Asn Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ile Ser Pro Leu Thr Phe Gly Gly Gly Thr Lys Val Glu Ile

```
                    100                 105                 110
Lys Arg Thr Val Ala Ala Pro Ser Val Phe Ile Phe Pro Pro Ser Asp
            115                 120                 125
Glu Gln Leu Lys Ser Gly Thr Ala Ser Val Val Cys Leu Leu Asn Asn
            130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
                180                 185                 190
Glu Lys His Lys Val Tyr Ala Cys Glu Val Thr His Gln Gly Leu Ser
            195                 200                 205
Ser Pro Val Thr Lys Ser Phe Asn Arg Gly Glu Cys
            210                 215                 220

<210> SEQ ID NO 92
<211> LENGTH: 220
<212> TYPE: PRT
<213> ORGANISM: Artificial Sequence
<220> FEATURE:
<223> OTHER INFORMATION: Synthetic LC-18 polypeptide

<400> SEQUENCE: 92

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys His Tyr Leu Ala Trp Tyr Arg Gln Lys Pro Gly Gln
        35                  40                  45
Pro Pro Lys Leu Leu Ile Tyr Arg Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Pro Glu Asp Val Ala Val Tyr Tyr Cys Gln Gln
                85                  90                  95
Tyr Tyr Ser Ser Pro Phe Thr Phe Gly Pro Gly Thr Lys Val Asp Ile
            100                 105                 110
Lys Arg Thr Val Ala Ala Pro Ser Val Phe Ile Phe Pro Pro Ser Asp
            115                 120                 125
Glu Gln Leu Lys Ser Gly Thr Ala Ser Val Val Cys Leu Leu Asn Asn
            130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
                180                 185                 190
Glu Lys His Lys Val Tyr Ala Cys Glu Val Thr His Gln Gly Leu Ser
            195                 200                 205
Ser Pro Val Thr Lys Ser Phe Asn Arg Gly Glu Cys
            210                 215                 220

<210> SEQ ID NO 93
<211> LENGTH: 220
<212> TYPE: PRT
```

<213> ORGANISM: Artificial Sequence
<220> FEATURE:
<223> OTHER INFORMATION: Synthetic LC-19 polypeptide

<400> SEQUENCE: 93

```
Asp Ile Val Met Thr Gln Ser Pro Asp Ser Leu Ala Val Ser Leu Gly
1               5                   10                  15

Glu Arg Ala Thr Ile His Cys Lys Ser Gln Ser Val Leu Tyr Ser
            20                  25                  30

Ser Asn Asn Lys Asn Phe Leu Thr Trp Tyr Gln Gln Lys Pro Gly Gln
        35                  40                  45

Pro Pro Lys Leu Leu Ile Tyr Arg Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Ala Pro Phe Thr Phe Gly Pro Gly Thr Arg Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 94
<211> LENGTH: 220
<212> TYPE: PRT
<213> ORGANISM: Artificial Sequence
<220> FEATURE:
<223> OTHER INFORMATION: Synthetic LC-20 polypeptide

<400> SEQUENCE: 94

```
Asp Ile Val Met Thr Gln Ser Pro Asp Ser Leu Ala Val Ser Leu Gly
1               5                   10                  15

Glu Arg Ala Thr Ile His Cys Lys Ser Gln Ser Val Leu Tyr Ser
            20                  25                  30

Ser Asn Asn Arg Asn Phe Leu Ser Trp Tyr Gln Gln Lys Pro Gly Gln
        35                  40                  45

Pro Pro Lys Leu Leu Ile Tyr Arg Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Ala Pro Phe Thr Phe Gly Pro Gly Thr Val Asp Ile
            100                 105                 110
```

```
Lys Arg Thr Val Ala Ala Pro Ser Val Phe Ile Phe Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 95
<211> LENGTH: 220
<212> TYPE: PRT
<213> ORGANISM: Artificial Sequence
<220> FEATURE:
<223> OTHER INFORMATION: Synthetic LC-21 polypeptide

<400> SEQUENCE: 95

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Arg Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Gln
                85                  90                  95

Tyr Tyr Ser Ser Pro Phe Thr Phe Gly Pro Gly Thr Lys Val Asp Ile
            100                 105                 110

Lys Arg Thr Val Ala Ala Pro Ser Val Phe Ile Phe Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 96
<211> LENGTH: 449
<212> TYPE: PRT
<213> ORGANISM: Artificial Sequence
<220> FEATURE:
```

<223> OTHER INFORMATION: Synthetic HC-01 polypeptide

<400> SEQUENCE: 96

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Ser Asn His Tyr Ala
    50                  55                  60

Val Ser Val Lys Ser Arg Ile Thr Ile Asn Pro Asp Thr Ser Lys Ser
65                  70                  75                  80

Gln Phe Ser Leu Gln Leu Asn Ser Val Thr Pro Glu Asp Thr Ala Val
                85                  90                  95

Tyr Tyr Cys Ala Arg Gly Thr Trp Lys Gln Leu Trp Phe Leu Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Lys

<210> SEQ ID NO 97
<211> LENGTH: 453
<212> TYPE: PRT
<213> ORGANISM: Artificial Sequence
<220> FEATURE:
<223> OTHER INFORMATION: Synthetic HC-02 polypeptide

<400> SEQUENCE: 97

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Ser Asn His Tyr Ala
50                  55                  60

Val Ser Val Lys Ser Arg Ile Thr Ile Asn Pro Asp Thr Ser Lys Ser
65                  70                  75                  80

Gln Phe Ser Leu Gln Leu Asn Ser Val Thr Pro Glu Asp Thr Ala Val
                85                  90                  95

Tyr Tyr Cys Ala Arg Gly Thr Trp Lys Gln Leu Trp Phe Leu Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Gly Ser
    290                 295                 300

Thr Tyr Arg Val Val Ser Val Leu Thr Val Leu His Gln Asp Trp Leu
```

```
              305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
            435                 440                 445
Leu Ser Pro Gly Lys
        450

<210> SEQ ID NO 98
<211> LENGTH: 446
<212> TYPE: PRT
<213> ORGANISM: Artificial Sequence
<220> FEATURE:
<223> OTHER INFORMATION: Synthetic HC-03 polypeptide

<400> SEQUENCE: 98

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Tyr Tyr
                20                  25                  30
Ala Ile His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Tyr Asp Leu Leu Thr Gly Tyr Pro Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Asn Phe Gly Thr Gln Thr Tyr Thr Cys Asn Val Asp His Lys
            195                 200                 205
Pro Ser Asn Thr Lys Val Asp Lys Thr Val Glu Arg Lys Cys Cys Val
```

```
                210                 215                 220
Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
        290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 99
<211> LENGTH: 450
<212> TYPE: PRT
<213> ORGANISM: Artificial Sequence
<220> FEATURE:
<223> OTHER INFORMATION: Synthetic HC-04 polypeptide

<400> SEQUENCE: 99

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Leu Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

| | | | | | | | | | | | | | | |
|---|---|---|---|---|---|---|---|---|---|---|---|---|---|---|
| | | | | 130 | | | | | 135 | | | | | 140 |

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 100
<211> LENGTH: 450
<212> TYPE: PRT
<213> ORGANISM: Artificial Sequence
<220> FEATURE:
<223> OTHER INFORMATION: Synthetic HC-05 polypeptide

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Ala Ile His Trp Val Arg Gln Ala Pro Gly Lys Gly Leu Glu Trp Val

```
                35                  40                  45
Ala Val Ile Ser Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Tyr Asp Leu Leu Thr Gly Tyr Pro Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Cys Glu Glu Gln Tyr Gly Ser Thr Tyr Arg
290                 295                 300
Cys Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450
```

<210> SEQ ID NO 101
<211> LENGTH: 446
<212> TYPE: PRT
<213> ORGANISM: Artificial Sequence
<220> FEATURE:
<223> OTHER INFORMATION: Synthetic HC-06 polypeptide

<400> SEQUENCE: 101

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Phe
                20                  25                  30

Ala Met His Trp Val Arg Ala Pro Gly Lys Gly Leu Glu Trp Val
            35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Asn
65                  70                  75                  80

Leu Leu Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
            290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365
```

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 102
<211> LENGTH: 450
<212> TYPE: PRT
<213> ORGANISM: Artificial Sequence
<220> FEATURE:
<223> OTHER INFORMATION: Synthetic HC-07 polypeptide

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Arg Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Asn
65                  70                  75                  80

Leu Leu Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 103
<211> LENGTH: 450
<212> TYPE: PRT
<213> ORGANISM: Artificial Sequence
<220> FEATURE:
<223> OTHER INFORMATION: Synthetic HC-08 polypeptide

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Arg Ala Pro Gly Lys Gly Leu Glu Trp Val
        35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Asn
65                  70                  75                  80

Leu Leu Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Cys Glu Glu Gln Tyr Gly Ser Thr Tyr Arg
        290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 104
<211> LENGTH: 446
<212> TYPE: PRT
<213> ORGANISM: Artificial Sequence
<220> FEATURE:
<223> OTHER INFORMATION: Synthetic HC-09 polypeptide

<400> SEQUENCE: 104

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Ala Glu Ser Val
    50                  55                  60

Lys Gly Arg Phe Thr Ile Ser Arg Asp Asn Ser Lys Asn Thr Leu Asn
65                  70                  75                  80

Leu Leu Met Asn Ser Leu Arg Ala Glu Asp Thr Ala Leu Phe Tyr Cys
                85                  90                  95
```

Ala Arg Gly Tyr Asp Val Leu Thr Gly Tyr Pro Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 105
<211> LENGTH: 450
<212> TYPE: PRT
<213> ORGANISM: Artificial Sequence
<220> FEATURE:
<223> OTHER INFORMATION: Synthetic HC-10 polypeptide

<400> SEQUENCE: 105

Gln Val Gln Leu Val Glu Ser Gly Gly Gly Val Val Gln Pro Gly Arg
1               5                   10                  15

-continued

```
Ser Leu Arg Leu Ser Cys Ala Ala Ser Gly Phe Thr Phe Ser Arg Phe
         20                  25                  30
Ala Met His Trp Val Arg Gln Ala Pro Gly Lys Gly Leu Glu Trp Val
         35                  40              45
Ala Val Ile Ser Tyr Asp Gly Asn Lys Tyr Tyr Ala Glu Ser Val
 50                  55                  60
Lys Gly Arg Phe Thr Ile Ser Arg Asp Asn Ser Lys Asn Thr Leu Asn
 65                  70                  75                  80
Leu Leu Met Asn Ser Leu Arg Ala Glu Asp Thr Ala Leu Phe Tyr Cys
             85                  90                  95
Ala Arg Gly Tyr Asp Val Leu Thr Gly Tyr Pro Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
 130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Gly Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
```

-continued

Glu Ala Leu His Asn His Tyr Thr Gln Lys Ser Leu Ser Leu Ser Pro
                435                 440                 445
Gly Lys
    450

<210> SEQ ID NO 106
<211> LENGTH: 450
<212> TYPE: PRT
<213> ORGANISM: Artificial Sequence
<220> FEATURE:
<223> OTHER INFORMATION: Synthetic HC-11 polypeptide

<400> SEQUENCE: 106

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
                20                  25                  30

Ala Met His Trp Val Arg Gln Ala Pro Gly Lys Gly Leu Glu Trp Val
            35                  40                  45

Ala Val Ile Ser Tyr Asp Gly Asn Lys Tyr Tyr Ala Glu Ser Val
        50                  55                  60

Lys Gly Arg Phe Thr Ile Ser Arg Asp Asn Ser Lys Asn Thr Leu Asn
65                  70                  75                  80

Leu Leu Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 107
<211> LENGTH: 446
<212> TYPE: PRT
<213> ORGANISM: Artificial Sequence
<220> FEATURE:
<223> OTHER INFORMATION: Synthetic HC-12 polypeptide

<400> SEQUENCE: 107

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 108
<211> LENGTH: 450
<212> TYPE: PRT
<213> ORGANISM: Artificial Sequence
<220> FEATURE:
<223> OTHER INFORMATION: Synthetic HC-13 polypeptide

<400> SEQUENCE: 108

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Gly Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 109
<211> LENGTH: 450
<212> TYPE: PRT
<213> ORGANISM: Artificial Sequence
<220> FEATURE:
<223> OTHER INFORMATION: Synthetic HC-14 polypeptide

<400> SEQUENCE: 109

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Arg Phe
            20                  25                  30
Ala Met His Trp Val Arg Gln Ala Pro Gly Lys Gly Leu Glu Trp Val
        35                  40                  45
Ala Val Ile Ser Tyr Asp Gly Gly Asn Lys Tyr Tyr Ala Glu Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Phe Tyr Cys
                 85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Cys Glu Glu Gln Tyr Gly Ser Thr Tyr Arg
290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 110
<211> LENGTH: 446
<212> TYPE: PRT
```

<213> ORGANISM: Artificial Sequence
<220> FEATURE:
<223> OTHER INFORMATION: Synthetic HC-15 polypeptide

<400> SEQUENCE: 110

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Arg Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Asn
65                  70                  75                  80

Leu Leu Met Asp Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
```

```
            385                 390                 395                 400
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 111
<211> LENGTH: 450
<212> TYPE: PRT
<213> ORGANISM: Artificial Sequence
<220> FEATURE:
<223> OTHER INFORMATION: Synthetic HC-16 polypeptide

<400> SEQUENCE: 111

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
                20                  25                  30

Ala Met His Trp Val Arg Arg Ala Pro Gly Lys Gly Leu Glu Trp Val
            35                  40                  45

Ala Val Ile Ser Tyr Asp Gly Asn Lys Tyr Tyr Ala Glu Ser Val
        50                  55                  60

Lys Gly Arg Phe Thr Ile Ser Arg Asp Asn Ser Lys Asn Thr Leu Asn
65                  70                  75                  80

Leu Leu Met Asp Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gly Ser Thr Tyr Arg
        290                 295                 300

Val Val Ser Val Leu Thr Val Leu His Gln Asp Trp Leu Asn Gly Lys
```

|     |     |     |     |     |     |     |     |     |     |     |     |     |     |     |     |
| --- | --- | --- | --- | --- | --- | --- | --- | --- | --- | --- | --- | --- | --- | --- | --- |
| 305 | | | | 310 | | | | 315 | | | | 320 | | | |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | 355 | | | | | 360 | | | | | 365 | | | |
| Thr | Cys | Leu | Val | Lys | Gly | Phe | Tyr | Pro | Ser | Asp | Ile | Ala | Val | Glu | Trp |
| 370 | | | | | 375 | | | | | 380 | | | | | |
| Glu | Ser | Asn | Gly | Gln | Pro | Glu | Asn | Asn | Tyr | Lys | Thr | Thr | Pro | Pro | Val |
| 385 | | | | 390 | | | | | 395 | | | | | 400 | |
| Leu | Asp | Ser | Asp | Gly | Ser | Phe | Phe | Leu | Tyr | Ser | Lys | Leu | Thr | Val | Asp |
| | | | 405 | | | | | 410 | | | | | 415 | | |
| Lys | Ser | Arg | Trp | Gln | Gln | Gly | Asn | Val | Phe | Ser | Cys | Ser | Val | Met | His |
| | | 420 | | | | | 425 | | | | | 430 | | | |
| Glu | Ala | Leu | His | Asn | His | Tyr | Thr | Gln | Lys | Ser | Leu | Ser | Leu | Ser | Pro |
| | | 435 | | | | | 440 | | | | | 445 | | | |
| Gly | Lys | | | | | | | | | | | | | | |
| 450 | | | | | | | | | | | | | | | |

<210> SEQ ID NO 112
<211> LENGTH: 450
<212> TYPE: PRT
<213> ORGANISM: Artificial Sequence
<220> FEATURE:
<223> OTHER INFORMATION: Synthetic HC-17 polypeptide

<400> SEQUENCE: 112

|     |     |     |     |     |     |     |     |     |     |     |     |     |     |     |     |
| --- | --- | --- | --- | --- | --- | --- | --- | --- | --- | --- | --- | --- | --- | --- | --- |
| Gln | Val | Gln | Leu | Val | Glu | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Arg | Phe |
| | | | 20 | | | | | 25 | | | | | 30 | | |
| Ala | Met | His | Trp | Val | Arg | Arg | Ala | Pro | Gly | Lys | Gly | Leu | Glu | Trp | Val |
| | | 35 | | | | | 40 | | | | | 45 | | | |
| Ala | Val | Ile | Ser | Tyr | Asp | Gly | Gly | Asn | Lys | Tyr | Tyr | Ala | Glu | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Asn |
| 65 | | | | | 70 | | | | | 75 | | | | | 80 |
| Leu | Leu | Met | Asp | Ser | Leu | Arg | Ala | Glu | Asp | Thr | Ala | Leu | Phe | Tyr | Cys |
| | | | | 85 | | | | | 90 | | | | | 95 | |
| Ala | Arg | Gly | Tyr | Asp | Val | Leu | Thr | Gly | Tyr | Pro | Asp | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | | | 115 | | | | | 120 | | | | | 125 | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |

```
            210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
                275                 280                 285

Asn Ala Lys Thr Lys Pro Cys Glu Glu Gln Tyr Gly Ser Thr Tyr Arg
            290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 113
<211> LENGTH: 446
<212> TYPE: PRT
<213> ORGANISM: Artificial Sequence
<220> FEATURE:
<223> OTHER INFORMATION: Synthetic HC-18 polypeptide

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
                20                  25                  30

Ala Met His Trp Val Arg Gln Ala Pro Gly Gln Gly Leu Glu Trp Met
            35                  40                  45

Gly Val Ile Ser Tyr Asp Gly Asn Lys Tyr Ala Glu Ser Val
        50                  55                  60

Lys Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
```

115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Asn Phe Gly Thr Gln Thr Tyr Thr Cys Asn Val Asp His Lys
        195                 200                 205
Pro Ser Asn Thr Lys Val Asp Lys Thr Val Glu Arg Lys Cys Cys Val
    210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 114
<211> LENGTH: 450
<212> TYPE: PRT
<213> ORGANISM: Artificial Sequence
<220> FEATURE:
<223> OTHER INFORMATION: Synthetic HC-19 polypeptide

<400> SEQUENCE: 114

Gln Val Gln Leu Val Gln Ser Gly Ala Glu Val Lys Lys Pro Gly Ala
1               5                   10                  15
Ser Val Lys Val Ser Cys Lys Ala Ser Gly Phe Thr Phe Ser Arg Phe
                20                  25                  30
Ala Met His Trp Val Arg Gln Ala Pro Gly Gln Gly Leu Glu Trp Met

```
                35                  40                  45
Gly Val Ile Ser Tyr Asp Gly Gly Asn Lys Tyr Tyr Ala Glu Ser Val
 50                  55                  60
Lys Gly Arg Val Thr Met Thr Arg Asp Thr Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Tyr Asp Val Leu Thr Gly Tyr Pro Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Gly Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450
```

<210> SEQ ID NO 115
<211> LENGTH: 450
<212> TYPE: PRT
<213> ORGANISM: Artificial Sequence
<220> FEATURE:
<223> OTHER INFORMATION: Synthetic HC-20 polypeptide

<400> SEQUENCE: 115

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Asn Lys Tyr Tyr Ala Glu Ser Val
    50                  55                  60

Lys Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 116
<211> LENGTH: 446
<212> TYPE: PRT
<213> ORGANISM: Artificial Sequence
<220> FEATURE:
<223> OTHER INFORMATION: Synthetic HC-21 polypeptide

<400> SEQUENCE: 116

Gln Val Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Gly Asn Lys Tyr Tyr Ala Glu Ser Val
    50                  55                  60

Lys Gly Arg Val Thr Met Thr Arg Asp Asn Ser Lys Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
        290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 117
<211> LENGTH: 450
<212> TYPE: PRT
<213> ORGANISM: Artificial Sequence
<220> FEATURE:
<223> OTHER INFORMATION: Synthetic HC-22 polypeptide

<400> SEQUENCE: 117

Gln Val Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Asn Lys Tyr Ala Glu Ser Val
    50                  55                  60

Lys Gly Arg Val Thr Met Thr Arg Asp Asn Ser Lys Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gly Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 118
<211> LENGTH: 450
<212> TYPE: PRT
<213> ORGANISM: Artificial Sequence
<220> FEATURE:
<223> OTHER INFORMATION: Synthetic HC-23 polypeptide

<400> SEQUENCE: 118

Gln Val Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Asn Lys Tyr Ala Glu Ser Val
    50                  55                  60

Lys Gly Arg Val Thr Met Thr Arg Asp Asn Ser Lys Asn Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 119
<211> LENGTH: 446
<212> TYPE: PRT
<213> ORGANISM: Artificial Sequence
<220> FEATURE:
<223> OTHER INFORMATION: Synthetic HC-24 polypeptide

<400> SEQUENCE: 119

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
            210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
            290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415
```

```
Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 120
<211> LENGTH: 450
<212> TYPE: PRT
<213> ORGANISM: Artificial Sequence
<220> FEATURE:
<223> OTHER INFORMATION: Synthetic HC-25 polypeptide

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 121
<211> LENGTH: 450
<212> TYPE: PRT
<213> ORGANISM: Artificial Sequence
<220> FEATURE:
<223> OTHER INFORMATION: Synthetic HC-26 polypeptide

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Cys Glu Glu Gln Tyr Gly Ser Thr Tyr Arg
290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 122
<211> LENGTH: 446
<212> TYPE: PRT
<213> ORGANISM: Artificial Sequence
<220> FEATURE:
<223> OTHER INFORMATION: Synthetic HC-27 polypeptide

<400> SEQUENCE: 122

Gln Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
        290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 123
<211> LENGTH: 450
<212> TYPE: PRT
<213> ORGANISM: Artificial Sequence
<220> FEATURE:
<223> OTHER INFORMATION: Synthetic HC-28 polypeptide

<400> SEQUENCE: 123

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 124
<211> LENGTH: 450
<212> TYPE: PRT
```

<213> ORGANISM: Artificial Sequence
<220> FEATURE:
<223> OTHER INFORMATION: Synthetic HC-29 polypeptide

<400> SEQUENCE: 124

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val

```
                385                 390                 395                 400
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 125
<211> LENGTH: 446
<212> TYPE: PRT
<213> ORGANISM: Artificial Sequence
<220> FEATURE:
<223> OTHER INFORMATION: Synthetic HC-30 polypeptide

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
                20                  25                  30

Ala Met His Trp Val Arg Gln Ala Pro Gly Gln Gly Leu Glu Trp Met
            35                  40                  45

Gly Val Ile Ser Tyr Asp Gly Asn Lys Tyr Tyr Ala Glu Ser Val
        50                  55                  60

Lys Gly Arg Val Thr Met Thr Arg Asp Thr Ser Thr Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
```

```
            290                 295                 300
Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 126
<211> LENGTH: 450
<212> TYPE: PRT
<213> ORGANISM: Artificial Sequence
<220> FEATURE:
<223> OTHER INFORMATION: Synthetic HC-31 polypeptide

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
                20                  25                  30

Ala Met His Trp Val Arg Gln Ala Pro Gly Gln Gly Leu Glu Trp Met
            35                  40                  45

Gly Val Ile Ser Tyr Asp Gly Gly Asn Lys Tyr Tyr Ala Glu Ser Val
        50                  55                  60

Lys Gly Arg Val Thr Met Thr Arg Asp Thr Ser Thr Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
            210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gly Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 127
<211> LENGTH: 450
<212> TYPE: PRT
<213> ORGANISM: Artificial Sequence
<220> FEATURE:
<223> OTHER INFORMATION: Synthetic HC-32 polypeptide

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Asn Lys Tyr Ala Glu Ser Val
    50                  55                  60

Lys Gly Arg Val Thr Met Thr Arg Asp Thr Ser Thr Thr Leu Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Cys Glu Glu Gln Tyr Gly Ser Thr Tyr Arg
    290                 295                 300
Cys Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 128
<211> LENGTH: 446
<212> TYPE: PRT
<213> ORGANISM: Artificial Sequence
<220> FEATURE:
<223> OTHER INFORMATION: Synthetic HC-33 polypeptide

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
```

```
                  20                  25                  30
Ala Met His Trp Val Arg Gln Ala Pro Gly Gln Gly Leu Glu Trp Met
            35                  40                  45
Gly Val Ile Ser Tyr Asp Gly Asn Lys Tyr Tyr Ala Glu Ser Val
        50                  55                  60
Lys Gly Arg Val Thr Met Thr Arg Asp Thr Ser Lys Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Tyr Asp Val Leu Thr Gly Tyr Pro Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Asn Phe Gly Thr Gln Thr Tyr Thr Cys Asn Val Asp His Lys
        195                 200                 205
Pro Ser Asn Thr Lys Val Asp Lys Thr Val Glu Arg Lys Cys Cys Val
        210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Phe Arg Val Val Ser Val
        290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445
```

<210> SEQ ID NO 129
<211> LENGTH: 450
<212> TYPE: PRT
<213> ORGANISM: Artificial Sequence
<220> FEATURE:
<223> OTHER INFORMATION: Synthetic HC-34 polypeptide

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Asn Lys Tyr Tyr Ala Glu Ser Val
    50                  55                  60

Lys Gly Arg Val Thr Met Thr Arg Asp Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 130
<211> LENGTH: 450
<212> TYPE: PRT
<213> ORGANISM: Artificial Sequence
<220> FEATURE:
<223> OTHER INFORMATION: Synthetic HC-35 polypeptide

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Gly Asn Lys Tyr Tyr Ala Glu Ser Val
    50                  55                  60

Lys Gly Arg Val Thr Met Thr Arg Asp Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
        290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 131
<211> LENGTH: 446
<212> TYPE: PRT
<213> ORGANISM: Artificial Sequence
<220> FEATURE:
<223> OTHER INFORMATION: Synthetic HC-36 polypeptide

<400> SEQUENCE: 131

Gln Val Gln Leu Val Glu Ser Gly Ala Glu Val Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Asn Lys Tyr Tyr Ala Glu Ser Val
    50                  55                  60

Lys Gly Arg Val Thr Met Thr Arg Asp Thr Ser Thr Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 132
<211> LENGTH: 450
<212> TYPE: PRT
<213> ORGANISM: Artificial Sequence
<220> FEATURE:
<223> OTHER INFORMATION: Synthetic HC-37 polypeptide

<400> SEQUENCE: 132

Gln Val Gln Leu Val Glu Ser Gly Ala Glu Val Val Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Asn Lys Tyr Ala Glu Ser Val
    50                  55                  60

Lys Gly Arg Val Thr Met Thr Arg Asp Thr Ser Thr Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 133
<211> LENGTH: 450
<212> TYPE: PRT
<213> ORGANISM: Artificial Sequence
<220> FEATURE:
<223> OTHER INFORMATION: Synthetic HC-38 polypeptide

<400> SEQUENCE: 133

-continued

```
Gln Val Gln Leu Val Glu Ser Gly Ala Glu Val Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
            35                  40                  45

Gly Val Ile Ser Tyr Asp Gly Asn Lys Tyr Tyr Ala Glu Ser Val
    50                  55                  60

Lys Gly Arg Val Thr Met Thr Arg Asp Thr Ser Thr Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
    275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 134
<211> LENGTH: 446
<212> TYPE: PRT
<213> ORGANISM: Artificial Sequence
<220> FEATURE:
<223> OTHER INFORMATION: Synthetic HC-39 polypeptide

<400> SEQUENCE: 134

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Tyr
                20                  25                  30

Ala Met His Trp Val Arg Gln Ala Ser Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Leu Met Ser Ser Leu Arg Ala Glu Asp Thr Ala Val Phe Tyr Cys
                85                  90                  95

Ala Arg Gly Tyr Asp Ile Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320
```

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Met Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 135
<211> LENGTH: 450
<212> TYPE: PRT
<213> ORGANISM: Artificial Sequence
<220> FEATURE:
<223> OTHER INFORMATION: Synthetic HC-40 polypeptide

<400> SEQUENCE: 135

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Ala Met His Trp Val Arg Gln Ala Ser Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Leu Met Ser Ser Leu Arg Ala Glu Asp Thr Ala Val Phe Tyr Cys
                85                  90                  95

Ala Arg Gly Tyr Asp Ile Leu Thr Gly Tyr Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 136
<211> LENGTH: 450
<212> TYPE: PRT
<213> ORGANISM: Artificial Sequence
<220> FEATURE:
<223> OTHER INFORMATION: Synthetic HC-41 polypeptide

<400> SEQUENCE: 136

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Ala Met His Trp Val Arg Gln Ala Ser Gly Lys Gly Leu Glu Trp Val
        35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Leu Met Ser Ser Leu Arg Ala Glu Asp Thr Ala Val Phe Tyr Cys
            85                  90                  95

Ala Arg Gly Tyr Asp Ile Leu Thr Gly Tyr Pro Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Cys Glu Glu Gln Tyr Gly Ser Thr Tyr Arg
290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
   450

<210> SEQ ID NO 137
<211> LENGTH: 449
<212> TYPE: PRT
<213> ORGANISM: Artificial Sequence
<220> FEATURE:
<223> OTHER INFORMATION: Synthetic HC-42 polypeptide

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

-continued

Gly Trp Ile Asn Ala Tyr Asn Gly His Thr Asn Tyr Ala Gln Thr Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Leu Glu Leu Arg Ser Phe Tyr Tyr Phe Gly Met Asp Val
            100                 105                 110

Trp Gly Gln Gly Thr Thr Val Pro Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 138

<211> LENGTH: 449
<212> TYPE: PRT
<213> ORGANISM: Artificial Sequence
<220> FEATURE:
<223> OTHER INFORMATION: Synthetic HC-43 polypeptide

<400> SEQUENCE: 138

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Asn | Ala | Tyr | Asn | Gly | His | Thr | Asn | Tyr | Ala | Gln | Thr | Phe |
| | 50 | | | | | 55 | | | | | 60 | | | | |
| Gln | Gly | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Glu | Leu | Glu | Leu | Arg | Ser | Phe | Tyr | Tyr | Phe | Gly | Met | Asp | Val |
| | | | 100 | | | | | 105 | | | | | 110 | | |
| Trp | Gly | Gln | Gly | Thr | Thr | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Cys | Ser | Arg | Ser | Thr | Ser | Glu | Ser |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Asn | Phe | Gly | Thr | Gln | Thr | Tyr | Thr | Cys | Asn | Val |
| | | 195 | | | | | 200 | | | | | 205 | | | |
| Asp | His | Lys | Pro | Ser | Asn | Thr | Lys | Val | Asp | Lys | Thr | Val | Glu | Arg | Lys |
| | 210 | | | | | 215 | | | | | 220 | | | | |
| Cys | Cys | Val | Glu | Cys | Pro | Pro | Cys | Pro | Ala | Pro | Pro | Val | Ala | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Gln | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Phe | Asn | Ser | Thr | Phe | Arg | Val |
| | 290 | | | | | 295 | | | | | 300 | | | | |
| Val | Ser | Val | Leu | Thr | Val | Val | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Gly | Leu | Pro | Ala | Pro | Ile | Glu | Lys |
| | | | | 325 | | | | | 330 | | | | | 335 | |
| Thr | Ile | Ser | Lys | Thr | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |

```
Ser Asn Gly Gln Pro Glu Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 139
<211> LENGTH: 447
<212> TYPE: PRT
<213> ORGANISM: Artificial Sequence
<220> FEATURE:
<223> OTHER INFORMATION: Synthetic HC-44 polypeptide

<400> SEQUENCE: 139

Gln Val Gln Leu Val Gln Ser Gly Ala Glu Val Lys Lys Ser Gly Ala
1               5                   10                  15

Ser Leu Lys Val Ser Cys Lys Ala Ser Gly Tyr Ile Phe Thr Arg Tyr
            20                  25                  30

Gly Val Ser Trp Val Arg Gln Ala Pro Gly Gln Gly Leu Glu Trp Met
        35                  40                  45

Gly Trp Ile Thr Thr Tyr Asn Gly Asn Thr Asn Tyr Ala Gln Lys Leu
50                  55                  60

Gln Gly Arg Val Thr Met Thr Ile Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Arg Val Arg Tyr Ser Gly Gly Tyr Ser Phe Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Asn Phe Gly Thr Gln Thr Tyr Thr Cys Asn Val Asp His
    195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Gln Phe Asn Trp Tyr Val Asp Gly Val Glu Val His Asn Ala Lys
    275                 280                 285
```

```
Thr Lys Pro Arg Glu Glu Gln Phe Asn Ser Thr Phe Arg Val Val Ser
    290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 140
<211> LENGTH: 447
<212> TYPE: PRT
<213> ORGANISM: Artificial Sequence
<220> FEATURE:
<223> OTHER INFORMATION: Synthetic HC-45 polypeptide

<400> SEQUENCE: 140

Gln Val Gln Leu Val Gln Ser Gly Ala Glu Val Lys Lys Ser Gly Ala
1               5                   10                  15
Ser Leu Lys Val Ser Cys Lys Ala Ser Gly Tyr Ile Phe Thr Arg Tyr
            20                  25                  30
Gly Val Ser Trp Val Arg Gln Ala Pro Gly Gln Gly Leu Glu Trp Met
        35                  40                  45
Gly Trp Ile Thr Thr Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Arg Val Arg Tyr Ser Gly Gly Tyr Ser Phe Asp Asn Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
```

Lys Pro Ser Asn Thr Lys Val Asp Lys Thr Val Glu Arg Lys Cys Cys
                210                 215                 220

Val Glu Cys Pro Pro Cys Pro Ala Pro Val Ala Gly Pro Ser Val
225             230              235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305             310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370             375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 141
<211> LENGTH: 447
<212> TYPE: PRT
<213> ORGANISM: Artificial Sequence
<220> FEATURE:
<223> OTHER INFORMATION: Synthetic HC-46 polypeptide

<400> SEQUENCE: 141

Gln Val Gln Leu Val Gln Ser Gly Ala Glu Val Lys Lys Ser Gly Ala
1               5                   10                  15

Ser Leu Lys Val Ser Cys Lys Ala Ser Gly Tyr Ile Phe Thr Arg Tyr
                20                  25                  30

Gly Val Ser Trp Val Arg Gln Ala Pro Gly Gln Gly Leu Glu Trp Met
            35                  40                  45

Gly Trp Ile Thr Thr Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Val Arg Tyr Ser Gly Gly Tyr Ser Phe Asp Asn Trp Gly
                100                 105                 110

Gln Gly Thr Leu Val Thr Val Ser Ser Ala Ser Thr Lys Gly Pro Ser
            115                 120                 125

```
Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 142
<211> LENGTH: 444
<212> TYPE: PRT
<213> ORGANISM: Artificial Sequence
<220> FEATURE:
<223> OTHER INFORMATION: Synthetic HC-47 polypeptide

<400> SEQUENCE: 142

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45
```

Gly Arg Ile Tyr Thr Ser Gly Ser Thr Asn Tyr Asn Pro Ser Leu Lys
    50                  55                  60

Ser Arg Val Thr Met Ser Ile Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ile Ile Ala Ser Arg Gly Trp Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 143
<211> LENGTH: 445
<212> TYPE: PRT

<213> ORGANISM: Artificial Sequence
<220> FEATURE:
<223> OTHER INFORMATION: Synthetic HC-48 polypeptide

<400> SEQUENCE: 143

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Gly Gly Ala Ala Arg Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
```

```
                385                 390                 395                 400
        Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro Gly Lys
                        435                 440                 445

<210> SEQ ID NO 144
<211> LENGTH: 449
<212> TYPE: PRT
<213> ORGANISM: Artificial Sequence
<220> FEATURE:
<223> OTHER INFORMATION: Synthetic HC-49 polypeptide

<400> SEQUENCE: 144

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Arg Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Val Phe Tyr Ser Lys Gly Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
```

```
            305                 310                 315                 320
Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 145
<211> LENGTH: 445
<212> TYPE: PRT
<213> ORGANISM: Artificial Sequence
<220> FEATURE:
<223> OTHER INFORMATION: Synthetic HC-50 polypeptide

<400> SEQUENCE: 145

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Arg Gly
                20                  25                  30

Gly Tyr Tyr Trp Ser Trp Ile Arg Gln His Pro Gly Lys G

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 146
<211> LENGTH: 445
<212> TYPE: PRT
<213> ORGANISM: Artificial Sequence
<220> FEATURE:
<223> OTHER INFORMATION: Synthetic HC-51 polypeptide

<400> SEQUENCE: 146

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Thr Arg Gly Gly Ala Ala Arg Gly Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Asn Phe Gly Thr Gln Thr Tyr Thr Cys Asn Val Asp His Lys Pro
    195                 200                 205

Ser Asn Thr Lys Val Asp Lys Thr Val Glu Arg Lys Cys Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Phe Arg Val Val Ser Val Leu
290                 295                 300

Thr Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 147
<211> LENGTH: 449
<212> TYPE: PRT
<213> ORGANISM: Artificial Sequence
<220> FEATURE:
<223> OTHER INFORMATION: Synthetic HC-52 polypeptide

<400> SEQUENCE: 147

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
50                  55                  60
```

```
Leu Lys Ser Arg Val Thr Ile Ser Gly Asp Thr Ser Lys Asn Gln Phe
 65                  70                  75                  80

Ser Leu Lys Leu Arg Ser Val Thr Ala Ala Asp Thr Ala Val Tyr Tyr
                 85                  90                  95

Cys Thr Arg Gly Gly Ala Ala Arg Gly Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 148
<211> LENGTH: 445
<212> TYPE: PRT
```

<213> ORGANISM: Artificial Sequence
<220> FEATURE:
<223> OTHER INFORMATION: Synthetic HC-53 polypeptide

<400> SEQUENCE: 148

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Ile Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Ala Ala Arg Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly

```
                385                 390                 395                 400
Ser Phe Phe Leu Tyr Ser Lys Leu Thr Val Asp Lys Ser Arg Trp Gln
                    405                 410                 415
Gln Gly Asn Val Phe Ser Cys Ser Val Met His Glu Ala Leu His Asn
                    420                 425                 430
His Tyr Thr Gln Lys Ser Leu Ser Leu Ser Pro Gly Lys
                    435                 440                 445

<210> SEQ ID NO 149
<211> LENGTH: 108
<212> TYPE: PRT
<213> ORGANISM: Artificial Sequence
<220> FEATURE:
<223> OTHER INFORMATION: Synthetic LV-01 polypeptide

<400> SEQUENCE: 149

Asp Ile Gln Met Thr Gln Ser Pro Ser Ser Leu Ser Ala Ser Val Gly
1               5                   10                  15
Asp Arg Ile Thr Ile Thr Cys Arg Ala Ser Gln Ser Ile Ser Arg Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Ile Pro Ser Arg Phe Ser Gly
        50                  55                  60
Ser Gly Ser Gly Thr Asp Phe Thr Leu Thr Ile Asn Ser Leu Gln Pro
65                  70                  75                  80
Glu Asp Phe Ala Thr Tyr Phe Cys Gln Gln Ser Tyr Ser Pro Pro Phe
                85                  90                  95
Thr Phe Gly Pro Gly Thr Lys Val Asp Ile Lys Arg
                100                 105

<210> SEQ ID NO 150
<211> LENGTH: 108
<212> TYPE: PRT
<213> ORGANISM: Artificial Sequence
<220> FEATURE:
<223> OTHER INFORMATION: Synthetic LV-02 polypeptide

<400> SEQUENCE: 150

Glu Ile Val Leu Thr Gln Ser Pro Asp Phe Gln Ser Val Thr Pro Lys
1               5                   10                  15
Glu Lys Val Thr Ile Thr Cys Arg Ala Ser Gln Ser Ile Gly Ser Ser
                20                  25                  30
Leu His Trp Tyr Gln Gln Lys Pro Asp Gln Ser Pro Lys Leu Leu Ile
            35                  40                  45
Lys Tyr Ala Ser Gln Ser Leu Ser Gly Ile Pro Ser Arg Phe Ser Gly
        50                  55                  60
Ser Gly Ser Gly Thr His Phe Thr Leu Thr Ile Asn Ser Leu Glu Ala
65                  70                  75                  80
Glu Asp Ala Ala Thr Tyr Tyr Cys His Gln Ser Ser Arg Leu Pro Phe
                85                  90                  95
Thr Phe Gly Pro Gly Thr Lys Val Asp Ile Lys Arg
                100                 105

<210> SEQ ID NO 151
<211> LENGTH: 108
<212> TYPE: PRT
<213> ORGANISM: Artificial Sequence
<220> FEATURE:
```

<223> OTHER INFORMATION: Synthetic LV-03 polypeptide

<400> SEQUENCE: 151

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Arg Ser
            20                  25                  30

Leu His Trp Tyr Gln Gln Lys Pro Gly Lys Ala Pro Lys Leu Leu Ile
        35                  40                  45

Lys Tyr Ala Ser Gln Ser Leu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys His Gln Ser Ser Arg Leu Pro Phe
                85                  90                  95

Thr Phe Gly Pro Gly Thr Lys Val Asp Ile Lys Arg
            100                 105

<210> SEQ ID NO 152
<211> LENGTH: 108
<212> TYPE: PRT
<213> ORGANISM: Artificial Sequence
<220> FEATURE:
<223> OTHER INFORMATION: Synthetic LV-04 polypeptide

<400> SEQUENCE: 152

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Val Gly Arg Ser
            20                  25                  30

Leu His Trp Tyr His Gln Lys Pro Asp Gln Ser Pro Lys Leu Leu Ile
        35                  40                  45

Lys Tyr Ala Ser Gln Ser Leu Ser Gly Val Pro Ser Arg Phe Ser Gly
    50                  55                  60

Ser Gly Ser Gly Thr Asp Phe Thr Leu Ile Ile Asn Ser Leu Glu Ala
65                  70                  75                  80

Glu Asp Ala Ala Thr Tyr Tyr Cys His Gln Ser Ser Arg Leu Pro Phe
                85                  90                  95

Thr Phe Gly Pro Gly Thr Lys Val Asp Ile Lys Arg
            100                 105

<210> SEQ ID NO 153
<211> LENGTH: 108
<212> TYPE: PRT
<213> ORGANISM: Artificial Sequence
<220> FEATURE:
<223> OTHER INFORMATION: Synthetic LV-05 polypeptide

<400> SEQUENCE: 153

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Arg Ser
            20                  25                  30

Leu His Trp Tyr Gln Gln Lys Pro Gly Lys Ala Pro Lys Leu Leu Ile
        35                  40                  45

Lys Tyr Ala Ser Gln Ser Leu Ser Gly Val Pro Ser Arg Phe Ser Gly
    50                  55                  60

Ser Gly Ser Gly Thr Glu Phe Thr Leu Thr Ile Ser Ser Leu Gln Pro

```
                65                  70                  75                  80
Glu Asp Phe Ala Thr Tyr Tyr Cys His Gln Ser Ser Arg Leu Pro Phe
                    85                  90                  95

Thr Phe Gly Pro Gly Thr Lys Val Asp Ile Lys Arg
            100                 105
```

<210> SEQ ID NO 154
<211> LENGTH: 108
<212> TYPE: PRT
<213> ORGANISM: Artificial Sequence
<220> FEATURE:
<223> OTHER INFORMATION: Synthetic LV-06 polypeptide

<400> SEQUENCE: 154

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Arg Ser
            20                  25                  30

Leu His Trp Tyr His Gln Lys Pro Gly Lys Ala Pro Lys Leu Leu Ile
        35                  40                  45

Lys Tyr Ala Ser Gln Ser Leu Ser Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Glu Asp Phe Ala Thr Tyr Tyr Cys His Gln Ser Ser Arg Leu Pro Phe
                85                  90                  95

Thr Phe Gly Pro Gly Thr Lys Val Asp Ile Lys Arg
            100                 105
```

<210> SEQ ID NO 155
<211> LENGTH: 108
<212> TYPE: PRT
<213> ORGANISM: Artificial Sequence
<220> FEATURE:
<223> OTHER INFORMATION: Synthetic LV-07 polypeptide

<400> SEQUENCE: 155

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Val Gly Arg Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Leu Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Arg Leu Pro Phe
                85                  90                  95

Thr Phe Gly Pro Gly Thr Lys Val Asp Ile Lys Arg
            100                 105
```

<210> SEQ ID NO 156
<211> LENGTH: 108
<212> TYPE: PRT
<213> ORGANISM: Artificial Sequence
<220> FEATURE:
<223> OTHER INFORMATION: Synthetic LV-08 polypeptide

<400> SEQUENCE: 156

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Ser
            20                  25                  30

Leu His Trp Tyr Gln Gln Lys Pro Gly Gln Ala Pro Arg Leu Leu Ile
                35                  40                  45

Lys Tyr Ala Ser Gln Ser Leu Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Ser Ser Arg Leu Pro Phe
                85                  90                  95

Thr Phe Gly Pro Gly Thr Lys Val Asp Ile Lys Arg
                100                 105
```

<210> SEQ ID NO 157
<211> LENGTH: 108
<212> TYPE: PRT
<213> ORGANISM: Artificial Sequence
<220> FEATURE:
<223> OTHER INFORMATION: Synthetic LV-09 polypeptide

<400> SEQUENCE: 157

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Arg Ser
            20                  25                  30

Leu His Trp Tyr Gln Gln Lys Pro Gly Gln Ala Pro Arg Leu Leu Ile
                35                  40                  45

Lys Tyr Ala Ser Gln Ser Leu Ser Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Thr Tyr Tyr Cys His Gln Ser Ser Arg Leu Pro Phe
                85                  90                  95

Thr Phe Gly Gln Gly Thr Lys Val Glu Ile Lys Arg
                100                 105
```

<210> SEQ ID NO 158
<211> LENGTH: 108
<212> TYPE: PRT
<213> ORGANISM: Artificial Sequence
<220> FEATURE:
<223> OTHER INFORMATION: Synthetic LV-10 polypeptide

<400> SEQUENCE: 158

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Arg Ser
            20                  25                  30

Leu His Trp Tyr Gln Gln Lys Pro Asp Gln Ser Pro Lys Leu Leu Phe
                35                  40                  45

Lys Tyr Ala Ser Gln Ser Leu Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Arg Leu Pro Phe
```

```
                        85                  90                  95

Thr Phe Gly Pro Gly Thr Lys Val Asp Ile Lys Arg
                100                 105

<210> SEQ ID NO 159
<211> LENGTH: 108
<212> TYPE: PRT
<213> ORGANISM: Artificial Sequence
<220> FEATURE:
<223> OTHER INFORMATION: Synthetic LV-11 polypeptide

<400> SEQUENCE: 159

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Arg Ser
                20                  25                  30

Leu His Trp Tyr Gln Gln Lys Pro Gly Lys Ala Pro Lys Leu Leu Phe
            35                  40                  45

Lys Tyr Ala Ser Gln Ser Leu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys His Gln Ser Ser Arg Leu Pro Phe
                85                  90                  95

Thr Phe Gly Pro Gly Thr Lys Val Asp Ile Lys Arg
                100                 105

<210> SEQ ID NO 160
<211> LENGTH: 108
<212> TYPE: PRT
<213> ORGANISM: Artificial Sequence
<220> FEATURE:
<223> OTHER INFORMATION: Synthetic LV-12 polypeptide

<400> SEQUENCE: 160

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Asn Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser Arg
                85                  90                  95

Thr Phe Gly Gln Gly Thr Lys Val Glu Ile Lys Arg
                100                 105

<210> SEQ ID NO 161
<211> LENGTH: 113
<212> TYPE: PRT
<213> ORGANISM: Artificial Sequence
<220> FEATURE:
<223> OTHER INFORMATION: Synthetic LV-13 polypeptide

<400> SEQUENCE: 161

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Leu Tyr Leu Gly Ser Asn Arg Ala Ser Gly Val Pro
    50                  55                  60

Asp Arg Phe Ser Gly Ser Gly Ser Gly Thr Asp Phe Thr Leu Gln Ile
65                  70                  75                  80

Ser Arg Val Glu Ala Glu Asp Val Gly Val Tyr Tyr Cys Met Gln Thr
                85                  90                  95

Leu Gln Thr Pro Phe Thr Phe Gly Pro Gly Thr Lys Val Asp Ile Lys
            100                 105                 110

Arg

<210> SEQ ID NO 162
<211> LENGTH: 113
<212> TYPE: PRT
<213> ORGANISM: Artificial Sequence
<220> FEATURE:
<223> OTHER INFORMATION: Synthetic LV-14 polypeptide

<400> SEQUENCE: 162

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Leu Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Phe Thr Phe Gly Pro Gly Thr Lys Val Asp Ile Lys
            100                 105                 110

Arg

<210> SEQ ID NO 163
<211> LENGTH: 109
<212> TYPE: PRT
<213> ORGANISM: Artificial Sequence
<220> FEATURE:
<223> OTHER INFORMATION: Synthetic LV-15 polypeptide

<400> SEQUENCE: 163

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Phe Tyr Cys Gln Gln Phe Gly Ser Ser Pro
                85                  90                  95

Trp Thr Phe Gly Gln Gly Thr Lys Val Glu Ile Lys Arg
            100                 105
```

<210> SEQ ID NO 164
<211> LENGTH: 114
<212> TYPE: PRT
<213> ORGANISM: Artificial Sequence
<220> FEATURE:
<223> OTHER INFORMATION: Synthetic LV-16 polypeptide

<400> SEQUENCE: 164

```
Asp Ile Val Met Thr Gln Ser Pro Asp Ser Leu Ala Val Ser Leu Gly
1               5                   10                  15

Glu Arg Ala Thr Ile His Cys Lys Ser Ser Gln Asn Val Leu Tyr Ser
            20                  25                  30

Ser Asn Asn Lys Asn Phe Leu Thr Trp Tyr Gln Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Ala Pro Phe Thr Phe Gly Pro Gly Thr Lys Val Asp Ile
            100                 105                 110

Lys Arg
```

<210> SEQ ID NO 165
<211> LENGTH: 114
<212> TYPE: PRT
<213> ORGANISM: Artificial Sequence
<220> FEATURE:
<223> OTHER INFORMATION: Synthetic LV-17 polypeptide

<400> SEQUENCE: 165

```
Asp Ile Val Met Thr Gln Ser Pro Asp Ser Leu Ala Val Ser Leu Gly
1               5                   10                  15

Glu Arg Thr Thr Ile Lys Cys Lys Ser Ser Gln Ser Val Leu Tyr Arg
            20                  25                  30

Ser Asn Asn Asn Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ile Ser Pro Leu Thr Phe Gly Gly Gly Thr Lys Val Glu Ile
            100                 105                 110

Lys Arg
```

<210> SEQ ID NO 166
<211> LENGTH: 114
<212> TYPE: PRT
<213> ORGANISM: Artificial Sequence
<220> FEATURE:
<223> OTHER INFORMATION: Synthetic LV-18 polypeptide

<400> SEQUENCE: 166

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys His Tyr Leu Ala Trp Tyr Arg Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Val Tyr Tyr Cys Gln Gln
                85                  90                  95

Tyr Tyr Ser Ser Pro Phe Thr Phe Gly Pro Gly Thr Lys Val Asp Ile
            100                 105                 110

Lys Arg
```

<210> SEQ ID NO 167
<211> LENGTH: 114
<212> TYPE: PRT
<213> ORGANISM: Artificial Sequence
<220> FEATURE:
<223> OTHER INFORMATION: Synthetic LV-19 polypeptide

<400> SEQUENCE: 167

```
Asp Ile Val Met Thr Gln Ser Pro Asp Ser Leu Ala Val Ser Leu Gly
1               5                   10                  15

Glu Arg Ala Thr Ile His Cys Lys Ser Ser Gln Ser Val Leu Tyr Ser
            20                  25                  30

Ser Asn Asn Lys Asn Phe Leu Thr Trp Tyr Gln Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Ala Pro Phe Thr Phe Gly Pro Gly Thr Arg Val Asp Ile
            100                 105                 110

Lys Arg
```

<210> SEQ ID NO 168
<211> LENGTH: 114
<212> TYPE: PRT
<213> ORGANISM: Artificial Sequence
<220> FEATURE:
<223> OTHER INFORMATION: Synthetic LV-20 polypeptide

<400> SEQUENCE: 168

```
Asp Ile Val Met Thr Gln Ser Pro Asp Ser Leu Ala Val Ser Leu Gly
1               5                   10                  15

Glu Arg Ala Thr Ile His Cys Lys Ser Ser Gln Ser Val Leu Tyr Ser
            20                  25                  30

Ser Asn Asn Arg Asn Phe Leu Ser Trp Tyr Gln Gln Lys Pro Gly Gln
        35                  40                  45

Pro Pro Lys Leu Leu Ile Tyr Arg Ala Ser Thr Arg Glu Ser Gly Val
```

-continued

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Ala Pro Phe Thr Phe Gly Pro Gly Thr Val Asp Ile
            100                 105                 110

Lys Arg

<210> SEQ ID NO 169
<211> LENGTH: 114
<212> TYPE: PRT
<213> ORGANISM: Artificial Sequence
<220> FEATURE:
<223> OTHER INFORMATION: Synthetic LV-21 polypeptide

<400> SEQUENCE: 169

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Arg Gln Lys Pro Gly Gln
            35                  40                  45

Pro Pro Lys Leu Leu Ile Tyr Arg Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Gln
                85                  90                  95

Tyr Tyr Ser Ser Pro Phe Thr Phe Gly Pro Gly Thr Lys Val Asp Ile
            100                 105                 110

Lys Arg

<210> SEQ ID NO 170
<211> LENGTH: 123
<212> TYPE: PRT
<213> ORGANISM: Artificial Sequence
<220> FEATURE:
<223> OTHER INFORMATION: Synthetic HV-01 polypeptide

<400> SEQUENCE: 170

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Thr Trp Asn Trp Ile Arg Gln Ser Pro Ser Arg Gly Leu Glu
            35                  40                  45

Trp Leu Gly Arg Thr Tyr Tyr Arg Ser Lys Trp Ser Asn His Tyr Ala
        50                  55                  60

Val Ser Val Lys Ser Arg Ile Thr Ile Asn Pro Asp Thr Ser Lys Ser
65                  70                  75                  80

Gln Phe Ser Leu Gln Leu Asn Ser Val Thr Pro Glu Asp Thr Ala Val
                85                  90                  95

Tyr Tyr Cys Ala Arg Gly Thr Trp Lys Gln Leu Trp Phe Leu Asp His
            100                 105                 110

Trp Gly Gln Gly Thr Leu Val Thr Val Ser Ser
        115                 120

-continued

```
<210> SEQ ID NO 171
<211> LENGTH: 120
<212> TYPE: PRT
<213> ORGANISM: Artificial Sequence
<220> FEATURE:
<223> OTHER INFORMATION: Synthetic HV-02 polypeptide

<400> SEQUENCE: 171

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Leu Leu Thr Gly Tyr Pro Asp Tyr Trp Gly Gln
            100                 105                 110

Gly Thr Leu Val Thr Val Ser Ser
        115                 120

<210> SEQ ID NO 172
<211> LENGTH: 120
<212> TYPE: PRT
<213> ORGANISM: Artificial Sequence
<220> FEATURE:
<223> OTHER INFORMATION: Synthetic HV-03 polypeptide

<400> SEQUENCE: 172

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Arg Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Asn
65                  70                  75                  80

Leu Leu Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
        115                 120

<210> SEQ ID NO 173
<211> LENGTH: 120
<212> TYPE: PRT
<213> ORGANISM: Artificial Sequence
<220> FEATURE:
<223> OTHER INFORMATION: Synthetic HV-04 polypeptide

<400> SEQUENCE: 173
```

-continued

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Asn
65                  70                  75                  80

Leu Leu Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
            115                 120

<210> SEQ ID NO 174
<211> LENGTH: 120
<212> TYPE: PRT
<213> ORGANISM: Artificial Sequence
<220> FEATURE:
<223> OTHER INFORMATION: Synthetic HV-05 polypeptide

<400> SEQUENCE: 174

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Phe Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
            115                 120

<210> SEQ ID NO 175
<211> LENGTH: 120
<212> TYPE: PRT
<213> ORGANISM: Artificial Sequence
<220> FEATURE:
<223> OTHER INFORMATION: Synthetic HV-06 polypeptide

<400> SEQUENCE: 175

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Ala Met His Trp Val Arg Arg Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

-continued

```
Lys Gly Arg Phe Thr Ile Ser Arg Asp Asn Ser Lys Asn Thr Leu Asn
 65                  70                  75                  80

Leu Leu Met Asp Ser Leu Arg Ala Glu Asp Thr Ala Leu Phe Tyr Cys
                 85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
        115                 120

<210> SEQ ID NO 176
<211> LENGTH: 120
<212> TYPE: PRT
<213> ORGANISM: Artificial Sequence
<220> FEATURE:
<223> OTHER INFORMATION: Synthetic HV-07 polypeptide

<400> SEQUENCE: 176

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Ser Arg Phe
                 20                  25                  30

Ala Met His Trp Val Arg Gln Ala Pro Gly Gln Gly Leu Glu Trp Met
             35                  40                  45

Gly Val Ile Ser Tyr Asp Gly Asn Lys Tyr Tyr Ala Glu Ser Val
         50                  55                  60

Lys Gly Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
        115                 120

<210> SEQ ID NO 177
<211> LENGTH: 120
<212> TYPE: PRT
<213> ORGANISM: Artificial Sequence
<220> FEATURE:
<223> OTHER INFORMATION: Synthetic HV-08 polypeptide

<400> SEQUENCE: 177

Gln Val Gln Leu Val Gln Ser Gly Ala Glu Val Lys Lys Pro Gly Ala
 1               5                  10                  15

Ser Val Lys Val Ser Cys Ala Ala Ser Gly Phe Thr Phe Ser Arg Phe
                 20                  25                  30

Ala Met His Trp Val Arg Gln Ala Pro Gly Gln Gly Leu Glu Trp Met
             35                  40                  45

Gly Val Ile Ser Tyr Asp Gly Asn Lys Tyr Tyr Ala Glu Ser Val
         50                  55                  60

Lys Gly Arg Val Thr Met Thr Arg Asp Asn Ser Lys Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
```

```
            115                 120

<210> SEQ ID NO 178
<211> LENGTH: 120
<212> TYPE: PRT
<213> ORGANISM: Artificial Sequence
<220> FEATURE:
<223> OTHER INFORMATION: Synthetic HV-09 polypeptide

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
        115                 120

<210> SEQ ID NO 179
<211> LENGTH: 120
<212> TYPE: PRT
<213> ORGANISM: Artificial Sequence
<220> FEATURE:
<223> OTHER INFORMATION: Synthetic HV-10 polypeptide

<400> SEQUENCE: 179

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
        115                 120

<210> SEQ ID NO 180
<211> LENGTH: 120
<212> TYPE: PRT
<213> ORGANISM: Artificial Sequence
<220> FEATURE:
<223> OTHER INFORMATION: Synthetic HV-11 polypeptide

<400> SEQUENCE: 180
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Gly Asn Lys Tyr Tyr Ala Glu Ser Val
    50                  55                  60

Lys Gly Arg Val Thr Met Thr Arg Asp Thr Ser Thr Ser Thr Leu Tyr
65              70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
        115                 120

<210> SEQ ID NO 181
<211> LENGTH: 120
<212> TYPE: PRT
<213> ORGANISM: Artificial Sequence
<220> FEATURE:
<223> OTHER INFORMATION: Synthetic HV-12 polypeptide

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Gly Asn Lys Tyr Tyr Ala Glu Ser Val
    50                  55                  60

Lys Gly Arg Val Thr Met Thr Arg Asp Thr Ser Lys Ser Thr Ala Tyr
65              70                  75                  80

Met Glu Leu Ser Ser Leu Arg Ser Glu Asp Thr Ala Val Tyr Tyr Cys
                85                  90                  95

Ala Arg Gly Tyr Asp Val Leu Thr Gly Tyr Pro Asp Tyr Trp Gly Gln
            100                 105                 110

Gly Thr Leu Val Thr Val Ser Ser
        115                 120

<210> SEQ ID NO 182
<211> LENGTH: 120
<212> TYPE: PRT
<213> ORGANISM: Artificial Sequence
<220> FEATURE:
<223> OTHER INFORMATION: Synthetic HV-13 polypeptide

<400> SEQUENCE: 182

Gln Val Gln Leu Val Glu Ser Gly Ala Glu Val Val Lys Pro Gly Ala
1               5                   10                  15

Ser Val Lys Val Ser Cys Lys Ala Ser Gly Phe Thr Phe Ser Arg Phe
            20                  25                  30

Ala Met His Trp Val Arg Gln Ala Pro Gly Gln Gly Leu Glu Trp Met
        35                  40                  45

Gly Val Ile Ser Tyr Asp Gly Gly Asn Lys Tyr Tyr Ala Glu Ser Val
```

```
                50                  55                  60
Lys Gly Arg Val Thr Met Thr Arg Asp Thr Ser Thr Ser Thr Leu Tyr
 65                  70                  75                  80

Met Glu Leu Ser Ser Leu Arg Ser Glu Asp Thr Ala Val Tyr Tyr Cys
                    85                  90                  95

Ala Arg Gly Tyr Asp Val Leu Thr Gly Tyr Pro Asp Tyr Trp Gly Gln
                100                 105                 110

Gly Thr Leu Val Thr Val Ser Ser
            115                 120

<210> SEQ ID NO 183
<211> LENGTH: 120
<212> TYPE: PRT
<213> ORGANISM: Artificial Sequence
<220> FEATURE:
<223> OTHER INFORMATION: Synthetic HV-14 polypeptide

<400> SEQUENCE: 183

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Arg Tyr
                20                  25                  30

Ala Met His Trp Val Arg Gln Ala Ser Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Leu Met Ser Ser Leu Arg Ala Glu Asp Thr Ala Val Phe Tyr Cys
                    85                  90                  95

Ala Arg Gly Tyr Asp Ile Leu Thr Gly Tyr Pro Asp Tyr Trp Gly Gln
                100                 105                 110

Gly Thr Leu Val Thr Val Ser Ser
            115                 120

<210> SEQ ID NO 184
<211> LENGTH: 123
<212> TYPE: PRT
<213> ORGANISM: Artificial Sequence
<220> FEATURE:
<223> OTHER INFORMATION: Synthetic HV-15 polypeptide

<400> SEQUENCE: 184

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Asn Ala Tyr Asn Gly His Thr Asn Tyr Ala Gln Thr Phe
        50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                    85                  90                  95

Ala Arg Glu Leu Glu Leu Arg Ser Phe Tyr Tyr Phe Gly Met Asp Val
                100                 105                 110
```

```
Trp Gly Gln Gly Thr Thr Val Pro Val Ser Ser
        115                 120
```

<210> SEQ ID NO 185
<211> LENGTH: 123
<212> TYPE: PRT
<213> ORGANISM: Artificial Sequence
<220> FEATURE:
<223> OTHER INFORMATION: Synthetic HV-16 polypeptide

<400> SEQUENCE: 185

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Asn Ala Tyr Asn Gly His Thr Asn Tyr Ala Gln Thr Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Leu Glu Leu Arg Ser Phe Tyr Tyr Phe Gly Met Asp Val
            100                 105                 110

Trp Gly Gln Gly Thr Thr Val Thr Val Ser Ser
        115                 120
```

<210> SEQ ID NO 186
<211> LENGTH: 121
<212> TYPE: PRT
<213> ORGANISM: Artificial Sequence
<220> FEATURE:
<223> OTHER INFORMATION: Synthetic HV-17 polypeptide

<400> SEQUENCE: 186

```
Gln Val Gln Leu Val Gln Ser Gly Ala Glu Val Lys Lys Ser Gly Ala
1               5                   10                  15

Ser Leu Lys Val Ser Cys Lys Ala Ser Gly Tyr Ile Phe Thr Arg Tyr
            20                  25                  30

Gly Val Ser Trp Val Arg Gln Ala Pro Gly Gln Gly Leu Glu Trp Met
        35                  40                  45

Gly Trp Ile Thr Thr Tyr Asn Gly Asn Thr Asn Tyr Ala Gln Lys Leu
    50                  55                  60

Gln Gly Arg Val Thr Met Thr Ile Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Val Arg Tyr Ser Gly Gly Tyr Ser Phe Asp Asn Trp Gly
            100                 105                 110

Gln Gly Thr Leu Val Thr Val Ser Ser
        115                 120
```

<210> SEQ ID NO 187
<211> LENGTH: 121
<212> TYPE: PRT
<213> ORGANISM: Artificial Sequence
<220> FEATURE:
<223> OTHER INFORMATION: Synthetic HV-18 polypeptide

<400> SEQUENCE: 187

```
Gln Val Gln Leu Val Gln Ser Gly Ala Glu Val Lys Lys Ser Gly Ala
1               5                   10                  15
Ser Leu Lys Val Ser Cys Lys Ala Ser Gly Tyr Ile Phe Thr Arg Tyr
            20                  25                  30
Gly Val Ser Trp Val Arg Gln Ala Pro Gly Gln Gly Leu Glu Trp Met
        35                  40                  45
Gly Trp Ile Thr Thr Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Arg Val Arg Tyr Ser Gly Gly Tyr Ser Phe Asp Asn Trp Gly
            100                 105                 110
Gln Gly Thr Leu Val Thr Val Ser Ser
        115                 120
```

<210> SEQ ID NO 188
<211> LENGTH: 121
<212> TYPE: PRT
<213> ORGANISM: Artificial Sequence
<220> FEATURE:
<223> OTHER INFORMATION: Synthetic HV-19 polypeptide

<400> SEQUENCE: 188

```
Gln Val Gln Leu Val Gln Ser Gly Ala Glu Val Lys Lys Ser Gly Ala
1               5                   10                  15
Ser Leu Lys Val Ser Cys Lys Ala Ser Gly Tyr Ile Phe Thr Arg Tyr
            20                  25                  30
Gly Val Ser Trp Val Arg Gln Ala Pro Gly Gln Gly Leu Glu Trp Met
        35                  40                  45
Gly Trp Ile Thr Thr Tyr Asn Gly Asn Thr Asn Tyr Ala Gln Lys Leu
    50                  55                  60
Gln Gly Arg Val Thr Met Thr Thr Asp Thr Ser Thr Asn Thr Ala Tyr
65                  70                  75                  80
Met Glu Leu Arg Ser Leu Arg Ser Asp Asp Thr Ala Val Tyr Tyr Cys
                85                  90                  95
Ala Arg Arg Val Arg Tyr Ser Gly Gly Tyr Ser Phe Asp Asn Trp Gly
            100                 105                 110
Gln Gly Thr Leu Val Thr Val Ser Ser
        115                 120
```

<210> SEQ ID NO 189
<211> LENGTH: 118
<212> TYPE: PRT
<213> ORGANISM: Artificial Sequence
<220> FEATURE:
<223> OTHER INFORMATION: Synthetic HV-20 polypeptide

<400> SEQUENCE: 189

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Ala Gly Lys Gly Leu Glu Trp Ile
        35                  40                  45
```

Gly Arg Ile Tyr Thr Ser Gly Ser Thr Asn Tyr Asn Pro Ser Leu Lys
            50                  55                  60

Ser Arg Val Thr Met Ser Ile Gly Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Ile Ile Ala Ser Arg Gly Trp Tyr Phe Asp Leu Trp Gly Arg Gly Thr
            100                 105                 110

Leu Val Thr Val Ser Ser
            115

<210> SEQ ID NO 190
<211> LENGTH: 119
<212> TYPE: PRT
<213> ORGANISM: Artificial Sequence
<220> FEATURE:
<223> OTHER INFORMATION: Synthetic HV-21 polypeptide

<400> SEQUENCE: 190

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Gly Asp Thr Ser Lys Asn Gln Phe
 65                 70                  75                  80

Ser Leu Lys Leu Arg Ser Val Thr Ala Ala Asp Thr Ala Val Tyr Tyr
                85                  90                  95

Cys Ala Arg Gly Gly Ala Ala Arg Gly Met Asp Val Trp Gly Gln Gly
            100                 105                 110

Thr Thr Val Thr Val Ser Ser
            115

<210> SEQ ID NO 191
<211> LENGTH: 123
<212> TYPE: PRT
<213> ORGANISM: Artificial Sequence
<220> FEATURE:
<223> OTHER INFORMATION: Synthetic HV-22 polypeptide

<400> SEQUENCE: 191

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Arg Trp Tyr Asn Asp Tyr Ala
    50                  55                  60

Val Ser Val Lys Ser Arg Ile Thr Ile Asn Pro Asp Thr Ser Lys Asn
 65                 70                  75                  80

Gln Phe Ser Leu Gln Leu Asn Ser Val Thr Pro Glu Asp Thr Ala Val
                85                  90                  95

Tyr Tyr Cys Ala Arg Gly Val Phe Tyr Ser Lys Gly Ala Phe Asp Ile
            100                 105                 110

Trp Gly Gln Gly Thr Met Val Thr Val Ser Ser
        115                 120

<210> SEQ ID NO 192
<211> LENGTH: 119
<212> TYPE: PRT
<213> ORGANISM: Artificial Sequence
<220> FEATURE:
<223> OTHER INFORMATION: Synthetic HV-23 polypeptide

<400> SEQUENCE: 192

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Arg Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
50                  55                  60

Leu Lys Ser Arg Val Ile Ile Ser Gly Asp Thr Ser Lys Asn Gln Leu
65                  70                  75                  80

Ser Leu Lys Leu Arg Ser Val Thr Ala Ala Asp Thr Ala Val Tyr Tyr
                85                  90                  95

Cys Ala Arg Gly Gly Ala Ala Arg Gly Met Asp Val Trp Gly Gln Gly
            100                 105                 110

Thr Thr Val Thr Val Ser Ser
        115

<210> SEQ ID NO 193
<211> LENGTH: 119
<212> TYPE: PRT
<213> ORGANISM: Artificial Sequence
<220> FEATURE:
<223> OTHER INFORMATION: Synthetic HV-24 polypeptide

<400> SEQUENCE: 193

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
50                  55                  60

Leu Lys Ser Arg Val Thr Ile Ser Gly Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Thr Arg Gly Gly Ala Ala Arg Gly Met Asp Val Trp Gly Gln Gly
            100                 105                 110

Thr Thr Val Thr Val Ser Ser
        115

<210> SEQ ID NO 194
<211> LENGTH: 119
<212> TYPE: PRT
<213> ORGANISM: Artificial Sequence
<220> FEATURE:
<223> OTHER INFORMATION: Synthetic HV-25 polypeptide

```
<400> SEQUENCE: 194

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Thr Arg Gly Gly Ala Ala Arg Gly Met Asp Val Trp Gly Gln Gly
            100                 105                 110

Thr Thr Val Thr Val Ser Ser
        115

<210> SEQ ID NO 195
<211> LENGTH: 119
<212> TYPE: PRT
<213> ORGANISM: Artificial Sequence
<220> FEATURE:
<223> OTHER INFORMATION: Synthetic HV-26 polypeptide

<400> SEQUENCE: 195

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Ile Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Ala Ala Arg Gly Met Asp Val Trp Gly Gln Gly
            100                 105                 110

Thr Thr Val Thr Val Ser Ser
        115

<210> SEQ ID NO 196
<211> LENGTH: 11
<212> TYPE: PRT
<213> ORGANISM: Artificial Sequence
<220> FEATURE:
<223> OTHER INFORMATION: Synthetic CDRL1-1 peptide

<400> SEQUENCE: 196

Arg Ala Ser Gln Ser Ile Gly Arg Ser Leu His
1               5                   10

<210> SEQ ID NO 197
<211> LENGTH: 11
<212> TYPE: PRT
<213> ORGANISM: Artificial Sequence
```

```
<220> FEATURE:
<223> OTHER INFORMATION: Synthetic CDRL1-2 peptide

<400> SEQUENCE: 197

Arg Ala Ser Gln Ser Val Gly Arg Ser Leu His
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Synthetic CDRL1-3 peptide

<400> SEQUENCE: 198

Arg Ala Ser Gln Ser Ile Ser Arg Tyr Leu Asn
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Synthetic CDRL1-4 peptide

<400> SEQUENCE: 199

Arg Ala Ser Gln Ser Val Ser Ser Ser Tyr Leu Ala
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Synthetic CDRL1-5 peptide

<400> SEQUENCE: 200

Arg Ala Ser Gln Thr Val Ser Arg Ser Tyr Leu Ala
1               5                   10

<210> SEQ ID NO 201
<211> LENGTH: 16
<212> TYPE: PRT
<213> ORGANISM: Artificial Sequence
<220> FEATURE:
<223> OTHER INFORMATION: Synthetic CDRL1-6 peptide

<400> SEQUENCE: 201

Arg Ser Ser Gln Ser Leu Leu His Ser Asn Gly Tyr Asn Tyr Leu Asp
1               5                   10                  15

<210> SEQ ID NO 202
<211> LENGTH: 17
<212> TYPE: PRT
<213> ORGANISM: Artificial Sequence
<220> FEATURE:
<223> OTHER INFORMATION: Synthetic CDRL1-7 peptide

<400> SEQUENCE: 202

Lys Ser Ser Gln Asn Val Leu Tyr Ser Ser Asn Asn Lys Asn Phe Leu
1               5                   10                  15

Thr

<210> SEQ ID NO 203
<211> LENGTH: 17
<212> TYPE: PRT
```

```
<213> ORGANISM: Artificial Sequence
<220> FEATURE:
<223> OTHER INFORMATION: Synthetic CDRL1-8 peptide

<400> SEQUENCE: 203

Lys Ser Ser Gln Ser Val Leu Tyr Arg Ser Asn Asn Asn Phe Leu
1               5                   10                  15

Ala

<210> SEQ ID NO 204
<211> LENGTH: 17
<212> TYPE: PRT
<213> ORGANISM: Artificial Sequence
<220> FEATURE:
<223> OTHER INFORMATION: Synthetic CDRL1-9 peptide

<400> SEQUENCE: 204

Lys Ser Ser Gln Ser Val Leu Tyr Ser Ser Asn Asn Lys His Tyr Leu
1               5                   10                  15

Ala

<210> SEQ ID NO 205
<211> LENGTH: 17
<212> TYPE: PRT
<213> ORGANISM: Artificial Sequence
<220> FEATURE:
<223> OTHER INFORMATION: Synthetic CDRL1-10 peptide

<400> SEQUENCE: 205

Lys Ser Ser Gln Ser Val Leu Tyr Ser Ser Asn Asn Lys Asn Phe Leu
1               5                   10                  15

Thr

<210> SEQ ID NO 206
<211> LENGTH: 17
<212> TYPE: PRT
<213> ORGANISM: Artificial Sequence
<220> FEATURE:
<223> OTHER INFORMATION: Synthetic CDRL1-11 peptide

<400> SEQUENCE: 206

Lys Ser Ser Gln Ser Val Leu Tyr Ser Ser Asn Asn Lys Asn Tyr Leu
1               5                   10                  15

Ala

<210> SEQ ID NO 207
<211> LENGTH: 17
<212> TYPE: PRT
<213> ORGANISM: Artificial Sequence
<220> FEATURE:
<223> OTHER INFORMATION: Synthetic CDRL1-12 peptide

<400> SEQUENCE: 207

Lys Ser Ser Gln Ser Val Leu Tyr Ser Ser Asn Asn Arg Asn Phe Leu
1               5                   10                  15

Ser

<210> SEQ ID NO 208
<211> LENGTH: 11
<212> TYPE: PRT
<213> ORGANISM: Artificial Sequence
<220> FEATURE:
<223> OTHER INFORMATION: Synthetic CDRL1-13 peptide
```

```
<400> SEQUENCE: 208

Arg Ala Ser Gln Ser Ile Gly Ser Ser Leu His
1               5                   10

<210> SEQ ID NO 209
<211> LENGTH: 7
<212> TYPE: PRT
<213> ORGANISM: Artificial Sequence
<220> FEATURE:
<223> OTHER INFORMATION: Synthetic CDRL2-1 peptide

<400> SEQUENCE: 209

Tyr Ala Ser Gln Ser Leu Ser
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic CDRL2-2 peptide

<400> SEQUENCE: 210

Ala Ala Ser Ser Leu Gln Ser
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic CDRL2-3 peptide

<400> SEQUENCE: 211

Gly Ala Ser Ser Arg Ala Thr
1               5

<210> SEQ ID NO 212
<211> LENGTH: 7
<212> TYPE: PRT
<213> ORGANISM: Artificial Sequence
<220> FEATURE:
<223> OTHER INFORMATION: Synthetic CDRL2-4 peptide

<400> SEQUENCE: 212

Leu Gly Ser Asn Arg Ala Ser
1               5

<210> SEQ ID NO 213
<211> LENGTH: 7
<212> TYPE: PRT
<213> ORGANISM: Artificial Sequence
<220> FEATURE:
<223> OTHER INFORMATION: Synthetic CDRL2-5 peptide

<400> SEQUENCE: 213

Arg Ala Ser Thr Arg Glu Ser
1               5

<210> SEQ ID NO 214
<211> LENGTH: 7
<212> TYPE: PRT
<213> ORGANISM: Artificial Sequence
<220> FEATURE:
<223> OTHER INFORMATION: Synthetic CDRL2-6 peptide

<400> SEQUENCE: 214
```

Trp Ala Ser Thr Arg Glu Ser
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic CDRL3-1 peptide

<400> SEQUENCE: 215

His Gln Ser Ser Arg Leu Pro Phe Thr
1               5

<210> SEQ ID NO 216
<211> LENGTH: 9
<212> TYPE: PRT
<213> ORGANISM: Artificial Sequence
<220> FEATURE:
<223> OTHER INFORMATION: Synthetic CDRL3-2 peptide

<400> SEQUENCE: 216

Gln Gln Ser Tyr Ser Pro Pro Phe Thr
1               5

<210> SEQ ID NO 217
<211> LENGTH: 8
<212> TYPE: PRT
<213> ORGANISM: Artificial Sequence
<220> FEATURE:
<223> OTHER INFORMATION: Synthetic CDRL3-3 peptide

<400> SEQUENCE: 217

Gln Arg Tyr Gly Ser Ser Arg Thr
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic CDRL3-4 peptide

<400> SEQUENCE: 218

Gln Gln Phe Gly Ser Ser Pro Trp Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic CDRL3-5 peptide

<400> SEQUENCE: 219

Met Gln Thr Leu Gln Thr Pro Phe Thr
1               5

<210> SEQ ID NO 220
<211> LENGTH: 9
<212> TYPE: PRT
<213> ORGANISM: Artificial Sequence
<220> FEATURE:
<223> OTHER INFORMATION: Synthetic CDRL3-6 peptide

<400> SEQUENCE: 220

Gln Gln Tyr Tyr Ser Ala Pro Phe Thr
1               5

<210> SEQ ID NO 221
<211> LENGTH: 9
<212> TYPE: PRT
<213> ORGANISM: Artificial Sequence
<220> FEATURE:
<223> OTHER INFORMATION: Synthetic CDRL3-7 peptide

<400> SEQUENCE: 221

Gln Gln Tyr Tyr Ile Ser Pro Leu Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic CDRL3-8 peptide

<400> SEQUENCE: 222

Gln Gln Tyr Tyr Ser Ser Pro Phe Thr
1               5

<210> SEQ ID NO 223
<211> LENGTH: 5
<212> TYPE: PRT
<213> ORGANISM: Artificial Sequence
<220> FEATURE:
<223> OTHER INFORMATION: Synthetic CDRH1-1 peptide

<400> SEQUENCE: 223

Arg Phe Ala Met His
1               5

<210> SEQ ID NO 224
<211> LENGTH: 7
<212> TYPE: PRT
<213> ORGANISM: Artificial Sequence
<220> FEATURE:
<223> OTHER INFORMATION: Synthetic CDRH1-2 peptide

<400> SEQUENCE: 224

Arg Gly Gly Tyr Tyr Trp Ser
1               5

<210> SEQ ID NO 225
<211> LENGTH: 5
<212> TYPE: PRT
<213> ORGANISM: Artificial Sequence
<220> FEATURE:
<223> OTHER INFORMATION: Synthetic CDRH1-3 peptide

<400> SEQUENCE: 225

Arg Tyr Ala Met His
1               5

<210> SEQ ID NO 226
<211> LENGTH: 5
<212> TYPE: PRT
<213> ORGANISM: Artificial Sequence
<220> FEATURE:
<223> OTHER INFORMATION: Synthetic CDRH1-4 peptide

<400> SEQUENCE: 226

Arg Tyr Gly Val Ser

```
1               5
```

<210> SEQ ID NO 227
<211> LENGTH: 7
<212> TYPE: PRT
<213> ORGANISM: Artificial Sequence
<220> FEATURE:
<223> OTHER INFORMATION: Synthetic CDRH1-5 peptide

<400> SEQUENCE: 227

```
Ser Gly Gly Phe Tyr Trp Ser
1               5
```

<210> SEQ ID NO 228
<211> LENGTH: 7
<212> TYPE: PRT
<213> ORGANISM: Artificial Sequence
<220> FEATURE:
<223> OTHER INFORMATION: Synthetic CDRH1-6 peptide

<400> SEQUENCE: 228

```
Ser Gly Gly Tyr Tyr Trp Ser
1               5
```

<210> SEQ ID NO 229
<211> LENGTH: 7
<212> TYPE: PRT
<213> ORGANISM: Artificial Sequence
<220> FEATURE:
<223> OTHER INFORMATION: Synthetic CDRH1-7 peptide

<400> SEQUENCE: 229

```
Ser Asn Ser Ala Ala Trp Asn
1               5
```

<210> SEQ ID NO 230
<211> LENGTH: 7
<212> TYPE: PRT
<213> ORGANISM: Artificial Sequence
<220> FEATURE:
<223> OTHER INFORMATION: Synthetic CDRH1-8 peptide

<400> SEQUENCE: 230

```
Ser Asn Ser Ala Thr Trp Asn
1               5
```

<210> SEQ ID NO 231
<211> LENGTH: 5
<212> TYPE: PRT
<213> ORGANISM: Artificial Sequence
<220> FEATURE:
<223> OTHER INFORMATION: Synthetic CDRH1-9 peptide

<400> SEQUENCE: 231

```
Ser Tyr Gly Ile Ser
1               5
```

<210> SEQ ID NO 232
<211> LENGTH: 5
<212> TYPE: PRT
<213> ORGANISM: Artificial Sequence
<220> FEATURE:
<223> OTHER INFORMATION: Synthetic CDRH1-10 peptide

<400> SEQUENCE: 232

```
Ser Tyr Tyr Trp Ser
1               5
```

<210> SEQ ID NO 233
<211> LENGTH: 5
<212> TYPE: PRT
<213> ORGANISM: Artificial Sequence
<220> FEATURE:
<223> OTHER INFORMATION: Synthetic CDRH1-11 peptide

<400> SEQUENCE: 233

Tyr Tyr Ala Ile His
1               5

<210> SEQ ID NO 234
<211> LENGTH: 16
<212> TYPE: PRT
<213> ORGANISM: Artificial Sequence
<220> FEATURE:
<223> OTHER INFORMATION: Synthetic CDRH2-1 peptide

<400> SEQUENCE: 234

Arg Ile Tyr Thr Ser Gly Ser Thr Asn Tyr Asn Pro Ser Leu Lys Ser
1               5                   10                  15

<210> SEQ ID NO 235
<211> LENGTH: 18
<212> TYPE: PRT
<213> ORGANISM: Artificial Sequence
<220> FEATURE:
<223> OTHER INFORMATION: Synthetic CDRH2-2 peptide

<400> SEQUENCE: 235

Arg Thr Tyr Tyr Arg Ser Lys Trp Ser Asn His Tyr Ala Val Ser Val
1               5                   10                  15

Lys Ser

<210> SEQ ID NO 236
<211> LENGTH: 18
<212> TYPE: PRT
<213> ORGANISM: Artificial Sequence
<220> FEATURE:
<223> OTHER INFORMATION: Synthetic CDRH2-3 peptide

<400> SEQUENCE: 236

Arg Thr Tyr Tyr Arg Ser Arg Trp Tyr Asn Asp Tyr Ala Val Ser Val
1               5                   10                  15

Lys Ser

<210> SEQ ID NO 237
<211> LENGTH: 17
<212> TYPE: PRT
<213> ORGANISM: Artificial Sequence
<220> FEATURE:
<223> OTHER INFORMATION: Synthetic CDRH2-4 peptide

<400> SEQUENCE: 237

Val Ile Ser Tyr Asp Gly Gly Asn Lys Tyr Tyr Ala Glu Ser Val Lys
1               5                   10                  15

Gly

<210> SEQ ID NO 238
<211> LENGTH: 17
<212> TYPE: PRT
<213> ORGANISM: Artificial Sequence
<220> FEATURE:
<223> OTHER INFORMATION: Synthetic CDRH2-5 peptide

<400> SEQUENCE: 238

Val Ile Ser Tyr Asp Gly Ser Asn Lys Tyr Tyr Ala Asp Ser Val Lys
1               5                   10                  15

Gly

<210> SEQ ID NO 239
<211> LENGTH: 17
<212> TYPE: PRT
<213> ORGANISM: Artificial Sequence
<220> FEATURE:
<223> OTHER INFORMATION: Synthetic CDRH2-6 peptide

<400> SEQUENCE: 239

Trp Ile Asn Ala Tyr Asn Gly His Thr Asn Tyr Ala Gln Thr Phe Gln
1               5                   10                  15

Gly

<210> SEQ ID NO 240
<211> LENGTH: 17
<212> TYPE: PRT
<213> ORGANISM: Artificial Sequence
<220> FEATURE:
<223> OTHER INFORMATION: Synthetic CDRH2-7 peptide

<400> SEQUENCE: 240

Trp Ile Thr Thr Tyr Asn Gly Asn Thr Asn Tyr Ala Gln Lys Leu Gln
1               5                   10                  15

Gly

<210> SEQ ID NO 241
<211> LENGTH: 16
<212> TYPE: PRT
<213> ORGANISM: Artificial Sequence
<220> FEATURE:
<223> OTHER INFORMATION: Synthetic CDRH2-8 peptide

<400> SEQUENCE: 241

Tyr Ile Tyr Tyr Ser Gly Asn Thr Tyr Tyr Asn Pro Ser Leu Lys Ser
1               5                   10                  15

<210> SEQ ID NO 242
<211> LENGTH: 14
<212> TYPE: PRT
<213> ORGANISM: Artificial Sequence
<220> FEATURE:
<223> OTHER INFORMATION: Synthetic CDRH3-1 peptide

<400> SEQUENCE: 242

Glu Leu Glu Leu Arg Ser Phe Tyr Tyr Phe Gly Met Asp Val
1               5                   10

<210> SEQ ID NO 243
<211> LENGTH: 9
<212> TYPE: PRT
<213> ORGANISM: Artificial Sequence
<220> FEATURE:
<223> OTHER INFORMATION: Synthetic CDRH3-2 peptide

<400> SEQUENCE: 243

Gly Gly Ala Ala Arg Gly Met Asp Val
1               5

<210> SEQ ID NO 244

```
<211> LENGTH: 11
<212> TYPE: PRT
<213> ORGANISM: Artificial Sequence
<220> FEATURE:
<223> OTHER INFORMATION: Synthetic CDRH3-3 peptide

<400> SEQUENCE: 244

Gly Thr Trp Lys Gln Leu Trp Phe Leu Asp His
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Synthetic CDRH3-4 peptide

<400> SEQUENCE: 245

Gly Val Phe Tyr Ser Lys Gly Ala Phe Asp Ile
1               5                   10

<210> SEQ ID NO 246
<211> LENGTH: 11
<212> TYPE: PRT
<213> ORGANISM: Artificial Sequence
<220> FEATURE:
<223> OTHER INFORMATION: Synthetic CDRH3-5 peptide

<400> SEQUENCE: 246

Gly Tyr Asp Ile Leu Thr Gly Tyr Pro Asp Tyr
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Synthetic CDRH3-6 peptide

<400> SEQUENCE: 247

Gly Tyr Asp Val Leu Thr Gly Tyr Pro Asp Tyr
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Synthetic CDRH3-7 peptide

<400> SEQUENCE: 248

Ile Ala Ser Arg Gly Trp Tyr Phe Asp Leu
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Synthetic CDRH3-8 peptide

<400> SEQUENCE: 249

Arg Val Arg Tyr Ser Gly Gly Tyr Ser Phe Asp Asn
1               5                   10

<210> SEQ ID NO 250
<211> LENGTH: 11
```

```
<212> TYPE: PRT
<213> ORGANISM: Artificial Sequence
<220> FEATURE:
<223> OTHER INFORMATION: Synthetic CDRH3-9 peptide

<400> SEQUENCE: 250

Gly Tyr Asp Leu Leu Thr Gly Tyr Pro Asp Tyr
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Synthetic CDRL1-C1 peptide
<220> FEATURE:
<221> NAME/KEY: misc_feature
<222> LOCATION: (1)..(12)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (5)..(5)
<223> OTHER INFORMATION: /replace="Thr"
<220> FEATURE:
<221> NAME/KEY: VARIANT
<222> LOCATION: (6)..(6)
<223> OTHER INFORMATION: /replace="Ile"
<220> FEATURE:
<221> NAME/KEY: VARIANT
<222> LOCATION: (7)..(7)
<223> OTHER INFORMATION: /replace="Gly"
<220> FEATURE:
<221> NAME/KEY: VARIANT
<222> LOCATION: (8)..(8)
<223> OTHER INFORMATION: /replace="Ser"
<220> FEATURE:
<221> NAME/KEY: VARIANT
<222> LOCATION: (9)..(9)
<223> OTHER INFORMATION: /replace=" "
<220> FEATURE:
<221> NAME/KEY: VARIANT
<222> LOCATION: (10)..(10)
<223> OTHER INFORMATION: /replace="Ser"
<220> FEATURE:
<221> NAME/KEY: VARIANT
<222> LOCATION: (12)..(12)
<223> OTHER INFORMATION: /replace="His" or "Asn"

<400> SEQUENCE: 251

Arg Ala Ser Gln Ser Val Ser Arg Ser Tyr Leu Ala
1               5                   10

<210> SEQ ID NO 252
<211> LENGTH: 17
<212> TYPE: PRT
<213> ORGANISM: Artificial Sequence
<220> FEATURE:
<223> OTHER INFORMATION: Synthetic CDRL1-C2 peptide
<220> FEATURE:
<221> NAME/KEY: misc_feature
<222> LOCATION: (1)..(17)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (5)..(5)
<223> OTHER INFORMATION: /replace="Asn"
<220> FEATURE:
<221> NAME/KEY: VARIANT
<222> LOCATION: (9)..(9)
<223> OTHER INFORMATION: /replace="Arg"
<220> FEATURE:
```

```
<221> NAME/KEY: VARIANT
<222> LOCATION: (13)..(13)
<223> OTHER INFORMATION: /replace="Asn" or "Arg"
<220> FEATURE:
<221> NAME/KEY: VARIANT
<222> LOCATION: (14)..(14)
<223> OTHER INFORMATION: /replace="His"
<220> FEATURE:
<221> NAME/KEY: VARIANT
<222> LOCATION: (15)..(15)
<223> OTHER INFORMATION: /replace="Tyr"
<220> FEATURE:
<221> NAME/KEY: VARIANT
<222> LOCATION: (17)..(17)
<223> OTHER INFORMATION: /replace="Ala" or "Ser"

<400> SEQUENCE: 252

Lys Ser Ser Gln Ser Val Leu Tyr Ser Ser Asn Asn Lys Asn Phe Leu
1               5                   10                  15

Thr

<210> SEQ ID NO 253
<211> LENGTH: 7
<212> TYPE: PRT
<213> ORGANISM: Artificial Sequence
<220> FEATURE:
<223> OTHER INFORMATION: Synthetic CDRL2-C1 peptide
<220> FEATURE:
<221> NAME/KEY: VARIANT
<222> LOCATION: (1)..(1)
<223> OTHER INFORMATION: /replace="Ala"
<220> FEATURE:
<221> NAME/KEY: misc_feature
<222> LOCATION: (1)..(7)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="Leu"
<220> FEATURE:
<221> NAME/KEY: VARIANT
<222> LOCATION: (6)..(6)
<223> OTHER INFORMATION: /replace="Gln"

<400> SEQUENCE: 253

Tyr Ala Ser Gln Ser Leu Ser
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic CDRL2-C2 peptide
<220> FEATURE:
<221> NAME/KEY: VARIANT
<222> LOCATION: (1)..(1)
<223> OTHER INFORMATION: /replace="Leu"
<220> FEATURE:
<221> NAME/KEY: misc_feature
<222> LOCATION: (1)..(7)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Gly"
```

```
<220> FEATURE:
<221> NAME/KEY: VARIANT
<222> LOCATION: (4)..(4)
<223> OTHER INFORMATION: /replace="Asn"
<220> FEATURE:
<221> NAME/KEY: VARIANT
<222> LOCATION: (7)..(7)
<223> OTHER INFORMATION: /replace="Ser"

<400> SEQUENCE: 254

Gly Ala Ser Ser Arg Ala Thr
1               5

<210> SEQ ID NO 255
<211> LENGTH: 7
<212> TYPE: PRT
<213> ORGANISM: Artificial Sequence
<220> FEATURE:
<223> OTHER INFORMATION: Synthetic CDRL2-C3 peptide
<220> FEATURE:
<221> NAME/KEY: VARIANT
<222> LOCATION: (1)..(1)
<223> OTHER INFORMATION: /replace="Trp"
<220> FEATURE:
<221> NAME/KEY: misc_feature
<222> LOCATION: (1)..(7)
<223> OTHER INFORMATION: /note="Variant residues given in the sequence
      have no preference with respect to those in the annotations for
      variant positions"

<400> SEQUENCE: 255

Arg Ala Ser Thr Arg Glu Ser
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic CDRL3-C1 peptide
<220> FEATURE:
<221> NAME/KEY: VARIANT
<222> LOCATION: (1)..(1)
<223> OTHER INFORMATION: /replace="His"
<220> FEATURE:
<221> NAME/KEY: misc_feature
<222> LOCATION: (1)..(9)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (3)..(3)
<223> OTHER INFORMATION: /replace="Tyr" or "Phe"
<220> FEATURE:
<221> NAME/KEY: VARIANT
<222> LOCATION: (4)..(4)
<223> OTHER INFORMATION: /replace="Ser" or "Gly"
<220> FEATURE:
<221> NAME/KEY: VARIANT
<222> LOCATION: (5)..(5)
<223> OTHER INFORMATION: /replace="Arg" or "Ile"
<220> FEATURE:
<221> NAME/KEY: VARIANT
<222> LOCATION: (6)..(6)
<223> OTHER INFORMATION: /replace="Ser" or "Ala" or "Leu"
<220> FEATURE:
<221> NAME/KEY: VARIANT
<222> LOCATION: (8)..(8)
<223> OTHER INFORMATION: /replace="Leu" or "Trp"

<400> SEQUENCE: 256

Gln Gln Ser Tyr Ser Pro Pro Phe Thr
1               5
```

```
<210> SEQ ID NO 257
<211> LENGTH: 5
<212> TYPE: PRT
<213> ORGANISM: Artificial Sequence
<220> FEATURE:
<223> OTHER INFORMATION: Synthetic CDRH1-C1 peptide
<220> FEATURE:
<221> NAME/KEY: VARIANT
<222> LOCATION: (1)..(1)
<223> OTHER INFORMATION: /replace="Ser" or "Tyr"
<220> FEATURE:
<221> NAME/KEY: misc_feature
<222> LOCATION: (1)..(5)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Phe"
<220> FEATURE:
<221> NAME/KEY: VARIANT
<222> LOCATION: (3)..(3)
<223> OTHER INFORMATION: /replace="Gly" or "Tyr"
<220> FEATURE:
<221> NAME/KEY: VARIANT
<222> LOCATION: (4)..(4)
<223> OTHER INFORMATION: /replace="Val" or "Ile" or "Trp"
<220> FEATURE:
<221> NAME/KEY: VARIANT
<222> LOCATION: (5)..(5)
<223> OTHER INFORMATION: /replace="Ser"

<400> SEQUENCE: 257

Arg Tyr Ala Met His
1               5

<210> SEQ ID NO 258
<211> LENGTH: 7
<212> TYPE: PRT
<213> ORGANISM: Artificial Sequence
<220> FEATURE:
<223> OTHER INFORMATION: Synthetic CDRH1-C2 peptide
<220> FEATURE:
<221> NAME/KEY: VARIANT
<222> LOCATION: (1)..(1)
<223> OTHER INFORMATION: /replace="Ser"
<220> FEATURE:
<221> NAME/KEY: misc_feature
<222> LOCATION: (1)..(7)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (4)..(4)
<223> OTHER INFORMATION: /replace="Phe" or "Ala"
<220> FEATURE:
<221> NAME/KEY: VARIANT
<222> LOCATION: (5)..(5)
<223> OTHER INFORMATION: /replace="Ala" or "Thr"
<220> FEATURE:
<221> NAME/KEY: VARIANT
<222> LOCATION: (7)..(7)
<223> OTHER INFORMATION: /replace="Asn"

<400> SEQUENCE: 258
```

Arg Gly Gly Tyr Tyr Trp Ser
1               5

<210> SEQ ID NO 259
<211> LENGTH: 18
<212> TYPE: PRT
<213> ORGANISM: Artificial Sequence
<220> FEATURE:
<223> OTHER INFORMATION: Synthetic CDRH2-C1 peptide
<220> FEATURE:
<221> NAME/KEY: VARIANT
<222> LOCATION: (1)..(1)
<223> OTHER INFORMATION: /replace="Tyr"
<220> FEATURE:
<221> NAME/KEY: misc_feature
<222> LOCATION: (1)..(18)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (7)..(7)
<223> OTHER INFORMATION: /replace="Arg"
<220> FEATURE:
<221> NAME/KEY: VARIANT
<222> LOCATION: (8)..(8)
<223> OTHER INFORMATION: /replace="Gly"
<220> FEATURE:
<221> NAME/KEY: VARIANT
<222> LOCATION: (9)..(9)
<223> OTHER INFORMATION: /replace="Asn" or "Tyr"
<220> FEATURE:
<221> NAME/KEY: VARIANT
<222> LOCATION: (10)..(10)
<223> OTHER INFORMATION: /replace="Thr"
<220> FEATURE:
<221> NAME/KEY: VARIANT
<222> LOCATION: (11)..(11)
<223> OTHER INFORMATION: /replace="Asn" or "Tyr" or "Asp"
<220> FEATURE:
<221> NAME/KEY: VARIANT
<222> LOCATION: (13)..(13)
<223> OTHER INFORMATION: /replace="Asn"
<220> FEATURE:
<221> NAME/KEY: VARIANT
<222> LOCATION: (14)..(14)
<223> OTHER INFORMATION: /replace="Pro"
<220> FEATURE:
<221> NAME/KEY: VARIANT
<222> LOCATION: (16)..(16)
<223> OTHER INFORMATION: /replace="Leu"

<400> SEQUENCE: 259

Arg Thr Tyr Tyr Arg Ser Lys Trp Ser Asn His Tyr Ala Val Ser Val
1               5                   10                  15

Lys Ser

<210> SEQ ID NO 260
<211> LENGTH: 17
<212> TYPE: PRT
<213> ORGANISM: Artificial Sequence
<220> FEATURE:
<223> OTHER INFORMATION: Synthetic CDRH2-C2 peptide
<220> FEATURE:
<221> NAME/KEY: misc_feature
<222> LOCATION: (1)..(17)

```
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (13)..(13)
<223> OTHER INFORMATION: /replace="Asp"

<400> SEQUENCE: 260

Val Ile Ser Tyr Asp Gly Gly Asn Lys Tyr Tyr Ala Glu Ser Val Lys
1               5                   10                  15

Gly

<210> SEQ ID NO 261
<211> LENGTH: 17
<212> TYPE: PRT
<213> ORGANISM: Artificial Sequence
<220> FEATURE:
<223> OTHER INFORMATION: Synthetic CDRH2-C3 peptide
<220> FEATURE:
<221> NAME/KEY: misc_feature
<222> LOCATION: (1)..(17)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (3)..(4)
<223> OTHER INFORMATION: /replace="Thr"
<220> FEATURE:
<221> NAME/KEY: VARIANT
<222> LOCATION: (8)..(8)
<223> OTHER INFORMATION: /replace="Asn"
<220> FEATURE:
<221> NAME/KEY: VARIANT
<222> LOCATION: (14)..(14)
<223> OTHER INFORMATION: /replace="Lys"
<220> FEATURE:
<221> NAME/KEY: VARIANT
<222> LOCATION: (15)..(15)
<223> OTHER INFORMATION: /replace="Leu"

<400> SEQUENCE: 261

Trp Ile Asn Ala Tyr Asn Gly His Thr Asn Tyr Ala Gln Thr Phe Gln
1               5                   10                  15

Gly

<210> SEQ ID NO 262
<211> LENGTH: 11
<212> TYPE: PRT
<213> ORGANISM: Artificial Sequence
<220> FEATURE:
<223> OTHER INFORMATION: Synthetic CDRH3-C1 peptide
<220> FEATURE:
<221> NAME/KEY: misc_feature
<222> LOCATION: (1)..(11)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Thr" or "Val"
<220> FEATURE:
<221> NAME/KEY: VARIANT
<222> LOCATION: (3)..(3)
<223> OTHER INFORMATION: /replace="Trp" or "Phe"
<220> FEATURE:
<221> NAME/KEY: VARIANT
```

```
<222> LOCATION: (4)..(4)
<223> OTHER INFORMATION: /replace="Lys" or "Tyr" or "Leu"
<220> FEATURE:
<221> NAME/KEY: VARIANT
<222> LOCATION: (5)..(5)
<223> OTHER INFORMATION: /replace="Gln" or "Ser"
<220> FEATURE:
<221> NAME/KEY: VARIANT
<222> LOCATION: (6)..(6)
<223> OTHER INFORMATION: /replace="Leu" or "Lys"
<220> FEATURE:
<221> NAME/KEY: VARIANT
<222> LOCATION: (7)..(7)
<223> OTHER INFORMATION: /replace="Trp"
<220> FEATURE:
<221> NAME/KEY: VARIANT
<222> LOCATION: (8)..(8)
<223> OTHER INFORMATION: /replace="Phe" or "Ala"
<220> FEATURE:
<221> NAME/KEY: VARIANT
<222> LOCATION: (9)..(9)
<223> OTHER INFORMATION: /replace="Leu" or "Phe"
<220> FEATURE:
<221> NAME/KEY: VARIANT
<222> LOCATION: (11)..(11)
<223> OTHER INFORMATION: /replace="His" or "Ile"

<400> SEQUENCE: 262

Gly Tyr Asp Ile Leu Thr Gly Tyr Pro Asp Tyr
1               5                   10
```

HUMAN PAC1 ANTIBODIES

PRIORITY

The present application is a continuation of U.S. application Ser. No. 14/775,995, filed Sep. 14, 2015, which is a national phase entry of International Application No. PCT/US2014/029128, filed Mar. 14, 2014, which claims priority benefit to U.S. Provisional Application Ser. No. 61/792,678, filed Mar. 15, 2013, all of which are hereby incorporated by reference in their entireties.

REFERENCE TO THE SEQUENCE LISTING

The present application contains a Sequence Listing which has been submitted electronically in ASCII format and is hereby incorporated by reference in its entirety. Said ASCII copy, created on May 1, 2017, is named A-1804-US-CNT2_ST25.txt and is 446,762 bytes in size.

BACKGROUND

There is a significant unmet need for effective therapies, particularly prophylaxis therapies, for migraine. Results from multiple studies indicate that ~14 million migraineurs in the US could qualify and benefit from an effective and safe preventive therapy. Currently approved migraine prophylactic therapies are only partially effective and have considerable side-effect profiles which significantly limit the acceptability of these medications. Despite these limitations, 4.5 million individuals with frequent migraine headache in the US take prophylactic medication for their migraines.

Pituitary adenylate cyclase-activating polypeptides (PACAP) are 38-amino acid (PACAP38), or 27-amino acid (PACAP27) peptides that were first isolated from an ovine hypothalamic extract on the basis of their ability to stimulate cAMP formation in anterior pituitary cells (Miyata, A., et al., "Isolation of a novel 38 residue-hypothalamic polypeptide which stimulates adenylate cyclase in pituitary cells.", Biochem Biophys Res Commun. 1989; 164:567-574; Miyata, A., et al., "Isolation of a neuropeptide corresponding to the N-terminal 27 residues of the pituitary adenylate cyclase activating polypeptide with 38 residues (PACAP38).", Biochem Biophys Res Commun. 1990; 170:643-648). PACAP peptides belong to the vasoactive intestinal polypeptide VIP-secretin-hormone-releasing hormone (GHRH)-glucagon superfamily with the sequence of human PACAP27 shares 68% identity with vasoactive intestinal polypeptide (VIP) (Campbell, R. M. and Scanes, C. G., "Evolution of the growth hormone-releasing factor (GRF) family of peptides. Growth Regul." 1992; 2:175-191). The major form of PACAP peptide in the human body is PACAP38 and the pharmacology of PACAP38 and PACAP27 has not been shown to be different from each other. Unless indicated otherwise herein, PACAP or PACAP38 will be used to represent PACAP38, and PACAP27 will be used to specify PACAP27.

Three PACAP receptors have been reported: one that binds PACAP with high affinity and has a much lower affinity for VIP (PAC1 receptor, or simply "PAC1"), and two that recognize PACAP and VIP essentially equally well (VPAC1 and VPAC2 receptors, or simply "VPAC1" or "VPAC2", respectively) (Vaudry, D., et al. "Pituitary adenylate cyclase-activating polypeptide and its receptors: 20 years after the discovery.", Pharmacol Rev. 2009; September 61(3):283-357).

PACAP is capable of binding all three receptors (PAC1, VPAC1, VPAC2) with similar potency and is thus not particularly selective. VIP, on the other hand, binds with significantly higher affinity to VPAC1 and VPAC2, as compared with PAC1. Maxadilan, a 65 amino acid peptide originally isolated from the sand-fly (Lerner, E. A., et al., "Isolation of maxadilan, a potent vasodilatory peptide from the salivary glands of the sand fly Lutzomyia longipalpis", J Biol Chem. 1991 Jun. 15; 266(17):11234-6; Lerner, E. A., et al., "Maxadilan, a PAC1 receptor agonist from sand flies", Peptides. September 2007; 28(9): 1651-1654.), is exquisitely selective for PAC1 compared with VPAC1 or VPAC2, and can thus be used as a PAC1-selective agonist.

SUMMARY

In one aspect, the invention includes an isolated antibody or antigen-binding fragment thereof that specifically binds human PAC1, comprising: (A) a light chain CDR1 comprising (i) an amino acid sequence selected from the group consisting of the LC CDR1 sequences set forth in Table 4A, (ii) an amino acid sequence at least 90% identical to an amino acid sequence selected from the group consisting of the LC CDR1 sequences set forth in Table 4A, or (iii) an amino acid sequence at least 95% identical to an amino acid sequence selected from the group consisting of the LC CDR1 sequences set forth in Table 4A; (B) a light chain CDR2 comprising (i) an amino acid sequence selected from the group consisting of the LC CDR2 sequences set forth in Table 4A, (ii) an amino acid sequence at least 90% identical to an amino acid sequence selected from the group consisting of the LC CDR2 sequences set forth in Table 4A, or (iii) an amino acid sequence at least 95% identical to an amino acid sequence selected from the group consisting of the LC CDR2 sequences set forth in Table 4A; and (C) a light chain CDR3 comprising (i) an amino acid sequence selected from the group consisting of the LC CDR3 sequences set forth in Table 4A, (ii) an amino acid sequence at least 90% identical to an amino acid sequence selected from the group consisting of the LC CDR3 sequences set forth in Table 4A, or (iii) an amino acid sequence at least 95% identical to an amino acid sequence selected from the group consisting of the LC CDR3 sequences set forth in Table 4A.

In another aspect, the invention includes an antibody or antigen binding fragment thereof, wherein (A) the antibody or antigen binding fragment thereof competes for binding, with a Ki of 10 nM or less (e.g., 5 nM or 1 nM), to human PAC1 with a reference antibody, said reference antibody selected from the group consisting of 01B, 14A, 14B, 26A, 26B, 28A, 29A, 29B, 39A, and 39B; and (B) the antibody or antigen binding fragment thereof specifically binds human PAC1.

In another aspect, the invention includes an isolated antibody or antigen-binding fragment thereof that specifically binds human PAC1, comprising: (A) a heavy chain CDR1 comprising (i) an amino acid sequence selected from the group consisting of the HC CDR1 sequences set forth in Table 4B, (ii) an amino acid sequence at least 90% identical to an amino acid sequence selected from the group consisting of the HC CDR1 sequences set forth in Table 4B, or (iii) an amino acid sequence at least 95% identical to an amino acid sequence selected from the group consisting of the HC CDR1 sequences set forth in Table 4B; (B) a heavy chain CDR2 comprising (i) an amino acid sequence selected from the group consisting of the HC CDR2 sequences set forth in Table 4B, (ii) an amino acid sequence at least 90% identical to an amino acid sequence selected from the group consisting of the HC CDR2 sequences set forth in Table 4B, or (iii) an amino acid sequence at least 95% identical to an amino acid sequence selected from the group consisting of the HC CDR2 sequences set forth in Table 4B; and (C) a heavy chain CDR3 comprising (i) an amino acid sequence selected from the group consisting of the HC CDR3 sequences set forth in Table 4B, (ii) an amino acid sequence at least 90% identical to an amino acid sequence selected from the group consisting of the HC CDR3 sequences set forth in Table 4B, or (iii) an amino acid sequence at least 95% identical to an amino acid sequence selected from the group consisting of the HC CDR3 sequences set forth in Table 4B.

In another aspect, the invention includes an antibody or antigen binding fragment thereof, wherein (A) the CDRLs comprise (i) a CDRL1 selected from the group consisting of CDRL1-C1 and CDRL1-C2, (ii) a CDRL2 selected from the group consisting of CDRL2-C1, CDRL2-C2, and CDRL2-C3, and (iii) a CDRL3 consisting of CDRL3-C1; (B) the CDRHs comprise (i) a CDRH1 selected from the group consisting of CDRH1-C1 and CDRH1-C2; (ii) a CDRH2 selected from the group consisting of CDRH2-C1, CDRH2-C2, and CDRH2-C3; and (iii) a CDRH3 consisting of CDRH3-C1, and (C) the antibody or antigen binding fragment thereof specifically binds human PAC1.

In one embodiment of the above, the antibody or antigen binding fragment thereof comprises CDRL1-C1, CDRL2-C1, CDRL3-C1, CDRH1-C1, CDRH2-C1, and CDRH3-C1.

In another embodiment of the above, the antibody or antigen binding fragment thereof comprises CDRL1-C1, CDRL2-C1, CDRL3-C1, CDRH1-C1, CDRH2-C2, and CDRH3-C1.

In another embodiment of the above, the antibody or antigen binding fragment thereof comprises CDRL1-C1, CDRL2-C1, CDRL3-C1, CDRH1-C1, CDRH2-C3, and CDRH3-C1.

In another embodiment of the above, the antibody or antigen binding fragment thereof comprises CDRL1-C1, CDRL2-C1, CDRL3-C1, CDRH1-C2, CDRH2-C1, and CDRH3-C1.

In another embodiment of the above, the antibody or antigen binding fragment thereof comprises CDRL1-C1, CDRL2-C1, CDRL3-C1, CDRH1-C2, CDRH2-C2, and CDRH3-C1.

In another embodiment of the above, the antibody or antigen binding fragment thereof comprises CDRL1-C1, CDRL2-C1, CDRL3-C1, CDRH1-C2, CDRH2-C3, and CDRH3-C1.

In another embodiment of the above, the antibody or antigen binding fragment thereof comprises CDRL1-C1, CDRL2-C2, CDRL3-C1, CDRH1-C1, CDRH2-C1, and CDRH3-C1.

In another embodiment of the above, the antibody or antigen binding fragment thereof comprises CDRL1-C1, CDRL2-C2, CDRL3-C1, CDRH1-C1, CDRH2-C2, and CDRH3-C1.

In another embodiment of the above, the antibody or antigen binding fragment thereof comprises CDRL1-C1, CDRL2-C2, CDRL3-C1, CDRH1-C1, CDRH2-C3, and CDRH3-C1.

In another embodiment of the above, the antibody or antigen binding fragment thereof comprises CDRL1-C1, CDRL2-C2, CDRL3-C1, CDRH1-C2, CDRH2-C1, and CDRH3-C1.

In another embodiment of the above, the antibody or antigen binding fragment thereof comprises CDRL1-C1, CDRL2-C2, CDRL3-C1, CDRH1-C2, CDRH2-C2, and CDRH3-C1.

In another embodiment of the above, the antibody or antigen binding fragment thereof comprises CDRL1-C1, CDRL2-C2, CDRL3-C1, CDRH1-C2, CDRH2-C3, and CDRH3-C1.

In another embodiment of the above, the antibody or antigen binding fragment thereof comprises CDRL1-C1, CDRL2-C3, CDRL3-C1, CDRH1-C1, CDRH2-C1, and CDRH3-C1.

In another embodiment of the above, the antibody or antigen binding fragment thereof comprises CDRL1-C1, CDRL2-C3, CDRL3-C1, CDRH1-C1, CDRH2-C2, and CDRH3-C1.

In another embodiment of the above, the antibody or antigen binding fragment thereof comprises CDRL1-C1, CDRL2-C3, CDRL3-C1, CDRH1-C1, CDRH2-C3, and CDRH3-C1.

In another embodiment of the above, the antibody or antigen binding fragment thereof comprises CDRL1-C1, CDRL2-C3, CDRL3-C1, CDRH1-C2, CDRH2-C1, and CDRH3-C1.

In another embodiment of the above, the antibody or antigen binding fragment thereof comprises CDRL1-C1, CDRL2-C3, CDRL3-C1, CDRH1-C2, CDRH2-C2, and CDRH3-C1.

In another embodiment of the above, the antibody or antigen binding fragment thereof comprises CDRL1-C1, CDRL2-C3, CDRL3-C1, CDRH1-C2, CDRH2-C3, and CDRH3-C1.

In another embodiment of the above, the antibody or antigen binding fragment thereof comprises CDRL1-C2, CDRL2-C1, CDRL3-C1, CDRH1-C1, CDRH2-C1, and CDRH3-C1.

In another embodiment of the above, the antibody or antigen binding fragment thereof comprises CDRL1-C2, CDRL2-C1, CDRL3-C1, CDRH1-C1, CDRH2-C2, and CDRH3-C1.

In another embodiment of the above, the antibody or antigen binding fragment thereof comprises CDRL1-C2, CDRL2-C1, CDRL3-C1, CDRH1-C1, CDRH2-C3, and CDRH3-C1.

In another embodiment of the above, the antibody or antigen binding fragment thereof comprises CDRL1-C2, CDRL2-C1, CDRL3-C1, CDRH1-C2, CDRH2-C1, and CDRH3-C1.

In another embodiment of the above, the antibody or antigen binding fragment thereof comprises CDRL1-C2, CDRL2-C1, CDRL3-C1, CDRH1-C2, CDRH2-C2, and CDRH3-C1.

In another embodiment of the above, the antibody or antigen binding fragment thereof comprises CDRL1-C2, CDRL2-C1, CDRL3-C1, CDRH1-C2, CDRH2-C3, and CDRH3-C1.

In another embodiment of the above, the antibody or antigen binding fragment thereof comprises CDRL1-C2, CDRL2-C2, CDRL3-C1, CDRH1-C1, CDRH2-C1, and CDRH3-C1.

In another embodiment of the above, the antibody or antigen binding fragment thereof comprises CDRL1-C2, CDRL2-C2, CDRL3-C1, CDRH1-C1, CDRH2-C2, and CDRH3-C1.

In another embodiment of the above, the antibody or antigen binding fragment thereof comprises CDRL1-C2, CDRL2-C2, CDRL3-C1, CDRH1-C1, CDRH2-C3, and CDRH3-C1.

In another embodiment of the above, the antibody or antigen binding fragment thereof comprises CDRL1-C2, CDRL2-C2, CDRL3-C1, CDRH1-C2, CDRH2-C1, and CDRH3-C1.

In another embodiment of the above, the antibody or antigen binding fragment thereof comprises CDRL1-C2, CDRL2-C2, CDRL3-C1, CDRH1-C2, CDRH2-C2, and CDRH3-C1.

In another embodiment of the above, the antibody or antigen binding fragment thereof comprises CDRL1-C2, CDRL2-C2, CDRL3-C1, CDRH1-C2, CDRH2-C3, and CDRH3-C1.

In another embodiment of the above, the antibody or antigen binding fragment thereof comprises CDRL1-C2, CDRL2-C3, CDRL3-C1, CDRH1-C1, CDRH2-C1, and CDRH3-C1.

In another embodiment of the above, the antibody or antigen binding fragment thereof comprises CDRL1-C2, CDRL2-C3, CDRL3-C1, CDRH1-C1, CDRH2-C2, and CDRH3-C1.

In another embodiment of the above, the antibody or antigen binding fragment thereof comprises CDRL1-C2, CDRL2-C3, CDRL3-C1, CDRH1-C1, CDRH2-C3, and CDRH3-C1.

In another embodiment of the above, the antibody or antigen binding fragment thereof comprises CDRL1-C2, CDRL2-C3, CDRL3-C1, CDRH1-C2, CDRH2-C1, and CDRH3-C1.

In another embodiment of the above, the antibody or antigen binding fragment thereof comprises CDRL1-C2, CDRL2-C3, CDRL3-C1, CDRH1-C2, CDRH2-C2, and CDRH3-C1.

In another embodiment of the above, the antibody or antigen binding fragment thereof comprises CDRL1-C2, CDRL2-C3, CDRL3-C1, CDRH1-C2, CDRH2-C3, and CDRH3-C1.

In another aspect, the invention includes an isolated antibody or antigen-binding fragment thereof that specifically binds human PAC1, comprising (i) heavy chain CDRs CDR1, CDR2 and CDR3, each having a sequence of the corresponding heavy chain CDR as above, and (ii) light chain CDRs CDR1, CDR2 and CDR3, each having a sequence of the corresponding heavy chain CDR as above.

In one embodiment the invention includes an antibody or antigen-binding fragment thereof, comprising heavy chain CDRs: CDRH1-8, CDRH2-2 and CDRH3-3; and light chain CDRs: CDRL1-3, CDRL2-2, CDRL3-2.

In another embodiment the invention includes an antibody or antigen-binding fragment thereof, comprising heavy chain CDRs: CDRH1-11, CDRH2-5 and CDRH3-9; and light chain CDRs: CDRL1-13, CDRL2-1, CDRL3-1.

In another embodiment the invention includes an antibody or antigen-binding fragment thereof, comprising heavy chain CDRs: CDRH1-1, CDRH2-4 and CDRH3-6; and light chain CDRs: CDRL1-2, CDRL2-1, CDRL3-1.

In another embodiment the invention includes an antibody or antigen-binding fragment thereof, comprising heavy chain CDRs: CDRH1-1, CDRH2-4 and CDRH3-6; and light chain CDRs: CDRL1-1, CDRL2-1, CDRL3-1.

In another embodiment the invention includes an antibody or antigen-binding fragment thereof, comprising heavy chain CDRs: CDRH1-3, CDRH2-5 and CDRH3-5; and light chain CDRs: CDRL1-1, CDRL2-1, CDRL3-1.

In another embodiment the invention includes an antibody or antigen-binding fragment In another embodiment the invention includes an antibody or antigen-binding fragment thereof, comprising heavy chain CDRs: CDRH1-9, CDRH2-6 and CDRH3-1; and light chain CDRs: CDRL1-4, CDRL2-3, CDRL3-3.

In another embodiment the invention includes an antibody or antigen-binding fragment thereof, comprising heavy chain CDRs: CDRH1-4, CDRH2-7 and CDRH3-8; and light chain CDRs: CDRL1-6, CDRL2-4, CDRL3-5.

In another embodiment the invention includes an antibody or antigen-binding fragment thereof, comprising heavy chain CDRs: CDRH1-10, CDRH2-1 and CDRH3-7; and light chain CDRs: CDRL1-5, CDRL2-3, CDRL3-4.

In another embodiment the invention includes an antibody or antigen-binding fragment thereof, comprising heavy chain CDRs: CDRH1-6, CDRH2-8 and CDRH3-2; and light chain CDRs: CDRL1-7, CDRL2-5, CDRL3-6.

In another embodiment the invention includes an antibody or antigen-binding fragment thereof, comprising heavy chain CDRs: CDRH1-7, CDRH2-3 and CDRH3-4; and light chain CDRs: CDRL1-8, CDRL2-6, CDRL3-7.

In another embodiment the invention includes an antibody or antigen-binding fragment thereof, comprising heavy chain CDRs: CDRH1-2, CDRH2-8 and CDRH3-2; and light chain CDRs: CDRL1-9, CDRL2-5, CDRL3-8.

In another embodiment the invention includes an antibody or antigen-binding fragment thereof, comprising heavy chain CDRs: CDRH1-6, CDRH2-8 and CDRH3-2; and light chain CDRs: CDRL1-10, CDRL2-5, CDRL3-6.

In another embodiment the invention includes an antibody or antigen-binding fragment thereof, comprising heavy chain CDRs: CDRH1-6, CDRH2-8 and CDRH3-2; and light chain CDRs: CDRL1-10, CDRL2-5, CDRL3-6.

In another embodiment the invention includes an antibody or antigen-binding fragment thereof, comprising heavy chain CDRs: CDRH1-6, CDRH2-8 and CDRH3-2; and light chain CDRs: CDRL1-12, CDRL2-5, CDRL3-6.

In another embodiment the invention includes an antibody or antigen-binding fragment thereof, comprising heavy chain CDRs: CDRH1-5, CDRH2-8 and CDRH3-2; and light chain CDRs: CDRL1-11, CDRL2-5, CDRL3-8.

In another aspect, the invention includes an isolated antibody or antigen-binding fragment thereof that specifically binds human PAC1, comprising a heavy chain CDR1 selected from the group consisting of CDRH1-1, CDRH1-2, CDRH1-3, CDRH1-4, CDRH1-5, CDRH1-6, CDRH1-7, CDRH1-8, CDRH1-9, CDRH1-10, and CDRH1-11.

In another aspect, the invention includes an isolated antibody or antigen-binding fragment thereof that specifically binds human PAC1, comprising a heavy chain CDR2 selected from the group consisting of CDRH2-1, CDRH2-2, CDRH2-3, CDRH2-4, CDRH2-5, CDRH2-6, CDRH2-7, and CDRH2-8.

In another aspect, the invention includes an isolated antibody or antigen-binding fragment thereof that specifically binds human PAC1, comprising a heavy chain CDR3 selected from the group consisting of CDRH3-1, CDRH3-2, CDRH3-3, CDRH3-4, CDRH3-5, CDRH3-6, CDRH3-7, CDRH3-8 and CDRH3-9.

In another aspect, the invention includes an isolated antibody or antigen-binding fragment thereof that specifically binds human PAC1, comprising a light chain CDR1 selected from the group consisting of CDRL1-1, CDRL1-2, CDRL1-3, CDRL1-4, CDRL1-5, CDRL1-6, CDRL1-7, CDRL1-8, CDRL1-9, CDRL1-10, CDRL1-11, CDRL1-12 and CDRL1-13.

In another aspect, the invention includes an isolated antibody or antigen-binding fragment thereof that specifically binds human PAC1, comprising a light chain CDR2 selected from the group consisting of CDRL2-1, CDRL2-2, CDRL2-3, CDRL2-4, CDRL2-5, and CDRL2-6.

In another aspect, the invention includes an isolated antibody or antigen-binding fragment thereof that specifically binds human PAC1, comprising a light chain CDR3 selected from the group consisting of CDRL3-1, CDRL3-2, CDRL3-3, CDRL3-4, CDRL3-5, CDRL3-6, CDRL3-7, and CDRL3-8.

In another aspect, the invention includes an isolated antibody or antigen-binding fragment thereof that optionally specifically binds human PAC1, comprising a heavy chain CDR1 as above, a heavy chain CDR2 as above, a heavy chain CDR3 as above, a light chain CDR1 as above, a light chain CDR2 as above, and a light chain CDR3 as above.

In another aspect, the invention includes an isolated antibody or antigen-binding fragment thereof that optionally specifically binds human PAC1, comprising a light chain variable region comprising (i) an amino acid sequence selected from the group consisting of the $V_L$ AA sequences set forth in Table 3A, (ii) an amino acid sequence at least 90% identical to an amino acid sequence selected from the group consisting of the $V_L$ AA sequences set forth in Table 3A, or (iii) an amino acid sequence at least 95% identical to an amino acid sequence selected from the group consisting of the $V_L$ AA sequences set forth in Table 3A.

In another aspect, the invention includes an isolated antibody or antigen-binding fragment thereof that specifically binds human PAC1, comprising a heavy chain variable region comprising (i) an amino acid sequence selected from the group consisting of the $V_H$ AA sequences set forth in Table 3B, (ii) an amino acid sequence at least 90% identical to an amino acid sequence selected from the group consisting of the $V_H$ AA sequences set forth in Table 3B, or (iii) an amino acid sequence at least 95% identical to an amino acid sequence selected from the group consisting of the $V_H$ AA sequences set forth in Table 3B.

In another aspect, the invention includes an isolated antibody or antigen-binding fragment thereof that specifically binds human PAC1, comprising a light chain variable region amino acid sequence selected from the group consisting of LV-01, LV-02, LV-03, LV-04, LV-05, LV-06, LV-07, LV-08, LV-09, LV-10, LV-11, LV-12, LV-13, LV-14, LV-15, LV-16, LV-17, LV-18, LV-19, LV-20, and LV-21.

In another aspect, the invention includes an isolated antibody or antigen-binding fragment thereof that specifically binds human PAC1, comprising a heavy chain variable region amino acid sequence selected from the group consisting of HV-01, HV-02, HV-03, HV-04, HV-05, HV-06, HV-07, HV-08, HV-09, HV-10, HV-11, HV-12, HV-13, HV-14, HV-15, HV-16, HV-17, HV-18, HV-19, HV-20, HV-21, HV-22, HV-23, HV-24, HV-25, and HV-26.

In one embodiment the invention includes an antibody or antigen-binding fragment thereof, comprising LV-01 and HV-01.

In another embodiment the invention includes an antibody or antigen-binding fragment thereof, comprising LV-02 and HV-02.

In another embodiment the invention includes an antibody or antigen-binding fragment thereof, comprising LV-03 and HV-02.

In another embodiment the invention includes an antibody or antigen-binding fragment thereof, comprising LV-04 and HV-03.

In another embodiment the invention includes an antibody or antigen-binding fragment thereof, comprising LV-05 and HV-03.

In another embodiment the invention includes an antibody or antigen-binding fragment thereof, comprising LV-06 and HV-03.

In another embodiment the invention includes an antibody or antigen-binding fragment thereof, comprising LV-04 and HV-04.

In another embodiment the invention includes an antibody or antigen-binding fragment thereof, comprising LV-04 and HV-05.

In another embodiment the invention includes an antibody or antigen-binding fragment thereof, comprising LV-07 and HV-04.

In another embodiment the invention includes an antibody or antigen-binding fragment thereof, comprising LV-07 and HV-05.

In another embodiment the invention includes an antibody or antigen-binding fragment thereof, comprising LV-07 and HV-03.

In another embodiment the invention includes an antibody or antigen-binding fragment thereof, comprising LV-04 and HV-06.

In another embodiment the invention includes an antibody or antigen-binding fragment thereof, comprising LV-04 and HV-06.

In another embodiment the invention includes an antibody or antigen-binding fragment thereof, comprising LV-05 and HV-05.

In another embodiment the invention includes an antibody or antigen-binding fragment thereof, comprising LV-08 and HV-05.

In another embodiment the invention includes an antibody or antigen-binding fragment thereof, comprising LV-09 and HV-05.

In another embodiment the invention includes an antibody or antigen-binding fragment thereof, comprising LV-05 and HV-07.

In another embodiment the invention includes an antibody or antigen-binding fragment thereof, comprising LV-05 and HV-08.

In another embodiment the invention includes an antibody or antigen-binding fragment thereof, comprising LV-09 and HV-07.

In another embodiment the invention includes an antibody or antigen-binding fragment thereof, comprising LV-09 and HV-08.

In another embodiment the invention includes an antibody or antigen-binding fragment thereof, comprising LV-09 and HV-09.

In another embodiment the invention includes an antibody or antigen-binding fragment thereof, comprising LV-05 and HV-09.

In another embodiment the invention includes an antibody or antigen-binding fragment thereof, comprising LV-05 and HV-10.

In another embodiment the invention includes an antibody or antigen-binding fragment thereof, comprising LV-08 and HV-10.

In another embodiment the invention includes an antibody or antigen-binding fragment thereof, comprising LV-05 and HV-11.

In another embodiment the invention includes an antibody or antigen-binding fragment thereof, comprising LV-05 and HV-12.

In another embodiment the invention includes an antibody or antigen-binding fragment thereof, comprising LV-05 and HV-13.

In another embodiment the invention includes an antibody or antigen-binding fragment thereof, comprising LV-08 and HV-13.

In another embodiment the invention includes an antibody or antigen-binding fragment thereof, comprising LV-10 and HV-14.

In another embodiment the invention includes an antibody or antigen-binding fragment thereof, comprising LV-11 and HV-14.

In another embodiment the invention includes an antibody or antigen-binding fragment thereof, comprising LV-12 and HV-15.

In another embodiment the invention includes an antibody or antigen-binding fragment thereof, comprising LV-12 and HV-16.

In another embodiment the invention includes an antibody or antigen-binding fragment thereof, comprising LV-13 and HV-17.

In another embodiment the invention includes an antibody or antigen-binding fragment thereof, comprising LV-14 and HV-18.

In another embodiment the invention includes an antibody or antigen-binding fragment thereof, comprising LV-14 and HV-19.

In another embodiment the invention includes an antibody or antigen-binding fragment thereof, comprising LV-15 and HV-20.

In another embodiment the invention includes an antibody or antigen-binding fragment thereof, comprising LV-16 and HV-21.

In another embodiment the invention includes an antibody or antigen-binding fragment thereof, comprising LV-17 and HV-22.

In another embodiment the invention includes an antibody or antigen-binding fragment thereof, comprising LV-18 and HV-23.

In another embodiment the invention includes an antibody or antigen-binding fragment thereof, comprising LV-19 and HV-24.

In another embodiment the invention includes an antibody or antigen-binding fragment thereof, comprising LV-19 and HV-25.

In another embodiment the invention includes an antibody or antigen-binding fragment thereof, comprising LV-20 and HV-21.

In another embodiment the invention includes an antibody or antigen-binding fragment thereof, comprising LV-21 and HV-26.

In another aspect, the invention includes an isolated antibody or antigen-binding fragment thereof that specifically binds human PAC1, comprising a (i) a sequence selected from the group consisting of the sequences set forth in Table 2A, or (ii) a sequence at least 90% identical to one of the sequences in set forth in Table 2A, or (iii) a sequence at least 95% identical to one of the sequences in set forth in Table 2A.

In another aspect, the invention includes an isolated antibody or antigen-binding fragment thereof that specifically binds human PAC1, comprising a (i) a sequence selected from the group consisting of the sequences set forth in Table 2B, or (ii) a sequence at least 90% identical to one of the sequences in set forth in Table 2B, or (iii) a sequence at least 95% identical to one of the sequences in set forth in Table 2B.

In another aspect, the invention includes an isolated antibody or antigen-binding fragment thereof that specifically binds human PAC1, comprising a light chain amino acid sequence selected from the group consisting of LC-01, LC-02, LC-03, LC-04, LC-05, LC-06, LC-07, LC-08, LC-09, LC-10, LC-11, LC-12, LC-13, LC-14, LC-15, LC-16, LC-17, LC-18, LC-19, LC-20, and LC-21.

In another aspect, the invention includes an isolated antibody or antigen-binding fragment thereof that specifically binds human PAC1, comprising a heavy chain amino acid sequence selected from the group consisting of HC-01, HC-02, HC-03, HC-04, HC-05, HC-06, HC-07, HC-08, HC-09, HC-10, HC-11, HC-12, HC-13, HC-14, HC-15, HC-16, HC-17, HC-18, HC-19, HC-20, HC-21, HC-22, HC-23, HC-24, HC-25, HC-26, HC-27, HC-28, HC-29, HC-30, HC-31, HC-32, HC-33, HC-34, HC-35, HC-36, HC-37, HC-38, HC-39, HC-40, HC-41, HC-42, HC-43, HC-44, HC-45, HC-46, HC-47, HC-48, HC-49, HC-50, HC-51, HC-52, and HC-53.

In one embodiment the invention includes an antibody or antigen-binding fragment thereof, comprising LC-01 and HC-01 (01A).

In another embodiment the invention includes an antibody or antigen-binding fragment thereof, comprising LC-01 and HC-02 (01B).

In another embodiment the invention includes an antibody or antigen-binding fragment thereof, comprising LC-02 and HC-03 (02A).

In another embodiment the invention includes an antibody or antigen-binding fragment thereof, comprising LC-02 and HC-04 (02B).

In another embodiment the invention includes an antibody or antigen-binding fragment thereof, comprising LC-02 and HC-05 (02C).

In another embodiment the invention includes an antibody or antigen-binding fragment thereof, comprising LC-03 and HC-03 (03A).

In another embodiment the invention includes an antibody or antigen-binding fragment thereof, comprising LC-04 and HC-06 (04A).

In another embodiment the invention includes an antibody or antigen-binding fragment thereof, comprising LC-04 and HC-07 (04B).

In another embodiment the invention includes an antibody or antigen-binding fragment thereof, comprising LC-04 and HC-08 (04C).

In another embodiment the invention includes an antibody or antigen-binding fragment thereof, comprising LC-05 and HC-06 (05A).

In another embodiment the invention includes an antibody or antigen-binding fragment thereof, comprising LC-05 and HC-07 (05B).

In another embodiment the invention includes an antibody or antigen-binding fragment thereof, comprising LC-05 and HC-08 (05C).

In another embodiment the invention includes an antibody or antigen-binding fragment thereof, comprising LC-06 and HC-06 (06A).

In another embodiment the invention includes an antibody or antigen-binding fragment thereof, comprising LC-06 and HC-07 (06B).

In another embodiment the invention includes an antibody or antigen-binding fragment thereof, comprising LC-06 and HC-08 (06C).

In another embodiment the invention includes an antibody or antigen-binding fragment thereof, comprising LC-04 and HC-09 (07A).

In another embodiment the invention includes an antibody or antigen-binding fragment thereof, comprising LC-04 and HC-10 (07B).

In another embodiment the invention includes an antibody or antigen-binding fragment thereof, comprising LC-04 and HC-11 (07C).

In another embodiment the invention includes an antibody or antigen-binding fragment thereof, comprising LC-04 and HC-12 (08A).

In another embodiment the invention includes an antibody or antigen-binding fragment thereof, comprising LC-04 and HC-13 (08B).

In another embodiment the invention includes an antibody or antigen-binding fragment thereof, comprising LC-04 and HC-14 (08C).

In another embodiment the invention includes an antibody or antigen-binding fragment thereof, comprising LC-07 and HC-09 (09A).

In another embodiment the invention includes an antibody or antigen-binding fragment thereof, comprising LC-07 and HC-10 (09B).

In another embodiment the invention includes an antibody or antigen-binding fragment thereof, comprising LC-07 and HC-11 (09C).

In another embodiment the invention includes an antibody or antigen-binding fragment thereof, comprising LC-07 and HC-12 (10A).

In another embodiment the invention includes an antibody or antigen-binding fragment thereof, comprising LC-07 and HC-13 (10B).

In another embodiment the invention includes an antibody or antigen-binding fragment thereof, comprising LC-07 and HC-14 (10C).

In another embodiment the invention includes an antibody or antigen-binding fragment thereof, comprising LC-07 and HC-06 (11A).

In another embodiment the invention includes an antibody or antigen-binding fragment thereof, comprising LC-07 and HC-07 (11B).

In another embodiment the invention includes an antibody or antigen-binding fragment thereof, comprising LC-07 and HC-08 (11C).

In another embodiment the invention includes an antibody or antigen-binding fragment thereof, comprising LC-04 and HC-15 (12A).

In another embodiment the invention includes an antibody or antigen-binding fragment thereof, comprising LC-04 and HC-16 (12B).

In another embodiment the invention includes an antibody or antigen-binding fragment thereof, comprising LC-04 and HC-17 (12C).

In another embodiment the invention includes an antibody or antigen-binding fragment thereof, comprising LC-05 and HC-12 (13A).

In another embodiment the invention includes an antibody or antigen-binding fragment thereof, comprising LC-05 and HC-13 (13B).

In another embodiment the invention includes an antibody or antigen-binding fragment thereof, comprising LC-05 and HC-14 (13C).

In another embodiment the invention includes an antibody or antigen-binding fragment thereof, comprising LC-08 and HC-12 (14A).

In another embodiment the invention includes an antibody or antigen-binding fragment thereof, comprising LC-08 and HC-13 (14B).

In another embodiment the invention includes an antibody or antigen-binding fragment thereof, comprising LC-08 and HC-14 (14C).

In another embodiment the invention includes an antibody or antigen-binding fragment thereof, comprising LC-09 and HC-12 (15A).

In another embodiment the invention includes an antibody or antigen-binding fragment thereof, comprising LC-09 and HC-13 (15B).

In another embodiment the invention includes an antibody or antigen-binding fragment thereof, comprising LC-09 and HC-14 (15C).

In another embodiment the invention includes an antibody or antigen-binding fragment thereof, comprising LC-05 and HC-18 (16A).

In another embodiment the invention includes an antibody or antigen-binding fragment thereof, comprising LC-05 and HC-19 (16B).

In another embodiment the invention includes an antibody or antigen-binding fragment thereof, comprising LC-05 and HC-20 (16C).

In another embodiment the invention includes an antibody or antigen-binding fragment thereof, comprising LC-05 and HC-21 (17A).

In another embodiment the invention includes an antibody or antigen-binding fragment thereof, comprising LC-05 and HC-22 (17B).

In another embodiment the invention includes an antibody or antigen-binding fragment thereof, comprising LC-05 and HC-23 (17C).

In another embodiment the invention includes an antibody or antigen-binding fragment thereof, comprising LC-09 and HC-18 (18A).

In another embodiment the invention includes an antibody or antigen-binding fragment thereof, comprising LC-09 and HC-19 (18B).

In another embodiment the invention includes an antibody or antigen-binding fragment thereof, comprising LC-09 and HC-20 (18C).

In another embodiment the invention includes an antibody or antigen-binding fragment thereof, comprising LC-09 and HC-21 (19A).

In another embodiment the invention includes an antibody or antigen-binding fragment thereof, comprising LC-09 and HC-22 (19B).

In another embodiment the invention includes an antibody or antigen-binding fragment thereof, comprising LC-09 and HC-23 (19C).

In another embodiment the invention includes an antibody or antigen-binding fragment thereof, comprising LC-09 and HC-24 (20A).

In another embodiment the invention includes an antibody or antigen-binding fragment thereof, comprising LC-09 and HC-25 (20B).

In another embodiment the invention includes an antibody or antigen-binding fragment thereof, comprising LC-09 and HC-26 (20C).

In another embodiment the invention includes an antibody or antigen-binding fragment thereof, comprising LC-05 and HC-24 (21A).

In another embodiment the invention includes an antibody or antigen-binding fragment thereof, comprising LC-05 and HC-25 (21B).

In another embodiment the invention includes an antibody or antigen-binding fragment thereof, comprising LC-05 and HC-26 (21C).

In another embodiment the invention includes an antibody or antigen-binding fragment thereof, comprising LC-05 and HC-27 (22A).

In another embodiment the invention includes an antibody or antigen-binding fragment thereof, comprising LC-05 and HC-28 (22B).

In another embodiment the invention includes an antibody or antigen-binding fragment thereof, comprising LC-05 and HC-29 (22C).

In another embodiment the invention includes an antibody or antigen-binding fragment thereof, comprising LC-08 and HC-27 (23A).

In another embodiment the invention includes an antibody or antigen-binding fragment thereof, comprising LC-08 and HC-28 (23B).

In another embodiment the invention includes an antibody or antigen-binding fragment thereof, comprising LC-08 and HC-29 (23C).

In another embodiment the invention includes an antibody or antigen-binding fragment thereof, comprising LC-05 and HC-30 (24A).

In another embodiment the invention includes an antibody or antigen-binding fragment thereof, comprising LC-05 and HC-31 (24B).

In another embodiment the invention includes an antibody or antigen-binding fragment thereof, comprising LC-05 and HC-32 (24C).

In another embodiment the invention includes an antibody or antigen-binding fragment thereof, comprising LC-05 and HC-33 (25A).

In another embodiment the invention includes an antibody or antigen-binding fragment thereof, comprising LC-05 and HC-34 (25B).

In another embodiment the invention includes an antibody or antigen-binding fragment thereof, comprising LC-05 and HC-35 (25C).

In another embodiment the invention includes an antibody or antigen-binding fragment thereof, comprising LC-05 and HC-36 (26A).

In another embodiment the invention includes an antibody or antigen-binding fragment thereof, comprising LC-05 and HC-37 (26B).

In another embodiment the invention includes an antibody or antigen-binding fragment thereof, comprising LC-05 and HC-38 (26C).

In another embodiment the invention includes an antibody or antigen-binding fragment thereof, comprising LC-08 and HC-36 (27A).

In another embodiment the invention includes an antibody or antigen-binding fragment thereof, comprising LC-08 and HC-37 (27B).

In another embodiment the invention includes an antibody or antigen-binding fragment thereof, comprising LC-08 and HC-38 (27C).

In another embodiment the invention includes an antibody or antigen-binding fragment thereof, comprising LC-10 and HC-39 (28A).

In another embodiment the invention includes an antibody or antigen-binding fragment thereof, comprising LC-10 and HC-40 (28B).

In another embodiment the invention includes an antibody or antigen-binding fragment thereof, comprising LC-10 and HC-41 (28C).

In another embodiment the invention includes an antibody or antigen-binding fragment thereof, comprising LC-11 and HC-39 (29A).

In another embodiment the invention includes an antibody or antigen-binding fragment thereof, comprising LC-11 and HC-40 (29B).

In another embodiment the invention includes an antibody or antigen-binding fragment thereof, comprising LC-11 and HC-41 (29C).

In another embodiment the invention includes an antibody or antigen-binding fragment thereof, comprising LC-12 and HC-42 (30A).

In another embodiment the invention includes an antibody or antigen-binding fragment thereof, comprising LC-12 and HC-43 (31A).

In another embodiment the invention includes an antibody or antigen-binding fragment thereof, comprising LC-13 and HC-44 (32A).

In another embodiment the invention includes an antibody or antigen-binding fragment thereof, comprising LC-14 and HC-45 (33A).

In another embodiment the invention includes an antibody or antigen-binding fragment thereof, comprising LC-14 and HC-46 (34A).

In another embodiment the invention includes an antibody or antigen-binding fragment thereof, comprising LC-15 and HC-47 (35A).

In another embodiment the invention includes an antibody or antigen-binding fragment thereof, comprising LC-16 and HC-48 (36A).

In another embodiment the invention includes an antibody or antigen-binding fragment thereof, comprising LC-17 and HC-49 (37A).

In another embodiment the invention includes an antibody or antigen-binding fragment thereof, comprising LC-18 and HC-50 (38A).

In another embodiment the invention includes an antibody or antigen-binding fragment thereof, comprising LC-19 and HC-51 (39A).

In another embodiment the invention includes an antibody or antigen-binding fragment thereof, comprising LC-19 and HC-52 (39B).

In another embodiment the invention includes an antibody or antigen-binding fragment thereof, comprising LC-20 and HC-48 (40A).

In another embodiment the invention includes an antibody or antigen-binding fragment thereof, comprising LC-21 and HC-53 (41A).

In another aspect, the invention includes an isolated antibody or antigen-binding fragment thereof of any of the foregoing, wherein the antibody is a polyclonal antibody.

In another aspect, the invention includes the isolated antibody of any of the above, wherein the isolated antibody is selected from the group consisting of a monoclonal antibody, a Fab fragment, an Fab' fragment, an F(ab')2 fragment, an Fv fragment, a diabody, and a single chain antibody.

In another aspect, the invention includes the isolated antibody as above, wherein the isolated antibody is a monoclonal antibody selected from the group consisting of a fully human antibody, a humanized antibody and a chimeric antibody.

In one embodiment of the above, the isolated antibody according to any of the above is a fully human monoclonal antibody.

In another aspect, the invention includes the isolated antibody as above, wherein the antibody is an IgG1-, IgG2-, IgG3-, or IgG4-type antibody.

In another aspect, the invention includes the isolated antibody as above, wherein the antibody is an aglycosylated IgG1 antibody.

In another aspect, the invention includes the isolated antibody as above, wherein the aglycosylated IgG1 antibody comprises a mutation at position N297 in its heavy chain.

In another aspect, the invention includes the isolated antibody as above, wherein the aglycosylated IgG1 antibody comprises the substitution N297G in its heavy chain.

In another aspect, the invention includes the isolated antibody as above, wherein the aglycosylated IgG1 antibody comprises the substitutions N297G, R292C and V302C in its heavy chain.

In another aspect, the invention includes the isolated antibody of any as above, wherein the antibody selectively inhibits hPAC1 relative to hVPA1 and hVPAC2.

In another aspect, the invention includes the isolated antibody as above, wherein the selectivity ratio is greater than 100:1.

In another aspect, the invention includes the isolated antibody as above, wherein the selectivity ratio is greater than 1000:1.

In another aspect, the invention includes an isolated polynucleotide that encodes an antibody of any as above.

In another aspect, the invention includes an isolated nucleic acid encoding an antibody or antigen-binding fragment thereof that specifically binds human PAC1, comprising (i) a sequence selected from the group consisting of the sequences set forth in Table 1A, or (ii) a sequence at least 90% identical to one of the sequences in set forth in Table 1A, or (iii) a sequence at least 95% identical to one of the sequences in set forth in Table 1A.

In another aspect, the invention includes an isolated nucleic acid encoding an antibody or antigen-binding fragment thereof that specifically binds human PAC1, comprising (i) a sequence selected from the group consisting of the sequences set forth in Table 1B, or (ii) a sequence at least 90% identical to one of the sequences in set forth in Table 1B, or (iii) a sequence at least 95% identical to one of the sequences in set forth in Table 1B.

In another aspect, the invention includes an isolated polynucleotide having a nucleic acid sequence selected from the group consisting of the sequences set forth in Table 1A, (ii) a nucleic acid sequence at least 80% identical to a nucleic acid sequence selected from the group consisting of the sequences set forth in Table 1A, (iii) a nucleic acid sequence at least 90% identical to a nucleic acid sequence selected from the group consisting of the sequences set forth in Table 1A, or (iv) a nucleic acid sequence at least 95% identical to a nucleic acid sequence selected from the group consisting of the sequences set forth in Table 1A.

In another aspect, the invention includes an isolated polynucleotide having a nucleic acid sequence selected from the group consisting of the sequences set forth in Table 1B, (ii) a nucleic acid sequence at least 80% identical to a nucleic acid sequence selected from the group consisting of the sequences set forth in Table 1B, (iii) a nucleic acid sequence at least 90% identical to a nucleic acid sequence selected from the group consisting of the sequences set forth in Table 1B, or (iv) a nucleic acid sequence at least 95% identical to a nucleic acid sequence selected from the group consisting of the sequences set forth in Table 1B.

In another aspect, the invention includes an isolated polynucleotide having a nucleic acid sequence selected from the group consisting of nucleic acid sequences encoding the variable regions set forth in Table 3A, (ii) a nucleic acid sequence at least 80% identical to a nucleic acid sequence selected from the group consisting of nucleic acid sequences encoding the variable regions set forth in Table 3A, (iii) a nucleic acid sequence at least 90% identical to a nucleic acid sequence selected from the group consisting of nucleic acid sequences encoding the variable regions set forth in Table 3A, or (iv) a nucleic acid sequence at least 95% identical to a nucleic acid sequence selected from the group consisting of nucleic acid sequences encoding the variable regions set forth in Table 3A. In another aspect, the invention includes an isolated polynucleotide having a nucleic acid sequence selected from the group consisting of nucleic acid sequences encoding the variable regions set forth in Table 3B, (ii) a nucleic acid sequence at least 80% identical to a nucleic acid sequence selected from the group consisting of nucleic acid sequences encoding the variable regions set forth in Table 3B, (iii) a nucleic acid sequence at least 90% identical to a nucleic acid sequence selected from the group consisting of nucleic acid sequences encoding the variable regions set forth in Table 3B, or (iv) a nucleic acid sequence at least 95% identical to a nucleic acid sequence selected from the group consisting of nucleic acid sequences encoding the variable regions set forth in Table 3A.

In another aspect, the invention includes an expression vector comprising an isolated nucleic acid or polynucleotide of any as above.

In another aspect, the invention includes a cell line transformed with expression vector as above.

In another aspect, the invention includes a method of making an antibody or antigen binding fragment thereof of any as above, comprising preparing the antibody or antigen binding fragment thereof from a host cell as above that secretes the antibody or antigen binding fragment thereof.

In another aspect, the invention includes a pharmaceutical composition comprising an antibody or antigen binding fragment thereof of any as above and a pharmaceutically acceptable excipient.

In another aspect, the invention includes a method for treating a condition associated with PAC1 in a patient, comprising administering to a patient an effective amount of an antibody or antigen binding fragment thereof of any as above.

In another aspect, the invention includes the method as above, wherein the condition is headache.

In another aspect, the invention includes the method as above, wherein the condition is migraine.

In another aspect, the invention includes the method as above, wherein the migraine is episodic migraine.

In another aspect, the invention includes the method as above, wherein the migraine is chronic migraine.

In another aspect, the invention includes the method as above, wherein the condition is cluster headache.

In another aspect, the invention includes the method of any as above, wherein the method comprises prophylactic treatment.

BRIEF DESCRIPTION OF THE FIGURES

FIG. 1 shows selected anti-hPAC1 light chain CDR sequences and defined anti-hPAC1 light chain CDR consensus sequences CDRL1-C1, CDRL1-C2, CDRL2-C1, CDRL2-C2, CDRL2-C3, and CDRL3-C1.

FIG. 2 shows selected anti-hPAC1 heavy chain CDR sequences and defined anti-hPAC1 heavy chain CDR consensus sequences CDRH1-C1, CDRH1-C2, CDRH2-C1, CDRH2-C2, CDRH2-C3, and CDRH3-C1.

DETAILED DESCRIPTION

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages means±10%.

Definitions

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transduction" means the transfer of genes from one bacterium to another, usually by bacteriophage. "Transduction" also refers to the acquisition and transfer of eukaryotic cellular sequences by replication defective retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier;

Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass antibodies, e.g., anti-PAC1 antibodies (aka PAC1 antibodies), PAC1 binding proteins, antibodies, or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a PAC1-binding antibody, useful fragments include but are not limited to a CDR region, a variable domain of a heavy or light chain, a portion of an antibody chain or just its variable domain including two CDRs, and the like.

The term "isolated protein" (e.g., isolated antibody), "isolated polypeptide" or "isolated antibody" means that a subject protein, polypeptide or antibody is free of most other proteins with which it would normally be found and has been separated from at least about 50 percent of polynucleotides, lipids, carbohydrates, or other materials with which it is associated in nature. Typically, an "isolated protein", "isolated polypeptide" or "isolated antibody" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein polypeptide or antibody is substantially free from other proteins or other polypeptides or other contaminants that are found in its natural environment that would interfere with its therapeutic, diagnostic, prophylactic, research or other use.

The terms "human PAC1", "human $PAC_1$", "hPAC1" and "$hPAC_1$", "human PAC1 receptor", "human $PAC_1$ receptor", "hPAC1 receptor" and "$hPAC_1$ receptor" are used interchangeably and refer to the human pituitary adenylate cyclase-activating polypeptide type I receptor. hPAC1 is a 468 amino acid protein designated as P41586 (PACK_HUMAN) in the UniProtKB/Swiss-Prot database and is encoded by the ADCYAP1R1 gene. PACAP-27 and PACAP-38 are the principal endogenous agonists of PAC1. Unless otherwise specified or clear from the context in which the term is used, "PAC1" refers to human hPAC1.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein, or an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

An antibody or antigen binding fragment thereof is said to "specifically bind" its target when the dissociation constant ($K_D$) is $\leq 10^{-6}$ M. The antibody specifically binds the target antigen with "high affinity" when the $K_D$ is $\leq 1\times 10^{-8}$ M. In one embodiment, the antibodies or antigen-binding fragments thereof will bind to PAC1, or human PAC1 with a $K_D \leq 5\times 10^{-7}$; in another embodiment the antibodies or antigen-binding fragments thereof will bind with a $K_D \leq 1\times 10^{-7}$; in another embodiment the antibodies or antigen-binding fragments thereof will bind with a $K_D \leq 5\times 10^{-8}$; in another embodiment the antibodies or antigen-binding fragments thereof will bind with a $K_D \leq 1\times 10^{-8}$; in another embodiment the antibodies or antigen-binding fragments thereof will bind with a $K_D \leq 5\times 10^{-9}$; in another embodiment the antibodies or antigen-binding fragments thereof will bind with a $K_D \leq 1\times 10^{-9}$; in another embodiment the antibodies or antigen-binding fragments thereof will bind with a $K_D \leq 5\times 10^{-10}$; in another embodiment the antibodies or antigen-binding fragments thereof will bind with a $K_D \leq 1\times 10^{-10}$.

An antibody, antigen binding fragment thereof or antigen binding protein "selectively inhibits" a specific receptor relative to other receptors when the IC50 of the antibody, antigen binding fragment thereof or antigen binding protein in an inhibition assay of the specific receptor is at least 50-fold lower than the IC50 in an inhibition assay of another "reference" receptor, e.g., a hVPAC1 or hVPAC2 receptor. The "selectivity ratio" is the IC50 of the reference receptor divided by IC50 of the specific receptor. For example, if hPAC1 is the specific receptor and hVPAC1 is the reference receptor, and the IC50 of a particular anti-PAC1 antibody described herein against hPAC1 is 10 nm and against hVPAC1 is 10 μm, that particular antibody can be characterized as having a selectivity ratio of 1000:1 for hPAC1 relative to hVPAC1. IC50 is the dose/concentration required to achieve 50% inhibition (of a biological or biochemical function). With radioactive ligands, IC50 is the concentration of a competing ligand that displaces 50% of the specific binding of the radioligand. EC50 is the concentration or dose required to induce a response 50% of the maximum response.

Ki data are typically generated in the context of competition binding experiments, which are typically done by attaching a radioactive isotope (e.g., a $^{125}$I) to an "agonist". The experiments measure the binding of the agonist in increasing concentrations of an "antagonist". Ki refers to the concentration of the "antagonist" or test compound, e.g., a test anti-PAC1 antibody, which would occupy 50% of the receptors if there was no radioligand present. Ki can be calculated using the equation Ki=IC50/(1+([L]/Kd)), where [L] is the concentration of the radioligand used (e.g., a $^{125}$I-labeled PAC-1 antibody) and Kd is the dissociation constant of the radioligand. See, e.g., Keen M, MacDermot J (1993) Analysis of receptors by radioligand binding. In: Wharton J, Polak J M (eds) Receptor autoradiography, principles and practice. Oxford University Press, Oxford.

"Antigen binding region" means a protein, or a portion of a protein, that specifically binds a specified antigen. For example, that portion of an antibody that contains the amino acid residues that interact with an antigen and confer on the antibody its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen.

In certain aspects, recombinant antibodies or antigen-binding fragments thereof that bind PAC1 protein, or human PAC1, are provided. In this context, a "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or an antigen binding fragment thereof that can compete with the intact antibody for specific binding to the target antigen, and includes, for instance, chimeric, humanized, fully human, and bispecific antibodies or antigen-binding fragments thereof. An "antibody" as such is a species of an antigen binding protein. An intact antibody generally will comprise at least two full-length heavy chains and two full-length light chains, but in some instances may include fewer chains such as antibodies naturally occurring in camelids which may comprise only heavy chains. Antibodies or antigen-binding fragments thereof may be derived solely from a single source, or may be "chimeric," that is, different portions of the antibody may be derived from two different antibodies as described further below. The antibodies or binding fragments thereof may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and mutations thereof, examples of which are described below.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains may be of any isotype, including IgG (including IgG1, IgG2, IgG3 and IgG4 subtypes), IgA (including IgA1 and IgA2 subtypes), IgM and IgE. In one embodiment, the heavy chain is an aglycosylated IgG1, e.g., an IgG1 HC with an N297G mutation.

The term "signal sequence", "leader sequence" or "signal peptide" refers to a short (3-60 amino acids long) peptide chain that directs the transport of a protein. Signal peptides may also be called targeting signals, signal sequences, transit peptides, or localization signals. Some signal peptides are cleaved from the protein by signal peptidase after the proteins are transported, such that the biologically active form of the protein (e.g., an antibody as described herein) is the cleaved, shorter form. Accordingly, terms such as "antibody comprising a heavy chain . . . ", "antibody comprising a light chain . . . ", etc., where the antibody is characterized as having a heavy and/or light chain with a particular identified sequence, are understood to include antibodies having the specific identified sequences, antibodies having the specific identified sequences except that the signal sequences are replaced by different signal sequences, as well as antibodies having the identified sequences, minus any signal sequences.

The term "antigen binding fragment" (or simply "fragment") of an antibody or immunoglobulin chain (heavy or light chain), as used herein, comprises a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antibodies or antigen-binding fragments thereof, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced, e.g., by enzymatic or chemical cleavage of intact antibodies. Immunologically functional immunoglobulin fragments include, but are not limited to, Fab, Fab', F(ab')$_2$, Fv, domain antibodies and single-chain antibodies, and may be derived from any mammalian source, including but not limited to human, mouse, rat, camelid or rabbit. It is contemplated further that a functional portion of the antibodies disclosed herein, for example, one or more CDRs, could be covalently bound to a second protein or to a small molecule to create a therapeutic agent directed to a particular target in the body, possessing bifunctional therapeutic properties, or having a prolonged serum half-life.

An "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')2 molecule.

An "F(ab')$_2$ fragment" contains two light chains and two heavy chains containing a portion of the constant region between the $C_H1$ and $C_H2$ domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. No. 4,946,778 and No. 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antigen binding protein" or "bivalent antibody" comprises two antigen binding sites. In some instances, the two binding sites have the same antigen specificities. Bivalent antibodies may be bispecific, see, infra.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antibodies are a species of multispecific antigen binding protein or multispecific antibody and may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which may reside on the same or different protein targets.

The term "neutralizing antigen binding protein" or "neutralizing antibody" refers to an antigen binding protein or antibody, respectively, that binds to a ligand, prevents binding of the ligand to its binding partner and interrupts the biological response that otherwise would result from the ligand binding to its binding partner. In assessing the binding and specificity of an antigen binding protein, e.g., an antibody or immunologically functional antigen binding fragment thereof, an antibody or fragment will substantially inhibit binding of a ligand to its binding partner when an excess of antibody reduces the quantity of binding partner bound to the ligand by at least about 20%, 30%, 40%, 50%, 60%, 70%, 80%, 85%, 90%, 95%, 97%, 99% or more (as measured in an in vitro competitive binding assay). In the case of a PAC1 binding protein, such a neutralizing molecule will diminish the ability of PAC1 to bind PACAP, e.g., PACAP-27 or PACAP-38.

The term "antigen" or "immunogen" refers to a molecule or a portion of a molecule capable of being bound by a selective binding agent, such as an antigen binding protein (including, e.g., an antibody or immunological functional antigen binding fragment thereof), and additionally capable of being used in an animal to produce antibodies capable of binding to that antigen. An antigen may possess one or more epitopes that are capable of interacting with different antibodies or fragments thereof.

The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., amino acid residues that are not contiguous to one another in the polypeptide sequence but that within in context of the molecule are bound by the antigen binding protein). In certain embodiments, epitopes may be mimetic in that they comprise a three dimensional structure that is similar to an epitope used to generate the antibody, yet comprise none or only some of the amino acid residues found in that epitope used to generate the antibody. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat migraine headaches either prophylactically or as an acute treatment, decreasing the frequency of migraine headaches, decreasing the severity of migraine headaches, and/or ameliorating a symptom associated with migraine headaches.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with migraine headache. In some embodiments, the effective amount is a therapeutically effective amount or a prophylactically effective amount. A "therapeutically effective amount" is an amount sufficient to remedy a disease state (e.g. migraine headache) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of migraine headache, or reducing the likelihood of the onset (or reoccurrence) of migraine headache or migraine headache symptoms. The full therapeutic or prophylactic effect does not necessarily occur by administration of one dose, and may occur only after administration of a series of doses. Thus, a therapeutically or prophylactically effective amount may be administered in one or more administrations.

"Amino acid" includes its normal meaning in the art. The twenty naturally-occurring amino acids and their abbreviations follow conventional usage. See, Immunology-A Synthesis, 2nd Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural amino acids such as α-,α-disubstituted amino acids, N-alkyl amino acids, and other unconventional amino acids may also be suitable components for polypeptides and are included in the phrase "amino acid." Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

PAC1 in Disease

Neuropeptides present in the perivascular space of cranial vessels have been implicated as important mediators of nociceptive input during migraine attacks. Pituitary adenylate cyclase-activating polypeptide (PACAP) is present in sensory trigeminal neurons and may modulate nociception at different levels of the nervous system. Human experimental studies have shown that PACAP38 induces both headache and migraine-like attacks (Schytz, et al., 2009, "PACAP38 induces migraine-like attacks in patients with migraine without aura", *Brain:*132 pp 16-25), supporting the idea that PAC1 receptor antagonists may be used in the prophylactic and/or acute treatment of migraine.

Antibodies

Antibodies that bind PAC1 protein, including human PAC1 (hPAC1) protein are provided herein. The antibodies provided are polypeptides into which one or more complementary determining regions (CDRs), as described herein, are embedded and/or joined. In some antibodies, the CDRs are embedded into a "framework" region, which orients the CDR(s) such that the proper antigen binding properties of the CDR(s) is achieved. In general, antibodies that are provided can interfere with, block, reduce or modulate the interaction between PAC1 and its ligand(s), e.g., PACAP, such as PACAP-38.

In certain embodiments, the antibodies include, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof. The various structures are further described herein below.

The antibodies provided herein have been demonstrated to bind to PAC1, in particular human PAC1 and cyno PAC1. As described further in the examples below, certain antibodies were tested and found to bind to epitopes different from those bound by a number of other antibodies directed against one or the other of the components of PAC1. The antibodies that are provided prevent PACAP (e.g., PACAP-38) from binding to its receptor. As a consequence, the antibodies provided herein are capable of inhibiting PAC1 activity. In particular, antibodies binding to these epitopes can have one or more of the following activities: inhibiting, inter alia, induction of PAC1 signal transduction pathways, inhibiting vasodialation, causing vasoconstriction, decreasing inflammation, e.g., neurogenic inflammation, and other physiological effects induced by PAC1 upon PACAP binding.

The antibodies that are disclosed herein have a variety of utilities. Some of the antibodies, for instance, are useful in specific binding assays, affinity purification of PAC1, in particular hPAC1 or its ligands and in screening assays to identify other antagonists of PAC1 activity. Some of the antibodies are useful for inhibiting binding of a PAC1 ligand (e.g., PACAP-38) to PAC1.

The antibodies can be used in a variety of treatment applications, as explained herein. For example, certain PAC1 antibodies are useful for treating conditions associated with PAC1 mediated signaling, such as reducing, alleviating, or treating the frequency and/or severity of migraine headache, reducing, alleviating, or treating cluster headache, reducing, alleviating, or treating chronic pain, alleviating or treating diabetes mellitus (type II), reducing, alleviating, or treating cardiovascular disorders, and reducing, alleviating, or treating hemodynamic derangements associated with endotoxemia and sepsis in a patient. Other uses for the antibodies include, for example, diagnosis of PAC1-associated diseases or conditions and screening assays to determine the presence or absence of PAC1. Some of the antibodies described herein are useful in treating consequences, symptoms, and/or the pathology associated with PAC1 activity. These include, but are not limited to, various types of headaches, including migraine (e.g., chronic and/or episodic migraine).

Some of the antibodies that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as $C_H1$, $C_H2$ and $C_H3$. The antibodies that are provided can have any of these isotypes and subtypes. In certain embodiments, the PAC1 antibody is of the IgG1, IgG2, or IgG4 subtype.

In full-length light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., PAC1). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, *Nature* 342: 878-883.

The various heavy chain and light chain variable regions provided herein are depicted in Tables 3A and 3B. Each of these variable regions may be attached to the above heavy and light chain constant regions to form a complete antibody heavy and light chain, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

Nucleic acids that encode for the antibodies described herein, or portions thereof, are also provided, including nucleic acids encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Tables 1A and 1B show exemplary nucleic acid sequences. Any variable region provided herein may be attached to these constant regions to form complete heavy and light chain sequences. However, it should be understood that these constant regions sequences are provided as specific examples only—one of skill in the art may employ other constant regions, including IgG1 heavy chain constant region, IgG3 or IgG4 heavy chain constant regions, any of the seven lambda light chain constant regions, including hCL-1, hCL-2, hCL-3 and hCL-7; constant regions that have been modified for improved stability, expression, manufacturability or other desired characteristics, and the like. In some embodiments, the variable region sequences are joined to other constant region sequences that are known in the art.

Specific examples of full length light and heavy chains of the antibodies that are provided and their corresponding nucleic and amino acid sequences are summarized in Tables 1A, 1B, 2A and 2B. Tables 1A and 2A show exemplary light chain sequences, and Tables 1B and 2B show exemplary heavy chain sequences, which are shown without the respective signal sequences.

TABLE 1A

Exemplary Anti-hPAC1 Antibody Light Chain Nucleic Acid Sequences

| SEQ ID NO: | Seq Group | Antibodies containing sequence | LC NA Sequence |
|---|---|---|---|
| 1 | LC-01 | 01A, 01B | GACATCCAGATGACCCAGTCTCCATCCTCCCTGTCTGCATCTGTAGGAGAC AGAATCACCATCACTTGCCGGGCAAGTCAGAGCATTAGCAGGTATTTAAATT GGTATCAACAGAAACCAGGGAAAGCCCCTAAACTCCTGATCTATGCTGCAT CCAGTTTGCAAAGTGGGATCCCATCAAGGTTCAGCGGCAGTGGATCTGGG ACAGATTTCACTCTCACCATCAACAGTCTGCAACCTGAAGATTTTGCAACTT ACTTCTGTCAACAGAGTTACAGTCCCCCATTCACTTTCGGCCCTGGGACCA AAGTGGATATCAAACGTACGGTGGCTGCACCATCTGTCTTCATCTTCCCGC CATCTGATGAGCAGTTGAAATCTGGAACTGCCTCTGTTGTGTGCCTGCTGA ATAACTTCTATCCCAGAGAGGCCAAAGTACAGTGGAAGGTGGATAACGCCC TCCAATCGGGTAACTCCCAGGAGAGTGTCACAGAGCAGGACAGCAAGGAC AGCACCTACAGCCTCAGCAGCACCCTGACGCTGAGCAAAGCAGACTACGA GAAACACAAAGTCTACGCCTGCGAAGTCACCCATCAGGGCCTGAGCTCGC CCGTCACAAAGAGCTTCAACAGGGGAGAGTGT |
| 2 | LC-02 | 02A, 02B, 02C | GAAATTGTGCTGACTCAGTCTCCAGACTTTCAGTCTGTGACTCCAAAGGAG AAAGTCACCATCACCTGCCGGGCCAGTCAGAGCATTGGTAGTAGCTTACAC TGGTACCAGCAGAAACCAGATCAGTCTCCAAAGCTCCTCATCAAGTATGCT TCCCAGTCCTTGTCAGGGATCCCCTCGAGGTTTAGTGGCAGTGGATCTGG GACACATTTCACCCTCACCATCAATAGCCTGGAAGCTGAAGATGCTGCAAC GTATTACTGTCATCAGAGTAGTCGTTTACCATTCACTTTCGGCCCTGGGACC AAAGTGGATATCAAACGAACGGTGGCTGCACCATCTGTCTTCATCTTCCCG CCATCTGATGAGCAGTTGAAATCTGGAACTGCTAGCGTTGTGTGCCTGCTG AATAACTTCTATCCCAGAGAGGCCAAAGTACAGTGGAAGGTGGATAACGCC CTCCAATCGGGTAACTCCCAGGAGAGTGTCACAGAGCAGGACAGCAAGGA CAGCACCTACAGCCTCAGCAGCACCCTGACGCTGAGCAAAGCAGACTACG AGAAACACAAAGTCTACGCCTGCGAAGTCACCCATCAGGGCCTGAGCTCG CCCGTCACAAAGAGCTTCAACAGGGGAGAGTGT |
| 3 | LC-03 | 03A | GATATCCAGCTCACTCAATCGCCATCATTTCTCTCCGCTTCGGTAGGCGAC CGGGTCACGATCACATGCAGGGCGTCGCAAAGCATTGGGAGGTCGTTGCA TTGGTATCAGCAGAAACCCGGAAAGGCCCCGAAACTTCTGATCAAATACGC ATCACAAAGCTTGAGCGGTGTGCCGTCGCGCTTCTCCGGTTCCGGAAGCG GAACGGAATTCACGCTTACAATCTCCTCACTGCAGCCCGAGGATTTCGCGA CCTATTACTGTCACCAGTCATCCAGACTCCCGTTTACTTTTGGCCCTGGGAC CAAGGTGGACATTAAGCGTACGGTGGCTGCACCATCTGTCTTCATCTTCCC GCCATCTGATGAGCAGTTGAAATCTGGAACTGCCTCTGTTGTGTGCCTGCT GAATAACTTCTATCCCAGAGAGGCCAAAGTACAGTGGAAGGTGGATAACGC CCTCCAATCGGGTAACTCCCAGGAGAGTGTCACAGAGCAGGACAGCAAGG ACAGCACCTACAGCCTCAGCAGCACCCTGACGCTGAGCAAAGCAGACTAC GAGAAACACAAAGTCTACGCCTGCGAAGTCACCCATCAGGGCCTGAGCTC GCCCGTCACAAAGAGCTTCAACAGGGGAGAGTGT |
| 4 | LC-04 | 04A, 04B, 04C, 07A, 07B, 07C, 08A, 08B, 08C, 12A, 12B, 12C | GAAATTGTGCTGACTCAGTCTCCAGACTTTCAGTCTGTGACTCCAAAGGAG AAAGTCACCATCACCTGCCGGGCCAGTCAGAGCGTTGGTCGTAGTTTACAC TGGTACCATCAGAAACCAGATCAGTCTCCAAAGCTCCTCATCAAGTATGCTT CCCAGTCCTTATCAGGGGTCCCCTCGAGGTTCAGTGGCAGTGGATCTGGG ACAGATTTCACCCTCATTATCAATAGCCTGGAAGCTGAAGATGCTGCAACGT ATTACTGTCATCAGAGTAGTCGTTTACCATTCACTTTCGGCCCTGGGACCAA |

TABLE 1A-continued

Exemplary Anti-hPAC1 Antibody Light Chain Nucleic Acid Sequences

| SEQ ID NO: | Seq Group | Antibodies containing sequence | LC NA Sequence |
|---|---|---|---|
| | | | AGTGGATATCAAACGAACGGTGGCTGCACCATCTGTCTTCATCTTCCCGCC<br>ATCTGATGAGCAGTTGAAATCTGGAACTGCTAGCGTTGTGTGCCTGCTGAA<br>TAACTTCTATCCCAGAGAGGCCAAAGTACAGTGGAAGGTGGATAACGCCCT<br>CCAATCGGGTAACTCCCAGGAGAGTGTCACAGAGCAGGACAGCAAGGACA<br>GCACCTACAGCCTCAGCAGCACCCTGACGCTGAGCAAAGCAGACTACGAG<br>AAACACAAAGTCTACGCCTGCGAAGTCACCCATCAGGGCCTGAGCTCGCC<br>CGTCACAAAGAGCTTCAACAGGGGAGAGTGT |
| 5 | LC-05 | 05A, 05B, 05C,<br>13A, 13B, 13C,<br>16A, 16B, 16C,<br>17A, 17B, 17C,<br>21A, 21B, 21C,<br>22A, 22B, 22C,<br>24A, 24B, 24C,<br>25A, 25B, 25C,<br>26A, 26B, 26C | GATATCCAGCTCACTCAATCGCCATCATTTCTCTCCGCTTCGGTAGGCGAC<br>CGGGTCACGATCACATGCAGGGCGTCGCAAAGCATTGGGAGGTCGTTGCA<br>TTGGTATCAGCAGAAACCCGGAAAGGCCCCGAAACTTCTGATCAAATACGC<br>ATCACAAAGCTTGAGCGGTGTGCCGTCGCGCTTCTCCGGTTCCGGAAGCG<br>GAACGGAATTCACGCTTACAATCTCCTCACTGCAGCCCGAGGATTTCGCGA<br>CCTATTACTGTCACCAGTCATCCAGACTCCCGTTTACTTTTGGCCCTGGGAC<br>CAAGGTGGACATTAAGCGTACGGTGGCTGCACCATCTGTCTTCATCTTCCC<br>GCCATCTGATGAGCAGTTGAAATCTGGAACTGCCTCTGTTGTGTGCCTGCT<br>GAATAACTTCTATCCCAGAGAGGCCAAAGTACAGTGGAAGGTGGATAACGC<br>CCTCCAATCGGGTAACTCCCAGGAGAGTGTCACAGAGCAGGACAGCAAGG<br>ACAGCACCTACAGCCTCAGCAGCACCCTGACGCTGAGCAAAGCAGACTAC<br>GAGAAACACAAAGTCTACGCCTGCGAAGTCACCCATCAGGGCCTGAGCTC<br>GCCCGTCACAAAGAGCTTCAACAGGGGAGAGTGT |
| 6 | LC-06 | 06A, 06B, 06C | GATATCCAGCTCACTCAATCGCCATCATTTCTCTCCGCTTCGGTAGGCGAC<br>CGGGTCACGATCACATGCAGGGCGTCGCAAAGCATTGGGAGGTCGTTGCA<br>TTGGTATCACCAGAAACCCGGAAAGGCCCCGAAACTTCTGATCAAATACGC<br>ATCACAAAGCTTGAGCGGTGTGCCGTCGCGCTTCTCCGGTTCCGGAAGCG<br>GAACGGAATTCACGCTTATCATCTCCTCACTGCAGCCCGAGGATTTCGCGA<br>CCTATTACTGTCACCAGTCATCCAGACTCCCGTTTACTTTTGGCCCTGGGAC<br>CAAGGTGGACATTAAGCGTACGGTGGCTGCACCATCTGTCTTCATCTTCCC<br>GCCATCTGATGAGCAGTTGAAATCTGGAACTGCCTCTGTTGTGTGCCTGCT<br>GAATAACTTCTATCCCAGAGAGGCCAAAGTACAGTGGAAGGTGGATAACGC<br>CCTCCAATCGGGTAACTCCCAGGAGAGTGTCACAGAGCAGGACAGCAAGG<br>ACAGCACCTACAGCCTCAGCAGCACCCTGACGCTGAGCAAAGCAGACTAC<br>GAGAAACACAAAGTCTACGCCTGCGAAGTCACCCATCAGGGCCTGAGCTC<br>GCCCGTCACAAAGAGCTTCAACAGGGGAGAGTGT |
| 7 | LC-07 | 09A, 09B, 09C,<br>10A, 10B, 10C,<br>11A, 11B, 11C | GAAATTGTGCTGACTCAGTCTCCAGACTTTCAGTCTGTGACTCCAAAGGAG<br>AAAGTCACCATCACCTGCCGGGCCAGTCAGAGCGTTGGTCGTAGTTTACAC<br>TGGTACCAGCAGAAACCAGATCAGTCTCCAAAGCTCCTCATCAAGTATGCT<br>TCCCAGTCCTTATCAGGGGTCCCCTCGAGGTTCAGTGGCAGTGGATCTGG<br>GACAGATTTCACCCTCACTATCAATAGCCTGGAAGCTGAAGATGCTGCAAC<br>GTATTACTGTCATCAGAGTAGTCGTTTACCATTCACTTTCGGCCCTGGGACC<br>AAAGTGGATATCAAACGAACGGTGGCTGCACCATCTGTCTTCATCTTCCCG<br>CCATCTGATGAGCAGTTGAAATCTGGAACTGCTAGCGTTGTGTGCCTGCTG<br>AATAACTTCTATCCCAGAGAGGCCAAAGTACAGTGGAAGGTGGATAACGCC<br>CTCCAATCGGGTAACTCCCAGGAGAGTGTCACAGAGCAGGACAGCAAGGA<br>CAGCACCTACAGCCTCAGCAGCACCCTGACGCTGAGCAAAGCAGACTACG<br>AGAAACACAAAGTCTACGCCTGCGAAGTCACCCATCAGGGCCTGAGCTCG<br>CCCGTCACAAAGAGCTTCAACAGGGGAGAGTGT |
| 8 | LC-08 | 14A, 14B, 14C,<br>23A, 23B, 23C,<br>27A, 27B, 27C | GAGATCGTACTTACTCAGTCACCCGCCACATTGTCCCTGAGCCCGGGTGAA<br>CGGGCGACCCTCAGCTGCCGAGCATCCGTCCGTCGGACGATCATTGCA<br>CTGGTACCAACAAAAACCGGGCAGGCCCCCAGACTTCTGATCAAGTATGC<br>GTCACAGAGCTTGTCGGGTATTCCCGCTCGCTTTTCGGGGTCGGGATCCG<br>GGACAGATTTCACGCTCACAATCTCCTCGCTGGAACCCGAGGACTTCGCG<br>GTCTACTATTGTCATCAGTCATCGAGGTTGCCTTTCACGTTTGGACCAGGG<br>ACCAAGGTGGACATTAAGCGTACGGTGGCTGCACCATCTGTCTTCATCTTC<br>CCGCCATCTGATGAGCAGTTGAAATCTGGAACTGCCTCTGTTGTGTGCCTG<br>CTGAATAACTTCTATCCCAGAGAGGCCAAAGTACAGTGGAAGGTGGATAAC<br>GCCCTCCAATCGGGTAACTCCCAGGAGAGTGTCACAGAGCAGGACAGCAA<br>GGACAGCACCTACAGCCTCAGCAGCACCCTGACGCTGAGCAAAGCAGACT<br>ACGAGAAACACAAAGTCTACGCCTGCGAAGTCACCCATCAGGGCCTGAGC<br>TCGCCCGTCACAAAGAGCTTCAACAGGGGAGAGTGT |
| 9 | LC-09 | 15A, 15B, 15C,<br>18A, 18B, 18C,<br>19A, 19B, 19C,<br>20A, 20B, 20C | GAGATCGTACTTACTCAGTCACCCGGCACATTGTCCCTGAGCCCGGGTGAA<br>CGGGCGACCCTCAGCTGCCGAGCATCCCAGTCCGTCGGACGATCATTGCA<br>CTGGTACCAACAAAAACCGGGCAGGCCCCCAGACTTCTGATCAAGTATGC<br>GTCACAGAGCTTGTCGGGTATTCCCGATCGCTTTCGGGGTCGGGATCCG<br>GGACAGATTTCACGCTCACAATCTCCCGACTGGAACCCGAGGACTTCGCG<br>CCTACTATTGTCATCAGTCATCGAGGTTGCCTTTCACGTTTGGACAGGGGA<br>CCAAGGTGGAGATTAAGCGTACGGTGGCTGCACCATCTGTCTTCATCTTCC<br>CGCCATCTGATGAGCAGTTGAAATCTGGAACTGCCTCTGTTGTGTGCCTGC<br>TGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAG |

TABLE 1A-continued

Exemplary Anti-hPAC1 Antibody Light Chain Nucleic Acid Sequences

| SEQ ID NO: | Seq Group | Antibodies containing sequence | LC NA Sequence |
|---|---|---|---|
| | | | GACAGCACCTACAGCCTCAGCAGCACCCTGACGCTGAGCAAAGCAGACTA CGAGAAACACAAAGTCTACGCCTGCGAAGTCACCCATCAGGGCCTGAGCT CGCCCGTCACAAAGAGCTTCAACAGGGGAGAGTGT |
| 10 | LC-10 | 28A, 28B, 28C | GAAATTGTGCTGACTCAGTCTCCAGACTTTCAGTCTGTGACTCCAAAGGAG AAAGTCACCATCACCTGCCGGGCCAGTCAGAGCATTGGTCGTAGTTTACAC TGGTACCAGCAGAAACCAGATCAGTCTCCAAAGCTCCTCTTCAAGTATGCTT CCCAGTCCTTATCAGGGGTCCCCTCGAGGTTCAGTGGCAGTGGATCTGGG ACAGATTTCACCCTCACAATCAATAGCCTGGAAGCTGAAGATGCTGCAACG TATTACTGTCATCAGAGTAGTCGTTTACCATTCACTTTCGGCCCTGGGACCA AAGTGGATATCAAACGAACGGTGGCTGCACCATCTGTCTTCATCTTCCCGC CATCTGATGAGCAGTTGAAATCTGGAACTGCTAGCGTTGTGTGCCTGCTGA ATAACTTCTATCCCAGAGAGGCCAAAGTACAGTGGAAGGTGGATAACGCCC TCCAATCGGGTAACTCCCAGGAGAGTGTCACAGAGCAGGACAGCAAGGAC AGCACCTACAGCCTCAGCAGCACCCTGACGCTGAGCAAAGCAGACTACGA GAAACACAAAGTCTACGCCTGCGAAGTCACCCATCAGGGCCTGAGCTCGC CCGTCACAAAGAGCTTCAACAGGGGAGAGTGT |
| 11 | LC-11 | 29A, 29B, 29C | GATATCCAGCTCACTCAATCGCCATCATTTCTCTCCGCTTCGGTAGGCGAC CGGGTCACGATCACATGCAGGGCGTCGCAAAGCATTGGGAGGTCGTTGCA TTGGTATCAGCAGAAACCCGGAAAGGCCCCGAAACTTCTGTTCAAATACGC ATCACAAAGCTTGAGCGGTGTGCCGTCGCGCTTCTCCGGTTCCGGAAGCG GAACGGAATTCACGCTTACAATCTCCTCACTGCAGCCCGAGGATTTCGCGA CCTATTACTGTCACCAGTCATCCAGACTCCCGTTTACTTTTGGCCCTGGGAC CAAGGTGGACATTAAGCGTACGGTGGCTGCACCATCTGTCTTCATCTTCCC GCCATCTGATGAGCAGTTGAAATCTGGAACTGCCTCTGTTGTGTGCCTGCT GAATAACTTCTATCCCAGAGAGGCCAAAGTACAGTGGAAGGTGGATAACGC CCTCCAATCGGGTAACTCCCAGGAGAGTGTCACAGAGCAGGACAGCAAGG ACAGCACCTACAGCCTCAGCAGCACCCTGACGCTGAGCAAAGCAGACTAC GAGAAACACAAAGTCTACGCCTGCGAAGTCACCCATCAGGGCCTGAGCTC GCCCGTCACAAAGAGCTTCAACAGGGGAGAGTGT |
| 12 | LC-12 | 30A, 31A | GAAATTGTGTTGACGCAGTCGCCAGGCACCCTGTCTTTGTCTCCAGGGGAA AGAGCCACCCTCTCCTGCAGGGCCAGTCAGAGTGTTAGCAGCAGCTACTTA GCCTGGTACCAGCAGAAACCTGGCCAGGCTCCCAGGCTCCTCATCTATGG TGCATCCAGCAGGGCCACTGGCATCCCAGACAGGTTCAGTAACAGTGGGT CTGGGACAGACTTCACTCTCACCATCAGCAGACTGGAGCCTGAAGATTTTG CAGTGTATTACTGTCAGAGGTATGGTAGCTCACGGACGTTCGGCCAAGGGA CCAAGGTGGAAATCAAACGAACTGTGGCTGCACCATCTGTCTTCATCTTCC CGCCATCTGATGAGCAGTTGAAATCTGGTACCGCCTCTGTTGTGTGCCTGC TGAATAACTTCTATCCCAGAGAGGCCAAAGTACAGTGGAAGGTGGATAACG CCCTCCAATCGGGTAACTCCCAGGAGAGTGTCACAGAGCAGGACAGCAAG GACAGCACCTACAGCCTCAGCAGCACCCTGACGCTGAGCAAAGCAGACTA CGAGAAACACAAAGTCTACGCCTGCGAAGTCACCCATCAGGGCCTGAGCT CGCCCGTCACAAAGAGCTTCAACAGGGGAGAGTGT |
| 13 | LC-13 | 32A | GATATTGTGATGACTCAGTCTCCACTCTCCCTGCCCGTCACCCCTGGAGAG CCGGCCTCCATCTCCTGCAGGTCTAGTCAGAGCCTCCTGCATAGTAATGGA TACAACTATTTGGATTGGTACCTGCAGAAGCCAGGGCAGTCTCCACAGCTC CTGCTCTATTTGGGTTCTAATCGGGCCTCCGGGGTCCCTGACAGGTTCAGT GGCAGTGGATCAGGCACAGATTTTACACTGCAAATCAGCAGAGTGGAGGCT GAGGATGTTGGGGTTTATTACTGCATGCAAACTCTACAAACTCCATTCACTT TCGGCCCTGGGACCAAAGTGGATATCAAACGTACGGTGGCTGCACCATCT GTCTTCATCTTCCCGCCATCTGATGAGCAGTTGAAATCTGGAACTGCCTCT GTTGTGTGCCTGCTGAATAACTTCTATCCCAGAGAGGCCAAAGTACAGTGG AAGGTGGATAACGCCCTCCAATCGGGTAACTCCCAGGAGAGTGTCACAGA GCAGGACAGCAAGGACAGCACCTACAGCCTCAGCAGCACCCTGACGCTGA GCAAAGCAGACTACGAGAAACACAAAGTCTACGCCTGCGAAGTCACCCATC AGGGCCTGAGCTCGCCCGTCACAAAGAGCTTCAACAGGGGAGAGTGT |
| 14 | LC-14 | 33A, 34A | GATATTGTGATGACTCAGTCTCCACTCTCCCTGCCCGTCACCCCTGGAGAG CCGGCCTCCATCTCCTGCAGGTCTAGTCAGAGCCTCCTGCATAGTAATGGA TACAACTATTTGGATTGGTACCTGCAGAAGCCAGGGCAGTCTCCACAGCTC CTGCTCTATTTGGGTTCTAATCGGGCCTCCGGGGTCCCTGACAGGTTCAGT GGCAGTGGATCAGGCACAGATTTTACACTGAAAATCAGCAGAGTGGAGGCT GAGGATGTTGGGGTTTATTACTGCATGCAAACTCTACAAACTCCATTCACTT TCGGCCCTGGGACCAAAGTGGATATCAAACGTACGGTGGCTGCACCATCT GTCTTCATCTTCCCGCCATCTGATGAGCAGTTGAAATCTGGAACTGCCTCT GTTGTGTGCCTGCTGAATAACTTCTATCCCAGAGAGGCCAAAGTACAGTGG AAGGTGGATAACGCCCTCCAATCGGGTAACTCCCAGGAGAGTGTCACAGA GCAGGACAGCAAGGACAGCACCTACAGCCTCAGCAGCACCCTGACGCTGA GCAAAGCAGACTACGAGAAACACAAAGTCTACGCCTGCGAAGTCACCCATC AGGGCCTGAGCTCGCCCGTCACAAAGAGCTTCAACAGGGGAGAGTGT |

TABLE 1A-continued

Exemplary Anti-hPAC1 Antibody Light Chain Nucleic Acid Sequences

| SEQ ID NO: | Seq Group | Antibodies containing sequence | LC NA Sequence |
|---|---|---|---|
| 15 | LC-15 | 35A | GAAATTGTGTTGACGCAGTCTCCAGGCACCCTGTCTTTGTCTCCAGGGGAA<br>AGAGCCACCCTCTCCTGCAGGGCCAGTCAGACTGTTAGCAGGAGCTACTTA<br>GCCTGGTACCAGCAGAAACCTGGCCAGGCTCCCAGGCTCCTCATCTATGG<br>TGCATCCAGCAGGGCCACTGGCATCCCAGACAGGTTCAGTGGCAGTGGGT<br>CTGGGACAGACTTCACTCTCACCATCAGCAGACTGGAGCCTGAAGATTTTG<br>CCGTGTTTTACTGTCAGCAGTTTGGTAGCTCACCGTGGACGTTCGGCCAAG<br>GGACCAAGGTGGAAATCAAACGTACGGTGGCTGCACCATCTGTCTTCATCT<br>TCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATA<br>ACGCCCTCCAATCGGGTAACTCCCAGGAGAGTGTCACAGAGCAGGACAGC<br>AAGGACAGCACCTACAGCCTCAGCAGCACCCTGACGCTGAGCAAAGCAGA<br>CTACGAGAAACACAAAGTCTACGCCTGCGAAGTCACCCATCAGGGCCTGA<br>GCTCGCCCGTCACAAAGAGCTTCAACAGGGGAGAGTGT |
| 16 | LC-16 | 36A | GACATCGTGATGACCCAGTCTCCAGACTCCCTGGCTGTGTCTCTGGGCGA<br>GAGGGCCACCATCCATTGCAAGTCCAGCCAGAATGTTTTATACAGCTCCAA<br>CAATAAGAACTTCTTAACTTGGTACCAGCAGAAACCAGGACAGCCCCCTAA<br>ACTGCTCATTTACCGGGCATCTACCCGGGAATCCGGGGTCCCTGACCGATT<br>CAGTGGCAGCGGGTCTGGGACGGATTTCACTCTCACTATCAGCAGTCTGCA<br>GGCTGAAGATGTGGCAGTTTATTTCTGTCAGCAATATTATAGTGCTCCATTC<br>ACTTTCGGCCCTGGGACCAAAGTGGATATCAAACGTACGGTGGCTGCACCA<br>TCTGTCTTCATCTTCCCGCCATCTGATGAGCAGTTGAAATCTGGAACTGCCT<br>CTGTTGTGTGCCTGCTGAATAACTTCTATCCCAGAGAGGCCAAAGTACAGT<br>GGAAGGTGGATAACGCCCTCCAATCGGGTAACTCCCAGGAGAGTGTCACA<br>GAGCAGGACAGCAAGGACAGCACCTACAGCCTCAGCAGCACCCTGACGCT<br>GAGCAAAGCAGACTACGAGAAACACAAAGTCTACGCCTGCGAAGTCACCCA<br>TCAGGGCCTGAGCTCGCCCGTCACAAAGAGCTTCAACAGGGGAGAGTGT |
| 17 | LC-17 | 37A | GACATCGTGATGACCCAGTCTCCAGACTCCCTGGCTGTGTCTCTGGGCGA<br>GAGGACCACCATCAAGTGCAAGTCCAGCCAGAGTGTTTTATACAGATCCAA<br>CAATAACAACTTCTTAGCTTGGTACCAGCAGAAACCAGGACAGCCTCCTAA<br>GCTGCTCATTTATTGGGCATCTACCCGGGAATCCGGGGTCCCTGACCGATT<br>CAGTGGCAGCGGGTCTGGGACAGATTTCACTCTCACCATCAGCAGCCTGC<br>AGGCTGAAGATGTGGCTGTTTATTTCTGTCAGCAATATTATATTTCTCCGCT<br>CACTTTCGGCGGAGGGACCAAGGTGGAGATCAAACGTACGGTGGCTGCAC<br>CATCTGTCTTCATCTTCCCGCCATCTGATGAGCAGTTGAAATCTGGAACTGC<br>CTCTGTTGTGTGCCTGCTGAATAACTTCTATCCCAGAGAGGCCAAAGTACA<br>GTGGAAGGTGGATAACGCCCTCCAATCGGGTAACTCCCAGGAGAGTGTCA<br>CAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACC<br>CATCAGGGCCTGAGCTCGCCCGTCACAAAGAGCTTCAACAGGGGAGAGTGT |
| 18 | LC-18 | 38A | GACATCGTGATGACCCAGTCTCCAGACTCCCTGGCTGTGTCTCTGGGCGA<br>GAGGGCCACCATCAACTGCAAGTCCAGCCAGAGTGTTTTATACAGTTCCAA<br>CAATAAGCACTACTTAGCTTGGTACCGGCAGAAACCAGGACAGCCTCCTAA<br>ACTGCTCATTTACAGGGCATCTACCCGGGAATCCGGGGTCCCTGACCGATT<br>CAGTGGCAGCGGGTCTGGGACAGATTTCACTCTCACCATCAGCAGCCTGC<br>AGCCTGAAGATGTGGCAGTGTATTACTGTCAGCAATATTATAGTTCTCCATT<br>CACTTTCGGCCCTGGGACCAAAGTGGATATCAAACGTACGGTGGCTGCAC<br>CATCTGTCTTCATCTTCCCGCCATCTGATGAGCAGTTGAAATCTGGAACTGC<br>CTCTGTTGTGTGCCTGCTGAATAACTTCTATCCCAGAGAGGCCAAAGTACA<br>GTGGAAGGTGGATAACGCCCTCCAATCGGGTAACTCCCAGGAGAGTGTCA<br>CAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACC<br>CATCAGGGCCTGAGCTCGCCCGTCACAAAGAGCTTCAACAGGGGAGAGTGT |
| 19 | LC-19 | 39A, 39B | GACATCGTGATGACCCAGTCTCCAGACTCCCTGGCTGTGTCTCTGGGCGA<br>GAGGGCCACCATCCACTGCAAGTCCAGCCAGAGTGTTTTATACAGCTCCAA<br>CAATAAGAACTTCTTAACTTGGTACCAGCAGAAACCAGGACAGCCTCCTAAA<br>CTTCTCATTTACCGGGCATCTACCCGGGAATCCGGGGTTCCTGACCGATTC<br>AGTGGCAGCGGGTCTGGGACAGATTTCACTCTCACCATCAGCAGCCTGCA<br>GGCTGAAGATGTGGCAGTTTATTTCTGTCAGCAATATTATAGTGCTCCATTC<br>ACTTTCGGCCCTGGGACCAGAGTGGATATCAAACGTACGGTGGCTGCACC<br>ATCTGTCTTCATCTTCCCGCCATCTGATGAGCAGTTGAAATCTGGAACTGCC<br>TCTGTTGTGTGCCTGCTGAATAACTTCTATCCCAGAGAGGCCAAAGTACAG<br>TGGAAGGTGGATAACGCCCTCCAATCGGGTAACTCCCAGGAGAGTGTCAC<br>AGAGCAGGACAGCAAGGACAGCACCTACAGCCTCAGCAGCACCCTGACGC<br>TGAGCAAAGCAGACTACGAGAAACACAAAGTCTACGCCTGCGAAGTCACCC<br>ATCAGGGCCTGAGCTCGCCCGTCACAAAGAGCTTCAACAGGGGAGAGTGT |
| 20 | LC-20 | 40A | GACATCGTGATGACTCAGTCTCCAGACTCCCTGGCTGTGTCTCTGGGCGAG<br>AGGGCCACCATCCACTGCAAGTCCAGCCAGAGTGTTTTATACAGCTCCAAC<br>AATAGGAACTTCTTAAGTTGGTACCAGCAGAAACCAGGACAGCCTCCTAAA<br>CTGCTCATTTACCGGGCATCTACCCGGGAATCCGGGGTCCCTGACCGATTC |

TABLE 1A-continued

Exemplary Anti-hPAC1 Antibody Light Chain Nucleic Acid Sequences

| SEQ ID NO: | Seq Group | Antibodies containing sequence | LC NA Sequence |
|---|---|---|---|
| | | | AGTGGCAGCGGGTCTGGGACAGATTTCACTCTCACCATCAGCAGCCTGCA<br>GGCTGAAGATGTGGCAGTTTATTTCTGTCAGCAATATTATAGTGCTCCATTC<br>ACTTTCGGCCCTGGGACCACAGTGGATATCAAACGTACGGTGGCTGCACC<br>ATCTGTCTTCATCTTCCCGCCATCTGATGAGCAGTTGAAATCTGGAACTGCC<br>TCTGTTGTGTGCCTGCTGAATAACTTCTATCCCAGAGAGGCCAAAGTACAG<br>TGGAAGGTGGATAACGCCCTCCAATCGGGTAACTCCCAGGAGAGTGTCAC<br>AGAGCAGGACAGCAAGGACAGCACCTACAGCCTCAGCAGCACCCTGACGC<br>TGAGCAAAGCAGACTACGAGAAACACAAAGTCTACGCCTGCGAAGTCACCC<br>ATCAGGGCCTGAGCTCGCCCGTCACAAAGAGCTTCAACAGGGGAGAGTGT |
| 21 | LC-21 | 41A | GACATCGTGATGACCCAGTCTCCAGACTCCCTGGCTGTGTCTCTGGGCGA<br>GAGGGCCACCATCAACTGCAAGTCCAGCCAGAGTGTTTTATACAGTTCCAA<br>CAATAAGAACTACTTAGCTTGGTACCGGCAGAAACCAGGACAGCCTCCTAA<br>GCTGCTCATTTACAGGGCATCTACCCGGGAATCCGGGGTCCCTGACCGATT<br>CAGTGGCAGCGGGTCTGGGACAGATTTCACTCTCACCATCAGCAGCCTGC<br>AGGCTGAAGATGTGGCAGTGTATCACTGTCAGCAATATTATAGTTCTCCATT<br>CACTTTCGGCCCTGGGACCAAAGTGGATATCAAACGTACGGTGGCTGCAC<br>CATCTGTCTTCATCTTCCCGCCATCTGATGAGCAGTTGAAATCTGGAACTGC<br>CTCTGTTGTGTGCCTGCTGAATAACTTCTATCCCAGAGAGGCCAAAGTACA<br>GTGGAAGGTGGATAACGCCCTCCAATCGGGTAACTCCCAGGAGAGTGTCA<br>CAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACC<br>CATCAGGGCCTGAGCTCGCCCGTCACAAAGAGCTTCAACAGGGGAGAGTGT |

TABLE 1B

Exemplary Anti-hPAC1 Antibody Heavy Chain Nucleic Acid Sequences

| SEQ ID NO: | Seq Group | Antibodies containing sequence | HC NA Sequence |
|---|---|---|---|
| 22 | HC-01 | 01A | CAGGTACAGCTGCAGCAGTCAGGTCCAGGACTGGTGAAGCCCTCGCAGAC<br>CCTCTCACTCACCTGTGCCATCTCCGGGGACAGTGTCTCTAGCAACAGTGC<br>TACTTGGAACTGGATCAGGCAGTCCCCATCGAGAGGCCTTGAGTGGCTGG<br>GAAGGACATATTACAGGTCCAAGTGGTCTAATCATTATGCAGTATCTGTGAA<br>AAGTCGAATAACCATCAACCCCGACACGTCCAAGAGCCAGTTCTCCCTGCA<br>GCTGAACTCTGTGACTCCCGAGGACACGGCTGTGTATTACTGTGCAAGAGG<br>AACGTGGAAACAGCTATGGTTCCTTGACCACTGGGGCCAGGGAACCCTGG<br>TCACCGTCTCTAGTGCCTCCACCAAGGGCCCATCGGTCTTCCCCCTGGCG<br>CCCTGCTCCAGGAGCACCTCCGAGAGCACAGCGGCCCTGGGCTGCCTGG<br>TCAAGGACTACTTCCCCGAACCGGTGACGGTGTCGTGGAACTCAGGCGCT<br>CTGACCAGCGGCGTGCACACCTTCCCAGCTGTCCTACAGTCCTCAGGACT<br>CTACTCCCTCAGCAGCGTGGTGACCGTGCCCTCCAGCAACTTCGGCACCC<br>AGACCTACACCTGCAACGTAGATCACAAGCCCAGCAACACCAAGGTGGACA<br>AGACAGTTGAGCGCAAATGTTGTGTCGAGTGCCCACCGTGCCCAGCACCA<br>CCTGTGGCAGGACCGTCAGTCTTCCTCTTCCCCCCAAAACCCAAGGACACC<br>CTCATGATCTCCCGGACCCCTGAGGTCACGTGCGTGGTGGTGGACGTGAG<br>CCACGAAGACCCCGAGGTCCAGTTCAACTGGTACGTGGACGGCGTGGAGG<br>TGCATAATGCCAAGACAAAGCCACGGGAGGAGCAGTTCAACAGCACGTTC<br>CGTGTGGTCAGCGTCCTCACCGTTGTGCACCAGGACTGGCTGAACGGCAA<br>GGAGTACAAGTGCAAGGTCTCCAACAAAGGCCTCCCAGCCCCCATCGAGA<br>AAACCATCTCCAAAACCAAAGGGCAGCCCCGAGAACCACAGGTGTACACC<br>CTGCCCCCATCCCGGGAGGAGATGACCAAGAACCAGGTCAGCCTGACCTG<br>CCTGGTCAAAGGCTTCTACCCCAGCGACATCGCCGTGGAGTGGGAGAGCA<br>ATGGGCAGCCGGAGAACAACTACAAGACCACACCTCCCATGCTGGACTCC<br>GACGGCTCCTTCTTCCTCTACAGCAAGCTCACCGTGGACAAGAGCAGGTG<br>GCAGCAGGGGAACGTCTTCTCATGCTCCGTGATGCATGAGGCTCTGCACA<br>ACCACTACACGCAGAAGAGCCTCTCCCTGTCTCCGGGTAAA |
| 23 | HC-02 | 01B | CAGGTACAGCTGCAGCAGTCAGGTCCAGGACTGGTGAAGCCCTCGCAGAC<br>CCTCTCACTCACCTGTGCCATCTCCGGGGACAGTGTCTCTAGCAACAGTGC<br>TACTTGGAACTGGATCAGGCAGTCCCCATCGAGAGGCCTTGAGTGGCTGG<br>GAAGGACATATTACAGGTCCAAGTGGTCTAATCATTATGCAGTATCTGTGAA<br>AAGTCGAATAACCATCAACCCCGACACGTCCAAGAGCCAGTTCTCCCTGCA<br>GCTGAACTCTGTGACTCCCGAGGACACGGCTGTGTATTACTGTGCAAGAGG<br>AACGTGGAAACAGCTATGGTTCCTTGACCACTGGGGCCAGGGAACCCTGG<br>TCACCGTCTCTAGTGCCTCCACCAAGGGCCCATCGGTCTTCCCCCTGGCAC<br>CCTCCTCCAAGAGCACCTCTGGGGGCACAGCGGCCCTGGGCTGCCTGGTC<br>AAGGACTACTTCCCCGAACCGGTGACGGTGTCGTGGAACTCAGGCGCCCT<br>GACCAGCGGCGTGCACACCTTCCCGGCTGTCCTACAGTCCTCAGGACTCT |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | ACTCCCTCAGCAGCGTGGTGACCGTGCCCTCCAGCAGCTTGGGCACCCAG ACCTACATCTGCAACGTGAATCACAAGCCCAGCAACACCAAGGTGGACAAG AAAGTTGAGCCCAAATCTTGTGACAAAACTCACACATGCCCACCGTGCCCA GCACCTGAACTCCTGGGGGGACCGTCAGTCTTCCTCTTCCCCCCAAAACCC AAGGACACCCTCATGATCTCCCGGACCCCTGAGGTCACATGCGTGGTGGT GGACGTGAGCCACGAAGACCCTGAGGTCAAGTTCAACTGGTACGTGGACG GCGTGGAGGTGCATAATGCCAAGACAAAGCCGCGGGAGGAGCAGTACGG CAGCACGTACCGTGTGGTCAGCGTCCTCACCGTCCTGCACCAGGACTGGC TGAATGGCAAGGAGTACAAGTGCAAGGTCTCCAACAAAGCCCTCCCAGCC CCCATCGAGAAAACCATCTCCAAAGCCAAAGGGCAGCCCCGAGAACCACA GGTGTACACCCTGCCCCCATCCCGGGAGGAGATGACCAAGAACCAGGTCA GCCTGACCTGCCTGGTCAAAGGCTTCTATCCCAGCGACATCGCCGTGGAG TGGGAGAGCAATGGGCAGCCGGAGAACAACTACAAGACCACGCCTCCCGT GCTGGACTCCGACGGCTCCTTCTTCCTCTATAGCAAGCTCACCGTGGACAA GAGCAGGTGGCAGCAGGGGAACGTCTTCTCATGCTCCGTGATGCATGAGG CTCTGCACAACCACTACACGCAGAAGAGCCTCTCCCTGTCTCCGGGTAAA |
| 24 | HC-03 | 02A, 03A | CAGGTGCAGTTGGTGGAGTCTGGGGGAGGCGTGGTCCAGCCTGGGAGGT CCCTGAGACTCTCCTGTGCAGCCTCTGGATTCACCTTCAGTTACTATGCCAT ACACTGGGTCCGCCAGGCTCCAGGCAAGGGGCTAGAGTGGGTGGCAGTTA TCTCATATGATGGAAGTAATAAATACTATGCAGACTCCGTGAAGGGCCGATT CACCATCTCCAGAGACAATTCCAAGAACACGCTGTATCTGCAAATGAACAG CCTGAGAGCTGAGGACACGGCTGTGTATTACTGTGCGAGAGGATACGATCT TTTGACTGGTTACCCCGACTACTGGGGCCAGGGAACCCTGGTCACCGTCT CCTCAGCTAGCACCAAGGGCCCATCGGTCTTCCCCCTGGCGCCCTGCTCC AGGAGCACCTCCGAGAGCACAGCGGCCCTGGGCTGCCTGGTCAAGGACTA CTTCCCCGAACCGGTGACGGTGTCGTGGAACTCAGGCGCTCTGACCAGCG GCGTGCACACCTTCCCAGCTGTCCTACAGTCCTCAGGACTCTACTCCCTCA GCAGCGTGGTGACCGTGCCCTCCAGCAACTTCGGCACCCAGACCTACACC TGCAACGTAGATCACAAGCCCAGCAACACCAAGGTGGACAAGACAGTTGA GCGCAAATGTTGTGTCGAGTGCCCACCGTGCCCAGCACCACCTGTGGCAG GACCGTCAGTCTTCCTCTTCCCCCCAAAACCCAAGGACACCCTCATGATCT CCCGGACCCCTGAGGTCACGTGCGTGGTGGTGGACGTGAGCCACGAAGA CCCCGAGGTCCAGTTCAACTGGTACGTGGACGGCGTGGAGGTGCATAATG CCAAGACAAAGCCACGGGAGGAGCAGTTCAACAGCACGTTCCGTGTGGTC AGCGTCCTCACCGTTGTGCACCAGGACTGGCTGAACGGCAAGGAGTACAA GTGCAAGGTCTCCAACAAAGGCCTCCCAGCCCCCATCGAGAAAACCATCTC CAAAACCAAAGGGCAGCCCCGAGAACCACAGGTGTACACCCTGCCCCCAT CCCGGGAGGAGATGACCAAGAACCAGGTCAGCCTGACCTGCCTGGTCAAA GGCTTCTACCCCAGCGACATCGCCGTGGAGTGGGAGAGCAATGGGCAGCC GGAGAACAACTACAAGACCACACCTCCCATGCTGGACTCCGACGGCTCCTT CTTCCTCTACAGCAAGCTCACCGTGGACAAGAGCAGGTGGCAGCAGGGGA ACGTCTTCTCATGCTCCGTGATGCATGAGGCTCTGCACAACCACTACACGC AGAAGAGCCTCTCCCTGTCTCCGGGTAAA |
| 25 | HC-04 | 02B | CAGGTGCAGTTGGTGGAGTCTGGGGGAGGCGTGGTCCAGCCTGGGAGGT CCCTGAGACTCTCCTGTGCAGCCTCTGGATTCACCTTCAGTTACTATGCCAT ACACTGGGTCCGCCAGGCTCCAGGCAAGGGGCTAGAGTGGGTGGCAGTTA TCTCATATGATGGAAGTAATAAATACTATGCAGACTCCGTGAAGGGCCGATT CACCATCTCCAGAGACAATTCCAAGAACACGCTGTATCTGCAAATGAACAG CCTGAGAGCTGAGGACACGGCTGTGTATTACTGTGCGAGAGGATACGATCT TTTGACTGGTTACCCCGACTACTGGGGCCAGGGAACCCTGGTCACCGTCT CCTCAGCCTCCACCAAGGGCCCATCGGTCTTCCCCCTGGCACCCTCCTCC AAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCG GCGTGCACACCTTCCCGGCTGTCCTACAGTCCTCAGGACTCTACTCCCTCA GCAGCGTGGTGACCGTGCCCTCCAGCAGCTTGGGCACCCAGACCTACATC TGCAACGTGAATCACAAGCCCAGCAACACCAAGGTGGACAAGAAAGTTGAG CCCAAATCTTGTGACAAAACTCACACATGCCCACCGTGCCCAGCACCTGAA CTCCTGGGGGGACCGTCAGTCTTCCTCTTCCCCCCAAAACCCAAGGACAC CCTCATGATCTCCCGGACCCCTGAGGTCACATGCGTGGTGGTGGACGTGA GCCACGAAGACCCTGAGGTCAAGTTCAACTGGTACGTGGACGGCGTGGAG GTGCATAATGCCAAGACAAAGCCGCGGGAGGAGCAGTACGGCAGCACGTA CCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAG AAAACCATCTCCAAAGCCAAAGGGCAGCCCCGAGAACCACAGGTGTACAC CCTGCCCCCATCCCGGGAGGAGATGACCAAGAACCAGGTCAGCCTGACCT GCCTGGTCAAAGGCTTCTATCCCAGCGACATCGCCGTGGAGTGGGAGAGC AATGGGCAGCCGGAGAACAACTACAAGACCACGCCTCCCGTGCTGGACTC CGACGGCTCCTTCTTCCTCTATAGCAAGCTCACCGTGGACAAGAGCAGGTG GCAGCAGGGGAACGTCTTCTCATGCTCCGTGATGCATGAGGCTCTGCACA ACCACTACACGCAGAAGAGCCTCTCCCTGTCTCCGGGTAAA |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| 26 | HC-05 | 02C | CAGGTGCAGTTGGTGGAGTCTGGGGGAGGCGTGGTCCAGCCTGGGAGGT CCCTGAGACTCTCCTGTGCAGCCTCTGGATTCACCTTCAGTTACTATGCCAT ACACTGGGTCCGCCAGGCTCCAGGCAAGGGGCTAGAGTGGGTGGCAGTTA TCTCATATGATGGAAGTAATAAATACTATGCAGACTCCGTGAAGGGCCGATT CACCATCTCCAGAGACAATTCCAAGAACACGCTGTATCTGCAAATGAACAG CCTGAGAGCTGAGGACACGGCTGTGTATTACTGTGCGAGAGGATACGATCT TTTGACTGGTTACCCCGACTACTGGGGCCAGGGAACCCTGGTCACCGTCT CCTCAGCCTCGACGAAGGGGCCGTCCGTATTTCCGCTTGCGCCCTCGTCG AAGTCAACTTCGGGAGGGACCGCGGCACTTGGCTGTCTTGTCAAAGATTAC TTCCCTGAGCCAGTGACAGTCAGCTGGAATTCCGGTGCCCTCACGTCAGG AGTACATACATTCCCTGCGGTATTGCAGTCCTCCGGACTCTACTCCCTGTC GTCGGTGGTAACGGTGCCCAGCTCCAGCTTGGGGACCCAGACGTACATTT GTAACGTGAATCACAAACCAAGCAATACTAAGGTAGATAAGAAAGTAGAAC CGAAGAGCTGCGACAAGACCCACACATGTCCTCCGTGCCCCGCACCCGAG CTGTTGGGAGGACCCTCGGTGTTTTTGTTTCCTCCCAAGCCAAAGGACACG TTGATGATTTCGCGCACTCCAGAGGTCACGTGTGTAGTCGTGGACGTGTCA CATGAGGACCCCGAGGTAAAGTTCAATTGGTATGTGGACGGAGTCGAGGT CCATAACGCCAAAACAAAGCCGTGCGAAGAACAGTACGGGTCAACGTATAG GTGCGTCAGCGTCCTCACTGTGCTGCACCAAGACTGGCTCAATGGTAAAGA ATACAAGTGCAAGGTGTCGAACAAGGCCCTCCCTGCCCCTATCGAGAAAAC CATCTCCAAAGCGAAGGGGCAGCCGCGAGAACCCCAAGTCTACACGCTGC CGCCCTCGCGGGAGGAAATGACCAAAAACCAGGTGTCGCTTACGTGTCTT GTGAAAGGGTTCTATCCATCAGATATCGCGGTCGAGTGGGAGTCGAACGG CCAGCCCGAAAACAATTACAAAACAACACCTCCGGTCCTCGATTCAGATGG AAGCTTCTTCTTGTATTCGAAGCTGACCGTCGATAAGTCAAGGTGGCAACA GGGAAATGTGTTCTCGTGCTCAGTGATGCACGAGGCTCTGCATAACCACTA TACGCAGAAATCATTGTCGCTCAGCCCCGGTAAA |
| 27 | HC-06 | 04A, 05A, 06A, 11A | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCGGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGAATCTGCTAATGAAC AGCCTGAGAGCTGAGGACACGGCTCTGTTTTACTGTGCGAGAGGATACGAT GTTTTGACTGGTTACCCCGACTACTGGGGCCAGGGAACCCTGGTCACCGT CTCCTCAGCTTCCACCAAGGGCCCATCCGTCTTCCCCCTGGCGCCCTGCT CCAGGAGCACCTCCGAGAGCACAGCCGCCCTGGGCTGCCTGGTCAAGGA CTACTTCCCCGAACCGGTGACGGTGTCGTGGAACTCAGGCGCTCTGACCA GCGGCGTGCACACCTTCCCAGCTGTCCTACAGTCCTCAGGACTCTACTCCC TCAGCAGCGTGGTGACCGTGCCCTCCAGCAACTTCGGCACCCAGACCTAC ACCTGCAACGTAGATCACAAGCCCAGCAACACCAAGGTGGACAAGACAGTT GAGCGCAAATGTTGTGTCGAGTGCCCACCGTGCCCAGCACCACCTGTGGC AGGACCGTCAGTCTTCCTCTTCCCCCCAAAACCCAAGGACACCCTCATGAT CTCCCGGACCCCTGAGGTCACGTGCGTGGTGGTGGACGTGAGCCACGAA GACCCCGAGGTCCAGTTCAACTGGTACGTGGACGGCGTGGAGGTGCATAA TGCCAAGACAAAGCCACGGGAGGAGCAGTTCAACAGCACGTTCCGTGTGG TCAGCGTCCTCACCGTTGTGCACCAGGACTGGCTGAACGGCAAGGAGTAC AAGTGCAAGGTCTCCAACAAAGGCCTCCCAGCCCCCATCGAGAAAACCATC TCCAAAACCAAAGGGCAGCCCCGAGAACCACAGGTGTACACCCTGCCCCC ATCCCGGGAGGAGATGACCAAGAACCAGGTCAGCCTGACCTGCCTGGTCA AAGGCTTCTACCCCAGCGACATCGCCGTGGAGTGGGAGAGCAATGGGCAG CCGGAGAACAACTACAAGACCACACCTCCCATGCTGGACTCCGACGGCTC CTTCTTCCTCTACAGCAAGCTCACCGTGGACAAGAGCAGGTGGCAGCAGG GGAACGTCTTCTCATGCTCCGTGATGCATGAGGCTCTGCACAACCACTACA CGCAGAAGAGCCTCTCCCTGTCTCCGGGTAAA |
| 28 | HC-07 | 04B, 05B, 06B, 11B | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCGGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGAATCTGCTAATGAAC AGCCTGAGAGCTGAGGACACGGCTCTGTTTTACTGTGCGAGAGGATACGAT GTTTTGACTGGTTACCCCGACTACTGGGGCCAGGGAACCCTGGTCACCGT CTCCTCAGCCTCCACCAAGGGCCCATCGGTCTTCCCCCTGGCACCCTCCT CCAAGAGCACCTCTGGGGGCACAGCGGCCCTGGGCTGCCTGGTCAAGGA CTACTTCCCCGAACCGGTGACGGTGTCGTGGAACTCAGGCGCCCTGACCA GCGGCGTGCACACCTTCCCGGCTGTCCTACAGTCCTCAGGACTCTACTCC CTCAGCAGCGTGGTGACCGTGCCCTCCAGCAGCTTGGGCACCCAGACCTA CATCTGCAACGTGAATCACAAGCCCAGCAACACCAAGGTGGACAAGAAAGT TGAGCCCAAATCTTGTGACAAAACTCACACATGCCCACCGTGCCCAGCACC TGAACTCCTGGGGGGACCGTCAGTCTTCCTCTTCCCCCCAAAACCCAAGGA CACCCTCATGATCTCCCGGACCCCTGAGGTCACATGCGTGGTGGTGGACG TGAGCCACGAAGACCCTGAGGTCAAGTTCAACTGGTACGTGGACGGCGTG |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | GAGGTGCATAATGCCAAGACAAAGCCGCGGGAGGAGCAGTACGGCAGCAC<br>GTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATC<br>GAGAAAACCATCTCCAAAGCCAAAGGGCAGCCCCGAGAACCACAGGTGTA<br>CACCCTGCCCCCATCCCGGGAGGAGATGACCAAGAACCAGGTCAGCCTGA<br>CCTGCCTGGTCAAAGGCTTCTATCCCAGCGACATCGCCGTGGAGTGGGAG<br>AGCAATGGGCAGCCGGAGAACAACTACAAGACCACGCCTCCCGTGCTGGA<br>CTCCGACGGCTCCTTCTTCCTCTATAGCAAGCTCACCGTGGACAAGAGCAG<br>GTGGCAGCAGGGGAACGTCTTCTCATGCTCCGTGATGCATGAGGCTCTGC<br>ACAACCACTACACGCAGAAGAGCCTCTCCCTGTCTCCGGGTAAA |
| 29 | HC-08 | 04C, 05C, 06C, 11C | CAGGTGCAGCTGGTGGAGTCTGGGGGAGGCGTGGTCCAGCCTGGGAGGT<br>CCCTGCGACTCTCCTGTGCAGCCTCTGGATTCACCTTCAGTAGATTTGCCA<br>TGCACTGGGTCCGCCGGGCTCCAGGCAAGGGGCTGGAGTGGGTGGCAGT<br>TATATCATATGATGGAGGAAATAAATACTATGCAGAGTCCGTGAAGGGCCG<br>GTTCACCATCTCCAGAGACAATTCCAAGAACACCCTGAATCTGCTAATGAAC<br>AGCCTGAGAGCTGAGGACACGGCTCTGTTTTACTGTGCGAGAGGATACGAT<br>GTTTTGACTGGTTACCCCGACTACTGGGGCCAGGGAACCCTGGTCACCGT<br>CTCCTCAGCCTCGACGAAGGGGCCGTCCGTATTTCCGCTTGCGCCCTCGT<br>CGAAGTCAACTTCGGGAGGGACCGCGGCACTTGGCTGTCTTGTCAAAGATT<br>ACTTCCCTGAGCCAGTGACAGTCAGCTGGAATTCCGGTGCCCTCACGTCAG<br>GAGTACATACATTCCCTGCGGTATTGCAGTCCTCCGGACTCTACTCCCTGT<br>CGTCGGTGGTAACGGTGCCCAGCTCCAGCTTGGGGACCCAGACGTACATT<br>TGTAACGTGAATCACAAACCAAGCAATACTAAGGTAGATAAGAAAGTAGAAC<br>CGAAGAGCTGCGACAAGACCCACACATGTCCTCCGTGCCCCGCACCCGAG<br>CTGTTGGGAGGACCCTCGGTGTTTTGTTTCCTCCCAAGCCAAAGGACACG<br>TTGATGATTTCGCGCACTCCAGAGGTCACGTGTGTAGTCGTGGACGTGTCA<br>CATGAGGACCCCGAGGTAAAGTTCAATTGGTATGTGGACGGAGTCGAGGT<br>CCATAACGCCAAAACAAAGCCGTGCGAAGAACAGTACGGGTCAACGTATAG<br>GTGCGTCAGCGTCCTCACTGTGCTGCACCAAGACTGGCTCAATGGTAAAGA<br>ATACAAGTGCAAGGTGTCGAACAAGGCCCTCCCTGCCCCTATCGAGAAAAC<br>CATCTCCAAAGCGAAGGGGCAGCCGCGAGAACCCCAAGTCTACACGCTGC<br>CGCCCTCGCGGGAGGAAATGACCAAAAACCAGGTGTCGCTTACGTGTCTT<br>GTGAAAGGGTTCTATCCATCAGATATCGCGGTCGAGTGGGAGTCGAACGG<br>CCAGCCCGAAAACAATTACAAAACAACACCTCCGGTCCTCGATTCAGATGG<br>AAGCTTCTTCTTGTATTCGAAGCTGACCGTCGATAAGTCAAGGTGGCAACA<br>GGGAAATGTGTTCTCGTGCTCAGTGATGCACGAGGCTCTGCATAACCACTA<br>TACGCAGAAATCATTGTCGCTCAGCCCCGGTAAA |
| 30 | HC-09 | 07A, 09A | CAGGTGCAGCTGGTGGAGTCTGGGGGAGGCGTGGTCCAGCCTGGGAGGT<br>CCCTGCGACTCTCCTGTGCAGCCTCTGGATTCACCTTCAGTAGATTTGCCA<br>TGCACTGGGTCCGCCAGGCTCCAGGCAAGGGGCTGGAGTGGGTGGCAGT<br>TATATCATATGATGGAGGAAATAAATACTATGCAGAGTCCGTGAAGGGCCG<br>GTTCACCATCTCCAGAGACAATTCCAAGAACACCCTGAATCTGCTAATGAAC<br>AGCCTGAGAGCTGAGGACACGGCTCTGTTTTACTGTGCGAGAGGATACGAT<br>GTTTTGACTGGTTACCCCGACTACTGGGGCCAGGGAACCCTGGTCACCGT<br>CTCCTCAGCTTCCACCAAGGGCCCATCCGTCTTCCCCCTGGCGCCCTGCT<br>CCAGGAGCACCTCCGAGAGCACAGCCGCCCTGGGCTGCCTGGTCAAGGA<br>CTACTTCCCCGAACCGGTGACGGTGTCGTGGAACTCAGGCGCTCTGACCA<br>GCGGCGTGCACACCTTCCCAGCTGTCCTACAGTCCTCAGGACTCTACTCCC<br>TCAGCAGCGTGGTGACCGTGCCCTCCAGCAACTTCGGCACCCAGACCTAC<br>ACCTGCAACGTAGATCACAAGCCCAGCAACACCAAGGTGGACAAGACAGTT<br>GAGCGCAAATGTTGTGTCGAGTGCCCACCGTGCCCAGCACCACCTGTGGC<br>AGGACCGTCAGTCTTCCTCTTCCCCCCAAAACCCAAGGACACCCTCATGAT<br>CTCCCGGACCCCTGAGGTCACGTGCGTGGTGGTGGACGTGAGCCACGAA<br>GACCCCGAGGTCCAGTTCAACTGGTACGTGGACGGCGTGGAGGTGCATAA<br>TGCCAAGACAAAGCCACGGGAGGAGCAGTTCAACAGCACGTTCCGTGTGG<br>TCAGCGTCCTCACCGTTGTGCACCAGGACTGGCTGAACGGCAAGGAGTAC<br>AAGTGCAAGGTCTCCAACAAAGGCCTCCCAGCCCCCATCGAGAAAACCATC<br>TCCAAAACCAAAGGGCAGCCCCGAGAACCACAGGTGTACACCCTGCCCCC<br>ATCCCGGGAGGAGATGACCAAGAACCAGGTCAGCCTGACCTGCCTGGTCA<br>AAGGCTTCTACCCCAGCGACATCGCCGTGGAGTGGGAGAGCAATGGGCAG<br>CCGGAGAACAACTACAAGACCACACCTCCCATGCTGGACTCCGACGGCTC<br>CTTCTTCCTCTACAGCAAGCTCACCGTGGACAAGAGCAGGTGGCAGCAGG<br>GGAACGTCTTCTCATGCTCCGTGATGCATGAGGCTCTGCACAACCACTACA<br>CGCAGAAGAGCCTCTCCCTGTCTCCGGGTAAA |
| 31 | HC-10 | 07B, 09B | CAGGTGCAGCTGGTGGAGTCTGGGGGAGGCGTGGTCCAGCCTGGGAGGT<br>CCCTGCGACTCTCCTGTGCAGCCTCTGGATTCACCTTCAGTAGATTTGCCA<br>TGCACTGGGTCCGCCAGGCTCCAGGCAAGGGGCTGGAGTGGGTGGCAGT<br>TATATCATATGATGGAGGAAATAAATACTATGCAGAGTCCGTGAAGGGCCG<br>GTTCACCATCTCCAGAGACAATTCCAAGAACACCCTGAATCTGCTAATGAAC<br>AGCCTGAGAGCTGAGGACACGGCTCTGTTTTACTGTGCGAGAGGATACGAT<br>GTTTTGACTGGTTACCCCGACTACTGGGGCCAGGGAACCCTGGTCACCGT |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | CTCCTCAGCCTCCACCAAGGGCCCATCGGTCTTCCCCCTGGCACCCTCCT CCAAGAGCACCTCTGGGGGCACAGCGGCCCTGGGCTGCCTGGTCAAGGA CTACTTCCCCGAACCGGTGACGGTGTCGTGGAACTCAGGCGCCCTGACCA GCGGCGTGCACACCTTCCCGGCTGTCCTACAGTCCTCAGGACTCTACTCC CTCAGCAGCGTGGTGACCGTGCCCTCCAGCAGCTTGGGCACCCAGACCTA CATCTGCAACGTGAATCACAAGCCCAGCAACACCAAGGTGGACAAGAAAGT TGAGCCCAAATCTTGTGACAAAACTCACACATGCCCACCGTGCCCAGCACC TGAACTCCTGGGGGGACCGTCAGTCTTCCTCTTCCCCCCAAAACCCAAGGA CACCCTCATGATCTCCCGGACCCCTGAGGTCACATGCGTGGTGGTGGACG TGAGCCACGAAGACCCTGAGGTCAAGTTCAACTGGTACGTGGACGGCGTG GAGGTGCATAATGCCAAGACAAAGCCGCGGGAGGAGCAGTACGGCAGCAC GTACCGTGTGGTCAGCGTCCTCACCGTCCTGCACCAGGACTGGCTGAATG GCAAGGAGTACAAGTGCAAGGTCTCCAACAAAGCCCTCCCAGCCCCCATC GAGAAAACCATCTCCAAAGCCAAAGGGCAGCCCCGAGAACCACAGGTGTA CACCCTGCCCCCATCCCGGGAGGAGATGACCAAGAACCAGGTCAGCCTGA CCTGCCTGGTCAAAGGCTTCTATCCCAGCGACATCGCCGTGGAGTGGGAG AGCAATGGGCAGCCGGAGAACAACTACAAGACCACGCCTCCCGTGCTGGA CTCCGACGGCTCCTTCTTCCTCTATAGCAAGCTCACCGTGGACAAGAGCAG GTGGCAGCAGGGGAACGTCTTCTCATGCTCCGTGATGCATGAGGCTCTGC ACAACCACTACACGCAGAAGAGCCTCTCCCTGTCTCCGGGTAAA |
| 32 | HC-11 | 07C, 09C | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCAGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGAATCTGCTAATGAAC AGCCTGAGAGCTGAGGACACGGCTCTGTTTTACTGTGCGAGAGGATACGAT GTTTTGACTGGTTACCCCGACTACTGGGGCCAGGGAACCCTGGTCACCGT CTCCTCAGCCTCGACGAAGGGGCCGTCCGTATTTCCGCTTGCGCCCTCGT CGAAGTCAACTTCGGGAGGGACCGCGGCACTTGGCTGTCTTGTCAAAGATT ACTTCCCTGAGCCAGTGACAGTCAGCTGGAATTCCGGTGCCCTCACGTCAG GAGTACATACATTCCCTGCGGTATTGCAGTCCTCCGGACTCTACTCCCTGT CGTCGGTGGTAACGGTGCCCAGCTCCAGCTTGGGGACCCAGACGTACATT TGTAACGTGAATCACAAACCAAGCAATACTAAGGTAGATAAGAAAGTAGAAC CGAAGAGCTGCGACAAGACCCACACATGTCCTCCGTGCCCCGCACCCGAG CTGTTGGGAGGACCCTCGGTGTTTTTGTTTCCTCCCAAGCCAAAGGACACG TTGATGATTTCGCGCACTCCAGAGGTCACGTGTGTAGTCGTGGACGTGTCA CATGAGGACCCCGAGGTAAAGTTCAATTGGTATGTGGACGGAGTCGAGGT CCATAACGCCAAAACAAAGCCGTGCGAAGAACAGTACGGGTCAACGTATAG GTGCGTCAGCGTCCTCACTGTGCTGCACCAAGACTGGCTCAATGGTAAAGA ATACAAGTGCAAGGTGTCGAACAAGGCCCTCCCTGCCCCTATCGAGAAAAC CATCTCCAAAGCGAAGGGGCAGCCGCGAGAACCCAAGTCTACACGCTGC CGCCCTCGCGGGAGGAAATGACCAAAAACCAGGTGTCGCTTACGTGTCTT GTGAAAGGGTTCTATCCATCAGATATCGCGGTCGAGTGGGAGTCGAACGG CCAGCCCGAAAACAATTACAAAACAACACCTCCGGTCCTCGATTCAGATGG AAGCTTCTTCTTGTATTCGAAGCTGACCGTCGATAAGTCAAGGTGGCAACA GGGAAATGTGTTCTCGTGCTCAGTGATGCACGAGGCTCTGCATAACCACTA TACGCAGAAATCATTGTCGCTCAGCCCCGGTAAA |
| 33 | HC-12 | 08A, 10A, 13A, 14A, 15A | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCAGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGTATCTGCAAATGAAC AGCCTGAGAGCTGAGGACACGGCTCTGTTTTACTGTGCGAGAGGATACGAT GTTTTGACTGGTTACCCCGACTACTGGGGCCAGGGAACCCTGGTCACCGT CTCCTCAGCTTCCACCAAGGGCCCATCCGTCTTCCCCCTGGCGCCCTGCT CCAGGAGCACCTCCGAGAGCACAGCCGCCCTGGGCTGCCTGGTCAAGGA CTACTTCCCCGAACCGGTGACGGTGTCGTGGAACTCAGGCGCTCTGACCA GCGGCGTGCACACCTTCCCAGCTGTCCTACAGTCCTCAGGACTCTACTCCC TCAGCAGCGTGGTGACCGTGCCCTCCAGCAACTTCGGCACCCAGACCTAC ACCTGCAACGTAGATCACAAGCCCAGCAACACCAAGGTGGACAAGACAGTT GAGCGCAAATGTTGTGTCGAGTGCCCACCGTGCCCAGCACCACCTGTGGC AGGACCGTCAGTCTTCCTCTTCCCCCCAAAACCCAAGGACACCCTCATGAT CTCCCGGACCCCTGAGGTCACGTGCGTGGTGGTGGACGTGAGCCACGAA GACCCCGAGGTCCAGTTCAACTGGTACGTGGACGGCGTGGAGGTGCATAA TGCCAAGACAAAGCCACGGGAGGAGCAGTTCAACAGCACGTTCCGTGTGG TCAGCGTCCTCACCGTTGTGCACCAGGACTGGCTGAACGGCAAGGAGTAC AAGTGCAAGGTCTCCAACAAAGCCCTCCCAGCCCCCATCGAGAAAACCATC TCCAAAACCAAAGGGCAGCCCCGAGAACCACAGGTGTACACCCTGCCCCC ATCCCGGGAGGAGATGACCAAGAACCAGGTCAGCCTGACCTGCCTGGTCA AAGGCTTCTACCCCAGCGACATCGCCGTGGAGTGGGAGAGCAATGGGCAG CCGGAGAACAACTACAAGACCACACCTCCCATGCTGGACTCCGACGGCTC CTTCTTCCTCTACAGCAAGCTCACCGTGGACAAGAGCAGGTGGCAGCAGG |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | GGAACGTCTTCTCATGCTCCGTGATGCATGAGGCTCTGCACAACCACTACA CGCAGAAGAGCCTCTCCCTGTCTCCGGGTAAA |
| 34 | HC-13 | 08B, 10B, 13B, 14B, 15B | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCAGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGTATCTGCAAATGAAC AGCCTGAGAGCTGAGGACACGGCTCTGTTTTACTGTGCGAGAGGATACGAT GTTTTGACTGGTTACCCCGACTACTGGGGCCAGGGAACCCTGGTCACCGT CTCCTCAGCCTCCACCAAGGGCCCATCGGTCTTCCCCCTGGCACCCTCCT CCAAGAGCACCTCTGGGGGCACAGCGGCCCTGGGCTGCCTGGTCAAGGA CTACTTCCCCGAACCGGTGACGGTGTCGTGGAACTCAGGCGCCCTGACCA GCGGCGTGCACACCTTCCCGGCTGTCCTACAGTCCTCAGGACTCTACTCC CTCAGCAGCGTGGTGACCGTGCCCTCCAGCAGCTTGGGCACCCAGACCTA CATCTGCAACGTGAATCACAAGCCCAGCAACACCAAGGTGGACAAGAAAGT TGAGCCCAAATCTTGTGACAAAACTCACACATGCCCACCGTGCCCAGCACC TGAACTCCTGGGGGGACCGTCAGTCTTCCTCTTCCCCCCAAAACCCAAGGA CACCCTCATGATCTCCCGGACCCCTGAGGTCACATGCGTGGTGGTGGACG TGAGCCACGAAGACCCTGAGGTCAAGTTCAACTGGTACGTGGACGGCGTG GAGGTGCATAATGCCAAGACAAAGCCGCGGGAGGAGCAGTACGGCAGCAC GTACCGTGTGGTCAGCGTCCTCACCGTCCTGCACCAGGACTGGCTGAATG GCAAGGAGTACAAGTGCAAGGTCTCCAACAAAGCCCTCCCAGCCCCCATC GAGAAAACCATCTCCAAAGCCAAAGGGCAGCCCCGAGAACCACAGGTGTA CACCCTGCCCCCATCCCGGGAGGAGATGACCAAGAACCAGGTCAGCCTGA CCTGCCTGGTCAAAGGCTTCTATCCCAGCGACATCGCCGTGGAGTGGGAG AGCAATGGGCAGCCGGAGAACAACTACAAGACCACGCCTCCCGTGCTGGA CTCCGACGGCTCCTTCTTCCTCTATAGCAAGCTCACCGTGGACAAGAGCAG GTGGCAGCAGGGGAACGTCTTCTCATGCTCCGTGATGCATGAGGCTCTGC ACAACCACTACACGCAGAAGAGCCTCTCCCTGTCTCCGGGTAAA |
| 35 | HC-14 | 08C, 10C, 13C, 14C, 15C | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCAGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGTATCTGCAAATGAAC AGCCTGAGAGCTGAGGACACGGCTCTGTTTTACTGTGCGAGAGGATACGAT GTTTTGACTGGTTACCCCGACTACTGGGGCCAGGGAACCCTGGTCACCGT CTCCTCAGCCTCGACGAAGGGCCGTCCGTATTTCCGCTTGCGCCCTCGT CGAAGTCAACTTCGGGAGGGACCGCGGCACTTGGCTGTCTTGTCAAAGATT ACTTCCCTGAGCCAGTGACAGTCAGCTGGAATTCCGGTGCCCTCACGTCAG GAGTACATACATTCCCTGCGGTATTGCAGTCCTCCGGACTCTACTCCCTGT CGTCGGTGGTAACGGTGCCCAGCTCCAGCTTGGGGACCCAGACGTACATT TGTAACGTGAATCACAAACCAAGCAATACTAAGGTAGATAAGAAAGTAGAAC CGAAGAGCTGCGACAAGACCCACACATGTCCTCCGTGCCCCGCACCCGAG CTGTTGGGAGGACCCTCGGTGTTTTTGTTTCCTCCCAAGCCAAAGGACACG TTGATGATTTCGCGCACTCCAGAGGTCACGTGTGTAGTCGTGGACGTGTCA CATGAGGACCCCGAGGTAAAGTTCAATTGGTATGTGGACGGAGTCGAGGT CCATAACGCCAAAACAAAGCCGTGCGAAGAACAGTACGGGTCAACGTATAG GTGCGTCAGCGTCCTCACTGTGCTGCACCAAGACTGGCTCAATGGTAAAGA ATACAAGTGCAAGGTGTCGAACAAGGCCCTCCCTGCCCCTATCGAGAAAAC CATCTCCAAAGCGAAGGGGCAGCCGCGAGAACCCCAAGTCTACACGCTGC CGCCCTCGCGGGAGGAAATGACCAAAAACCAGGTGTCGCTTACGTGTCTT GTGAAAGGGTTCTATCCATCAGATATCGCGGTCGAGTGGGAGTCGAACGG CCAGCCCGAAAACAATTACAAAACAACACCTCCGGTCCTCGATTCAGATGG AAGCTTCTTCTTGTATTCGAAGCTGACCGTCGATAAGTCAAGGTGGCAACA GGGAAATGTTCTCGTGCTCAGTGATGCACGAGGCTCTGCATAACCACTA TACGCAGAAATCATTGTCGCTCAGCCCCGGTAAA |
| 36 | HC-15 | 12A | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTGCCA TGCACTGGGTCCGCCGGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGAATCTGCTAATGGA CAGCCTGAGAGCTGAGGACACGGCTCTGTTTTACTGTGCGAGAGGATACG ATGTTTTGACTGGTTACCCCGACTACTGGGGCCAGGGAACCCTGGTCACC GTCTCCTCAGCTTCCACCAAGGGCCCATCGGTCTTCCCCCTGGCGCCCTG CTCCAGGAGCACCTCCGAGAGCACAGCCGCCCTGGGCTGCCTGGTCAAG GACTACTTCCCCGAACCGGTGACGGTGTCGTGGAACTCAGGCGCTCTGAC CAGCGGCGTGCACACCTTCCCAGCTGTCCTACAGTCCTCAGGACTCTACTC CCTCAGCAGCGTGGTGACCGTGCCCTCCAGCAACTTCGGCACCCAGACCT ACACCTGCAACGTAGATCACAAGCCCAGCAACACCAAGGTGGACAAGACA GTTGAGCGCAAATGTTGTGTCGAGTGCCCACCGTGCCCAGCACCACCTGT GGCAGGACCGTCAGTCTTCCTCTTCCCCCCAAAACCCAAGGACACCCTCAT |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | GATCTCCCGGACCCCTGAGGTCACGTGCGTGGTGGTGGACGTGAGCCACG AAGACCCCGAGGTCCAGTTCAACTGGTACGTGGACGGCGTGGAGGTGCAT AATGCCAAGACAAAGCCACGGGAGGAGCAGTTCAACAGCACGTTCCGTGT GGTCAGCGTCCTCACCGTTGTGCACCAGGACTGGCTGAACGGCAAGGAGT ACAAGTGCAAGGTCTCCAACAAAGGCCTCCCAGCCCCCATCGAGAAAACCA TCTCCAAAACCAAAGGGCAGCCCCGAGAACCACAGGTGTACACCCTGCCC CCATCCCGGGAGGAGATGACCAAGAACCAGGTCAGCCTGACCTGCCTGGT CAAAGGCTTCTACCCCAGCGACATCGCCGTGGAGTGGGAGAGCAATGGGC AGCCGGAGAACAACTACAAGACCACACCTCCCATGCTGGACTCCGACGGC TCCTTCTTCCTCTACAGCAAGCTCACCGTGGACAAGAGCAGGTGGCAGCAG GGGAACGTCTTCTCATGCTCCGTGATGCATGAGGCTCTGCACAACCACTAC ACGCAGAAGAGCCTCTCCCTGTCTCCGGGTAAA |
| 37 | HC-16 | 12B | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCGGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGAATCTGCTAATGGA CAGCCTGAGAGCTGAGGACACGGCTCTGTTTTACTGTGCGAGAGGATACG ATGTTTTGACTGGTTACCCCGACTACTGGGGCCAGGGAACCCTGGTCACC GTCTCCTCAGCCTCCACCAAGGGCCCATCGGTCTTCCCCCTGGCACCCTC CTCCAAGAGCACCTCTGGGGGCACAGCGGCCCTGGGCTGCCTGGTCAAG GACTACTTCCCCGAACCGGTGACGGTGTCGTGGAACTCAGGCGCCCTGAC CAGCGGCGTGCACACCTTCCCGGCTGTCCTACAGTCCTCAGGACTCTACTC CCTCAGCAGCGTGGTGACCGTGCCCTCCAGCAGCTTGGGCACCCAGACCT ACATCTGCAACGTGAATCACAAGCCCAGCAACACCAAGGTGGACAAGAAAG TTGAGCCCAAATCTTGTGACAAAACTCACACATGCCCACCGTGCCCAGCAC CTGAACTCCTGGGGGGACCGTCAGTCTTCCTCTTCCCCCCAAAACCCAAGG ACACCCTCATGATCTCCCGGACCCCTGAGGTCACATGCGTGGTGGTGGAC GTGAGCCACGAAGACCCTGAGGTCAAGTTCAACTGGTACGTGGACGGCGT GGAGGTGCATAATGCCAAGACAAAGCCGCGGGAGGAGCAGTACGGCAGC ACGTACCGTGTGGTCAGCGTCCTCACCGTCCTGCACCAGGACTGGCTGAA TGGCAAGGAGTACAAGTGCAAGGTCTCCAACAAAGCCCTCCCAGCCCCCA TCGAGAAAACCATCTCCAAAGCCAAAGGGCAGCCCCGAGAACCACAGGTG TACACCCTGCCCCCATCCCGGGAGGAGATGACCAAGAACCAGGTCAGCCT GACCTGCCTGGTCAAAGGCTTCTATCCCAGCGACATCGCCGTGGAGTGGG AGAGCAATGGGCAGCCGGAGAACAACTACAAGACCACGCCTCCCGTGCTG GACTCCGACGGCTCCTTCTTCCTCTATAGCAAGCTCACCGTGGACAAGAGC AGGTGGCAGCAGGGGAACGTCTTCTCATGCTCCGTGATGCATGAGGCTCT GCACAACCACTACACGCAGAAGAGCCTCTCCCTGTCTCCGGGTAAA |
| 38 | HC-17 | 12C | CAGGTGCAGCTGGTGGAGTCTGGGGGAGGCGTGGTCCAGCCTGGGAGGT CCCTGCGACTCTCCTGTGCAGCCTCTGGATTCACCTTCAGTAGATTTGCCA TGCACTGGGTCCGCCGGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGAATCTGCTAATGGA CAGCCTGAGAGCTGAGGACACGGCTCTGTTTTACTGTGCGAGAGGATACG ATGTTTTGACTGGTTACCCCGACTACTGGGGCCAGGGAACCCTGGTCACC GTCTCCTCAGCCTCGACGAAGGGGCCGTCCGTATTTCCGCTTGCGCCCTC GTCGAAGTCAACTTCGGGAGGGACCGCGGCACTTGGCTGTCTTGTCAAAG ATTACTTCCCTGAGCCAGTGACAGTCAGCTGGAATTCCGGTGCCCTCACGT CAGGAGTACATACATTCCCTGCGGTATTGCAGTCCTCCGGACTCTACTCCC TGTCGTCGGTGGTAACGGTGCCCAGCTCCAGCTTGGGGACCCAGACGTAC ATTTGTAACGTGAATCACAAACCAAGCAATACTAAGGTAGATAAGAAAGTAG AACCGAAGAGCTGCGACAAGACCCACACATGTCCTCCGTGCCCCGCACCC GAGCTGTTGGGAGGACCCTCGGTGTTTTTGTTTCCTCCCAAGCCAAAGGAC ACGTTGATGATTTCGCGCACTCCAGAGGTCACGTGTGTAGTCGTGGACGTG TCACATGAGGACCCCGAGGTAAAGTTCAATTGGTATGTGGACGGAGTCGAG GTCCATAACGCCAAAACAAAGCCGTGCGAAGAACAGTACGGGTCAACGTAT AGGTGCGTCAGCGTCCTCACTGTGCTGCACCAAGACTGGCTCAATGGTAAA GAATACAAGTGCAAGGTGTCGAACAAGCCCTCCCTGCCCCTATCGAGAAA ACCATCTCCAAAGCGAAGGGGCAGCCGCGAGAACCCCAAGTCTACACGCT GCCGCCCTCGCGGGAGGAAATGACCAAAAACCAGGTGTCGCTTACGTGTC TTGTGAAAGGGTTCTATCCATCAGATATCGCGGTCGAGTGGGAGTCGAACG GCCAGCCCGAAAACAATTACAAAACAACACCTCCGGTCCTCGATTCAGATG GAAGCTTCTTCTTGTATTCGAAGCTGACCGTCGATAAGTCAAGGTGGCAAC AGGGAAATGTGTTCTCGTGCTCAGTGATGCACGAGGCTCTGCATAACCACT ATACGCAGAAATCATTGTCGCTCAGCCCCGGTAAA |
| 39 | HC-18 | 16A, 18A | CAAGTTCAGTTGGTGCAATCTGGAGCCGAAGTAAAGAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGCAATAAGTACTACGCCGAGTCTGTTAAGGGTCGGG TCACAATGACACGGGACACCTCAACCAGTACAGCCTATATGGAACTGTCTA |

TABLE 1B-continued

Exemplary Anti-hPAC1 Antibody Heavy Chain Nucleic Acid Sequences

| SEQ ID Seq NO:Group | Antibodies containing sequence | HC NA Sequence |
|---|---|---|
| | | GCCTGAGATCCGAGGACACCGCTGTGTATTATTGCGCTAGGGGGTACGAT GTATTGACGGGTTATCCTGATTACTGGGGGCAGGGGACACTCGTAACCGTC TCTAGTGCCTCCACCAAGGGCCCATCGGTCTTCCCCCTGGCGCCCTGCTC CAGGAGCACCTCCGAGAGCACAGCGGCCCTGGGCTGCCTGGTCAAGGAC TACTTCCCCGAACCGGTGACGGTGTCGTGGAACTCAGGCGCTCTGACCAG CGGCGTGCACACCTTCCCAGCTGTCCTACAGTCCTCAGGACTCTACTCCCT CAGCAGCGTGGTGACCGTGCCCTCCAGCAACTTCGGCACCCAGACCTACA CCTGCAACGTAGATCACAAGCCCAGCAACACCAAGGTGGACAAGACAGTT GAGCGCAAATGTTGTGTCGAGTGCCCACCGTGCCCAGCACCACCTGTGGC AGGACCGTCAGTCTTCCTCTTCCCCCCAAAACCCAAGGACACCCTCATGAT CTCCCGGACCCCTGAGGTCACGTGCGTGGTGGTGGACGTGAGCCACGAA GACCCCGAGGTCCAGTTCAACTGGTACGTGGACGGCGTGGAGGTGCATAA TGCCAAGACAAAGCCACGGGAGGAGCAGTTCAACAGCACGTTCCGTGTGG TCAGCGTCCTCACCGTTGTGCACCAGGACTGGCTGAACGGCAAGGAGTAC AAGTGCAAGGTCTCCAACAAAGGCCTCCCAGCCCCCATCGAGAAAACCATC TCCAAAACCAAAGGGCAGCCCCGAGAACCACAGGTGTACACCCTGCCCCC ATCCCGGGAGGAGATGACCAAGAACCAGGTCAGCCTGACCTGCCTGGTCA AAGGCTTCTACCCCAGCGACATCGCCGTGGAGTGGGAGAGCAATGGGCAG CCGGAGAACAACTACAAGACCACACCTCCCATGCTGGACTCCGACGGCTC CTTCTTCCTCTACAGCAAGCTCACCGTGGACAAGAGCAGGTGGCAGCAGG GGAACGTCTTCTCATGCTCCGTGATGCATGAGGCTCTGCACAACCACTACA CGCAGAAGAGCCTCTCCCTGTCTCCGGGTAAA |
| 40 HC-19 | 16B, 18B | CAAGTTCAGTTGGTGCAATCTGGAGCCGAAGTAAAGAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAACCAGTACAGCCTATATGGAACTGTCTA GCCTGAGATCCGAGGACACCGCTGTGTATTATTGCGCTAGGGGGTACGAT GTATTGACGGGTTATCCTGATTACTGGGGCAGGGGACACTCGTAACCGTC TCTAGTGCCTCCACCAAGGGCCCATCGGTCTTCCCCCTGGCACCCTCCTCC AAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCG GCGTGCACACCTTCCCGGCTGTCCTACAGTCCTCAGGACTCTACTCCCTCA GCAGCGTGGTGACCGTGCCCTCCAGCAGCTTGGGCACCCAGACCTACATC TGCAACGTGAATCACAAGCCCAGCAACACCAAGGTGGACAAGAAAGTTGAG CCCAAATCTTGTGACAAAACTCACACATGCCCACCGTGCCCAGCACCTGAA CTCCTGGGGGGACCGTCAGTCTTCCTCTTCCCCCCAAAACCCAAGGACAC CCTCATGATCTCCCGGACCCCTGAGGTCACATGCGTGGTGGTGGACGTGA GCCACGAAGACCCTGAGGTCAAGTTCAACTGGTACGTGGACGGCGTGGAG GTGCATAATGCCAAGACAAAGCCGCGGGAGGAGCAGTACGGCAGCACGTA CCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAG AAAACCATCTCCAAAGCCAAAGGGCAGCCCCGAGAACCACAGGTGTACAC CCTGCCCCCATCCCGGGAGGAGATGACCAAGAACCAGGTCAGCCTGACCT GCCTGGTCAAAGGCTTCTATCCCAGCGACATCGCCGTGGAGTGGGAGAGC AATGGGCAGCCGGAGAACAACTACAAGACCACGCCTCCCGTGCTGGACTC CGACGGCTCCTTCTTCCTCTATAGCAAGCTCACCGTGGACAAGAGCAGGTG GCAGCAGGGGAACGTCTTCTCATGCTCCGTGATGCATGAGGCTCTGCACA ACCACTACACGCAGAAGAGCCTCTCCCTGTCTCCGGGTAAA |
| 41 HC-20 | 16C, 18C | CAAGTTCAGTTGGTGCAATCTGGAGCCGAAGTAAAGAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAACCAGTACAGCCTATATGGAACTGTCTA GCCTGAGATCCGAGGACACCGCTGTGTATTATTGCGCTAGGGGGTACGAT GTATTGACGGGTTATCCTGATTACTGGGGCAGGGGACACTCGTAACCGTC TCTAGTGCCTCGACGAAGGGGCCGTCGTATTTCCGCTTGCGCCCTCGTC GAAGTCAACTTCGGGAGGGACCGCGGCACTTGGCTGTCTTGTCAAAGATTA CTTCCCTGAGCCAGTGACAGTCAGCTGGAATTCCGGTGCCCTCACGTCAG GAGTACATACATTCCCTGCGGTATTGCAGTCCTCCGGACTCTACTCCCTGT CGTCGGTGGTAACGGTGCCCAGCTCCAGCTTGGGACCCAGACGTACATT TGTAACGTGAATCACAAACCAAGCAATACTAAGGTAGATAAGAAAGTAGAAC CGAAGAGCTGCGACAAGACCCACACATGTCCTCCGTGCCCCGCACCCGAG CTGTTGGGAGGACCCTCGGTGTTTTTGTTTCCTCCCAAGCCAAAGGACACG TTGATGATTTCGCGCACTCCAGAGGTCACGTGTGTAGTCGTGGACGTGTCA CATGAGGACCCCGAGGTAAAGTTCAATTGGTATGTGGACGGAGTCGAGGT CCATAACGCCAAAACAAAGCCGTGCGAAGAACGATCGGGTCAACGTATAG GTGCGTCAGCGTCCTCACTGTGCTGCACCAAGACTGGCTCAATGGTAAAGA ATACAAGTGCAAGGTGTCGAACAAGGCCCTCCCTGCCCCTATCGAGAAAAC CATCTCCAAAGCGAAGGGGCAGCCGCGAGAACCCAAGTCTACACGCTGC CGCCCCTCGCGGGAGGAAATGACCAAAAACCAGGTGTCGCTTACGTGTCTT GTGAAAGGGGTTCTATCCATCAGATATCGCGGTCGAGTGGGAGTCGAACGG |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | CCAGCCCGAAAACAATTACAAAACAACACCTCCGGTCCTCGATTCAGATGG<br>AAGCTTCTTCTTGTATTCGAAGCTGACCGTCGATAAGTCAAGGTGGCAACA<br>GGGAAATGTGTTCTCGTGCTCAGTGATGCACGAGGCTCTGCATAACCACTA<br>TACGCAGAAATCATTGTCGCTCAGCCCCGGTAAA |
| 42 | HC-21 | 17A, 19A | CAAGTTCAGTTGGTGCAATCTGGAGCCGAAGTAAAGAAGCCAGGAGCTTCA<br>GTGAAAGTCTCTTGTGCCGCAAGTGGATTCACGTTTAGCCGCTTTGCCATG<br>CATTGGGTGCGGCAAGCTCCCGGTCAGGGGTTGGAGTGGATGGGAGTTAT<br>TAGCTATGACGGGGGCAATAAGTACTACGCCGAGTCTGTTAAGGGTCGGG<br>TCACAATGACACGGGACAACTCAAAAAATACAGCCTATATGGAACTGTCTAG<br>CCTGAGATCCGAGGACACCGCTGTGTATTATTGCGCTAGGGGGTACGATGT<br>ATTGACGGGTTATCCTGATTACTGGGGGCAGGGGACACTCGTAACCGTCTC<br>TAGTGCCTCCACCAAGGGCCCATCGGTCTTCCCCCTGGCGCCCTGCTCCA<br>GGAGCACCTCCGAGAGCACAGCGGCCCTGGGCTGCCTGGTCAAGGACTA<br>CTTCCCCGAACCGGTGACGGTGTCGTGGAACTCAGGCGCTCTGACCAGCG<br>GCGTGCACACCTTCCCAGCTGTCCTACAGTCCTCAGGACTCTACTCCCTCA<br>GCAGCGTGGTGACCGTGCCCTCCAGCAACTTCGGCACCCAGACCTACACC<br>TGCAACGTAGATCACAAGCCCAGCAACACCAAGGTGGACAAGACAGTTGA<br>GCGCAAATGTTGTGTCGAGTGCCCACCGTGCCCAGCACCACCTGTGGCAG<br>GACCGTCAGTCTTCCTCTTCCCCCCAAAACCCAAGGACACCCTCATGATCT<br>CCCCGGACCCCTGAGGTCACGTGCGTGGTGGTGGACGTGAGCCACGAAGA<br>CCCCGAGGTCCAGTTCAACTGGTACGTGGACGGCGTGGAGGTGCATAATG<br>CCAAGACAAAGCCACGGGAGGAGCAGTTCAACAGCACGTTCCGTGTGGTC<br>AGCGTCCTCACCGTTGTGCACCAGGACTGGCTGAACGGCAAGGAGTACAA<br>GTGCAAGGTCTCCAACAAAGGCCTCCCAGCCCCCATCGAGAAAACCATCTC<br>CAAAACCAAAGGGCAGCCCCGAGAACCACAGGTGTACACCCTGCCCCCAT<br>CCCGGGAGGAGATGACCAAGAACCAGGTCAGCCTGACCTGCCTGGTCAAA<br>GGCTTCTACCCCAGCGACATCGCCGTGGAGTGGGAGAGCAATGGGCAGCC<br>GGAGAACAACTACAAGACCACACCTCCCATGCTGGACTCCGACGGCTCCTT<br>CTTCCTCTACAGCAAGCTCACCGTGGACAAGAGCAGGTGGCAGCAGGGGA<br>ACGTCTTCTCATGCTCCGTGATGCATGAGGCTCTGCACAACCACTACACGC<br>AGAAGAGCCTCTCCCTGTCTCCGGGTAAA |
| 43 | HC-22 | 17B, 19B | CAAGTTCAGTTGGTGCAATCTGGAGCCGAAGTAAAGAAGCCAGGAGCTTCA<br>GTGAAAGTCTCTTGTGCCGCAAGTGGATTCACGTTTAGCCGCTTTGCCATG<br>CATTGGGTGCGGCAAGCTCCCGGTCAGGGGTTGGAGTGGATGGGAGTTAT<br>TAGCTATGACGGGGGCAATAAGTACTACGCCGAGTCTGTTAAGGGTCGGG<br>TCACAATGACACGGGACAACTCAAAAAATACAGCCTATATGGAACTGTCTAG<br>CCTGAGATCCGAGGACACCGCTGTGTATTATTGCGCTAGGGGGTACGATGT<br>ATTGACGGGTTATCCTGATTACTGGGGGCAGGGGACACTCGTAACCGTCTC<br>TAGTGCCTCCACCAAGGGCCCATCGGTCTTCCCCCTGGCACCCTCCTCCAA<br>GAGCACCTCTGGGGGCACAGCGGCCCTGGGCTGCCTGGTCAAGGACTACT<br>TCCCCGAACCGGTGACGGTGTCGTGGAACTCAGGCGCCCTGACCAGCGG<br>CGTGCACACCTTCCCGGCTGTCCTACAGTCCTCAGGACTCTACTCCCTCAG<br>CAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAG<br>CCCAAATCTTGTGACAAAACTCACACATGCCCACCGTGCCCAGCACCTGAA<br>CTCCTGGGGGGACCGTCAGTCTTCCTCTTCCCCCCAAAACCCAAGGACAC<br>CCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAG<br>GTGCATAATGCCAAGACAAAGCCGCGGGAGGAGCAGTACGGCAGCACGTA<br>CCGTGTGGTCAGCGTCCTCACCGTCCTGCACCAGGACTGGCTGAATGGCA<br>AGGAGTACAAGTGCAAGGTCTCCAACAAAGCCCTCCCAGCCCCCATCGAG<br>AAAACCATCTCCAAAGCCAAAGGGCAGCCCCGAGAACCACAGGTGTACAC<br>CCTGCCCCCATCCCGGGAGGAGATGACCAAGAACCAGGTCAGCCTGACCT<br>GCCTGGTCAAAGGCTTCTATCCCAGCGACATCGCCGTGGAGTGGGAGAGC<br>AATGGGCAGCCGGAGAACAACTACAAGACCACGCCTCCCGTGCTGGACTC<br>CGACGGCTCCTTCTTCCTCTATAGCAAGCTCACCGTGGACAAGAGCAGGTG<br>GCAGCAGGGGAACGTCTTCTCATGCTCCGTGATGCATGAGGCTCTGCACA<br>ACCACTACACGCAGAAGAGCCTCTCCCTGTCTCCGGGTAAA |
| 44 | HC-23 | 17C, 19C | CAAGTTCAGTTGGTGCAATCTGGAGCCGAAGTAAAGAAGCCAGGAGCTTCA<br>GTGAAAGTCTCTTGTGCCGCAAGTGGATTCACGTTTAGCCGCTTTGCCATG<br>CATTGGGTGCGGCAAGCTCCCGGTCAGGGGTTGGAGTGGATGGGAGTTAT<br>TAGCTATGACGGGGGCAATAAGTACTACGCCGAGTCTGTTAAGGGTCGGG<br>TCACAATGACACGGGACAACTCAAAAAATACAGCCTATATGGAACTGTCTAG<br>CCTGAGATCCGAGGACACCGCTGTGTATTATTGCGCTAGGGGGTACGATGT<br>ATTGACGGGTTATCCTGATTACTGGGGGCAGGGGACACTCGTAACCGTCTC<br>TAGTGCCTCGACGAAGGGGCCGTCCGTATTTCCGTTGCGCCCTCGTCGA<br>AGTCAACTTCGGGAGGGACCGCGGCACTTGGCTGTCTTGTCAAAGATTACT<br>TCCCTGAGCCAGTGACAGTCAGCTGGAATTCCGGTGCCCTCACGTCAGGA<br>GTACATACATTCCCTGCGGTATTGCAGTCCTCCGGACTCTACTCCCTGTCG<br>TCGGTGGTAACGGTGCCCAGCTCCAGCTTGGGGACCCAGACGTACATTTG<br>TAACGTGAATCACAAACCAAGCAATACTAAGGTAGATAAGAAAGTAGAACC |

TABLE 1B-continued

Exemplary Anti-hPAC1 Antibody Heavy Chain Nucleic Acid Sequences

| SEQ ID NO | Seq Group | Antibodies containing sequence | HC NA Sequence |
|---|---|---|---|
| | | | GAAGAGCTGCGACAAGACCCACACATGTCCTCCGTGCCCCGCACCCGAGC TGTTGGGAGGACCCCTCGGTGTTTTTGTTTCCTCCCAAGCCAAAGGACACGT TGATGATTTCGCGCACTCCAGAGGTCACGTGTGTAGTCGTGGACGTGTCAC ATGAGGACCCCGAGGTAAAGTTCAATTGGTATGTGGACGGAGTCGAGGTC CATAACGCCAAAACAAAGCCGTGCGAAGAACAGTACGGGTCAACGTATAGG TGCGTCAGCGTCCTCACTGTGCTGCACCAAGACTGGCTCAATGGTAAAGAA TACAAGTGCAAGGTGTCGAACAAGGCCCTCCCTGCCCCTATCGAGAAAACC ATCTCCAAAGCGAAGGGGCAGCCGCGAGAACCCCAAGTCTACACGCTGCC GCCCTCGCGGGAGGAAATGACCAAAAACCAGGTGTCGCTTACGTGTCTTGT GAAAGGGTTCTATCCATCAGATATCGCGGTCGAGTGGGAGTCGAACGGCC AGCCCGAAAACAATTACAAAACAACACCTCCGGTCCTCGATTCAGATGGAA GCTTCTTCTTGTATTCGAAGCTGACCGTCGATAAGTCAAGGTGGCAACAGG GAAATGTGTTCTCGTGCTCAGTGATGCACGAGGCTCTGCATAACCACTATA CGCAGAAATCATTGTCGCTCAGCCCCGGTAAA |
| 45 | HC-24 | 20A, 21A | GAGGTGCAGCTGCTGGAGTCTGGGGGAGGCCTGGTCCAGCCTGGGGGGT CCCTGCGACTCTCCTGTGCAGCCTCTGGATTCACCTTCAGTAGATTTGCCA TGCACTGGGTCCGCCAGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGTATCTGCAAATGAAC AGCCTGAGAGCTGAGGACACGGCTGTGTATTACTGTGCGAGAGGATACGA TGTTTTGACTGGTTACCCCGACTACTGGGGCCAGGGAACCCTGGTCACCGT CTCCTCAGCTTCCACCAAGGGCCCATCCGTCTTCCCCCTGGCGCCCTGCT CCAGGAGCACCTCCGAGAGCACAGCCGCCCTGGGCTGCCTGGTCAAGGA CTACTTCCCCGAACCGGTGACGGTGTCGTGGAACTCAGGCGCTCTGACCA GCGGCGTGCACACCTTCCCAGCTGTCCTACAGTCCTCAGGACTCTACTCCC TCAGCAGCGTGGTGACCGTGCCCTCCAGCAACTTCGGCACCCAGACCTAC ACCTGCAACGTAGATCACAAGCCCAGCAACACCAAGGTGGACAAGACAGTT GAGCGCAAATGTTGTGTCGAGTGCCCACCGTGCCCAGCACCACCTGTGGC AGGACCGTCAGTCTTCCTCTTCCCCCCAAAACCCAAGGACACCCTCATGAT CTCCCGGACCCCTGAGGTCACGTGCGTGGTGGTGGACGTGAGCCACGAA GACCCCGAGGTCCAGTTCAACTGGTACGTGGACGGCGTGGAGGTGCATAA TGCCAAGACAAAGCCACGGGAGGAGCAGTTCAACAGCACGTTCCGTGTGG TCAGCGTCCTCACCGTTGTGCACCAGGACTGGCTGAACGGCAAGGAGTAC AAGTGCAAGGTCTCCAACAAAGGCCTCCCAGCCCCCATCGAGAAAACCATC TCCAAAACCAAAGGGCAGCCCCGAGAACCACAGGTGTACACCCTGCCCCC ATCCCGGGAGGAGATGACCAAGAACCAGGTCAGCCTGACCTGCCTGGTCA AAGGCTTCTACCCCAGCGACATCGCCGTGGAGTGGGAGAGCAATGGGCAG CCGGAGAACAACTACAAGACCACACCTCCCATGCTGGACTCCGACGGCTC CTTCTTCCTCTACAGCAAGCTCACCGTGGACAAGAGCAGGTGGCAGCAGG GGAACGTCTTCTCATGCTCCGTGATGCATGAGGCTCTGCACAACCACTACA CGCAGAAGAGCCTCTCCCTGTCTCCGGGTAAA |
| 46 | HC-25 | 20B, 21B | GAGGTGCAGCTGCTGGAGTCTGGGGGAGGCCTGGTCCAGCCTGGGGGGT CCCTGCGACTCTCCTGTGCAGCCTCTGGATTCACCTTCAGTAGATTTGCCA TGCACTGGGTCCGCCAGGCTCCAGGCAAGGGGCTGGAGTGGGTGGCAGT TATATCATATGATGGAGGAAATAAATACTATGCAGAGTCCGTGAAGGGCCG GTTCACCATCTCCAGAGACAATTCCAAGAACACCCTGTATCTGCAAATGAAC AGCCTGAGAGCTGAGGACACGGCTGTGTATTACTGTGCGAGAGGATACGA TGTTTTGACTGGTTACCCCGACTACTGGGGCCAGGGAACCCTGGTCACCGT CTCCTCAGCCTCCACCAAGGGCCCATCGGTCTTCCCCCTGGCACCCTCCT CCAAGAGCACCTCTGGGGGCACAGCGGCCCTGGGCTGCCTGGTCAAGGA CTACTTCCCCGAACCGGTGACGGTGTCGTGGAACTCAGGCGCCCTGACCA GCGGCGTGCACACCTTCCCGGCTGTCCTACAGTCCTCAGGACTCTACTCC CTCAGCAGCGTGGTGACCGTGCCCTCCAGCAGCTTGGGCACCCAGACCTA CATCTGCAACGTGAATCACAAGCCCAGCAACACCAAGGTGGACAAGAAAGT TGAGCCCAAATCTTGTGACAAAACTCACACATGCCCACCGTGCCCAGCACC TGAACTCCTGGGGGGACCGTCAGTCTTCCTCTTCCCCCCAAAACCCAAGGA CACCCTCATGATCTCCCGGACCCCTGAGGTCACATGCGTGGTGGTGGACG TGAGCCACGAAGACCCTGAGGTCAAGTTCAACTGGTACGTGGACGGCGTG GAGGTGCATAATGCCAAGACAAAGCCGCGGGAGGAGCAGTACGGCAGCAC GTACCGTGTGGTCAGCGTCCTCACCGTCCTGCACCAGGACTGGCTGAATG GCAAGGAGTACAAGTGCAAGGTCTCCAACAAAGCCCTCCCAGCCCCCATC GAGAAAACCATCTCCAAAGCCAAAGGGCAGCCCCGAGAACCACAGGTGTA CACCCTGCCCCCATCCCGGGAGGAGATGACCAAGAACCAGGTCAGCCTGA CCTGCCTGGTCAAAGGCTTCTATCCCAGCGACATCGCCGTGGAGTGGGAG AGCAATGGGCAGCCGGAGAACAACTACAAGACCACGCCTCCCGTGCTGGA CTCCGACGGCTCCTTCTTCCTCTATAGCAAGCTCACCGTGGACAAGAGCAG GTGGCAGCAGGGGAACGTCTTCTCATGCTCCGTGATGCATGAGGCTCTGC ACAACCACTACACGCAGAAGAGCCTCTCCCTGTCTCCGGGTAAA |
| 47 | HC-26 | 20C, 21C | GAGGTGCAGCTGCTGGAGTCTGGGGGAGGCCTGGTCCAGCCTGGGGGGT CCCTGCGACTCTCCTGTGCAGCCTCTGGATTCACCTTCAGTAGATTTGCCA TGCACTGGGTCCGCCAGGCTCCAGGCAAGGGGCTGGAGTGGGTGGCAGT |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | TATATCATATGATGGAGGAAATAAATACTATGCAGAGTCCGTGAAGGGCCG<br>GTTCACCATCTCCAGAGACAATTCCAAGAACACCCTGTATCTGCAAATGAAC<br>AGCCTGAGAGCTGAGGACACGGCTGTGTATTACTGTGCGAGAGGATACGA<br>TGTTTTGACTGGTTACCCCGACTACTGGGGCCAGGGAACCCTGGTCACCGT<br>CTCCTCAGCCTCGACGAAGGGGCCGTCCGTATTTCCGCTTGCGCCCTCGT<br>CGAAGTCAACTTCGGGAGGGACCGCGGCACTTGGCTGTCTTGTCAAAGATT<br>ACTTCCCTGAGCCAGTGACAGTCAGCTGGAATTCCGGTGCCCTCACGTCAG<br>GAGTACATACATTCCCTGCGGTATTGCAGTCCTCCGGACTCTACTCCCTGT<br>CGTCGGTGGTAACGGTGCCCAGCTCCAGCTTGGGGACCCAGACGTACATT<br>TGTAACGTGAATCACAAACCAAGCAATACTAAGGTAGATAAGAAAGTAGAAC<br>CGAAGAGCTGCGACAAGACCCACACATGTCCTCCGTGCCCCGCACCCGAG<br>CTGTTGGGAGGACCCTCGGTGTTTTGTTTCCTCCCAAGCCAAAGGACACG<br>TTGATGATTTCGCGCACTCCAGAGGTCACGTGTGTAGTCGTGGACGTGTCA<br>CATGAGGACCCCGAGGTAAAGTTCAATTGGTATGTGGACGGAGTCGAGGT<br>CCATAACGCCAAAACAAAGCCGTGCGAAGAACAGTACGGGTCAACGTATAG<br>GTGCGTCAGCGTCCTCACTGTGCTGCACCAAGACTGGCTCAATGGTAAAGA<br>ATACAAGTGCAAGGTGTCGAACAAGGCCCTCCCTGCCCCTATCGAGAAAAC<br>CATCTCCAAAGCGAAGGGGCAGCCGCGAGAACCCCAAGTCTACACGCTGC<br>CGCCCTCGCGGGAGGAAATGACCAAAAACCAGGTGTCGCTTACGTGTCTT<br>GTGAAAGGGTTCTATCCATCAGATATCGCGGTCGAGTGGGAGTCGAACGG<br>CCAGCCCGAAAACAATTACAAAACAACACCTCCGGTCCTCGATTCAGATGG<br>AAGCTTCTTCTTGTATTCGAAGCTGACCGTCGATAAGTCAAGGTGGCAACA<br>GGGAAATGTGTTCTCGTGCTCAGTGATGCACGAGGCTCTGCATAACCACTA<br>TACGCAGAAATCATTGTCGCTCAGCCCCGGTAAA |
| 48 | HC-27 | 22A, 23A | CAGGTGCAGCTGCTGGAGTCTGGGGGAGGCCTGGTCCAGCCTGGGGGGT<br>CCCTGCGACTCTCCTGTGCAGCCTCTGGATTCACCTTCAGTAGATTTGCCA<br>TGCACTGGGTCCGCCAGGCTCCAGGCAAGGGGCTGGAGTGGGTGGCAGT<br>TATATCATATGATGGAGGAAATAAATACTATGCAGAGTCCGTGAAGGGCCG<br>GTTCACCATCTCCAGAGACAATTCCAAGAACACCCTGTATCTGCAAATGAAC<br>AGCCTGAGAGCTGAGGACACGGCTGTGTATTACTGTGCGAGAGGATACGA<br>TGTTTTGACTGGTTACCCCGACTACTGGGGCCAGGGAACCCTGGTCACCGT<br>CTCCTCAGCTTCCACCAAGGGCCCATCCGTCTTCCCCCTGGCGCCCTGCT<br>CCAGGAGCACCTCCGAGAGCACAGCCGCCCTGGGCTGCCTGGTCAAGGA<br>CTACTTCCCCGAACCGGTGACGGTGTCGTGGAACTCAGGCGCTCTGACCA<br>GCGGCGTGCACACCTTCCCAGCTGTCCTACAGTCCTCAGGACTCTACTCCC<br>TCAGCAGCGTGGTGACCGTGCCCTCCAGCAACTTCGGCACCCAGACCTAC<br>ACCTGCAACGTAGATCACAAGCCCAGCAACACCAAGGTGGACAAGACAGTT<br>GAGCGCAAATGTTGTGTCGAGTGCCCACCGTGCCCAGCACCACCTGTGGC<br>AGGACCGTCAGTCTTCCTCTTCCCCCCAAAACCCAAGGACACCCTCATGAT<br>CTCCCGGACCCCTGAGGTCACGTGCGTGGTGGTGGACGTGAGCCACGAA<br>GACCCCGAGGTCCAGTTCAACTGGTACGTGGACGGCGTGGAGGTGCATAA<br>TGCCAAGACAAAGCCACGGGAGGAGCAGTTCAACAGCACGTTCCGTGTGG<br>TCAGCGTCCTCACCGTTGTGCACCAGGACTGGCTGAACGGCAAGGAGTAC<br>AAGTGCAAGGTCTCCAACAAAGGCCTCCCAGCCCCCATCGAGAAAACCATC<br>TCCAAAACCAAAGGGCAGCCCCGAGAACCACAGGTGTACACCCTGCCCCC<br>ATCCCGGGAGGAGATGACCAAGAACCAGGTCAGCCTGACCTGCCTGGTCA<br>AAGGCTTCTACCCCAGCGACATCGCCGTGGAGTGGGAGAGCAATGGGCAG<br>CCGGAGAACAACTACAAGACCACACCTCCCATGCTGGACTCCGACGGCTC<br>CTTCTTCCTCTACAGCAAGCTCACCGTGGACAAGAGCAGGTGGCAGCAGG<br>GGAACGTCTTCTCATGCTCCGTGATGCATGAGGCTCTGCACAACCACTACA<br>CGCAGAAGAGCCTCTCCCTGTCTCCGGGTAAA |
| 49 | HC-28 | 22B, 23B | CAGGTGCAGCTGCTGGAGTCTGGGGGAGGCCTGGTCCAGCCTGGGGGGT<br>CCCTGCGACTCTCCTGTGCAGCCTCTGGATTCACCTTCAGTAGATTTGCCA<br>TGCACTGGGTCCGCCAGGCTCCAGGCAAGGGGCTGGAGTGGGTGGCAGT<br>TATATCATATGATGGAGGAAATAAATACTATGCAGAGTCCGTGAAGGGCCG<br>GTTCACCATCTCCAGAGACAATTCCAAGAACACCCTGTATCTGCAAATGAAC<br>AGCCTGAGAGCTGAGGACACGGCTGTGTATTACTGTGCGAGAGGATACGA<br>TGTTTTGACTGGTTACCCCGACTACTGGGGCCAGGGAACCCTGGTCACCGT<br>CTCCTCAGCCTCCACCAAGGGCCCATCGGTCTTCCCCCTGGCACCCTCCT<br>CCAAGAGCACCTCTGGGGGCACAGCGGCCCTGGGCTGCCTGGTCAAGGA<br>CTACTTCCCCGAACCGGTGACGGTGTCGTGGAACTCAGGCGCCCTGACCA<br>GCGGCGTGCACACCTTCCCGGCTGTCCTACAGTCCTCAGGACTCTACTCC<br>CTCAGCAGCGTGGTGACCGTGCCCTCCAGCAGCTTGGGCACCCAGACCTA<br>CATCTGCAACGTGAATCACAAGCCCAGCAACACCAAGGTGGACAAGAAAGT<br>TGAGCCCAAATCTTGTGACAAAACTCACACATGCCCACCGTGCCCAGCACC<br>TGAACTCCTGGGGGGACCGTCAGTCTTCCTCTTCCCCCCAAAACCCAAGGA<br>CACCCTCATGATCTCCCGGACCCCTGAGGTCACATGCGTGGTGGTGGACG<br>TGAGCCACGAAGACCCTGAGGTCAAGTTCAACTGGTACGTGGACGGCGTG<br>GAGGTGCATAATGCCAAGACAAAGCCGCGGGAGGAGCAGTACGGCAGCAC<br>GTACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCATC<br>GAGAAAACCATCTCCAAAGCCAAAGGGCAGCCCCGAGAACCACAGGTGTA |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | CACCCTGCCCCCATCCCGGGAGGAGATGACCAAGAACCAGGTCAGCCTGA<br>CCTGCCTGGTCAAAGGCTTCTATCCCAGCGACATCGCCGTGGAGTGGGAG<br>AGCAATGGGCAGCCGGAGAACAACTACAAGACCACGCCTCCCGTGCTGGA<br>CTCCGACGGCTCCTTCTTCCTCTATAGCAAGCTCACCGTGGACAAGAGCAG<br>GTGGCAGCAGGGGAACGTCTTCTCATGCTCCGTGATGCATGAGGCTCTGC<br>ACAACCACTACACGCAGAAGAGCCTCTCCCTGTCTCCGGGTAAA |
| 50 | HC-29 | 22C, 23C | CAGGTGCAGCTGCTGGAGTCTGGGGGAGGCCTGGTCCAGCCTGGGGGGT<br>CCCTGCGACTCTCCTGTGCAGCCTCTGGATTCACCTTCAGTAGATTTGCCA<br>TGCACTGGGTCCGCCAGGCTCCAGGCAAGGGGCTGGAGTGGGTGGCAGT<br>TATATCATATGATGGAGGAAATAAATACTATGCAGAGTCCGTGAAGGGCCG<br>GTTCACCATCTCCAGAGACAATTCCAAGAACACCCTGTATCTGCAAATGAAC<br>AGCCTGAGAGCTGAGGACACGGCTGTGTATTACTGTGCGAGAGGATACGA<br>TGTTTTGACTGGTTACCCCGACTACTGGGGCCAGGGAACCCTGGTCACCGT<br>CTCCTCAGCCTCGACGAAGGGGCCGTCCGTATTTCCGCTTGCGCCCTCGT<br>CGAAGTCAACTTCGGGAGGGACCGCGGCACTTGGCTGTCTTGTCAAAGATT<br>ACTTCCCTGAGCCAGTGACAGTCAGCTGGAATTCCGGTGCCCTCACGTCAG<br>GAGTACATACATTCCCTGCGGTATTGCAGTCCTCCGGACTCTACTCCCTGT<br>CGTCGGTGGTAACGGTGCCCAGCTCCAGCTTGGGGACCCAGACGTACATT<br>TGTAACGTGAATCACAAACCAAGCAATACTAAGGTAGATAAGAAAGTAGAAC<br>CGAAGAGCTGCGACAAGACCCACACATGTCCTCCGTGCCCCGCACCCGAG<br>CTGTTGGGAGGACCCTCGGTGTTTTTGTTTCCTCCCAAGCCAAAGGACACG<br>TTGATGATTTCGCGCACTCCAGAGGTCACGTGTGTAGTCGTGGACGTGTCA<br>CATGAGGACCCCGAGGTAAAGTTCAATTGGTATGTGGACGGAGTCGAGGT<br>CCATAACGCCAAAACAAAGCCGTGCGAAGAACAGTACGGGTCAACGTATAG<br>GTGCGTCAGCGTCCTCACTGTGCTGCACCAAGACTGGCTCAATGGTAAAGA<br>ATACAAGTGCAAGGTGTCGAACAAGGCCCTCCCTGCCCCTATCGAGAAAAC<br>CATCTCCAAAGCGAAGGGGCAGCCGCGAGAACCCCAAGTCTACACGCTGC<br>CGCCCTCGCGGGAGGAAATGACCAAAAACCAGGTGTCGCTTACGTGTCTT<br>GTGAAAGGGTTCTATCCATCAGATATCGCGGTCGAGTGGGAGTCGAACGG<br>CCAGCCCGAAAACAATTACAAAACAACACCTCCGGTCCTCGATTCAGATGG<br>AAGCTTCTTCTTGTATTCGAAGCTGACCGTCGATAAGTCAAGGTGGCAACA<br>GGGAAATGTGTTCTCGTGCTCAGTGATGCACGAGGCTCTGCATAACCACTA<br>TACGCAGAAATCATTGTCGCTCAGCCCCGGTAAA |
| 51 | HC-30 | 24A | CAAGTTCAGTTGGTGCAATCTGGAGCCGAAGTAAAGAAGCCAGGAGCTTCA<br>GTGAAAGTCTCTTGTAAAGCAAGTGGATTCACGTTTAGCCGCTTTGCCATG<br>CATTGGGTGCGGCAAGCTCCCGGTCAGGGGTTGGAGTGGATGGGAGTTAT<br>TAGCTATGACGGGGCAATAAGTACTACGCCGAGTCTGTTAAGGGTCGGG<br>TCACAATGACACGGGACACCTCAACCAGTACACTCTATATGGAACTGTCTA<br>GCCTGAGATCCGAGGACACCGCTGTGTATTATTGCGCTAGGGGGTACGAT<br>GTATTGACGGGTTATCCTGATTACTGGGGCAGGGGACACTCGTAACCGTC<br>TCTAGTGCCTCCACCAAGGGCCCATCGGTCTTCCCCCTGGCGCCCTGCTC<br>CAGGAGCACCTCCGAGAGCACAGCGGCCCTGGGCTGCCTGGTCAAGGAC<br>TACTTCCCCGAACCGGTGACGGTGTCGTGGAACTCAGGCGCTCTGACCAG<br>CGGCGTGCACACCTTCCCAGCTGTCCTACAGTCCTCAGGACTCTACTCCCT<br>CAGCAGCGTGGTGACCGTGCCCTCCAGCAACTTCGGCACCCAGACCTACA<br>CCTGCAACGTAGATCACAAGCCCAGCAACACCAAGGTGGACAAGACAGTT<br>GAGCGCAAATGTTGTGTCGAGTGCCCACCGTGCCCAGCACCACCTGTGGC<br>AGGACCGTCAGTCTTCCTCTTCCCCCCAAAACCCAAGGACACCCTCATGAT<br>CTCCCGGACCCCTGAGGTCACGTGCGTGGTGGTGGACGTGAGCCACGAA<br>GACCCCGAGGTCCAGTTCAACTGGTACGTGGACGGCGTGGAGGTGCATAA<br>TGCCAAGACAAAGCCACGGGAGGAGCAGTTCAACAGCACGTTCCGTGTGG<br>TCAGCGTCCTCACCGTTGTGCACCAGGACTGGCTGAACGGCAAGGAGTAC<br>AAGTGCAAGGTCTCCAACAAAGGCCTCCCAGCCCCCATCGAGAAAACCATC<br>TCCAAAACCAAAGGGCAGCCCCGAGAACCACAGGTGTACACCCTGCCCCC<br>ATCCCGGGAGGAGATGACCAAGAACCAGGTCAGCCTGACCTGCCTGGTCA<br>AAGGCTTCTACCCCAGCGACATCGCCGTGGAGTGGGAGAGCAATGGGCAG<br>CCGGAGAACAACTACAAGACCACACCTCCCATGCTGGACTCCGACGGCTC<br>CTTCTTCCTCTACAGCAAGCTCACCGTGGACAAGAGCAGGTGGCAGCAGG<br>GGAACGTCTTCTCATGCTCCGTGATGCATGAGGCTCTGCACAACCACTACA<br>CGCAGAAGAGCCTCTCCCTGTCTCCGGGTAAA |
| 52 | HC-31 | 24B | CAAGTTCAGTTGGTGCAATCTGGAGCCGAAGTAAAGAAGCCAGGAGCTTCA<br>GTGAAAGTCTCTTGTAAAGCAAGTGGATTCACGTTTAGCCGCTTTGCCATG<br>CATTGGGTGCGGCAAGCTCCCGGTCAGGGGTTGGAGTGGATGGGAGTTAT<br>TAGCTATGACGGGGCAATAAGTACTACGCCGAGTCTGTTAAGGGTCGGG<br>TCACAATGACACGGGACACCTCAACCAGTACACTCTATATGGAACTGTCTA<br>GCCTGAGATCCGAGGACACCGCTGTGTATTATTGCGCTAGGGGGTACGAT<br>GTATTGACGGGTTATCCTGATTACTGGGGCAGGGGACACTCGTAACCGTC<br>TCTAGTGCCTCCACCAAGGGCCCATCGGTCTTCCCCCTGGCACCCTCCTCC<br>AAGAGCACCTCTGGGGGCACAGCGGCCCTGGGCTGCCTGGTCAAGGACTA<br>CTTCCCCGAACCGGTGACGGTGTCGTGGAACTCAGGCGCCCTGACCAGCG<br>GCGTGCACACCTTCCCGGCTGTCCTACAGTCCTCAGGACTCTACTCCCTCA |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | GCAGCGTGGTGACCGTGCCCTCCAGCAGCTTGGGCACCCAGACCTACATC TGCAACGTGAATCACAAGCCCAGCAACACCAAGGTGGACAAGAAAGTTGAG CCCAAATCTTGTGACAAAACTCACACATGCCCACCGTGCCCAGCACCTGAA CTCCTGGGGGGACCGTCAGTCTTCCTCTTCCCCCCAAAACCCAAGGACAC CCTCATGATCTCCCGGACCCCTGAGGTCACATGCGTGGTGGTGGACGTGA GCCACGAAGACCCTGAGGTCAAGTTCAACTGGTACGTGGACGGCGTGGAG GTGCATAATGCCAAGACAAAGCCGCGGGAGGAGCAGTACGGCAGCACGTA CCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAG AAAACCATCTCCAAAGCCAAAGGGCAGCCCCGAGAACCACAGGTGTACAC CCTGCCCCCATCCCGGGAGGAGATGACCAAGAACCAGGTCAGCCTGACCT GCCTGGTCAAAGGCTTCTATCCCAGCGACATCGCCGTGGAGTGGGAGAGC AATGGGCAGCCGGAGAACAACTACAAGACCACGCCTCCCGTGCTGGACTC CGACGGCTCCTTCTTCCTCTATAGCAAGCTCACCGTGGACAAGAGCAGGTG GCAGCAGGGGAACGTCTTCTCATGCTCCGTGATGCATGAGGCTCTGCACA ACCACTACACGCAGAAGAGCCTCTCCCTGTCTCCGGGTAAA |
| 53 | HC-32 | 24C | CAAGTTCAGTTGGTGCAATCTGGAGCCGAAGTAAAGAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAACCAGTACACTCTATATGGAACTGTCTA GCCTGAGATCCGAGGACACCGCTGTGTATTATTGCGCTAGGGGGTACGAT GTATTGACGGGTTATCCTGATTACTGGGGGCAGGGGACACTCGTAACCGTC TCTAGTGCCTCGACGAAGGGGCCGTCCGTATTTCCGCTTGCGCCCTCGTC GAAGTCAACTTCGGGAGGGACCGCGGCACTTGGCTGTCTTGTCAAAGATTA CTTCCCTGAGCCAGTGACAGTCAGCTGGAATTCCGGTGCCCTCACGTCAG GAGTACATACATTCCCTGCGGTATTGCAGTCCTCCGGACTCTACTCCCTGT CGTCGGTGGTAACGGTGCCCAGCTCCAGCTTGGGGACCCAGACGTACATT TGTAACGTGAATCACAAACCAAGCAATACTAAGGTAGATAAGAAAGTAGAAC CGAAGAGCTGCGACAAGACCCACACATGTCCTCCGTGCCCCGCACCCGAG CTGTTGGGAGGACCCTCGGTGTTTTTGTTTCCTCCCAAGCCAAAGGACACG TTGATGATTTCGCGCACTCCAGAGGTCACGTGTGTAGTCGTGGACGTGTCA CATGAGGACCCCGAGGTAAAGTTCAATTGGTATGTGGACGGAGTCGAGGT CCATAACGCCAAAACAAAGCCGTGCGAAGAACAGTACGGGTCAACGTATAG GTGCGTCAGCGTCCTCACTGTGCTGCACCAAGACTGGCTCAATGGTAAAGA ATACAAGTGCAAGGTGTCGAACAAGGCCCTCCCTGCCCCTATCGAGAAAAC CATCTCCAAAGCGAAGGGGCAGCCGCGAGAACCCCAAGTCTACACGCTGC CGCCCTCGCGGGAGGAAATGACCAAAAACCAGGTGTCGCTTACGTGTCTT GTGAAAGGGTTCTATCCATCAGATATCGCGGTCGAGTGGGAGTCGAACGG CCAGCCCGAAAACAATTACAAAACAACACCTCCGGTCCTCGATTCAGATGG AAGCTTCTTCTTGTATTCGAAGCTGACCGTCGATAAGTCAAGGTGGCAACA GGGAAATGTGTTCTCGTGCTCAGTGATGCACGAGGCTCTGCATAACCACTA TACGCAGAAATCATTGTCGCTCAGCCCCGGTAAA |
| 54 | HC-33 | 25A | CAAGTTCAGTTGGTGCAATCTGGAGCCGAAGTAAAGAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAAAGAGTACAGCCTATATGGAACTGTCTA GCCTGAGATCCGAGGACACCGCTGTGTATTATTGCGCTAGGGGGTACGAT GTATTGACGGGTTATCCTGATTACTGGGGGCAGGGGACACTCGTAACCGTC TCTAGTGCCTCCACCAAGGGCCCATCGGTCTTCCCCCTGGCGCCCTGCTC CAGGAGCACCTCCGAGAGCACAGCGGCCCTGGGCTGCCTGGTCAAGGAC TACTTCCCCGAACCGGTGACGGTGTCGTGGAACTCAGGCGCTCTGACCAG CGGCGTGCACACCTTCCCAGCTGTCCTACAGTCCTCAGGACTCTACTCCCT CAGCAGCGTGGTGACCGTGCCCTCCAGCAACTTCGGCACCCAGACCTACA CCTGCAACGTAGATCACAAGCCCAGCAACACCAAGGTGGACAAGACAGTT GAGCGCAAATGTTGTGTCGAGTGCCCACCGTGCCCAGCACCACCTGTGGC AGGACCGTCAGTCTTCCTCTTCCCCCCAAAACCCAAGGACACCCTCATGAT CTCCCGGACCCCTGAGGTCACGTGCGTGGTGGTGGACGTGAGCCACGAA GACCCCGAGGTCCAGTTCAACTGGTACGTGGACGGCGTGGAGGTGCATAA TGCCAAGACAAAGCCACGGGAGGAGCAGTTCAACAGCACGTTCCGTGTGG TCAGCGTCCTCACCGTTGTGCACCAGGACTGGCTGAACGGCAAGGAGTAC AAGTGCAAGGTCTCCAACAAAGGCCTCCCAGCCCCCATCGAGAAAACCATC TCCAAAACCAAAGGGCAGCCCCGAGAACCACAGGTGTACACCCTGCCCCC ATCCCGGGAGGAGATGACCAAGAACCAGGTCAGCCTGACCTGCCTGGTCA AAGGCTTCTACCCCAGCGACATCGCCGTGGAGTGGGAGAGCAATGGGCAG CCGGAGAACAACTACAAGACCACACCTCCCATGCTGGACTCCGACGGCTC CTTCTTCCTCTACAGCAAGCTCACCGTGGACAAGAGCAGGTGGCAGCAGG GGAACGTCTTCTCATGCTCCGTGATGCATGAGGCTCTGCACAACCACTACA CGCAGAAGAGCCTCTCCCTGTCTCCGGGTAAA |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| 55 | HC-34 | 25B | CAAGTTCAGTTGGTGCAATCTGGAGCCGAAGTAAAGAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAAAGAGTACAGCCTATATGGAACTGTCTA GCCTGAGATCCGAGGACACCGCTGTGTATTATTGCGCTAGGGGGTACGAT GTATTGACGGGTTATCCTGATTACTGGGGGCAGGGGACACTCGTAACCGTC TCTAGTGCCTCCACCAAGGGCCCATCGGTCTTCCCCCTGGCACCCTCCTCC AAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCG GCGTGCACACCTTCCCGGCTGTCCTACAGTCCTCAGGACTCTACTCCCTCA GCAGCGTGGTGACCGTGCCCTCCAGCAGCTTGGGCACCCAGACCTACATC TGCAACGTGAATCACAAGCCCAGCAACACCAAGGTGGACAAGAAAGTTGAG CCCAAATCTTGTGACAAAACTCACACATGCCCACCGTGCCCAGCACCTGAA CTCCTGGGGGGACCGTCAGTCTTCCTCTTCCCCCCAAAACCCAAGGACAC CCTCATGATCTCCCGGACCCCTGAGGTCACATGCGTGGTGGTGGACGTGA GCCACGAAGACCCTGAGGTCAAGTTCAACTGGTACGTGGACGGCGTGGAG GTGCATAATGCCAAGACAAAGCCGCGGGAGGAGCAGTACGGCAGCACGTA CCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAG AAAACCATCTCCAAAGCCAAAGGGCAGCCCCGAGAACCACAGGTGTACAC CCTGCCCCCATCCCGGGAGGAGATGACCAAGAACCAGGTCAGCCTGACCT GCCTGGTCAAAGGCTTCTATCCCAGCGACATCGCCGTGGAGTGGGAGAGC AATGGGCAGCCGGAGAACAACTACAAGACCACGCCTCCCGTGCTGGACTC CGACGGCTCCTTCTTCCTCTATAGCAAGCTCACCGTGGACAAGAGCAGGTG GCAGCAGGGGAACGTCTTCTCATGCTCCGTGATGCATGAGGCTCTGCACA ACCACTACACGCAGAAGAGCCTCTCCCTGTCTCCGGGTAAA |
| 56 | HC-35 | 25C | CAAGTTCAGTTGGTGCAATCTGGAGCCGAAGTAAAGAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAAAGAGTACAGCCTATATGGAACTGTCTA GCCTGAGATCCGAGGACACCGCTGTGTATTATTGCGCTAGGGGGTACGAT GTATTGACGGGTTATCCTGATTACTGGGGGCAGGGGACACTCGTAACCGTC TCTAGTGCCTCGACGAAGGGGCCGTCCGTATTTCCGCTTGCGCCCTCGTC GAAGTCAACTTCGGGAGGGACCGCGGCACTTGGCTGTCTTGTCAAAGATTA CTTCCCTGAGCCAGTGACAGTCAGCTGGAATTCCGGTGCCCTCACGTCAG GAGTACATACATTCCCTGCGGTATTGCAGTCCTCCGGACTCTACTCCCTGT CGTCGGTGGTAACGGTGCCCAGCTCCAGCTTGGGGACCCAGACGTACATT TGTAACGTGAATCACAAACCAAGCAATACTAAGGTAGATAAGAAAGTAGAAC CGAAGAGCTGCGACAAGACCCACACATGTCCTCCGTGCCCCGCACCCGAG CTGTTGGGAGGACCCTCGGTGTTTTTGTTTCCTCCCAAGCCAAAGGACACG TTGATGATTTCGCGCACTCCAGAGGTCACGTGTGTAGTCGTGGACGTGTCA CATGAGGACCCCGAGGTAAAGTTCAATTGGTATGTGGACGGAGTCGAGGT CCATAACGCCAAAACAAAGCCGTGCGAAGAACAGTACGGGTCAACGTATAG GTGCGTCAGCGTCCTCACTGTGCTGCACCAAGACTGGCTCAATGGTAAAGA ATACAAGTGCAAGGTGTCGAACAAGGCCCTCCCTGCCCCTATCGAGAAAAC CATCTCCAAAGCGAAGGGGCAGCCGCGAGAACCCAAGTCTACACGCTGC CGCCCTCGCGGGAGGAAATGACCAAAAACCAGGTGTCGCTTACGTGTCTT GTGGAAAGGGTTCTATCCATCAGATATCGCGGTCGAGTGGGAGTCGAACGG CCAGCCCGAAAACAATTACAAAACAACACCTCCGGTCCTCGATTCAGATGG AAGCTTCTTCTTGTATTCGAAGCTGACCGTCGATAAGTCAAGGTGGCAACA GGGAAATGTGTTCTCGTGCTCAGTGATGCACGAGGCTCTGCATAACCACTA TACGCAGAAATCATTGTCGCTCAGCCCCGGTAAA |
| 57 | HC-36 | 26A, 27A | CAAGTTCAGTTGGTGGAGTCTGGAGCCGAAGTAGTAAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAACCAGTACACTCTATATGGAACTGTCTA GCCTGAGATCCGAGGACACCGCTGTGTATTATTGCGCTAGGGGGTACGAT GTATTGACGGGTTATCCTGATTACTGGGGGCAGGGGACACTCGTAACCGTC TCTAGTGCCTCCACCAAGGGCCCATCGGTCTTCCCCCTGGCGCCCTGCTC CAGGAGCACCTCCGAGAGCACAGCGGCCCTGGGCTGCCTGGTCAAGGAC TACTTCCCCGAACCGGTGACGGTGTCGTGGAACTCAGGCGCTCTGACCAG CGGCGTGCACACCTTCCCAGCTGTCCTACAGTCCTCAGGACTCTACTCCCT CAGCAGCGTGGTGACCGTGCCCTCCAGCAACTTCGGCACCCAGACCTACA CCTGCAACGTAGATCACAAGCCCAGCAACACCAAGGTGGACAAGACAGTT GAGCGCAAATGTTGTGTCGAGTGCCCACCGTGCCCAGCACCACCTGTGGC AGGACCGTCAGTCTTCCTCTTCCCCCCAAAACCCAAGGACACCCTCATGAT CTCCCGGACCCCTGAGGTCACGTGCGTGGTGGTGGACGTGAGCCACGAA GACCCCGAGGTCCAGTTCAACTGGTACGTGGACGGCGTGGAGGTGCATAA |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | TGCCAAGACAAAGCCACGGGAGGAGCAGTTCAACAGCACGTTCCGTGTGG TCAGCGTCCTCACCGTTGTGCACCAGGACTGGCTGAACGGCAAGGAGTAC AAGTGCAAGGTCTCCAACAAAGGCCTCCCAGCCCCCATCGAGAAAACCATC TCCAAAACCAAAGGGCAGCCCCGAGAACCACAGGTGTACACCCTGCCCCC ATCCCGGGAGGAGATGACCAAGAACCAGGTCAGCCTGACCTGCCTGGTCA AAGGCTTCTACCCCAGCGACATCGCCGTGGAGTGGGAGAGCAATGGGCAG CCGGAGAACAACTACAAGACCACACCTCCCATGCTGGACTCCGACGGCTC CTTCTTCCTCTACAGCAAGCTCACCGTGGACAAGAGCAGGTGGCAGCAGG GGAACGTCTTCTCATGCTCCGTGATGCATGAGGCTCTGCACAACCACTACA CGCAGAAGAGCCTCTCCCTGTCTCCGGGTAAA |
| 58 | HC-37 | 26B, 27B | CAAGTTCAGTTGGTGGAGTCTGGAGCCGAAGTAGTAAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAACCAGTACACTCTATATGGAACTGTCTA GCCTGAGATCCGAGGACACCGCTGTGTATTATTGCGCTAGGGGGTACGAT GTATTGACGGGTTATCCTGATTACTGGGGCAGGGGACACTCGTAACCGTC TCTAGTGCCTCCACCAAGGGCCCATCGGTCTTCCCCCTGGCACCCTCCTCC AAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCG GCGTGCACACCTTCCCGGCTGTCCTACAGTCCTCAGGACTCTACTCCCTCA GCAGCGTGGTGACCGTGCCCTCCAGCAGCTTGGGCACCCAGACCTACATC TGCAACGTGAATCACAAGCCCAGCAACACCAAGGTGGACAAGAAAGTTGAG CCCAAATCTTGTGACAAAACTCACACATGCCCACCGTGCCCAGCACCTGAA CTCCTGGGGGGACCGTCAGTCTTCCTCTTCCCCCCAAAACCCAAGGACAC CCTCATGATCTCCCGGACCCCTGAGGTCACATGCGTGGTGGTGGACGTGA GCCACGAAGACCCTGAGGTCAAGTTCAACTGGTACGTGGACGGCGTGGAG GTGCATAATGCCAAGACAAAGCCGCGGGAGGAGCAGTACGGCAGCACGTA CCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAG AAAACCATCTCCAAAGCCAAAGGGCAGCCCCGAGAACCACAGGTGTACAC CCTGCCCCCATCCCGGGAGGAGATGACCAAGAACCAGGTCAGCCTGACCT GCCTGGTCAAAGGCTTCTATCCCAGCGACATCGCCGTGGAGTGGGAGAGC AATGGGCAGCCGGAGAACAACTACAAGACCACGCCTCCCGTGCTGGACTC CGACGGCTCCTTCTTCCTCTATAGCAAGCTCACCGTGGACAAGAGCAGGTG GCAGCAGGGGAACGTCTTCTCATGCTCCGTGATGCATGAGGCTCTGCACA ACCACTACACGCAGAAGAGCCTCTCCCTGTCTCCGGGTAAA |
| 59 | HC-38 | 26C, 27C | CAAGTTCAGTTGGTGGAGTCTGGAGCCGAAGTAGTAAAGCCAGGAGCTTCA GTGAAAGTCTCTTGTAAAGCAAGTGGATTCACGTTTAGCCGCTTTGCCATG CATTGGGTGCGGCAAGCTCCCGGTCAGGGGTTGGAGTGGATGGGAGTTAT TAGCTATGACGGGGGCAATAAGTACTACGCCGAGTCTGTTAAGGGTCGGG TCACAATGACACGGGACACCTCAACCAGTACACTCTATATGGAACTGTCTA GCCTGAGATCCGAGGACACCGCTGTGTATTATTGCGCTAGGGGGTACGAT GTATTGACGGGTTATCCTGATTACTGGGGCAGGGGACACTCGTAACCGTC TCTAGTGCCTCGACGAAGGGGCCGTCCGTATTTCCGCTTGCGCCCTCGTC GAAGTCAACTTGGGAGGGACCGCGGCACTTGGCTGTCTTGTCAAAGATTA CTTCCCTGAGCCAGTGACAGTCAGCTGGAATTCCGGTGCCCTCACGTCAG GAGTACATACATTCCCTGCGGTATTGCAGTCCTCCGGACTCTACTCCCTGT CGTCGGTGGTAACGGTGCCCAGCTCCAGCTTGGGGACCCAGACGTACATT TGTAACGTGAATCACAAACCAAGCAATACTAAGGTAGATAAGAAAGTAGAAC CGAAGAGCTGCGACAAGACCCACACATGTCCTCCGTGCCCCGCACCCGAG CTGTTGGGAGGACCCTCGGTGTTTTTGTTTCCTCCCAAGCCAAAGGACACG TTGATGATTTCGCGCACTCCAGAGGTCACGTGTGTAGTCGTGGACGTGTCA CATGAGGACCCCGAGGTAAAGTTCAATTGGTATGTGGACGGAGTCGAGGT CCATAACGCCAAAACAAAGCCGTGCGAAGAACAGTACGGGTCAACGTATAG GTGCGTCAGCGTCCTCACTGTGCTGCACCAAGACTGGCTCAATGGTAAAGA ATACAAGTGCAAGGTGTCGAACAAGGCCCTCCTGCCCCCATCGAGAAAAC CATCTCCAAAGCGAAGGGGCAGCCGCGAGAACCCCAAGTCTACACGCTGC CGCCCTCGCGGGAGGAAATGACCAAAAACCAGGTGTCGCTTACGTGTCTT GTGAAAGGGTTCTATCCATCAGATATCGCGGTCGAGTGGGAGTCGAACGG CCAGCCCGAAAACAATTACAAAACAACACCTCCGGTCCTCGATTCAGATGG AAGCTTCTTCTTGTATTCGAAGCTGACCGTCGATAAGTCAAGGTGGCAACA GGGAAATGTGTTCTCGTGCTCAGTGATGCACGAGGCTCTGCATAACCACTA TACGCAGAAATCATTGTCGCTCAGCCCCGGTAAA |
| 60 | HC-39 | 28A, 29A | CAGGTGCAGCTGGTGGAGTCTGGGGGAGGCGTGGTCCAGCCTGGGAGGT CCCTGCGACTCTCCTGTGCAGCTCTGGATTCACCTTCAGTCGCTATGCCA TGCACTGGGTCCGCCAGGCTTCAGGCAAGGGGCTGGAGTGGGTGGCAGT TATATCATATGATGGAAGTAATAAATACTATGCAGACTCCGTGAAGGGCCGA TTCACCATCTCCAGAGACAATTCCAAGAACACCCTGTATCTGCTAATGAGCA GCCTGAGAGCTGAGGACACGGCTGTGTTTTACTGTGCGAGAGGATACGAT ATTTTGACTGGTTACCCCGACTACTGGGGCCAGGGAACCCTGGTCACCGTC |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | TCCTCAGCTAGCACCAAGGGCCCATCGGTCTTCCCCCTGGCGCCCTGCTC
CAGGAGCACCTCCGAGAGCACAGCGGCCCTGGGCTGCCTGGTCAAGGAC
TACTTCCCCGAACCGGTGACGGTGTCGTGGAACTCAGGCGCTCTGACCAG
CGGCGTGCACACCTTCCCAGCTGTCCTACAGTCCTCAGGACTCTACTCCCT
CAGCAGCGTGGTGACCGTGCCCTCCAGCAACTTCGGCACCCAGACCTACA
CCTGCAACGTAGATCACAAGCCCAGCAACACCAAGGTGGACAAGACAGTT
GAGCGCAAATGTTGTGTCGAGTGCCCACCGTGCCCAGCACCACCTGTGGC
AGGACCGTCAGTCTTCCTCTTCCCCCCAAAACCCAAGGACACCCTCATGAT
CTCCCGGACCCCTGAGGTCACGTGCGTGGTGGTGGACGTGAGCCACGAA
GACCCCGAGGTCCAGTTCAACTGGTACGTGGACGGCGTGGAGGTGCATAA
TGCCAAGACAAAGCCACGGGAGGAGCAGTTCAACAGCACGTTCCGTGTGG
TCAGCGTCCTCACCGTTGTGCACCAGGACTGGCTGAACGGCAAGGAGTAC
AAGTGCAAGGTCTCCAACAAAGGCCTCCCAGCCCCCATCGAGAAAACCATC
TCCAAAACCAAAGGGCAGCCCCGAGAACCACAGGTGTACACCCTGCCCCC
ATCCCGGGAGGAGATGACCAAGAACCAGGTCAGCCTGACCTGCCTGGTCA
AAGGCTTCTACCCCAGCGACATCGCCGTGGAGTGGGAGAGCAATGGGCAG
CCGGAGAACAACTACAAGACCACACCTCCCATGCTGGACTCCGACGGCTC
CTTCTTCCTCTACAGCAAGCTCACCGTGGACAAGAGCAGGTGGCAGCAGG
GGAACGTCTTCTCATGCTCCGTGATGCATGAGGCTCTGCACAACCACTACA
CGCAGAAGAGCCTCTCCCTGTCTCCGGGTAAA |
| 61 | HC-40 | 28B, 29B | CAGGTGCAGCTGGTGGAGTCTGGGGGAGGCGTGGTCCAGCCTGGGAGGT
CCCTGCGACTCTCCTGTGCAGCCTCTGGATTCACCTTCAGTCGCTATGCCA
TGCACTGGGTCCGCCAGGCTTCAGGCAAGGGGCTGGAGTGGGTGGCAGT
TATATCATATGATGGAAGTAATAAATACTATGCAGACTCCGTGAAGGGCCGA
TTCACCATCTCCAGAGACAATTCCAAGAACACCCTGTATCTGCTAATGAGCA
GCCTGAGAGCTGAGGACACGGCTGTGTTTTACTGTGCGAGAGGATACGAT
ATTTTGACTGGTTACCCCGACTACTGGGGCCAGGGAACCCTGGTCACCGTC
TCCTCAGCCTCCACCAAGGGCCCATCGGTCTTCCCCCTGGCACCCTCCTC
CAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAG
CGGCGTGCACACCTTCCCGGCTGTCCTACAGTCCTCAGGACTCTACTCCCT
CAGCAGCGTGGTGACCGTGCCCTCCAGCAGCTTGGGCACCCAGACCTACA
TCTGCAACGTGAATCACAAGCCCAGCAACACCAAGGTGGACAAGAAAGTTG
AGCCCAAATCTTGTGACAAAACTCACACATGCCCACCGTGCCCAGCACCTG
AACTCCTGGGGGGACCGTCAGTCTTCCTCTTCCCCCCAAAACCCAAGGACA
CCCTCATGATCTCCCGGACCCCTGAGGTCACATGCGTGGTGGTGGACGTG
AGCCACGAAGACCCTGAGGTCAAGTTCAACTGGTACGTGGACGGCGTGGA
GGTGCATAATGCCAAGACAAAGCCGCGGGAGGAGCAGTACGGCAGCACGT
ACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGA
GAAAACCATCTCCAAAGCCAAAGGGCAGCCCCGAGAACCACAGGTGTACA
CCCTGCCCCCATCCCGGGAGGAGATGACCAAGAACCAGGTCAGCCTGACC
TGCCTGGTCAAAGGCTTCTATCCCAGCGACATCGCCGTGGAGTGGGAGAG
CAATGGGCAGCCGGAGAACAACTACAAGACCACGCCTCCCGTGCTGGACT
CCGACGGCTCCTTCTTCCTCTATAGCAAGCTCACCGTGGACAAGAGCAGGT
GGCAGCAGGGGAACGTCTTCTCATGCTCCGTGATGCATGAGGCTCTGCAC
AACCACTACACGCAGAAGAGCCTCTCCCTGTCTCCGGGTAAA |
| 62 | HC-41 | 28C, 29C | CAGGTGCAGCTGGTGGAGTCTGGGGGAGGCGTGGTCCAGCCTGGGAGGT
CCCTGCGACTCTCCTGTGCAGCCTCTGGATTCACCTTCAGTCGCTATGCCA
TGCACTGGGTCCGCCAGGCTTCAGGCAAGGGGCTGGAGTGGGTGGCAGT
TATATCATATGATGGAAGTAATAAATACTATGCAGACTCCGTGAAGGGCCGA
TTCACCATCTCCAGAGACAATTCCAAGAACACCCTGTATCTGCTAATGAGCA
GCCTGAGAGCTGAGGACACGGCTGTGTTTTACTGTGCGAGAGGATACGAT
ATTTTGACTGGTTACCCCGACTACTGGGGCCAGGGAACCCTGGTCACCGTC
TCCTCAGCCTCGACGAAGGGGCCGTCCGTATTTCCGCTTGCGCCCTCGTC
GAAGTCAACTTCGGGAGGGACCGCGGCACTTGGCTGTCTTGTCAAAGATTA
CTTCCCTGAGCCAGTGACAGTCAGCTGGAATTCCGGTGCCCTCACGTCAG
GAGTACATACATTCCCTGCGGTATTGCAGTCCTCCGGACTCTACTCCCTGT
CGTCGGTGGTAACGGTGCCAGCTCCAGCTTGGGGACCCAGACGTACATT
TGTAACGTGAATCACAAACCAAGCAATACTAAGGTAGATAAGAAAGTAGAAC
CGAAGAGCTGCGACAAGACCCACACATGTCCTCCGTGCCCCGCACCCGAG
CTGTTGGGAGGACCCTCGGTGTTTTTGTTTCCTCCCAAGCCAAAGGACACG
TTGATGATTTCGCGCACTCCAGAGGTCACGTGTGTAGTCGTGGACGTGTCA
CATGAGGACCCCGAGGTAAAGTTCAATTGGTATGTGGACGGAGTCGAGGT
CCATAACGCCAAAACAAAGCCGTGCGAAGAACAGTACGGGTCAACGTATAG
GTGCGTCAGCGTCCTCACTGTGCTGCACCAAGACTGGCTCAATGGTAAAGA
ATACAAGTGCAAGGTGTCGAACAAGGCCCTCCCTGCCCCTATCGAGAAAAC
CATCTCCAAAGCGAAGGGGCAGCCGCGAGAACCCCAAGTCTACACGCTGC
CGCCCTCGCGGGAGGAAATGACCAAAAACCAGGTGTCGCTTACGTGTCTT
GTGAAAGGGTTCTATCCATCAGATATCGCGGTCGAGTGGGAGTCGAACGG
CCAGCCCGAAAACAATTACAAAACAACACCTCCGGTCCTCGATTCAGATGG
AAGCTTCTTCTTGTATTCGAAGCTGACCGTCGATAAGTCAAGGTGGCAACA |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | GGGAAATGTGTTCTCGTGCTCAGTGATGCACGAGGCTCTGCATAACCACTA TACGCAGAAATCATTGTCGCTCAGCCCCGGTAAA |
| 63 | HC-42 | 30A | CAGGTTCAGCTGGTGCAGTCTGGAGCTGAGGTGAAGAAGCCTGGGGCCTC AGTGAAGGTCTCCTGCAAGGCTTCTGGTTACACCTTTACCAGCTATGGTAT CAGCTGGGTGCGACAGGCCCCTGGACAAGGGCTTGAGTGGATGGGATGG ATCAACGCTTACAATGGTCACACAAACTATGCACAGACGTTCCAGGGCAGA GTCACCATGACCACAGACACATCCACGAGCACAGCCTACATGGAGCTGAG GAGCCTGAGATCTGACGACACGGCCGTGTATTACTGTGCGAGGGAACTGG AACTACGCTCCTTCTATTACTTCGGTATGGACGTCTGGGGCCAAGGGACCA CGGTCCCCGTCTCTAGTGCCTCCACCAAGGGCCCATCGGTCTTCCCCCTG GCGCCCTGCTCCAGGAGCACCTCCGAGAGCACAGCGGCCCTGGGCTGCC TGGTCAAGGACTACTTCCCCGAACCGGTGACGGTGTCGTGGAACTCAGGC GCTCTGACCAGCGGCGTGCACACCTTCCCAGCTGTCCTACAGTCCTCAGG ACTCTACTCCCTCAGCAGCGTGGTGACCGTGCCCTCCAGCAACTTCGGCA CCCAGACCTACACCTGCAACGTAGATCACAAGCCCAGCAACACCAAGGTG GACAAGACAGTTGAGCGCAAATGTTGTGTCGAGTGCCCACCGTGCCCAGC ACCACCTGTGGCAGGACCGTCAGTCTTCCTCTTCCCCCCAAAACCCAAGGA CACCCTCATGATCTCCCGGACCCCTGAGGTCACGTGCGTGGTGGTGGACG TGAGCCACGAAGACCCCGAGGTCCAGTTCAACTGGTACGTGGACGGCGTG GAGGTGCATAATGCCAAGACAAAGCCACGGGAGGAGCAGTTCAACAGCAC GTTCCGTGTGGTCAGCGTCCTCACCGTTGTGCACCAGGACTGGCTGAACG GCAAGGAGTACAAGTGCAAGGTCTCCAACAAAGGCCTCCCAGCCCCCATC GAGAAAACCATCTCCAAAACCAAAGGGCAGCCCCGAGAACCACAGGTGTA CACCCTGCCCCCATCCCGGGAGGAGATGACCAAGAACCAGGTCAGCCTGA CCTGCCTGGTCAAAGGCTTCTACCCCAGCGACATCGCCGTGGAGTGGGAG AGCAATGGGCAGCCGGAGAACAACTACAAGACCACACCTCCCATGCTGGA CTCCGACGGCTCCTTCTTCCTCTACAGCAAGCTCACCGTGGACAAGAGCAG GTGGCAGCAGGGGAACGTCTTCTCATGCTCCGTGATGCATGAGGCTCTGC ACAACCACTACACGCAGAAGAGCCTCTCCCTGTCTCCGGGTAAA |
| 64 | HC-43 | 31A | CAGGTTCAGCTGGTGCAGTCTGGAGCTGAAGTGAAGAAGCCTGGGGCCTC AGTGAAGGTCTCCTGCAAGGCTTCTGGTTACACCTTTACCAGCTATGGTAT CAGCTGGGTGCGACAGGCCCCTGGACAAGGGCTTGAGTGGATGGGATGG ATCAACGCTTACAATGGTCACACAAACTATGCACAGACGTTCCAGGGCAGA GTCACCATGACCACAGACACATCCACGAGCACAGCCTACATGGAACTGAG GAGCCTGAGATCTGACGACACGGCCGTGTATTACTGTGCGAGGGAACTGG AACTACGCTCCTTCTATTACTTCGGTATGGACGTCTGGGGCCAAGGGACCA CGGTCACCGTCTCTAGTGCCTCCACCAAGGGCCCATCGGTCTTCCCCCTG GCGCCCTGCTCCAGGAGCACCTCCGAGAGCACAGCGGCCCTGGGCTGCC TGGTCAAGGACTACTTCCCCGAACCGGTGACGGTGTCGTGGAACTCAGGC GCTCTGACCAGCGGCGTGCACACCTTCCCAGCTGTCCTACAGTCCTCAGG ACTCTACTCCCTCAGCAGCGTGGTGACCGTGCCCTCCAGCAACTTCGGCA CCCAGACCTACACCTGCAACGTAGATCACAAGCCCAGCAACACCAAGGTG GACAAGACAGTTGAGCGCAAATGTTGTGTCGAGTGCCCACCGTGCCCAGC ACCACCTGTGGCAGGACCGTCAGTCTTCCTCTTCCCCCCAAAACCCAAGGA CACCCTCATGATCTCCCGGACCCCTGAGGTCACGTGCGTGGTGGTGGACG TGAGCCACGAAGACCCCGAGGTCCAGTTCAACTGGTACGTGGACGGCGTG GAGGTGCATAATGCCAAGACAAAGCCACGGGAGGAGCAGTTCAACAGCAC GTTCCGTGTGGTCAGCGTCCTCACCGTTGTGCACCAGGACTGGCTGAACG GCAAGGAGTACAAGTGCAAGGTCTCCAACAAAGGCCTCCCAGCCCCCATC GAGAAAACCATCTCCAAAACCAAAGGGCAGCCCCGAGAACCACAGGTGTA CACCCTGCCCCCATCCCGGGAGGAGATGACCAAGAACCAGGTCAGCCTGA CCTGCCTGGTCAAAGGCTTCTACCCCAGCGACATCGCCGTGGAGTGGGAG AGCAATGGGCAGCCGGAGAACAACTACAAGACCACACCTCCCATGCTGGA CTCCGACGGCTCCTTCTTCCTCTACAGCAAGCTCACCGTGGACAAGAGCAG GTGGCAGCAGGGGAACGTCTTCTCATGCTCCGTGATGCATGAGGCTCTGC ACAACCACTACACGCAGAAGAGCCTCTCCCTGTCTCCGGGTAAA |
| 65 | HC-44 | 32A | CAGGTTCAGCTGGTGCAGTCTGGAGCTGAGGTGAAGAAGTCTGGGGCCTC TTTGAAGGTCTCCTGCAAGGCTTCTGGTTACATTTTTACCCGCTATGGTGTC AGCTGGGTGCGACAGGCCCCTGGACAAGGGCTTGAGTGGATGGGATGGAT CACCACTTACAATGGTAACACAAACTATGCACAGAAGCTCCAGGGCAGAGT CACCATGACCATAGACACATCCACGAGCACAGCCTACATGGAACTGAGAAG CCTCAGATCTGACGACACGGCCGTGTATTACTGTGCGAGAAGAGTGCGGT ATAGTGGGGCTACTCGTTTGACAACTGGGGCCAGGGAACCCTGGTCACC GTCTCTAGTGCCTCCACCAAGGGCCCATCGGTCTTCCCCCTGGCGCCCTG CTCCAGGAGCACCTCCGAGAGCACAGCGGCCCTGGGCTGCCTGGTCAAG GACTACTTCCCCGAACCGGTGACGGTGTCGTGGAACTCAGGCGCTCTGAC CAGCGGCGTGCACACCTTCCCAGCTGTCCTACAGTCCTCAGGACTCTACTC CCTCAGCAGCGTGGTGACCGTGCCCTCCAGCAACTTCGGCACCCAGACCT ACACCTGCAACGTAGATCACAAGCCCAGCAACACCAAGGTGGACAAGACA GTTGAGCGCAAATGTTGTGTCGAGTGCCCACCGTGCCCAGCACCACCTGT GGCAGGACCGTCAGTCTTCCTCTTCCCCCCAAAACCCAAGGACACCCTCAT |

TABLE 1B-continued

Exemplary Anti-hPAC1 Antibody Heavy Chain Nucleic Acid Sequences

| SEQ ID NO | Seq Group | Antibodies containing sequence | HC NA Sequence |
|---|---|---|---|
| | | | GATCTCCCGGACCCCTGAGGTCACGTGCGTGGTGGTGGACGTGAGCCACG<br>AAGACCCCGAGGTCCAGTTCAACTGGTACGTGGACGGCGTGGAGGTGCAT<br>AATGCCAAGACAAAGCCACGGGAGGAGCAGTTCAACAGCACGTTCCGTGT<br>GGTCAGCGTCCTCACCGTTGTGCACCAGGACTGGCTGAACGGCAAGGAGT<br>ACAAGTGCAAGGTCTCCAACAAAGGCCTCCCAGCCCCCATCGAGAAAACCA<br>TCTCCAAAACCAAAGGGCAGCCCCGAGAACCACAGGTGTACACCCTGCCC<br>CCATCCCGGGAGGAGATGACCAAGAACCAGGTCAGCCTGACCTGCCTGGT<br>CAAAGGCTTCTACCCCAGCGACATCGCCGTGGAGTGGGAGAGCAATGGGC<br>AGCCGGAGAACAACTACAAGACCACACCTCCCATGCTGGACTCCGACGGC<br>TCCTTCTTCCTCTACAGCAAGCTCACCGTGGACAAGAGCAGGTGGCAGCAG<br>GGGAACGTCTTCTCATGCTCCGTGATGCATGAGGCTCTGCACAACCACTAC<br>ACGCAGAAGAGCCTCTCCCTGTCTCCGGGTAAA |
| 66 | HC-45 | 33A | CAGGTTCAGCTGGTGCAGTCTGGAGCTGAGGTGAAGAAGTCTGGGGCCTC<br>TTTGAAGGTCTCCTGCAAGGCTTCTGGTTACATTTTTACCCGCTATGGTGTC<br>AGCTGGGTGCGACAGGCCCCTGGACAAGGGCTTGAGTGGATGGGATGGAT<br>CACCACTTACAATGGTAATACAAACTATGCACAGAAGCTCCAGGGCAGAGT<br>CACCATGACCACAGACACATCCACGAGCACAGCCTACATGGAACTGAGGA<br>GCCTCAGATCTGACGACACGGCCGTGTATTACTGTGCGAGAAGAGTGCGG<br>TACAGTGGGGGCTACTCGTTTGACAACTGGGGCCAGGGAACCCTGGTCAC<br>CGTCTCTAGTGCCTCCACCAAGGGCCCATCGGTCTTCCCCCTGGCGCCCT<br>GCTCCAGGAGCACCTCCGAGAGCACAGCGGCCCTGGGCTGCCTGGTCAA<br>GGACTACTTCCCCGAACCGGTGACGGTGTCGTGGAACTCAGGCGCTCTGA<br>CCAGCGGCGTGCACACCTTCCCAGCTGTCCTACAGTCCTCAGGACTCTACT<br>CCCTCAGCAGCGTGGTGACCGTGCCCTCCAGCAACTTCGGCACCCAGACC<br>TACACCTGCAACGTAGATCACAAGCCCAGCAACACCAAGGTGGACAAGACA<br>GTTGAGCGCAAATGTTGTGTCGAGTGCCCACCGTGCCCAGCACCACCTGT<br>GGCAGGACCGTCAGTCTTCCTCTTCCCCCCAAAACCCAAGGACACCCTCAT<br>GATCTCCCGGACCCCTGAGGTCACGTGCGTGGTGGTGGACGTGAGCCACG<br>AAGACCCCGAGGTCCAGTTCAACTGGTACGTGGACGGCGTGGAGGTGCAT<br>AATGCCAAGACAAAGCCACGGGAGGAGCAGTTCAACAGCACGTTCCGTGT<br>GGTCAGCGTCCTCACCGTTGTGCACCAGGACTGGCTGAACGGCAAGGAGT<br>ACAAGTGCAAGGTCTCCAACAAAGGCCTCCCAGCCCCCATCGAGAAAACCA<br>TCTCCAAAACCAAAGGGCAGCCCCGAGAACCACAGGTGTACACCCTGCCC<br>CCATCCCGGGAGGAGATGACCAAGAACCAGGTCAGCCTGACCTGCCTGGT<br>CAAAGGCTTCTACCCCAGCGACATCGCCGTGGAGTGGGAGAGCAATGGGC<br>AGCCGGAGAACAACTACAAGACCACACCTCCCATGCTGGACTCCGACGGC<br>TCCTTCTTCCTCTACAGCAAGCTCACCGTGGACAAGAGCAGGTGGCAGCAG<br>GGGAACGTCTTCTCATGCTCCGTGATGCATGAGGCTCTGCACAACCACTAC<br>ACGCAGAAGAGCCTCTCCCTGTCTCCGGGTAAA |
| 67 | HC-46 | 34A | CAGGTTCAGCTGGTGCAGTCTGGAGCTGAGGTGAAGAAGTCTGGGGCCTC<br>TTTGAAGGTCTCCTGCAAGGCTTCTGGTTACATTTTTACCCGCTATGGTGTC<br>AGCTGGGTGCGACAGGCCCCTGGACAAGGGCTTGAGTGGATGGGATGGAT<br>CACCACTTACAATGGTAATACAAACTATGCACAGAAACTCCAGGGCAGAGT<br>CACCATGACCACAGACACATCCACGAACACAGCCTACATGGAACTGAGGAG<br>CCTCAGATCTGACGACACGGCCGTGTATTACTGTGCGAGAAGAGTGCGGT<br>ATAGTGGGGGCTACTCGTTTGACAACTGGGGCCAGGGAACCCTGGTCACC<br>GTCTCTAGTGCCTCCACCAAGGGCCCATCGGTCTTCCCCCTGGCGCCCTG<br>CTCCAGGAGCACCTCCGAGAGCACAGCGGCCCTGGGCTGCCTGGTCAAG<br>GACTACTTCCCCGAACCGGTGACGGTGTCGTGGAACTCAGGCGCTCTGAC<br>CAGCGGCGTGCACACCTTCCCAGCTGTCCTACAGTCCTCAGGACTCTACTC<br>CCTCAGCAGCGTGGTGACCGTGCCCTCCAGCAACTTCGGCACCCAGACCT<br>ACACCTGCAACGTAGATCACAAGCCCAGCAACACCAAGGTGGACAAGACA<br>GTTGAGCGCAAATGTTGTGTCGAGTGCCCACCGTGCCCAGCACCACCTGT<br>GGCAGGACCGTCAGTCTTCCTCTTCCCCCCAAAACCCAAGGACACCCTCAT<br>GATCTCCCGGACCCCTGAGGTCACGTGCGTGGTGGTGGACGTGAGCCACG<br>AAGACCCCGAGGTCCAGTTCAACTGGTACGTGGACGGCGTGGAGGTGCAT<br>AATGCCAAGACAAAGCCACGGGAGGAGCAGTTCAACAGCACGTTCCGTGT<br>GGTCAGCGTCCTCACCGTTGTGCACCAGGACTGGCTGAACGGCAAGGAGT<br>ACAAGTGCAAGGTCTCCAACAAAGGCCTCCCAGCCCCCATCGAGAAAACCA<br>TCTCCAAAACCAAAGGGCAGCCCCGAGAACCACAGGTGTACACCCTGCCC<br>CCATCCCGGGAGGAGATGACCAAGAACCAGGTCAGCCTGACCTGCCTGGT<br>CAAAGGCTTCTACCCCAGCGACATCGCCGTGGAGTGGGAGAGCAATGGGC<br>AGCCGGAGAACAACTACAAGACCACACCTCCCATGCTGGACTCCGACGGC<br>TCCTTCTTCCTCTACAGCAAGCTCACCGTGGACAAGAGCAGGTGGCAGCAG<br>GGGAACGTCTTCTCATGCTCCGTGATGCATGAGGCTCTGCACAACCACTAC<br>ACGCAGAAGAGCCTCTCCCTGTCTCCGGGTAAA |
| 68 | HC-47 | 35A | CAGGTGCAGCTGCAGGAGTCGGGCCCAGGACTGGTGAAGCCTTCGGAGA<br>CCCTGTCCCTCACCTGCACTGTCTCTGGTGGCTCCATCAGTAGTTACTACT<br>GGAGCTGGATCCGGCAGCCCGCCGGGAAGGGACTGGAATGGATTGGGCG<br>TATCTATACCAGTGGGAGCACCAACTACAACCCCTCCCTCAAGAGTCGAGT<br>CACCATGTCAATAGGCACGTCCAAGAACCAGTTCTCCCTGAAGCTGAGCTC |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | TGTGACCGCCGCGGACACGGCCGTGTATTACTGTGCGATTATTGCATCTCG
TGGCTGGTACTTCGATCTCTGGGGCCGTGGCACCCTGGTCACCGTCTCTA
GTGCCTCCACCAAGGGCCCATCGGTCTTCCCCCTGGCGCCCTGCTCCAGG
AGCACCTCCGAGAGCACAGCGGCCCTGGGCTGCCTGGTCAAGGACTACTT
CCCCGAACCGGTGACGGTGTCGTGGAACTCAGGCGCTCTGACCAGCGGC
GTGCACACCTTCCCAGCTGTCCTACAGTCCTCAGGACTCTACTCCCTCAGC
AGCGTGGTGACCGTGCCCTCCAGCAACTTCGGCACCCAGACCTACACCTG
CAACGTAGATCACAAGCCCAGCAACACCAAGGTGGACAAGACAGTTGAGC
GCAAATGTTGTGTCGAGTGCCCACCGTGCCCAGCACCACCTGTGGCAGGA
CCGTCAGTCTTCCTCTTCCCCCCAAAACCCAAGGACACCCTCATGATCTCC
CGGACCCCTGAGGTCACGTGCGTGGTGGTGGACGTGAGCCACGAAGACC
CCGAGGTCCAGTTCAACTGGTACGTGGACGGCGTGGAGGTGCATAATGCC
AAGACAAAGCCACGGGAGGAGCAGTTCAACAGCACGTTCCGTGTGGTCAG
CGTCCTCACCGTTGTGCACCAGGACTGGCTGAACGGCAAGGAGTACAAGT
GCAAGGTCTCCAACAAAGGCCTCCCAGCCCCCATCGAGAAAACCATCTCCA
AAACCAAAGGGCAGCCCCGAGAACCACAGGTGTACACCCTGCCCCCATCC
CGGGAGGAGATGACCAAGAACCAGGTCAGCCTGACCTGCCTGGTCAAAGG
CTTCTACCCCAGCGACATCGCCGTGGAGTGGGAGAGCAATGGGCAGCCGG
AGAACAACTACAAGACCACACCTCCCATGCTGGACTCCGACGGCTCCTTCT
TCCTCTACAGCAAGCTCACCGTGGACAAGAGCAGGTGGCAGCAGGGGAAC
GTCTTCTCATGCTCCGTGATGCATGAGGCTCTGCACAACCACTACACGCAG
AAGAGCCTCTCCCTGTCTCCGGGTAAA |
| 69 | HC-48 | 36A, 40A | CAGGTGCAGCTGCAGGAGTCGGGCCCAGGACTGGTGAAGCCTTCACAGAC
CCTGTCCCTCACCTGCACTGTCTCTGGTGGCTCCATCAGCAGTGGTGGTTA
CTACTGGAGCTGGATCCGCCAGCACCCAGGGAAGGGCCTGGAGTGGATTG
GGTACATCTATTACAGTGGGAACACCTACTACAACCCGTCCCTCAAGAGTC
GAGTTACCATATCAGGAGACACGTCTAAGAACCAGTTCTCCCTGAAGCTGA
GGTCTGTGACTGCCGCGGACACGGCCGTGTATTACTGTGCGAGAGGAGGA
GCAGCTCGCGGTATGGACGTCTGGGGCCAAGGGACCACGGTCACCGTCTC
TAGTGCCTCCACCAAGGGCCCATCGGTCTTCCCCCTGGCGCCCTGCTCCA
GGAGCACCTCCGAGAGCACAGCGGCCCTGGGCTGCCTGGTCAAGGACTA
CTTCCCCGAACCGGTGACGGTGTCGTGGAACTCAGGCGCTCTGACCAGCG
GCGTGCACACCTTCCCAGCTGTCCTACAGTCCTCAGGACTCTACTCCCTCA
GCAGCGTGGTGACCGTGCCCTCCAGCAACTTCGGCACCCAGACCTACACC
TGCAACGTAGATCACAAGCCCAGCAACACCAAGGTGGACAAGACAGTTGA
GCGCAAATGTTGTGTCGAGTGCCCACCGTGCCCAGCACCACCTGTGGCAG
GACCGTCAGTCTTCCTCTTCCCCCCAAAACCCAAGGACACCCTCATGATCT
CCCGGACCCCTGAGGTCACGTGCGTGGTGGTGGACGTGAGCCACGAAGA
CCCCGAGGTCCAGTTCAACTGGTACGTGGACGGCGTGGAGGTGCATAATG
CCAAGACAAAGCCACGGGAGGAGCAGTTCAACAGCACGTTCCGTGTGGTC
AGCGTCCTCACCGTTGTGCACCAGGACTGGCTGAACGGCAAGGAGTACAA
GTGCAAGGTCTCCAACAAAGGCCTCCCAGCCCCCATCGAGAAAACCATCTC
CAAAACCAAAGGGCAGCCCCGAGAACCACAGGTGTACACCCTGCCCCCAT
CCCGGGAGGAGATGACCAAGAACCAGGTCAGCCTGACCTGCCTGGTCAAA
GGCTTCTACCCCAGCGACATCGCCGTGGAGTGGGAGAGCAATGGGCAGCC
GGAGAACAACTACAAGACCACACCTCCCATGCTGGACTCCGACGGCTCCTT
CTTCCTCTACAGCAAGCTCACCGTGGACAAGAGCAGGTGGCAGCAGGGGA
ACGTCTTCTCATGCTCCGTGATGCATGAGGCTCTGCACAACCACTACACGC
AGAAGAGCCTCTCCCTGTCTCCGGGTAAA |
| 70 | HC-49 | 37A | CAGGTACAGCTGCAGCAGTCAGGTCCAGGACTGGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGAGTGGCTGG
GAAGGACATACTACAGGTCCAGGTGGTATAATGATTATGCAGTATCTGTGA
AAAGTCGAATAACCATCAACCCAGACACATCCAAGAACCAGTTCTCCCTGC
AGCTGAACTCTGTGACTCCCGAGGACACGGCTGTGTATTACTGTGCAAGAG
GGGTCTTTTATAGCAAAGGTGCTTTTGATATCTGGGGCCAAGGGACAATGG
TCACCGTCTCTAGTGCCTCCACCAAGGGCCCATCGGTCTTCCCCCTGGCG
CCCTGCTCCAGGAGCACCTCCGAGAGCACAGCGGCCCTGGGCTGCCTGG
TCAAGGACTACTTCCCCGAACCGGTGACGGTGTCGTGGAACTCAGGCGCT
CTGACCAGCGGCGTGCACACCTTCCCAGCTGTCCTACAGTCCTCAGGACT
CTACTCCCTCAGCAGCGTGGTGACCGTGCCCTCCAGCAACTTCGGCACCC
AGACCTACACCTGCAACGTAGATCACAAGCCCAGCAACACCAAGGTGGACA
AGACAGTTGAGCGCAAATGTTGTGTCGAGTGCCCACCGTGCCCAGCACCA
CCTGTGGCAGGACCGTCAGTCTTCCTCTTCCCCCCAAAACCCAAGGACACC
CTCATGATCTCCCGGACCCCTGAGGTCACGTGCGTGGTGGTGGACGTGAG
CCACGAAGACCCCGAGGTCCAGTTCAACTGGTACGTGGACGGCGTGGAGG
TGCATAATGCCAAGACAAAGCCACGGGAGGAGCAGTTCAACAGCACGTTC
CGTGTGGTCAGCGTCCTCACCGTTGTGCACCAGGACTGGCTGAACGGCAA
GGAGTACAAGTGCAAGGTCTCCAACAAAGGCCTCCCAGCCCCCATCGAGA
AAACCATCTCCAAAACCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTACCCCAGCGACATCGCCGTGGAGTGGGAGAGCA |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | ATGGGCAGCCGGAGAACAACTACAAGACCACACCTCCCATGCTGGACTCC GACGGCTCCTTCTTCCTCTACAGCAAGCTCACCGTGGACAAGAGCAGGTG GCAGCAGGGGAACGTCTTCTCATGCTCCGTGATGCATGAGGCTCTGCACA ACCACTACACGCAGAAGAGCCTCTCCCTGTCTCCGGGTAAA |
| 71 | HC-50 | 38A | CAGGTGCAGCTGCAGGAGTCGGGCCCAGGACTGGTGAAGCCTTCACAGAC CCTGTCCCTCACCTGCACTGTCTCTGGTGGCTCCATCAGCCGTGGTGGTTA CTACTGGAGCTGGATCCGCCAGCACCCAGGGAAGGGCCTGGAGTGGATTG GGTACATATATTACAGTGGGAATACCTACTACAACCCGTCCCTCAAGAGTC GAGTTATCATATCAGGAGACACGTCTAAGAACCAGCTCTCCCTGAAGCTGA GGTCTGTGACTGCCGCGGACACGGCCGTGTATTATTGTGCGAGAGGAGGA GCAGCTCGCGGTATGGACGTCTGGGGCCAAGGGACCACGGTCACCGTCTC TAGTGCCTCCACCAAGGGCCCATCGGTCTTCCCCCTGGCGCCCTGCTCCA GGAGCACCTCCGAGAGCACAGCGGCCCTGGGCTGCCTGGTCAAGGACTA CTTCCCCGAACCGGTGACGGTGTCGTGGAACTCAGGCGCTCTGACCAGCG GCGTGCACACCTTCCCAGCTGTCCTACAGTCCTCAGGACTCTACTCCCTCA GCAGCGTGGTGACCGTGCCCTCCAGCAACTTCGGCACCCAGACCTACACC TGCAACGTAGATCACAAGCCCAGCAACACCAAGGTGGACAAGACAGTTGA GCGCAAATGTTGTGTCGAGTGCCCACCGTGCCCAGCACCACCTGTGGCAG GACCGTCAGTCTTCCTCTTCCCCCCAAAACCCAAGGACACCCTCATGATCT CCCGGACCCCTGAGGTCACGTGCGTGGTGGTGGACGTGAGCCACGAAGA CCCCGAGGTCCAGTTCAACTGGTACGTGGACGGCGTGGAGGTGCATAATG CCAAGACAAAGCCACGGGAGGAGCAGTTCAACAGCACGTTCCGTGTGGTC AGCGTCCTCACCGTTGTGCACCAGGACTGGCTGAACGGCAAGGAGTACAA GTGCAAGGTCTCCAACAAAGGCCTCCCAGCCCCCATCGAGAAAACCATCTC CAAAACCAAAGGGCAGCCCCGAGAACCACAGGTGTACACCCTGCCCCCAT CCCGGGAGGAGATGACCAAGAACCAGGTCAGCCTGACCTGCCTGGTCAAA GGCTTCTACCCCAGCGACATCGCCGTGGAGTGGGAGAGCAATGGGCAGCC GGAGAACAACTACAAGACCACACCTCCCATGCTGGACTCCGACGGCTCCTT CTTCCTCTACAGCAAGCTCACCGTGGACAAGAGCAGGTGGCAGCAGGGGA ACGTCTTCTCATGCTCCGTGATGCATGAGGCTCTGCACAACCACTACACGC AGAAGAGCCTCTCCCTGTCTCCGGGTAAA |
| 72 | HC-51 | 39A | CAGGTGCAGCTGCAGGAGTCGGGCCCAGGACTGGTGAAGCCTTCACAGAC CCTGTCCCTCACCTGCACTGTCTCTGGTGGCTCCATCAGCAGTGGTGGTTA CTACTGGAGCTGGATCCGCCAGCACCCAGGGAAGGGCCTGGAGTGGATTG GGTACATCTATTACAGTGGGAACACCTACTACAACCCGTCCCTCAAGAGTC GAGTTACCATATCAGGAGACACGTCTAAGAACCAGTTCTCCCTGAAGCTGA GGTCTGTGACTGCCGCGGACACGGCCGTGTATTACTGTACGAGAGGAGGA GCAGCTCGCGGTATGGACGTCTGGGGCCAAGGGACCACGGTCACCGTCTC TAGTGCCTCCACCAAGGGCCCATCGGTCTTCCCCCTGGCGCCCTGCTCCA GGAGCACCTCCGAGAGCACAGCGGCCCTGGGCTGCCTGGTCAAGGACTA CTTCCCCGAACCGGTGACGGTGTCGTGGAACTCAGGCGCTCTGACCAGCG GCGTGCACACCTTCCCAGCTGTCCTACAGTCCTCAGGACTCTACTCCCTCA GCAGCGTGGTGACCGTGCCCTCCAGCAACTTCGGCACCCAGACCTACACC TGCAACGTAGATCACAAGCCCAGCAACACCAAGGTGGACAAGACAGTTGA GCGCAAATGTTGTGTCGAGTGCCCACCGTGCCCAGCACCACCTGTGGCAG GACCGTCAGTCTTCCTCTTCCCCCCAAAACCCAAGGACACCCTCATGATCT CCCGGACCCCTGAGGTCACGTGCGTGGTGGTGGACGTGAGCCACGAAGA CCCCGAGGTCCAGTTCAACTGGTACGTGGACGGCGTGGAGGTGCATAATG CCAAGACAAAGCCACGGGAGGAGCAGTTCAACAGCACGTTCCGTGTGGTC AGCGTCCTCACCGTTGTGCACCAGGACTGGCTGAACGGCAAGGAGTACAA GTGCAAGGTCTCCAACAAAGGCCTCCCAGCCCCCATCGAGAAAACCATCTC CAAAACCAAAGGGCAGCCCCGAGAACCACAGGTGTACACCCTGCCCCCAT CCCGGGAGGAGATGACCAAGAACCAGGTCAGCCTGACCTGCCTGGTCAAA GGCTTCTACCCCAGCGACATCGCCGTGGAGTGGGAGAGCAATGGGCAGCC GGAGAACAACTACAAGACCACACCTCCCATGCTGGACTCCGACGGCTCCTT CTTCCTCTACAGCAAGCTCACCGTGGACAAGAGCAGGTGGCAGCAGGGGA ACGTCTTCTCATGCTCCGTGATGCATGAGGCTCTGCACAACCACTACACGC AGAAGAGCCTCTCCCTGTCTCCGGGTAAA |
| 73 | HC-52 | 39B | CAGGTGCAGCTGCAGGAGTCGGGCCCAGGACTGGTGAAGCCTTCACAGAC CCTGTCCCTCACCTGCACTGTCTCTGGTGGCTCCATCAGCAGTGGTGGTTA CTACTGGAGCTGGATCCGCCAGCACCCAGGGAAGGGCCTGGAGTGGATTG GGTACATCTATTACAGTGGGAACACCTACTACAACCCGTCCCTCAAGAGTC GAGTTACCATATCAGGAGACACGTCTAAGAACCAGTTCTCCCTGAAGCTGA GGTCTGTGACTGCCGCGGACACGGCCGTGTATTACTGTACGAGAGGAGGA GCAGCTCGCGGTATGGACGTCTGGGGCCAAGGGACCACGGTCACCGTCTC TAGTGCCTCCACCAAGGGCCCATCGGTCTTCCCCCTGGCACCCTCCTCCAA GAGCACCTCTGGGGGCACAGCGGCCCTGGGCTGCCTGGTCAAGGACTACT TCCCCGAACCGGTGACGGTGTCGTGGAACTCAGGCGCCCTGACCAGCGG CGTGCACACCTTCCCGGCTGTCCTACAGTCCTCAGGACTCTACTCCCTCAG CAGCGTGGTGACCGTGCCCTCCAGCAGCTTGGGCACCCAGACCTACATCT GCAACGTGAATCACAAGCCCAGCAACACCAAGGTGGACAAGAAAGTTGAG |

TABLE 1B-continued

Exemplary Anti-hPAC1 Antibody Heavy Chain Nucleic Acid Sequences

| SEQ ID NO: | Seq Group | Antibodies containing sequence | HC NA Sequence |
|---|---|---|---|
| | | | CCCAAATCTTGTGACAAAACTCACACATGCCCACCGTGCCCAGCACCTGAA<br>CTCCTGGGGGGACCGTCAGTCTTCCTCTTCCCCCCAAAACCCAAGGACAC<br>CCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAG<br>GTGCATAATGCCAAGACAAAGCCGCGGGAGGAGCAGTACGGCAGCACGTA<br>CCGTGTGGTCAGCGTCCTCACCGTCCTGCACCAGGACTGGCTGAATGGCA<br>AGGAGTACAAGTGCAAGGTCTCCAACAAAGCCCTCCCAGCCCCCATCGAG<br>AAAACCATCTCCAAAGCCAAAGGGCAGCCCCGAGAACCACAGGTGTACAC<br>CCTGCCCCCATCCCGGGAGGAGATGACCAAGAACCAGGTCAGCCTGACCT<br>GCCTGGTCAAAGGCTTCTATCCCAGCGACATCGCCGTGGAGTGGGAGAGC<br>AATGGGCAGCCGGAGAACAACTACAAGACCACGCCTCCCGTGCTGGACTC<br>CGACGGCTCCTTCTTCCTCTATAGCAAGCTCACCGTGGACAAGAGCAGGT<br>GGCAGCAGGGGAACGTCTTCTCATGCTCCGTGATGCATGAGGCTCTGCACA<br>ACCACTACACGCAGAAGAGCCTCTCCCTGTCTCCGGGTAAA |
| 74 | HC-53 | 41A | CAGGTGCAGCTGCAGGAGTCGGGCCCAGGACTGGTGAAGCCTTCACAGAC<br>CCTGTCCCTCACCTGCACTGTCTCTGGTGGCTCCATCAGCAGTGGTGGTTT<br>CTACTGGAGCTGGATCCGCCAGCACCCAGGGAAGGGCCTGGAGTGGATTG<br>GGTACATCTATTACAGTGGGAATACCTACTACAACCCGTCCCTCAAGAGTC<br>GAGTTATCATATCAGGAGACACGTCTAAGAACCAGTTCTCCCTGAAGCTGA<br>GCTCTGTGACGGCCGCGGACACGGCCGTGTATTACTGTGCGAGAGGAGGA<br>GCAGCTCGCGGTATGGACGTCTGGGGCCAAGGGACCACGGTCACCGTCTC<br>TAGTGCCTCCACCAAGGGCCCATCGGTCTTCCCCCTGGCGCCCTGCTCCA<br>GGAGCACCTCCGAGAGCACAGCGGCCCTGGGCTGCCTGGTCAAGGACTA<br>CTTCCCCGAACCGGTGACGGTGTCGTGGAACTCAGGCGCTCTGACCAGCG<br>GCGTGCACACCTTCCCAGCTGTCCTACAGTCCTCAGGACTCTACTCCCTCA<br>GCAGCGTGGTGACCGTGCCCTCCAGCAACTTCGGCACCCAGACCTACACC<br>TGCAACGTAGATCACAAGCCCAGCAACACCAAGGTGGACAAGACAGTTGA<br>GCGCAAATGTTGTGTCGAGTGCCCACCGTGCCCAGCACCACCTGTGGCAG<br>GACCGTCAGTCTTCCTCTTCCCCCCAAAACCCAAGGACACCCTCATGATCT<br>CCCGGACCCCTGAGGTCACGTGCGTGGTGGTGGACGTGAGCCACGAAGA<br>CCCCGAGGTCCAGTTCAACTGGTACGTGGACGGCGTGGAGGTGCATAATG<br>CCAAGACAAAGCCACGGGAGGAGCAGTTCAACAGCACGTTCCGTGTGGTC<br>AGCGTCCTCACCGTTGTGCACCAGGACTGGCTGAACGGCAAGGAGTACAA<br>GTGCAAGGTCTCCAACAAAGGCCTCCCAGCCCCCATCGAGAAAACCATCTC<br>CAAAACCAAAGGGCAGCCCCGAGAACCACAGGTGTACACCCTGCCCCCAT<br>CCCGGGAGGAGATGACCAAGAACCAGGTCAGCCTGACCTGCCTGGTCAAA<br>GGCTTCTACCCCAGCGACATCGCCGTGGAGTGGGAGAGCAATGGGCAGCC<br>GGAGAACAACTACAAGACCACACCTCCCATGCTGGACTCCGACGGCTCCTT<br>CTTCCTCTACAGCAAGCTCACCGTGGACAAGAGCAGGTGGCAGCAGGGGA<br>ACGTCTTCTCATGCTCCGTGATGCATGAGGCTCTGCACAACCACTACACGC<br>AGAAGAGCCTCTCCCTGTCTCCGGGTAAA |

TABLE 2A

Exemplary Anti-hPAC1 Antibody Light Chain Amino Acid Sequences

| SEQ ID NO: | Seq Group | Antibodies containing sequence | LC AA Sequence |
|---|---|---|---|
| 75 | LC-01 | 01A, 01B | DIQMTQSPSSLSASVGDRITITCRASQSISRYLNWYQQKPGKAPKLLIYAASSLQ<br>SGIPSRFSGSGSGTDFTLTINSLQPEDFATYFCQQSYSPPFTFGPGTKVDIKRT<br>VAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 76 | LC-02 | 02A, 02B, 02C | EIVLTQSPDFQSVTPKEKVTITCRASQSIGSSLHWYQQKPDQSPKLLIKYASQSL<br>SGIPSRFSGSGSGTHFTLTINSLEAEDAATYYCHQSSRLPFTFGPGTKVDIKRT<br>VAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 77 | LC-03 | 03A | DIQLTQSPSFLSASVGDRVTITCRASQSIGRSLHWYQQKPGKAPKLLIKYASQS<br>LSGVPSRFSGSGSGTEFTLTISSLQPEDFATYYCHQSSRLPFTFGPGTKVDIKR<br>TVAAPSVFIFPPSDEQLKSGTASVVCLLNNFYPREAKVQWKVDNALQSGNSQE<br>SVTEQDSKDSTYSLSSTLTLSKADYEKHKVYACEVTHQGLSSPVTKSFNRGEC |
| 78 | LC-04 | 04A, 04B, 04C,<br>07A, 07B, 07C,<br>08A, 08B, 08C,<br>12A, 12B, 12C | EIVLTQSPDFQSVTPKEKVTITCRASQSVGRSLHWYHQKPDQSPKLLIKYASQS<br>LSGVPSRFSGSGSGTDFTLIINSLEAEDAATYYCHQSSRLPFTFGPGTKVDIKRT<br>VAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |

TABLE 2A-continued

Exemplary Anti-hPAC1 Antibody Light Chain Amino Acid Sequences

| SEQ ID NO: | Seq Group | Antibodies containing sequence | LC AA Sequence |
|---|---|---|---|
| 79 | LC-05 | 05A, 05B, 05C, 13A, 13B, 13C, 16A, 16B, 16C, 17A, 17B, 17C, 21A, 21B, 21C, 22A, 22B, 22C, 24A, 24B, 24C, 25A, 25B, 25C, 26A, 26B, 26C | DIQLTQSPSFLSASVGDRVTITCRASQSIGRSLHWYQQKPGKAPKLLIKYASQS LSGVPSRFSGSGSGTEFTLTISSLQPEDFATYYCHQSSRLPFTFGPGTKVDIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 80 | LC-06 | 06A, 06B, 06C | DIQLTQSPSFLSASVGDRVTITCRASQSIGRSLHWYHQKPGKAPKLLIKYASQS LSGVPSRFSGSGSGTEFTLIISSLQPEDFATYYCHQSSRLPFTFGPGTKVDIKRT VAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| 81 | LC-07 | 09A, 09B, 09C, 10A, 10B, 10C, 11A, 11B, 11C | EIVLTQSPDFQSVTPKEKVTITCRASQSVGRSLHWYQQKPDQSPKLLIKYASQS LSGVPSRFSGSGSGTDFTLTINSLEAEDAATYYCHQSSRLPFTFGPGTKVDIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 82 | LC-08 | 14A, 14B, 14C, 23A, 23B, 23C, 27A, 27B, 27C | EIVLTQSPATLSLSPGERATLSCRASQSVGRSLHWYQQKPGQAPRLLIKYASQ SLSGIPARFSGSGSGTDFTLTISSLEPEDFAVYYCHQSSRLPFTFGPGTKVDIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 83 | LC-09 | 15A, 15B, 15C, 18A, 18B, 18C, 19A, 19B, 19C, 20A, 20B, 20C | EIVLTQSPGTLSLSPGERATLSCRASQSVGRSLHWYQQKPGQAPRLLIKYASQ SLSGIPDRFSGSGSGTDFTLTISRLEPEDFATYYCHQSSRLPFTFGQGTKVEIK RTVAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSFNRGE C |
| 84 | LC-10 | 28A, 28B, 28C | EIVLTQSPDFQSVTPKEKVTITCRASQSIGRSLHWYQQKPDQSPKLLFKYASQS LSGVPSRFSGSGSGTDFTLTINSLEAEDAATYYCHQSSRLPFTFGPGTKVDIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 85 | LC-11 | 29A, 29B, 29C | DIQLTQSPSFLSASVGDRVTITCRASQSIGRSLHWYQQKPGKAPKLLFKYASQS LSGVPSRFSGSGSGTEFTLTISSLQPEDFATYYCHQSSRLPFTFGPGTKVDIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 86 | LC-12 | 30A, 31A | EIVLTQSPGTLSLSPGERATLSCRASQSVSSSYLAWYQQKPGQAPRLLIYGASS RATGIPDRFSNSGSGTDFTLTISRLEPEDFAVYYCQRYGSSRTFGQGTKVEIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 87 | LC-13 | 32A | DIVMTQSPLSLPVTPGEPASISCRSSQSLLHSNGYNYLDWYLQKPGQSPQLLL YLGSNRASGVPDRFSGSGSGTDFTLQISRVEAEDVGVYYCMQTLQTPFTFGP GTKVDIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVTK SFNRGEC |
| 88 | LC-14 | 33A, 34A | DIVMTQSPLSLPVTPGEPASISCRSSQSLLHSNGYNYLDWYLQKPGQSPQLLL YLGSNRASGVPDRFSGSGSGTDFTLKISRVEAEDVGVYYCMQTLQTPFTFGP GTKVDIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVTK SFNRGEC |
| 89 | LC-15 | 35A | EIVLTQSPGTLSLSPGERATLSCRASQTVSRSYLAWYQQKPGQAPRLLIYGASS RATGIPDRFSGSGSGTDFTLTISRLEPEDFAVFYCQQFGSSPWTFGQGTKVEIK RTVAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSFNRGE C |
| 90 | LC-16 | 36A | DIVMTQSPDSLAVSLGERATIHCKSSQNVLYSSNNKNFLTWYQQKPGQPPKLLI YRASTRESGVPDRFSGSGSGTDFTLTISSLQAEDVAVYFCQQYYSAPFTFGPG TKVDIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |

TABLE 2A-continued

Exemplary Anti-hPAC1 Antibody Light Chain Amino Acid Sequences

| SEQ ID NO: | Seq Group | Antibodies containing sequence | LC AA Sequence |
|---|---|---|---|
| 91 | LC-17 | 37A | DIVMTQSPDSLAVSLGERTTIKCKSSQSVLYRSNNNNFLAWYQQKPGQPPKLLI YWASTRESGVPDRFSGSGSGTDFTLTISSLQAEDVAVYFCQQYYISPLTFGGG TKVEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |
| 92 | LC-18 | 38A | DIVMTQSPDSLAVSLGERATINCKSSQSVLYSSNNKHYLAWYRQKPGQPPKLLI YRASTRESGVPDRFSGSGSGTDFTLTISSLQPEDVAVYYCQQYYSSPFTFGPG TKVDIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |
| 93 | LC-19 | 39A, 39B | DIVMTQSPDSLAVSLGERATIHCKSSQSVLYSSNNKNFLTWYQQKPGQPPKLLI YRASTRESGVPDRFSGSGSGTDFTLTISSLQAEDVAVYFCQQYYSAPFTFGPG TRVDIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |
| 94 | LC-20 | 40A | DIVMTQSPDSLAVSLGERATIHCKSSQSVLYSSNNRNFLSWYQQKPGQPPKLLI YRASTRESGVPDRFSGSGSGTDFTLTISSLQAEDVAVYFCQQYYSAPFTFGPG TTVDIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |
| 95 | LC-21 | 41A | DIVMTQSPDSLAVSLGERATINCKSSQSVLYSSNNKNYLAWYRQKPGQPPKLLI YRASTRESGVPDRFSGSGSGTDFTLTISSLQAEDVAVYHCQQYYSSPFTFGPG TKVDIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |

TABLE 2B

Exemplary Anti-hPAC1 Antibody Heavy Chain Amino Acid Sequences

| SEQ ID NO: | Seq Group | Antibodies containing sequence | HC AA Sequence |
|---|---|---|---|
| 96 | HC-01 | 01A | QVQLQQSGPGLVKPSQTLSLTCAISGDSVSSNSATWNWIRQSPSRGLEWLGR TYYRSKWSNHYAVSVKSRITINPDTSKSQFSLQLNSVTPEDTAVYYCARGTWK QLWFLDHWGQGTLVTVSSASTKGPSVFPLAPCSRSTSESTAALGCLVKDYFPE PVTVSWNSGALTSGVHTFPAVLQSSGLYSLSSVVTVPSSNFGTQTYTCNVDHK PSNTKVDKTVERKCCVECPPCPAPPVAGPSVFLFPPKPKDTLMISRTPEVTCV VVDVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |
| 97 | HC-02 | 01B | QVQLQQSGPGLVKPSQTLSLTCAISGDSVSSNSATWNWIRQSPSRGLEWLGR TYYRSKWSNHYAVSVKSRITINPDTSKSQFSLQLNSVTPEDTAVYYCARGTWK QLWFLDHWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTPE VTCVVVDVSHEDPEVKFNWYVDGVEVHNAKTKPREEQYGSTYRVVSVLTVLH QDWLNGKEYKCKVSNKALPAPIEKTISKAKGQPREPQVYTLPPSREEMTKNQV SLTCLVKGFYPSDIAVEWESNGQPENNYKTTPPVLDSDGSFFLYSKLTVDKSR WQQGNVFSCSVMHEALHNHYTQKSLSLSPGK |
| 98 | HC-03 | 02A, 03A | QVQLVESGGGVVQPGRSLRLSCAASGFTFSYYAIHWVRQAPGKGLEWVAVIS YDGSNKYYADSVKGRFTISRDNSKNTLYLQMNSLRAEDTAVYYCARGYDLLTG YPDYWGQGTLVTVSSASTKGPSVFPLAPCSRSTSESTAALGCLVKDYFPEPVT VSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 99 | HC-04 | 02B | QVQLVESGGGVVQPGRSLRLSCAASGFTFSYYAIHWVRQAPGKGLEWVAVIS YDGSNKYYADSVKGRFTISRDNSKNTLYLQMNSLRAEDTAVYYCARGYDLLTG |

TABLE 2B-continued

Exemplary Anti-hPAC1 Antibody Heavy Chain Amino Acid Sequences

| SEQ ID NO: | Seq Group | Antibodies containing sequence | HC AA Sequence |
|---|---|---|---|
| | | | YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYGSTYRVVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |
| 100 | HC-05 | 02C | QVQLVESGGGVVQPGRSLRLSCAASGFTFSYYAIHWVRQAPGKGLEWVAVIS YDGSNKYYADSVKGRFTISRDNSKNTLYLQMNSLRAEDTAVYYCARGYDLLTG YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPCEEQYGSTYRCVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |
| 101 | HC-06 | 04A, 05A, 06A, 11A | QVQLVESGGGVVQPGRSLRLSCAASGFTFSRFAMHWVRRAPGKGLEWVAVI SYDGGNKYYAESVKGRFTISRDNSKNTLNLLMNSLRAEDTALFYCARGYDVLT GYPDYWGQGTLVTVSSASTKGPSVFPLAPCSRSTSESTAALGCLVKDYFPEPV TVSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 102 | HC-07 | 04B, 05B, 06B, 11B | QVQLVESGGGVVQPGRSLRLSCAASGFTFSRFAMHWVRRAPGKGLEWVAVI SYDGGNKYYAESVKGRFTISRDNSKNTLNLLMNSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 103 | HC-08 | 04C, 05C, 06C, 11C | QVQLVESGGGVVQPGRSLRLSCAASGFTFSRFAMHWVRRAPGKGLEWVAVI SYDGGNKYYAESVKGRFTISRDNSKNTLNLLMNSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 104 | HC-09 | 07A, 09A | QVQLVESGGGVVQPGRSLRLSCAASGFTFSRFAMHWVRQAPGKGLEWVAVI SYDGGNKYYAESVKGRFTISRDNSKNTLNLLMNSLRAEDTALFYCARGYDVLT GYPDYWGQGTLVTVSSASTKGPSVFPLAPCSRSTSESTAALGCLVKDYFPEPV TVSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 105 | HC-10 | 07B, 09B | QVQLVESGGGVVQPGRSLRLSCAASGFTFSRFAMHWVRQAPGKGLEWVAVI SYDGGNKYYAESVKGRFTISRDNSKNTLNLLMNSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 106 | HC-11 | 07C, 09C | QVQLVESGGGVVQPGRSLRLSCAASGFTFSRFAMHWVRQAPGKGLEWVAVI SYDGGNKYYAESVKGRFTISRDNSKNTLNLLMNSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD |

TABLE 2B-continued

Exemplary Anti-hPAC1 Antibody Heavy Chain Amino Acid Sequences

| SEQ ID NO: | Seq Group | Antibodies containing sequence | HC AA Sequence |
|---|---|---|---|
| | | | WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 107 | HC-12 | 08A, 10A, 13A, 14A, 15A | QVQLVESGGGVVQPGRSLRLSCAASGFTFSRFAMHWVRQAPGKGLEWVAVI SYDGGNKYYAESVKGRFTISRDNSKNTLYLQMNSLRAEDTALFYCARGYDVLT GYPDYWGQGTLVTVSSASTKGPSVFPLAPCSRSTSESTAALGCLVKDYFPEPV TVSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 108 | HC-13 | 08B, 10B, 13B, 14B, 15B | QVQLVESGGGVVQPGRSLRLSCAASGFTFSRFAMHWVRQAPGKGLEWVAVI SYDGGNKYYAESVKGRFTISRDNSKNTLYLQMNSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 109 | HC-14 | 08C, 10C, 13C, 14C, 15C | QVQLVESGGGVVQPGRSLRLSCAASGFTFSRFAMHWVRQAPGKGLEWVAVI SYDGGNKYYAESVKGRFTISRDNSKNTLYLQMNSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 110 | HC-15 | 12A | QVQLVESGGGVVQPGRSLRLSCAASGFTFSRFAMHWVRRAPGKGLEWVAVI SYDGGNKYYAESVKGRFTISRDNSKNTLNLLMDSLRAEDTALFYCARGYDVLT GYPDYWGQGTLVTVSSASTKGPSVFPLAPCSRSTSESTAALGCLVKDYFPEPV TVSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 111 | HC-16 | 12B | QVQLVESGGGVVQPGRSLRLSCAASGFTFSRFAMHWVRRAPGKGLEWVAVI SYDGGNKYYAESVKGRFTISRDNSKNTLNLLMDSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 112 | HC-17 | 12C | QVQLVESGGGVVQPGRSLRLSCAASGFTFSRFAMHWVRRAPGKGLEWVAVI SYDGGNKYYAESVKGRFTISRDNSKNTLNLLMDSLRAEDTALFYCARGYDVLT GYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 113 | HC-18 | 16A, 18A | QVQLVQSGAEVKKPGASVKVSCKASGFTFSRFAMHWVRQAPGQGLEWMGVI SYDGGNKYYAESVKGRVTMTRDTSTSTAYMELSSLRSEDTAVYYCARGYDVL TGYPDYWGQGTLVTVSSASTKGPSVFPLAPCSRSTSESTAALGCLVKDYFPEP VTVSWNSGALTSGVHTFPAVLQSSGLYSLSSVVTVPSSNFGTQTYTCNVDHKP SNTKVDKTVERKCCVECPPCPAPPVAGPSVFLFPPKPKDTLMISRTPEVTCVV VDVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |

TABLE 2B-continued

Exemplary Anti-hPAC1 Antibody Heavy Chain Amino Acid Sequences

| SEQ ID NO: | Seq Group | Antibodies containing sequence | HC AA Sequence |
|---|---|---|---|
| 114 | HC-19 | 16B, 18B | QVQLVQSGAEVKKPGASVKVSCKASGFTFSRFAMHWVRQAPGQGLEWMGVI SYDGGNKYYAESVKGRVTMTRDTSTSTAYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 115 | HC-20 | 16C, 18C | QVQLVQSGAEVKKPGASVKVSCKASGFTFSRFAMHWVRQAPGQGLEWMGVI SYDGGNKYYAESVKGRVTMTRDTSTSTAYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 116 | HC-21 | 17A, 19A | QVQLVQSGAEVKKPGASVKVSCAASGFTFSRFAMHWVRQAPGQGLEWMGVI SYDGGNKYYAESVKGRVTMTRDNSKNTAYMELSSLRSEDTAVYYCARGYDVL TGYPDYWGQGTLVTVSSASTKGPSVFPLAPCSRSTSESTAALGCLVKDYFPEP VTVSWNSGALTSGVHTFPAVLQSSGLYSLSSVVTVPSSNFGTQTYTCNVDHKP SNTKVDKTVERKCCVECPPCPAPPVAGPSVFLFPPKPKDTLMISRTPEVTCVV VDVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |
| 117 | HC-22 | 17B, 19B | QVQLVQSGAEVKKPGASVKVSCAASGFTFSRFAMHWVRQAPGQGLEWMGVI SYDGGNKYYAESVKGRVTMTRDNSKNTAYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 118 | HC-23 | 17C, 19C | QVQLVQSGAEVKKPGASVKVSCAASGFTFSRFAMHWVRQAPGQGLEWMGVI SYDGGNKYYAESVKGRVTMTRDNSKNTAYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 119 | HC-24 | 20A, 21A | EVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSSASTKGPSVFPLAPCSRSTSESTAALGCLVKDYFPEPVT VSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 120 | HC-25 | 20B, 21B | EVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYGSTYRVVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |
| 121 | HC-26 | 20C, 21C | EVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN |

TABLE 2B-continued

Exemplary Anti-hPAC1 Antibody Heavy Chain Amino Acid Sequences

| SEQ ID NO: | Seq Group | Antibodies containing sequence | HC AA Sequence |
|---|---|---|---|
| | | | TKVDKKVEPKSCDKTHTCPPCPAPELLGGPSVFLFPPKPKDTLMISRTPEVTCV VVDVSHEDPEVKFNWYVDGVEVHNAKTKPCEEQYGSTYRCVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |
| 122 | HC-27 | 22A, 23A | QVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSSASTKGPSVFPLAPCSRSTSESTAALGCLVKDYFPEPVT VSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 123 | HC-28 | 22B, 23B | QVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYGSTYRVVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |
| 124 | HC-29 | 22C, 23C | QVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPCEEQYGSTYRCVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |
| 125 | HC-30 | 24A | QVQLVQSGAEVKKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSSASTKGPSVFPLAPCSRSTSESTAALGCLVKDYFPEP VTVSWNSGALTSGVHTFPAVLQSSGLYSLSSVVTVPSSNFGTQTYTCNVDHKP SNTKVDKTVERKCCVECPPCPAPPVAGPSVFLFPPKPKDTLMISRTPEVTCVV VDVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |
| 126 | HC-31 | 24B | QVQLVQSGAEVKKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 127 | HC-32 | 24C | QVQLVQSGAEVKKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 128 | HC-33 | 25A | QVQLVQSGAEVKKPGASVKVSCKASGFTFSRFAMHWVRQAPGQGLEWMGVI SYDGGNKYYAESVKGRVTMTRDTSKSTAYMELSSLRSEDTAVYYCARGYDVL TGYPDYWGQGTLVTVSSASTKGPSVFPLAPCSRSTSESTAALGCLVKDYFPEP VTVSWNSGALTSGVHTFPAVLQSSGLYSLSSVVTVPSSNFGTQTYTCNVDHKP SNTKVDKTVERKCCVECPPCPAPPVAGPSVFLFPPKPKDTLMISRTPEVTCVV VDVSHEDPEVQFNWYVDGVEVHNAKTKPREEQFNSTFRVVSVLTVVHQDWL |

TABLE 2B-continued

Exemplary Anti-hPAC1 Antibody Heavy Chain Amino Acid Sequences

| SEQ ID NO: | Seq Group | Antibodies containing sequence | HC AA Sequence |
|---|---|---|---|
| | | | NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |
| 129 | HC-34 | 25B | QVQLVQSGAEVKKPGASVKVSCKASGFTFSRFAMHWVRQAPGQGLEWMGVI SYDGGNKYYAESVKGRVTMTRDTSKSTAYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 130 | HC-35 | 25C | QVQLVQSGAEVKKPGASVKVSCKASGFTFSRFAMHWVRQAPGQGLEWMGVI SYDGGNKYYAESVKGRVTMTRDTSKSTAYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 131 | HC-36 | 26A, 27A | QVQLVESGAEVVKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSSASTKGPSVFPLAPCSRSTSESTAALGCLVKDYFPEP VTVSWNSGALTSGVHTFPAVLQSSGLYSLSSVVTVPSSNFGTQTYTCNVDHKP SNTKVDKTVERKCCVECPPCPAPPVAGPSVFLFPPKPKDTLMISRTPEVTCVV VDVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |
| 132 | HC-37 | 26B, 27B | QVQLVESGAEVVKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPREEQYGSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 133 | HC-38 | 26C, 27C | QVQLVESGAEVVKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVT CVVVDVSHEDPEVKFNWYVDGVEVHNAKTKPCEEQYGSTYRCVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| 134 | HC-39 | 28A, 29A | QVQLVESGGGVVQPGRSLRLSCAASGFTFSRYAMHWVRQASGKGLEWVAVI SYDGSNKYYADSVKGRFTISRDNSKNTLYLLMSSLRAEDTAVFYCARGYDILTG YPDYWGQGTLVTVSSASTKGPSVFPLAPCSRSTSESTAALGCLVKDYFPEPVT VSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVV DVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGN VFSCSVMHEALHNHYTQKSLSLSPGK |
| 135 | HC-40 | 28B, 29B | QVQLVESGGGVVQPGRSLRLSCAASGFTFSRYAMHWVRQASGKGLEWVAVI SYDGSNKYYADSVKGRFTISRDNSKNTLYLLMSSLRAEDTAVFYCARGYDILTG YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPREEQYGSTYRVVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |

TABLE 2B-continued

Exemplary Anti-hPAC1 Antibody Heavy Chain Amino Acid Sequences

| SEQ ID NO: | Seq Group | Antibodies containing sequence | HC AA Sequence |
|---|---|---|---|
| 136 | HC-41 | 28C, 29C | QVQLVESGGGVVQPGRSLRLSCAASGFTFSRYAMHWVRQASGKGLEWVAVI SYDGSNKYYADSVKGRFTISRDNSKNTLYLLMSSLRAEDTAVFYCARGYDILTG YPDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTCV VVDVSHEDPEVKFNWYVDGVEVHNAKTKPCEEQYGSTYRCVSVLTVLHQDWL NGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQG NVFSCSVMHEALHNHYTQKSLSLSPGK |
| 137 | HC-42 | 30A | QVQLVQSGAEVKKPGASVKVSCKASGYTFTSYGISWVRQAPGQGLEWMGWI NAYNGHTNYAQTFQGRVTMTTDTSTSTAYMELRSLRSDDTAVYYCARELELR SFYYFGMDVWGQGTTVPVSSASTKGPSVFPLAPCSRSTSESTAALGCLVKDY FPEPVTVSWNSGALTSGVHTFPAVLQSSGLYSLSSVVTVPSSNFGTQTYTCNV DHKPSNTKVDKTVERKCCVECPPCPAPPVAGPSVFLFPPKPKDTLMISRTPEV TCVVVDVSHEDPEVQFNWYVDGVEVHNAKTKPREEQFNSTFRVVSVLTVVHQ DWLNGKEYKCKVSNKGLPAPIEKTISKTKGQPREPQVYTLPPSREEMTKNQVS LTCLVKGFYPSDIAVEWESNGQPENNYKTTPPMLDSDGSFFLYSKLTVDKSRW QQGNVFSCSVMHEALHNHYTQKSLSLSPGK |
| 138 | HC-43 | 31A | QVQLVQSGAEVKKPGASVKVSCKASGYTFTSYGISWVRQAPGQGLEWMGWI NAYNGHTNYAQTFQGRVTMTTDTSTSTAYMELRSLRSDDTAVYYCARELELR SFYYFGMDVWGQGTTVTVSSASTKGPSVFPLAPCSRSTSESTAALGCLVKDY FPEPVTVSWNSGALTSGVHTFPAVLQSSGLYSLSSVVTVPSSNFGTQTYTCNV DHKPSNTKVDKTVERKCCVECPPCPAPPVAGPSVFLFPPKPKDTLMISRTPEV TCVVVDVSHEDPEVQFNWYVDGVEVHNAKTKPREEQFNSTFRVVSVLTVVHQ DWLNGKEYKCKVSNKGLPAPIEKTISKTKGQPREPQVYTLPPSREEMTKNQVS LTCLVKGFYPSDIAVEWESNGQPENNYKTTPPMLDSDGSFFLYSKLTVDKSRW QQGNVFSCSVMHEALHNHYTQKSLSLSPGK |
| 139 | HC-44 | 32A | QVQLVQSGAEVKKSGASLKVSCKASGYIFTRYGVSWVRQAPGQGLEWMGWI TTYNGNTNYAQKLQGRVTMTIDTSTSTAYMELRSLRSDDTAVYYCARRVRYSG GYSFDNWGQGTLVTVSSASTKGPSVFPLAPCSRSTSESTAALGCLVKDYFPEP VTVSWNSGALTSGVHTFPAVLQSSGLYSLSSVVTVPSSNFGTQTYTCNVDHKP SNTKVDKTVERKCCVECPPCPAPPVAGPSVFLFPPKPKDTLMISRTPEVTCVV VDVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |
| 140 | HC-45 | 33A | QVQLVQSGAEVKKSGASLKVSCKASGYIFTRYGVSWVRQAPGQGLEWMGWI TTYNGNTNYAQKLQGRVTMTTDTSTSTAYMELRSLRSDDTAVYYCARRVRYS GGYSFDNWGQGTLVTVSSASTKGPSVFPLAPCSRSTSESTAALGCLVKDYFP EPVTVSWNSGALTSGVHTFPAVLQSSGLYSLSSVVTVPSSNFGTQTYTCNVDH KPSNTKVDKTVERKCCVECPPCPAPPVAGPSVFLFPPKPKDTLMISRTPEVTC VVVDVSHEDPEVQFNWYVDGVEVHNAKTKPREEQFNSTFRVVSVLTVVHQD WLNGKEYKCKVSNKGLPAPIEKTISKTKGQPREPQVYTLPPSREEMTKNQVSL TCLVKGFYPSDIAVEWESNGQPENNYKTTPPMLDSDGSFFLYSKLTVDKSRW QQGNVFSCSVMHEALHNHYTQKSLSLSPGK |
| 141 | HC-46 | 34A | QVQLVQSGAEVKKSGASLKVSCKASGYIFTRYGVSWVRQAPGQGLEWMGWI TTYNGNTNYAQKLQGRVTMTTDTSTNTAYMELRSLRSDDTAVYYCARRVRYS GGYSFDNWGQGTLVTVSSASTKGPSVFPLAPCSRSTSESTAALGCLVKDYFP EPVTVSWNSGALTSGVHTFPAVLQSSGLYSLSSVVTVPSSNFGTQTYTCNVDH KPSNTKVDKTVERKCCVECPPCPAPPVAGPSVFLFPPKPKDTLMISRTPEVTC VVVDVSHEDPEVQFNWYVDGVEVHNAKTKPREEQFNSTFRVVSVLTVVHQD WLNGKEYKCKVSNKGLPAPIEKTISKTKGQPREPQVYTLPPSREEMTKNQVSL TCLVKGFYPSDIAVEWESNGQPENNYKTTPPMLDSDGSFFLYSKLTVDKSRW QQGNVFSCSVMHEALHNHYTQKSLSLSPGK |
| 142 | HC-47 | 35A | QVQLQESGPGLVKPSETLSLTCTVSGGSISSYYWSWIRQPAGKGLEWIGRIYT SGSTNYNPSLKSRVTMSIGTSKNQFSLKLSSVTAADTAVYYCAIIASRGWYFDL WGRGTLVTVSSASTKGPSVFPLAPCSRSTSESTAALGCLVKDYFPEPVTVSWN SGALTSGVHTFPAVLQSSGLYSLSSVVTVPSSNFGTQTYTCNVDHKPSNTKVD KTVERKCCVECPPCPAPPVAGPSVFLFPPKPKDTLMISRTPEVTCVVVDVSHE DPEVQFNWYVDGVEVHNAKTKPREEQFNSTFRVVSVLTVVHQDWLNGKEYK CKVSNKGLPAPIEKTISKTKGQPREPQVYTLPPSREEMTKNQVSLTCLVKGFYP SDIAVEWESNGQPENNYKTTPPMLDSDGSFFLYSKLTVDKSRWQQGNVFSCS VMHEALHNHYTQKSLSLSPGK |
| 143 | HC-48 | 36A, 40A | QVQLQESGPGLVKPSQTLSLTCTVSGGSISSGGYYWSWIRQHPGKGLEWIGYI YYSGNTYYNPSLKSRVTISGDTSKNQFSLKLRSVTAADTAVYYCARGGAARGM DVWGQGTTVTVSSASTKGPSVFPLAPCSRSTSESTAALGCLVKDYFPEPVTVS WNSGALTSGVHTFPAVLQSSGLYSLSSVVTVPSSNFGTQTYTCNVDHKPSNTK |

TABLE 2B-continued

Exemplary Anti-hPAC1 Antibody Heavy Chain Amino Acid Sequences

| SEQ ID NO: | Seq Group | Antibodies containing sequence | HC AA Sequence |
|---|---|---|---|
| | | | VDKTVERKCCVECPPCPAPPVAGPSVFLFPPKPKDTLMISRTPEVTCVVVDVS HEDPEVQFNWYVDGVEVHNAKTKPREEQFNSTFRVVSVLTVVHQDWLNGKE YKCKVSNKGLPAPIEKTISKTKGQPREPQVYTLPPSREEMTKNQVSLTCLVKGF YPSDIAVEWESNGQPENNYKTTPPMLDSDGSFFLYSKLTVDKSRWQQGNVFS CSVMHEALHNHYTQKSLSLSPGK |
| 144 | HC-49 | 37A | QVQLQQSGPGLVKPSQTLSLTCAISGDSVSSNSAAWNWIRQSPSRGLEWLGR TYYRSRWYNDYAVSVKSRITINPDTSKNQFSLQLNSVTPEDTAVYYCARGVFY SKGAFDIWGQGTMVTVSSASTKGPSVFPLAPCSRSTSESTAALGCLVKDYFPE PVTVSWNSGALTSGVHTFPAVLQSSGLYSLSSVVTVPSSNFGTQTYTCNVDHK PSNTKVDKTVERKCCVECPPCPAPPVAGPSVFLFPPKPKDTLMISRTPEVTCV VVDVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVSLTCL VKGFYPSDIAVEWESNGQPENNYKTTPPMLDSDGSFFLYSKLTVDKSRWQQG NVFSCSVMHEALHNHYTQKSLSLSPGK |
| 145 | HC-50 | 38A | QVQLQESGPGLVKPSQTLSLTCTVSGGSISRGGYYWSWIRQHPGKGLEWIGYI YYSGNTYYNPSLKSRVIISGDTSKNQLSLKLRSVTAADTAVYYCARGGAARGM DVWGQGTTVTVSSASTKGPSVFPLAPCSRSTSESTAALGCLVKDYFPEPVTVS WNSGALTSGVHTFPAVLQSSGLYSLSSVVTVPSSNFGTQTYTCNVDHKPSNTK VDKTVERKCCVECPPCPAPPVAGPSVFLFPPKPKDTLMISRTPEVTCVVVDVS HEDPEVQFNWYVDGVEVHNAKTKPREEQFNSTFRVVSVLTVVHQDWLNGKE YKCKVSNKGLPAPIEKTISKTKGQPREPQVYTLPPSREEMTKNQVSLTCLVKGF YPSDIAVEWESNGQPENNYKTTPPMLDSDGSFFLYSKLTVDKSRWQQGNVFS CSVMHEALHNHYTQKSLSLSPGK |
| 146 | HC-51 | 39A | QVQLQESGPGLVKPSQTLSLTCTVSGGSISSGGYYWSWIRQHPGKGLEWIGYI YYSGNTYYNPSLKSRVTISGDTSKNQFSLKLRSVTAADTAVYYCTRGGAARGM DVWGQGTTVTVSSASTKGPSVFPLAPCSRSTSESTAALGCLVKDYFPEPVTVS WNSGALTSGVHTFPAVLQSSGLYSLSSVVTVPSSNFGTQTYTCNVDHKPSNTK VDKTVERKCCVECPPCPAPPVAGPSVFLFPPKPKDTLMISRTPEVTCVVVDVS HEDPEVQFNWYVDGVEVHNAKTKPREEQFNSTFRVVSVLTVVHQDWLNGKE YKCKVSNKGLPAPIEKTISKTKGQPREPQVYTLPPSREEMTKNQVSLTCLVKGF YPSDIAVEWESNGQPENNYKTTPPMLDSDGSFFLYSKLTVDKSRWQQGNVFS CSVMHEALHNHYTQKSLSLSPGK |
| 147 | HC-52 | 39B | QVQLQESGPGLVKPSQTLSLTCTVSGGSISSGGYYWSWIRQHPGKGLEWIGYI YYSGNTYYNPSLKSRVTISGDTSKNQFSLKLRSVTAADTAVYYCTRGGAARGM DVWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVVV DVSHEDPEVKFNWYVDGVEVHNAKTKPREEQYGSTYRVVSVLTVLHQDWLN GKEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGN VFSCSVMHEALHNHYTQKSLSLSPGK |
| 148 | HC-53 | 41A | QVQLQESGPGLVKPSQTLSLTCTVSGGSISSGGFYWSWIRQHPGKGLEWIGYI YYSGNTYYNPSLKSRVIISGDTSKNQFSLKLSSVTAADTAVYYCARGGAARGM DVWGQGTTVTVSSASTKGPSVFPLAPCSRSTSESTAALGCLVKDYFPEPVTVS WNSGALTSGVHTFPAVLQSSGLYSLSSVVTVPSSNFGTQTYTCNVDHKPSNTK VDKTVERKCCVECPPCPAPPVAGPSVFLFPPKPKDTLMISRTPEVTCVVVDVS HEDPEVQFNWYVDGVEVHNAKTKPREEQFNSTFRVVSVLTVVHQDWLNGKE YKCKVSNKGLPAPIEKTISKTKGQPREPQVYTLPPSREEMTKNQVSLTCLVKGF YPSDIAVEWESNGQPENNYKTTPPMLDSDGSFFLYSKLTVDKSRWQQGNVFS CSVMHEALHNHYTQKSLSLSPGK |

Variable Domains of Antibodies

Also provided are antibodies (and corresponding nucleic acid sequences) that contain an antibody light chain variable region or an antibody heavy chain variable region, as shown in Tables 3A and 3B below, and immunologically functional fragments, derivatives, muteins and variants of these light chain and heavy chain variable regions.

Also included are nucleic acid sequences encoding the variable regions shown in Tables 3A and 3B. Because those sequences are contained in the full-length nucleic acid sequences of the corresponding antibodies shown in Tables 1A and 1B, they are not culled out as separate sequences in a table or in the Sequence Listing, but can be readily ascertained by one of skill in the art based on the variable regions provided in Tables 3A and 3B, together with the full length DNA sequences in Tables 1A and 1B.

Antibodies of this type can generally be designated by the formula "$V_{Hx}/V_{Ly}$," where "x" corresponds to the number of heavy chain variable regions and "y" corresponds to the number of the light chain variable regions.

TABLE 3A

Exemplary Anti-hPAC1 Antibody Light Chain Variable Region Amino Acid Sequences

| SEQ ID NO: | Seq Group | Antibodies containing sequence | V_L AA Sequence |
|---|---|---|---|
| 149 | LV-01 | 01A, 01B | DIQMTQSPSSLSASVGDRITITCRASQSISRYLNWYQQKPGKAPKLLIYAASSLQSGIPSRFSGSGSGTDFTLTINSLQPEDFATYFCQQSYSPPFTFGPGTKVDIKR |
| 150 | LV-02 | 02A, 02B, 02C | EIVLTQSPDFQSVTPKEKVTITCRASQSIGSSLHWYQQKPDQSPKLLIKYASQSLSGIPSRFSGSGSGTHFTLTINSLEAEDAATYYCHQSSRLPFTFGPGTKVDIKR |
| 151 | LV-03 | 03A | DIQLTQSPSFLSASVGDRVTITCRASQSIGRSLHWYQQKPGKAPKLLIKYASQSLSGVPSRFSGSGSGTEFTLTISSLQPEDFATYYCHQSSRLPFTFGPGTKVDIKR |
| 152 | LV-04 | 04A, 04B, 04C, 07A, 07B, 07C, 08A, 08B, 08C, 12A, 12B, 12C | EIVLTQSPDFQSVTPKEKVTITCRASQSVGRSLHWYHQKPDQSPKLLIKYASQSLSGVPSRFSGSGSGTDFTLIINSLEAEDAATYYCHQSSRLPFTFGPGTKVDIKR |
| 153 | LV-05 | 05A, 05B, 05C, 13A, 13B, 13C, 16A, 16B, 16C, 17A, 17B, 17C, 21A, 21B, 21C, 22A, 22B, 22C, 24A, 24B, 24C, 25A, 25B, 25C, 26A, 26B, 26C | DIQLTQSPSFLSASVGDRVTITCRASQSIGRSLHWYQQKPGKAPKLLIKYASQSLSGVPSRFSGSGSGTEFTLTISSLQPEDFATYYCHQSSRLPFTFGPGTKVDIKR |
| 154 | LV-06 | 06A, 06B, 06C | DIQLTQSPSFLSASVGDRVTITCRASQSIGRSLHWYHQKPGKAPKLLIKYASQSLSGVPSRFSGSGSGTEFTLIISSLQPEDFATYYCHQSSRLPFTFGPGTKVDIKR |
| 155 | LV-07 | 09A, 09B, 09C, 10A, 10B, 10C, 11A, 11B, 11C | EIVLTQSPDFQSVTPKEKVTITCRASQSVGRSLHWYQQKPDQSPKLLIKYASQSLSGVPSRFSGSGSGTDFTLTINSLEAEDAATYYCHQSSRLPFTFGPGTKVDIKR |
| 156 | LV-08 | 14A, 14B, 14C, 23A, 23B, 23C, 27A, 27B, 27C | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIKR |
| 157 | LV-09 | 15A, 15B, 15C, 18A, 18B, 18C, 19A, 19B, 19C, 20A, 20B, 20C | EIVLTQSPGTLSLSPGERATLSCRASQSVGRSLHWYQQKPGQAPRLLIKYASQSLSGIPDRFSGSGSGTDFTLTISRLEPEDFATYYCHQSSRLPFTFGQGTKVEIKR |
| 158 | LV-10 | 28A, 28B, 28C | EIVLTQSPDFQSVTPKEKVTITCRASQSIGRSLHWYQQKPDQSPKLLFKYASQSLSGVPSRFSGSGSGTDFTLTINSLEAEDAATYYCHQSSRLPFTFGPGTKVDIKR |
| 159 | LV-11 | 29A, 29B, 29C | DIQLTQSPSFLSASVGDRVTITCRASQSIGRSLHWYQQKPGKAPKLLFKYASQSLSGVPSRFSGSGSGTEFTLTISSLQPEDFATYYCHQSSRLPFTFGPGTKVDIKR |
| 160 | LV-12 | 30A, 31A | EIVLTQSPGTLSLSPGERATLSCRASQSVSSSYLAWYQQKPGQAPRLLIYGASSRATGIPDRFSNSGSGTDFTLTISRLEPEDFAVYYCQRYGSSRTFGQGTKVEIKR |
| 161 | LV-13 | 32A | DIVMTQSPLSLPVTPGEPASISCRSSQSLLHSNGYNYLDWYLQKPGQSPQLLLYLGSNRASGVPDRFSGSGSGTDFTLQISRVEAEDVGVYYCMQTLQTPFTFGPGTKVDIKR |
| 162 | LV-14 | 33A, 34A | DIVMTQSPLSLPVTPGEPASISCRSSQSLLHSNGYNYLDWYLQKPGQSPQLLLYLGSNRASGVPDRFSGSGSGTDFTLKISRVEAEDVGVYYCMQTLQTPFTFGPGTKVDIKR |
| 163 | LV-15 | 35A | EIVLTQSPGTLSLSPGERATLSCRASQTVSRSYLAWYQQKPGQAPRLLIYGASSRATGIPDRFSGSGSGTDFTLTISRLEPEDFAVFYCQQFGSSPWTFGQGTKVEIKR |
| 164 | LV-16 | 36A | DIVMTQSPDSLAVSLGERATIHCKSSQNVLYSSNNKNFLTWYQQKPGQPPKLLIYRASTRESGVPDRFSGSGSGTDFTLTISSLQAEDVAVYFCQQYYSAPFTFGPGTKVDIKR |
| 165 | LV-17 | 37A | DIVMTQSPDSLAVSLGERTTIKCKSSQSVLYRSNNNNFLAWYQQKPGQPPKLLIYWASTRESGVPDRFSGSGSGTDFTLTISSLQAEDVAVYFCQQYYISPLTFGGGTKVEIKR |
| 166 | LV-18 | 38A | DIVMTQSPDSLAVSLGERATINCKSSQSVLYSSNNKHYLAWYRQKPGQPPKLLIYRASTRESGVPDRFSGSGSGTDFTLTISSLQPEDVAVYYCQQYYSSPFTFGPGTKVDIKR |

TABLE 3A-continued

Exemplary Anti-hPAC1 Antibody Light Chain Variable Region Amino Acid Sequences

| SEQ ID NO: | Seq Group | Antibodies containing sequence | $V_L$ AA Sequence |
|---|---|---|---|
| 167 | LV-19 | 39A, 39B | DIVMTQSPDSLAVSLGERATIHCKSSQSVLYSSNNKNFLTWYQQKPGQPPKLLI YRASTRESGVPDRFSGSGSGTDFTLTISSLQAEDVAVYFCQQYYSAPFTFGPG TRVDIKR |
| 168 | LV-20 | 40A | DIVMTQSPDSLAVSLGERATIHCKSSQSVLYSSNNRNFLSWYQQKPGQPPKLLI YRASTRESGVPDRFSGSGSGTDFTLTISSLQAEDVAVYFCQQYYSAPFTFGPG TTVDIKR |
| 169 | LV-21 | 41A | DIVMTQSPDSLAVSLGERATINCKSSQSVLYSSNNKNYLAWYRQKPGQPPKLLI YRASTRESGVPDRFSGSGSGTDFTLTISSLQAEDVAVYHCQQYYSSPFTFGPG TKVDIKR |

TABLE 3B

Exemplary Anti-hPAC1 Antibody Heavy Chain Variable Region Amino Acid Sequences

| SEQ ID NO: | Seq Group | Antibodies containing sequence | $V_H$ AA Sequence |
|---|---|---|---|
| 170 | HV-01 | 01A, 01B | QVQLQQSGPGLVKPSQTLSLTCAISGDSVSSNSATWNWIRQSPSRGLEWLGR TYYRSKWSNHYAVSVKSRITINPDTSKSQFSLQLNSVTPEDTAVYYCARGTWK QLWFLDHWGQGTLVTVSS |
| 171 | HV-02 | 02A, 02B, 02C, 03A | QVQLVESGGGVVQPGRSLRLSCAASGFTFSYYAIHWVRQAPGKGLEWVAVIS YDGSNKYYADSVKGRFTISRDNSKNTLYLQMNSLRAEDTAVYYCARGYDLLTG YPDYWGQGTLVTVSS |
| 172 | HV-03 | 04A, 04B, 04C, 05A, 05B, 05C, 06A, 06B, 06C, 11A, 11B, 11C | QVQLVESGGGVVQPGRSLRLSCAASGFTFSRFAMHWVRRAPGKGLEWVAVI SYDGGNKYYAESVKGRFTISRDNSKNTLNLLMNSLRAEDTALFYCARGYDVLT GYPDYWGQGTLVTVSS |
| 173 | HV-04 | 07A, 07B, 07C, 09A, 09B, 09C | QVQLVESGGGVVQPGRSLRLSCAASGFTFSRFAMHWVRQAPGKGLEWVAVI SYDGGNKYYAESVKGRFTISRDNSKNTLNLLMNSLRAEDTALFYCARGYDVLT GYPDYWGQGTLVTVSS |
| 174 | HV-05 | 08A, 08B, 08C, 10A, 10B, 10C, 13A, 13B, 13C, 14A, 14B, 14C, 15A, 15B, 15C | QVQLVESGGGVVQPGRSLRLSCAASGFTFSRFAMHWVRQAPGKGLEWVAVI SYDGGNKYYAESVKGRFTISRDNSKNTLYLQMNSLRAEDTALFYCARGYDVLT GYPDYWGQGTLVTVSS |
| 175 | HV-06 | 12A, 12B, 12C | QVQLVESGGGVVQPGRSLRLSCAASGFTFSRFAMHWVRRAPGKGLEWVAVI SYDGGNKYYAESVKGRFTISRDNSKNTLNLLMDSLRAEDTALFYCARGYDVLT GYPDYWGQGTLVTVSS |
| 176 | HV-07 | 16A, 16B, 16C, 18A, 18B, 18C | QVQLVQSGAEVKKPGASVKVSCKASGFTFSRFAMHWVRQAPGQGLEWMGVI SYDGGNKYYAESVKGRVTMTRDTSTSTAYMELSSLRSEDTAVYYCARGYDVL TGYPDYWGQGTLVTVSS |
| 177 | HV-08 | 17A, 17B, 17C, 19A, 19B, 19C | QVQLVQSGAEVKKPGASVKVSCKASGFTFSRFAMHWVRQAPGQGLEWMGVI SYDGGNKYYAESVKGRVTMTRDNSKNTAYMELSSLRSEDTAVYYCARGYDVL TGYPDYWGQGTLVTVSS |
| 178 | HV-09 | 20A, 20B, 20C, 21A, 21B, 21C | EVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSS |
| 179 | HV-10 | 22A, 22B, 22C, 23A, 23B, 23C | QVQLLESGGGLVQPGGSLRLSCAASGFTFSRFAMHWVRQAPGKGLEWVAVIS YDGGNKYYAESVKGRFTISRDNSKNTLYLQMNSLRAEDTAVYYCARGYDVLTG YPDYWGQGTLVTVSS |
| 180 | HV-11 | 24A, 24B, 24C | QVQLVQSGAEVKKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSS |

TABLE 3B-continued

Exemplary Anti-hPAC1 Antibody Heavy Chain Variable Region Amino Acid Sequences

| SEQ ID NO: | Seq Group | Antibodies containing sequence | $V_H$ AA Sequence |
|---|---|---|---|
| 181 | HV-12 | 25A, 25B, 25C | QVQLVQSGAEVKKPGASVKVSCKASGFTFSRFAMHWVRQAPGQGLEWMGVI SYDGGNKYYAESVKGRVTMTRDTSKSTAYMELSSLRSEDTAVYYCARGYDVL TGYPDYWGQGTLVTVSS |
| 182 | HV-13 | 26A, 26B, 26C, 27A, 27B, 27C | QVQLVESGAEVVKPGASVKVSCKASGFTFSRFAMHWVRQAPGQGLEWMGVI SYDGGNKYYAESVKGRVTMTRDTSTSTLYMELSSLRSEDTAVYYCARGYDVL TGYPDYWGQGTLVTVSS |
| 183 | HV-14 | 28A, 28B, 28C, 29A, 29B, 29C | QVQLVESGGGVVQPGRSLRLSCAASGFTFSRYAMHWVRQASGKGLEWVAVI SYDGSNKYYADSVKGRFTISRDNSKNTLYLLMSSLRAEDTAVFYCARGYDILTG YPDYWGQGTLVTVSS |
| 184 | HV-15 | 30A | QVQLVQSGAEVKKPGASVKVSCKASGYTFTSYGISWVRQAPGQGLEWMGWI NAYNGHTNYAQTFQGRVTMTTDTSTSTAYMELRSLRSDDTAVYYCARELELR SFYYFGMDVWGQGTTVPVSS |
| 185 | HV-16 | 31A | QVQLVQSGAEVKKPGASVKVSCKASGYTFTSYGISWVRQAPGQGLEWMGWI NAYNGHTNYAQTFQGRVTMTTDTSTSTAYMELRSLRSDDTAVYYCARELELR SFYYFGMDVWGQGTTVTVSS |
| 186 | HV-17 | 32A | QVQLVQSGAEVKKSGASLKVSCKASGYIFTRYGVSWVRQAPGQGLEWMGWI TTYNGNTNYAQKLQGRVTMTIDTSTSTAYMELRSLRSDDTAVYYCARRVRYSG GYSFDNWGQGTLVTVSS |
| 187 | HV-18 | 33A | QVQLVQSGAEVKKSGASLKVSCKASGYIFTRYGVSWVRQAPGQGLEWMGWI TTYNGNTNYAQKLQGRVTMTTDTSTSTAYMELRSLRSDDTAVYYCARRVRYS GGYSFDNWGQGTLVTVSS |
| 188 | HV-19 | 34A | QVQLVQSGAEVKKSGASLKVSCKASGYIFTRYGVSWVRQAPGQGLEWMGWI TTYNGNTNYAQKLQGRVTMTTDTSTNTAYMELRSLRSDDTAVYYCARRVRYS GGYSFDNWGQGTLVTVSS |
| 189 | HV-20 | 35A | QVQLQESGPGLVKPSETLSLTCTVSGGSISSYYWSWIRQPAGKGLEWIGRIYT SGSTNYNPSLKSRVTMSIGTSKNQFSLKLSSVTAADTAVYYCAIIASRGWYFDL WGRGTLVTVSS |
| 190 | HV-21 | 36A, 40A | QVQLQESGPGLVKPSQTLSLTCTVSGGSISSGGYYWSWIRQHPGKGLEWIGYI YYSGNTYYNPSLKSRVTISGDTSKNQFSLKLRSVTAADTAVYYCARGGAARGM DVWGQGTTVTVSS |
| 191 | HV-22 | 37A | QVQLQQSGPGLVKPSQTLSLTCAISGDSVSSNSAAWNWIRQSPSRGLEWLGR TYYRSRWYNDYAVSVKSRITINPDTSKNQFSLQLNSVTPEDTAVYYCARGVFY SKGAFDIWGQGTMVTVSS |
| 192 | HV-23 | 38A | QVQLQESGPGLVKPSQTLSLTCTVSGGSISRGGYYWSWIRQHPGKGLEWIGYI YYSGNTYYNPSLKSRVIISGDTSKNQLSLKLRSVTAADTAVYYCARGGAARGM DVWGQGTTVTVSS |
| 193 | HV-24 | 39A | QVQLQESGPGLVKPSQTLSLTCTVSGGSISSGGYYWSWIRQHPGKGLEWIGYI YYSGNTYYNPSLKSRVTISGDTSKNQFSLKLRSVTAADTAVYYCTRGGAARGM DVWGQGTTVTVSS |
| 194 | HV-25 | 39B | QVQLQESGPGLVKPSQTLSLTCTVSGGSISSGGYYWSWIRQHPGKGLEWIGYI YYSGNTYYNPSLKSRVTISGDTSKNQFSLKLRSVTAADTAVYYCTRGGAARGM DVWGQGTTVTVSS |
| 195 | HV-26 | 41A | QVQLQESGPGLVKPSQTLSLTCTVSGGSISSGGFYWSWIRQHPGKGLEWIGYI YYSGNTYYNPSLKSRVIISGDTSKNQFSLKLSSVTAADTAVYYCARGGAARGM DVWGQGTTVTVSS |

Each of the heavy chain variable regions listed in Table 3B may be combined with any of the light chain variable regions shown in Table 3A to form an antibody.

CDRs

The antibodies disclosed herein are polypeptides into which one or more CDRs are grafted, inserted and/or joined. An antibody can have 1, 2, 3, 4, 5 or 6 CDRs. An antibody thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antibodies include both a CDRH3 and a CDRL3. Specific heavy and light chain CDRs are identified in Tables 3A and 3B, respectively.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical or have substantial sequence identity to the amino acid sequences of one or more of the CDRs presented in Table 4A (CDRLs) and Table 4B (CDRHs).

TABLE 4A

Exemplary Anti-hPAC1 Antibody Light Chain CDR Amino Acid Sequences

| SEQ ID NO: | Seq Group | Antibodies containing sequence | CDR Sequence |
|---|---|---|---|
| 196 | CDRL1-1 | 05A, 05B, 05C, 06A, 06B, 06C, 13A, 13B, 13C, 16A, 16B, 16C, 17A, 17B, 17C, 21A, 21B, 21C, 22A, 22B, 22C, 24A, 24B, 24C, 25A, 25B, 25C, 26A, 26B, 26C, 28A, 28B, 28C, 29A, 29B, 29C | RASQSIGRSLH |
| 197 | CDRL1-2 | 04A, 04B, 04C, 07A, 07B, 07C, 08A, 08B, 08C, 09A, 09B, 09C, 10A, 10B, 10C, 11A, 11B, 11C, 12A, 12B, 12C, 14A, 14B, 14C, 15A, 15B, 15C, 18A, 18B, 18C, 19A, 19B, 19C, 20A, 20B, 20C, 23A, 23B, 23C, 27A, 27B, 27C | RASQSVGRSLH |
| 198 | CDRL1-3 | 01A, 01B | RASQSISRYLN |
| 199 | CDRL1-4 | 30A, 31A | RASQSVSSSYLA |
| 200 | CDRL1-5 | 35A | RASQTVSRSYLA |
| 201 | CDRL1-6 | 32A, 33A, 34A | RSSQSLLHSNGYNYLD |
| 202 | CDRL1-7 | 36A | KSSQNVLYSSNNKNFLT |
| 203 | CDRL1-8 | 37A | KSSQSVLYRSNNNNFLA |
| 204 | CDRL1-9 | 38A | KSSQSVLYSSNNKHYLA |
| 205 | CDRL1-10 | 39A, 39B | KSSQSVLYSSNNKNFLT |
| 206 | CDRL1-11 | 41A | KSSQSVLYSSNNKNYLA |
| 207 | CDRL1-12 | 40A | KSSQSVLYSSNNRNFLS |
| 208 | CDRL1-13 | 02A, 02B, 02C, 03A | RASQSIGSSLH |
| 209 | CDRL2-1 | 02A, 02B, 02C, 03A, 04A, 04B, 04C, 05A, 05B, 05C, 06A, 06B, 06C, 07A, 07B, 07C, 08A, 08B, 08C, 09A, 09B, 09C, 10A, 10B, 10C, 11A, 11B, 11C, 12A, 12B, 12C, 13A, 13B, 13C, 14A, 14B, 14C, 15A, 15B, 15C, 16A, 16B, 16C, 17A, 17B, 17C, 18A, 18B, 18C, 19A, 19B, 19C, 20A, 20B, 20C, 21A, 21B, 21C, 22A, 22B, 22C, 23A, 23B, 23C, 24A, 24B, 24C, 25A, 25B, 25C, 26A, 26B, 26C, 27A, 27B, 27C, 28A, 28B, 28C, 29A, 29B, 29C | YASQSLS |
| 210 | CDRL2-2 | 01A, 01B | AASSLQS |
| 211 | CDRL2-3 | 30A, 31A, 35A | GASSRAT |
| 212 | CDRL2-4 | 32A, 33A, 34A | LGSNRAS |
| 213 | CDRL2-5 | 36A, 37A, 38A, 39A, 39B, 40A, 41A | RASTRES |
| 214 | CDRL2-6 | 37A | WASTRES |
| 215 | CDRL3-1 | 02A, 02B, 02C, 03A, 04A, 04B, 04C, 05A, 05B, 05C, 06A, 06B, 06C, 07A, 07B, 07C, 08A, 08B, 08C, 09A, 09B, 09C, 10A, 10B, 10C, 11A, 11B, 11C, 12A, 12B, 12C, 13A, 13B, 13C, 14A, 14B, 14C, 15A, 15B, 15C, 16A, 16B, 16C, 17A, 17B, 17C, 18A, 18B, 18C, 19A, 19B, 19C, 20A, 20B, 20C, 21A, 21B, 21C, 22A, 22B, 22C, 23A, 23B, 23C, 24A, 24B, 24C, 25A, 25B, 25C, 26A, 26B, 26C, 27A, 27B, 27C, 28A, 28B, 28C, 29A, 29B, 29C | HQSSRLPFT |
| 216 | CDRL3-2 | 01A, 01B | QQSYSPPFT |
| 217 | CDRL3-3 | 30A, 31A | QRYGSSRT |
| 218 | CDRL3-4 | 35A | QQFGSSPWT |
| 219 | CDRL3-5 | 32A, 33A, 34A | MQTLQTPFT |
| 220 | CDRL3-6 | 36A, 39A, 39B, 40A | QQYYSAPFT |

TABLE 4A-continued

Exemplary Anti-hPAC1 Antibody Light Chain CDR Amino Acid Sequences

| SEQ ID NO: | Seq Group | Antibodies containing sequence | CDR Sequence |
|---|---|---|---|
| 221 | CDRL3-7 | 37A | QQYYISPLT |
| 222 | CDRL3-8 | 38A, 41A | QQYYSSPFT |

TABLE 4B

Exemplary Anti-hPAC1 Antibody Heavy Chain CDR Amino Acid Sequences

| SEQ ID NO: | Seq Group | Antibodies containing sequence | CDR Sequence |
|---|---|---|---|
| 223 | CDRH1-1 | 04A, 04B, 04C, 05A, 05B, 05C, 06A, 06B, 06C, 07A, 07B, 07C, 08A, 08B, 08C, 09A, 09B, 09C, 10A, 10B, 10C, 11A, 11B, 11C, 12A, 12B, 12C, 13A, 13B, 13C, 14A, 14B, 14C, 15A, 15B, 15C, 16A, 16B, 16C, 17A, 17B, 17C, 18A, 18B, 18C, 19A, 19B, 19C, 20A, 20B, 20C, 21A, 21B, 21C, 22A, 22B, 22C, 23A, 23B, 23C, 24A, 24B, 24C, 25A, 25B, 25C, 26A, 26B, 26C, 27A, 27B, 27C | RFAMH |
| 224 | CDRH1-2 | 38A | RGGYYWS |
| 225 | CDRH1-3 | 28A, 28B, 28C, 29A, 29B, 29C | RYAMH |
| 226 | CDRH1-4 | 32A, 33A, 34A | RYGVS |
| 227 | CDRH1-5 | 41A | SGGFYWS |
| 228 | CDRH1-6 | 36A, 39A, 39B, 40A | SGGYYWS |
| 229 | CDRH1-7 | 37A | SNSAAWN |
| 230 | CDRH1-8 | 01A, 01B | SNSATWN |
| 231 | CDRH1-9 | 30A, 31A | SYGIS |
| 232 | CDRH1-10 | 35A | SYYWS |
| 233 | CDRH1-11 | 02A, 02B, 02C, 03A | YYAIH |
| 234 | CDRH2-1 | 35A | RIYTSGSTNYNPSLKS |
| 235 | CDRH2-2 | 01A, 01B | RTYYRSKWSNHYAVSVKS |
| 236 | CDRH2-3 | 37A | RTYYRSRWYNDYAVSVKS |
| 237 | CDRH2-4 | 04A, 04B, 04C, 05A, 05B, 05C, 06A, 06B, 06C, 07A, 07B, 07C, 08A, 08B, 08C, 09A, 09B, 09C, 10A, 10B, 10C, 11A, 11B, 11C, 12A, 12B, 12C, 13A, 13B, 13C, 14A, 14B, 14C, 15A, 15B, 15C, 16A, 16B, 16C, 17A, 17B, 17C, 18A, 18B, 18C, 19A, 19B, 19C, 20A, 20B, 20C, 21A, 21B, 21C, 22A, 22B, 22C, 23A, 23B, 23C, 24A, 24B, 24C, 25A, 25B, 25C, 26A, 26B, 26C, 27A, 27B, 27C | VISYDGGNKYYAESVKG |
| 238 | CDRH2-5 | 02A, 02B, 02C, 03A, 28A, 28B, 28C, 29A, 29B, 29C | VISYDGSNKYYADSVKG |
| 239 | CDRH2-6 | 30A, 31A | WINAYNGHTNYAQTFQG |
| 240 | CDRH2-7 | 32A, 33A, 34A | WITTYNGNTNYAQKLQG |
| 241 | CDRH2-8 | 36A, 38A, 39A, 39B, 40A, 41A | YIYYSGNTYYNPSLKS |
| 242 | CDRH3-1 | 30A, 31A | ELELRSFYYFGMDV |
| 243 | CDRH3-2 | 36A, 38A, 39A, 39B, 40A, 41A | GGAARGMDV |
| 244 | CDRH3-3 | 01A, 01B | GTWKQLWFLDH |
| 245 | CDRH3-4 | 37A | GVFYSKGAFDI |
| 246 | CDRH3-5 | 28A, 28B, 28C, 29A, 29B, 29C | GYDILTGYPDY |

TABLE 4B-continued

Exemplary Anti-hPAC1 Antibody Heavy Chain CDR Amino Acid Sequences

| SEQ ID NO: | Seq Group | Antibodies containing sequence | CDR Sequence |
|---|---|---|---|
| 247 | CDRH3-6 | 04A, 04B, 04C, 05A, 05B, 05C, 06A, 06B, 06C, 07A, 07B, 07C, 08A, 08B, 08C, 09A, 09B, 09C, 10A, 10B, 10C, 11A, 11B, 11C, 12A, 12B, 12C, 13A, 13B, 13C, 14A, 14B, 14C, 15A, 15B, 15C, 16A, 16B, 16C, 17A, 17B, 17C, 18A, 18B, 18C, 19A, 19B, 19C, 20A, 20B, 20C, 21A, 21B, 21C, 22A, 22B, 22C, 23A, 23B, 23C, 24A, 24B, 24C, 25A, 25B, 25C, 26A, 26B, 26C, 27A, 27B, 27C | GYDVLTGYPDY |
| 248 | CDRH3-7 | 35A | IASRGWYFDL |
| 249 | CDRH3-8 | 32A, 33A, 34A | RVRYSGGYSFDN |
| 250 | CDRH3-9 | 02A, 02B, 02C, 03A | GYDLLTGYPDY |

TABLE 5A

Exemplary Anti-hPAC1 Antibody LC Sequence Organization

| Ab ID | LC ID | SEQ ID NO: | V$_L$ ID | SEQ ID NO: | LC CDR1 | SEQ ID NO: | LC CDR2 | SEQ ID NO: | LC CDR3 | SEQ ID NO: |
|---|---|---|---|---|---|---|---|---|---|---|
| 01A | LC-01 | 75 | LV-01 | 149 | CDRL1-3 | 198 | CDRL2-2 | 210 | CDRL3-2 | 216 |
| 01B | LC-01 | 75 | LV-01 | 149 | CDRL1-3 | 198 | CDRL2-2 | 210 | CDRL3-2 | 216 |
| 02A | LC-02 | 76 | LV-02 | 150 | CDRL1-13 | 208 | CDRL2-1 | 209 | CDRL3-1 | 215 |
| 02B | LC-02 | 76 | LV-02 | 150 | CDRL1-13 | 208 | CDRL2-1 | 209 | CDRL3-1 | 215 |
| 02C | LC-02 | 76 | LV-02 | 150 | CDRL1-13 | 208 | CDRL2-1 | 209 | CDRL3-1 | 215 |
| 03A | LC-03 | 77 | LV-03 | 151 | CDRL1-13 | 208 | CDRL2-1 | 209 | CDRL3-1 | 215 |
| 04A | LC-04 | 78 | LV-04 | 152 | CDRL1-2 | 197 | CDRL2-1 | 209 | CDRL3-1 | 215 |
| 04B | LC-04 | 78 | LV-04 | 152 | CDRL1-2 | 197 | CDRL2-1 | 209 | CDRL3-1 | 215 |
| 04C | LC-04 | 78 | LV-04 | 152 | CDRL1-2 | 197 | CDRL2-1 | 209 | CDRL3-1 | 215 |
| 05A | LC-05 | 79 | LV-05 | 153 | CDRL1-1 | 196 | CDRL2-1 | 209 | CDRL3-1 | 215 |
| 05B | LC-05 | 79 | LV-05 | 153 | CDRL1-1 | 196 | CDRL2-1 | 209 | CDRL3-1 | 215 |
| 05C | LC-05 | 79 | LV-05 | 153 | CDRL1-1 | 196 | CDRL2-1 | 209 | CDRL3-1 | 215 |
| 06A | LC-06 | 80 | LV-06 | 154 | CDRL1-1 | 196 | CDRL2-1 | 209 | CDRL3-1 | 215 |
| 06B | LC-06 | 80 | LV-06 | 154 | CDRL1-1 | 196 | CDRL2-1 | 209 | CDRL3-1 | 215 |
| 06C | LC-06 | 80 | LV-06 | 154 | CDRL1-1 | 196 | CDRL2-1 | 209 | CDRL3-1 | 215 |
| 07A | LC-04 | 78 | LV-04 | 152 | CDRL1-2 | 197 | CDRL2-1 | 209 | CDRL3-1 | 215 |
| 07B | LC-04 | 78 | LV-04 | 152 | CDRL1-2 | 197 | CDRL2-1 | 209 | CDRL3-1 | 215 |
| 07C | LC-04 | 78 | LV-04 | 152 | CDRL1-2 | 197 | CDRL2-1 | 209 | CDRL3-1 | 215 |
| 08A | LC-04 | 78 | LV-04 | 152 | CDRL1-2 | 197 | CDRL2-1 | 209 | CDRL3-1 | 215 |
| 08B | LC-04 | 78 | LV-04 | 152 | CDRL1-2 | 197 | CDRL2-1 | 209 | CDRL3-1 | 215 |
| 08C | LC-04 | 78 | LV-04 | 152 | CDRL1-2 | 197 | CDRL2-1 | 209 | CDRL3-1 | 215 |
| 09A | LC-07 | 81 | LV-07 | 155 | CDRL1-2 | 197 | CDRL2-1 | 209 | CDRL3-1 | 215 |
| 09B | LC-07 | 81 | LV-07 | 155 | CDRL1-2 | 197 | CDRL2-1 | 209 | CDRL3-1 | 215 |
| 09C | LC-07 | 81 | LV-07 | 155 | CDRL1-2 | 197 | CDRL2-1 | 209 | CDRL3-1 | 215 |
| 10A | LC-07 | 81 | LV-07 | 155 | CDRL1-2 | 197 | CDRL2-1 | 209 | CDRL3-1 | 215 |
| 10B | LC-07 | 81 | LV-07 | 155 | CDRL1-2 | 197 | CDRL2-1 | 209 | CDRL3-1 | 215 |
| 10C | LC-07 | 81 | LV-07 | 155 | CDRL1-2 | 197 | CDRL2-1 | 209 | CDRL3-1 | 215 |
| 11A | LC-07 | 81 | LV-07 | 155 | CDRL1-2 | 197 | CDRL2-1 | 209 | CDRL3-1 | 215 |
| 11B | LC-07 | 81 | LV-07 | 155 | CDRL1-2 | 197 | CDRL2-1 | 209 | CDRL3-1 | 215 |
| 11C | LC-07 | 81 | LV-07 | 155 | CDRL1-2 | 197 | CDRL2-1 | 209 | CDRL3-1 | 215 |
| 12A | LC-04 | 78 | LV-04 | 152 | CDRL1-2 | 197 | CDRL2-1 | 209 | CDRL3-1 | 215 |
| 12B | LC-04 | 78 | LV-04 | 152 | CDRL1-2 | 197 | CDRL2-1 | 209 | CDRL3-1 | 215 |
| 12C | LC-04 | 78 | LV-04 | 152 | CDRL1-2 | 197 | CDRL2-1 | 209 | CDRL3-1 | 215 |
| 13A | LC-05 | 79 | LV-05 | 153 | CDRL1-1 | 196 | CDRL2-1 | 209 | CDRL3-1 | 215 |
| 13B | LC-05 | 79 | LV-05 | 153 | CDRL1-1 | 196 | CDRL2-1 | 209 | CDRL3-1 | 215 |
| 13C | LC-05 | 79 | LV-05 | 153 | CDRL1-1 | 196 | CDRL2-1 | 209 | CDRL3-1 | 215 |
| 14A | LC-08 | 82 | LV-08 | 156 | CDRL1-2 | 197 | CDRL2-1 | 209 | CDRL3-1 | 215 |
| 14B | LC-08 | 82 | LV-08 | 156 | CDRL1-2 | 197 | CDRL2-1 | 209 | CDRL3-1 | 215 |
| 14C | LC-08 | 82 | LV-08 | 156 | CDRL1-2 | 197 | CDRL2-1 | 209 | CDRL3-1 | 215 |
| 15A | LC-09 | 83 | LV-09 | 157 | CDRL1-2 | 197 | CDRL2-1 | 209 | CDRL3-1 | 215 |
| 15B | LC-09 | 83 | LV-09 | 157 | CDRL1-2 | 197 | CDRL2-1 | 209 | CDRL3-1 | 215 |
| 15C | LC-09 | 83 | LV-09 | 157 | CDRL1-2 | 197 | CDRL2-1 | 209 | CDRL3-1 | 215 |
| 16A | LC-05 | 79 | LV-05 | 153 | CDRL1-1 | 196 | CDRL2-1 | 209 | CDRL3-1 | 215 |
| 16B | LC-05 | 79 | LV-05 | 153 | CDRL1-1 | 196 | CDRL2-1 | 209 | CDRL3-1 | 215 |
| 16C | LC-05 | 79 | LV-05 | 153 | CDRL1-1 | 196 | CDRL2-1 | 209 | CDRL3-1 | 215 |
| 17A | LC-05 | 79 | LV-05 | 153 | CDRL1-1 | 196 | CDRL2-1 | 209 | CDRL3-1 | 215 |
| 17B | LC-05 | 79 | LV-05 | 153 | CDRL1-1 | 196 | CDRL2-1 | 209 | CDRL3-1 | 215 |
| 17C | LC-05 | 79 | LV-05 | 153 | CDRL1-1 | 196 | CDRL2-1 | 209 | CDRL3-1 | 215 |
| 18A | LC-09 | 83 | LV-09 | 157 | CDRL1-2 | 197 | CDRL2-1 | 209 | CDRL3-1 | 215 |
| 18B | LC-09 | 83 | LV-09 | 157 | CDRL1-2 | 197 | CDRL2-1 | 209 | CDRL3-1 | 215 |
| 18C | LC-09 | 83 | LV-09 | 157 | CDRL1-2 | 197 | CDRL2-1 | 209 | CDRL3-1 | 215 |

TABLE 5A-continued

Exemplary Anti-hPAC1 Antibody LC Sequence Organization

| Ab ID | LC ID | SEQ ID NO: | V$_L$ ID | SEQ ID NO: | LC CDR1 | SEQ ID NO: | LC CDR2 | SEQ ID NO: | LC CDR3 | SEQ ID NO: |
|---|---|---|---|---|---|---|---|---|---|---|
| 19A | LC-09 | 83 | LV-09 | 157 | CDRL1-2 | 197 | CDRL2-1 | 209 | CDRL3-1 | 215 |
| 19B | LC-09 | 83 | LV-09 | 157 | CDRL1-2 | 197 | CDRL2-1 | 209 | CDRL3-1 | 215 |
| 19C | LC-09 | 83 | LV-09 | 157 | CDRL1-2 | 197 | CDRL2-1 | 209 | CDRL3-1 | 215 |
| 20A | LC-09 | 83 | LV-09 | 157 | CDRL1-2 | 197 | CDRL2-1 | 209 | CDRL3-1 | 215 |
| 20B | LC-09 | 83 | LV-09 | 157 | CDRL1-2 | 197 | CDRL2-1 | 209 | CDRL3-1 | 215 |
| 20C | LC-09 | 83 | LV-09 | 157 | CDRL1-2 | 197 | CDRL2-1 | 209 | CDRL3-1 | 215 |
| 21A | LC-05 | 79 | LV-05 | 153 | CDRL1-1 | 196 | CDRL2-1 | 209 | CDRL3-1 | 215 |
| 21B | LC-05 | 79 | LV-05 | 153 | CDRL1-1 | 196 | CDRL2-1 | 209 | CDRL3-1 | 215 |
| 21C | LC-05 | 79 | LV-05 | 153 | CDRL1-1 | 196 | CDRL2-1 | 209 | CDRL3-1 | 215 |
| 22A | LC-05 | 79 | LV-05 | 153 | CDRL1-1 | 196 | CDRL2-1 | 209 | CDRL3-1 | 215 |
| 22B | LC-05 | 79 | LV-05 | 153 | CDRL1-1 | 196 | CDRL2-1 | 209 | CDRL3-1 | 215 |
| 22C | LC-05 | 79 | LV-05 | 153 | CDRL1-1 | 196 | CDRL2-1 | 209 | CDRL3-1 | 215 |
| 23A | LC-08 | 82 | LV-08 | 156 | CDRL1-2 | 197 | CDRL2-1 | 209 | CDRL3-1 | 215 |
| 23B | LC-08 | 82 | LV-08 | 156 | CDRL1-2 | 197 | CDRL2-1 | 209 | CDRL3-1 | 215 |
| 23C | LC-08 | 82 | LV-08 | 156 | CDRL1-2 | 197 | CDRL2-1 | 209 | CDRL3-1 | 215 |
| 24A | LC-05 | 79 | LV-05 | 153 | CDRL1-1 | 196 | CDRL2-1 | 209 | CDRL3-1 | 215 |
| 24B | LC-05 | 79 | LV-05 | 153 | CDRL1-1 | 196 | CDRL2-1 | 209 | CDRL3-1 | 215 |
| 24C | LC-05 | 79 | LV-05 | 153 | CDRL1-1 | 196 | CDRL2-1 | 209 | CDRL3-1 | 215 |
| 25A | LC-05 | 79 | LV-05 | 153 | CDRL1-1 | 196 | CDRL2-1 | 209 | CDRL3-1 | 215 |
| 25B | LC-05 | 79 | LV-05 | 153 | CDRL1-1 | 196 | CDRL2-1 | 209 | CDRL3-1 | 215 |
| 25C | LC-05 | 79 | LV-05 | 153 | CDRL1-1 | 196 | CDRL2-1 | 209 | CDRL3-1 | 215 |
| 26A | LC-05 | 79 | LV-05 | 153 | CDRL1-1 | 196 | CDRL2-1 | 209 | CDRL3-1 | 215 |
| 26B | LC-05 | 79 | LV-05 | 153 | CDRL1-1 | 196 | CDRL2-1 | 209 | CDRL3-1 | 215 |
| 26C | LC-05 | 79 | LV-05 | 153 | CDRL1-1 | 196 | CDRL2-1 | 209 | CDRL3-1 | 215 |
| 27A | LC-08 | 82 | LV-08 | 156 | CDRL1-2 | 197 | CDRL2-1 | 209 | CDRL3-1 | 215 |
| 27B | LC-08 | 82 | LV-08 | 156 | CDRL1-2 | 197 | CDRL2-1 | 209 | CDRL3-1 | 215 |
| 27C | LC-08 | 82 | LV-08 | 156 | CDRL1-2 | 197 | CDRL2-1 | 209 | CDRL3-1 | 215 |
| 28A | LC-10 | 84 | LV-10 | 158 | CDRL1-1 | 196 | CDRL2-1 | 209 | CDRL3-1 | 215 |
| 28B | LC-10 | 84 | LV-10 | 158 | CDRL1-1 | 196 | CDRL2-1 | 209 | CDRL3-1 | 215 |
| 28C | LC-10 | 84 | LV-10 | 158 | CDRL1-1 | 196 | CDRL2-1 | 209 | CDRL3-1 | 215 |
| 29A | LC-11 | 85 | LV-11 | 159 | CDRL1-1 | 196 | CDRL2-1 | 209 | CDRL3-1 | 215 |
| 29B | LC-11 | 85 | LV-11 | 159 | CDRL1-1 | 196 | CDRL2-1 | 209 | CDRL3-1 | 215 |
| 29C | LC-11 | 85 | LV-11 | 159 | CDRL1-1 | 196 | CDRL2-1 | 209 | CDRL3-1 | 215 |
| 30A | LC-12 | 86 | LV-12 | 160 | CDRL1-4 | 199 | CDRL2-3 | 211 | CDRL3-3 | 217 |
| 31A | LC-12 | 86 | LV-12 | 160 | CDRL1-4 | 199 | CDRL2-3 | 211 | CDRL3-3 | 217 |
| 32A | LC-13 | 87 | LV-13 | 161 | CDRL1-6 | 201 | CDRL2-4 | 212 | CDRL3-5 | 219 |
| 33A | LC-14 | 88 | LV-14 | 162 | CDRL1-6 | 201 | CDRL2-4 | 212 | CDRL3-5 | 219 |
| 34A | LC-14 | 88 | LV-14 | 162 | CDRL1-6 | 201 | CDRL2-4 | 212 | CDRL3-5 | 219 |
| 35A | LC-15 | 89 | LV-15 | 163 | CDRL1-5 | 200 | CDRL2-3 | 211 | CDRL3-4 | 218 |
| 36A | LC-16 | 90 | LV-16 | 164 | CDRL1-7 | 202 | CDRL2-5 | 213 | CDRL3-6 | 220 |
| 37A | LC-17 | 91 | LV-17 | 165 | CDRL1-8 | 203 | CDRL2-6 | 214 | CDRL3-7 | 221 |
| 38A | LC-18 | 92 | LV-18 | 166 | CDRL1-9 | 204 | CDRL2-5 | 213 | CDRL3-8 | 222 |
| 39A | LC-19 | 93 | LV-19 | 167 | CDRL1-10 | 205 | CDRL2-5 | 213 | CDRL3-6 | 220 |
| 39B | LC-19 | 93 | LV-19 | 167 | CDRL1-10 | 205 | CDRL2-5 | 213 | CDRL3-6 | 220 |
| 40A | LC-20 | 94 | LV-20 | 168 | CDRL1-12 | 207 | CDRL2-5 | 213 | CDRL3-6 | 220 |
| 41A | LC-21 | 95 | LV-21 | 169 | CDRL1-11 | 206 | CDRL2-5 | 213 | CDRL3-8 | 222 |

TABLE 5B

Exemplary Anti-hPAC1 Antibody HC Sequence Organization

| Ab ID | HC ID | SEQ ID NO: | V$_H$ ID | SEQ ID NO: | HC CDR1 | SEQ ID NO: | HC CDR2 | SEQ ID NO: | HC CDR3 | SEQ ID NO: |
|---|---|---|---|---|---|---|---|---|---|---|
| 01A | HC-01 | 96 | HV-01 | 170 | CDRH1-8 | 230 | CDRH2-2 | 235 | CDRH3-3 | 244 |
| 01B | HC-02 | 97 | HV-01 | 170 | CDRH1-8 | 230 | CDRH2-2 | 235 | CDRH3-3 | 244 |
| 02A | HC-03 | 98 | HV-02 | 171 | CDRH1-11 | 233 | CDRH2-5 | 238 | CDRH3-9 | 250 |
| 02B | HC-04 | 99 | HV-02 | 171 | CDRH1-11 | 233 | CDRH2-5 | 238 | CDRH3-9 | 250 |
| 02C | HC-05 | 100 | HV-02 | 171 | CDRH1-11 | 233 | CDRH2-5 | 238 | CDRH3-9 | 250 |
| 03A | HC-03 | 98 | HV-02 | 171 | CDRH1-11 | 233 | CDRH2-5 | 238 | CDRH3-9 | 250 |
| 04A | HC-06 | 101 | HV-03 | 172 | CDRH1-1 | 223 | CDRH2-4 | 237 | CDRH3-6 | 247 |
| 04B | HC-07 | 102 | HV-03 | 172 | CDRH1-1 | 223 | CDRH2-4 | 237 | CDRH3-6 | 247 |
| 04C | HC-08 | 103 | HV-03 | 172 | CDRH1-1 | 223 | CDRH2-4 | 237 | CDRH3-6 | 247 |
| 05A | HC-06 | 101 | HV-03 | 172 | CDRH1-1 | 223 | CDRH2-4 | 237 | CDRH3-6 | 247 |
| 05B | HC-07 | 102 | HV-03 | 172 | CDRH1-1 | 223 | CDRH2-4 | 237 | CDRH3-6 | 247 |
| 05C | HC-08 | 103 | HV-03 | 172 | CDRH1-1 | 223 | CDRH2-4 | 237 | CDRH3-6 | 247 |
| 06A | HC-06 | 101 | HV-03 | 172 | CDRH1-1 | 223 | CDRH2-4 | 237 | CDRH3-6 | 247 |
| 06B | HC-07 | 102 | HV-03 | 172 | CDRH1-1 | 223 | CDRH2-4 | 237 | CDRH3-6 | 247 |
| 06C | HC-08 | 103 | HV-03 | 172 | CDRH1-1 | 223 | CDRH2-4 | 237 | CDRH3-6 | 247 |
| 07A | HC-09 | 104 | HV-04 | 173 | CDRH1-1 | 223 | CDRH2-4 | 237 | CDRH3-6 | 247 |
| 07B | HC-10 | 105 | HV-04 | 173 | CDRH1-1 | 223 | CDRH2-4 | 237 | CDRH3-6 | 247 |
| 07C | HC-11 | 106 | HV-04 | 173 | CDRH1-1 | 223 | CDRH2-4 | 237 | CDRH3-6 | 247 |

TABLE 5B-continued

Exemplary Anti-hPAC1 Antibody HC Sequence Organization

| Ab ID | HC ID | SEQ ID NO: | $V_H$ ID | SEQ ID NO: | HC CDR1 | SEQ ID NO: | HC CDR2 | SEQ ID NO: | HC CDR3 | SEQ ID NO: |
|---|---|---|---|---|---|---|---|---|---|---|
| 08A | HC-12 | 107 | HV-05 | 174 | CDRH1-1 | 223 | CDRH2-4 | 237 | CDRH3-6 | 247 |
| 08B | HC-13 | 108 | HV-05 | 174 | CDRH1-1 | 223 | CDRH2-4 | 237 | CDRH3-6 | 247 |
| 08C | HC-14 | 109 | HV-05 | 174 | CDRH1-1 | 223 | CDRH2-4 | 237 | CDRH3-6 | 247 |
| 09A | HC-09 | 104 | HV-04 | 173 | CDRH1-1 | 223 | CDRH2-4 | 237 | CDRH3-6 | 247 |
| 09B | HC-10 | 105 | HV-04 | 173 | CDRH1-1 | 223 | CDRH2-4 | 237 | CDRH3-6 | 247 |
| 09C | HC-11 | 106 | HV-04 | 173 | CDRH1-1 | 223 | CDRH2-4 | 237 | CDRH3-6 | 247 |
| 10A | HC-12 | 107 | HV-05 | 174 | CDRH1-1 | 223 | CDRH2-4 | 237 | CDRH3-6 | 247 |
| 10B | HC-13 | 108 | HV-05 | 174 | CDRH1-1 | 223 | CDRH2-4 | 237 | CDRH3-6 | 247 |
| 10C | HC-14 | 109 | HV-05 | 174 | CDRH1-1 | 223 | CDRH2-4 | 237 | CDRH3-6 | 247 |
| 11A | HC-06 | 101 | HV-03 | 172 | CDRH1-1 | 223 | CDRH2-4 | 237 | CDRH3-6 | 247 |
| 11B | HC-07 | 102 | HV-03 | 172 | CDRH1-1 | 223 | CDRH2-4 | 237 | CDRH3-6 | 247 |
| 11C | HC-08 | 103 | HV-03 | 172 | CDRH1-1 | 223 | CDRH2-4 | 237 | CDRH3-6 | 247 |
| 12A | HC-15 | 110 | HV-06 | 175 | CDRH1-1 | 223 | CDRH2-4 | 237 | CDRH3-6 | 247 |
| 12B | HC-16 | 111 | HV-06 | 175 | CDRH1-1 | 223 | CDRH2-4 | 237 | CDRH3-6 | 247 |
| 12C | HC-17 | 112 | HV-06 | 175 | CDRH1-1 | 223 | CDRH2-4 | 237 | CDRH3-6 | 247 |
| 13A | HC-12 | 107 | HV-05 | 174 | CDRH1-1 | 223 | CDRH2-4 | 237 | CDRH3-6 | 247 |
| 13B | HC-13 | 108 | HV-05 | 174 | CDRH1-1 | 223 | CDRH2-4 | 237 | CDRH3-6 | 247 |
| 13C | HC-14 | 109 | HV-05 | 174 | CDRH1-1 | 223 | CDRH2-4 | 237 | CDRH3-6 | 247 |
| 14A | HC-12 | 107 | HV-05 | 174 | CDRH1-1 | 223 | CDRH2-4 | 237 | CDRH3-6 | 247 |
| 14B | HC-13 | 108 | HV-05 | 174 | CDRH1-1 | 223 | CDRH2-4 | 237 | CDRH3-6 | 247 |
| 14C | HC-14 | 109 | HV-05 | 174 | CDRH1-1 | 223 | CDRH2-4 | 237 | CDRH3-6 | 247 |
| 15A | HC-12 | 107 | HV-05 | 174 | CDRH1-1 | 223 | CDRH2-4 | 237 | CDRH3-6 | 247 |
| 15B | HC-13 | 108 | HV-05 | 174 | CDRH1-1 | 223 | CDRH2-4 | 237 | CDRH3-6 | 247 |
| 15C | HC-14 | 109 | HV-05 | 174 | CDRH1-1 | 223 | CDRH2-4 | 237 | CDRH3-6 | 247 |
| 16A | HC-18 | 113 | HV-07 | 176 | CDRH1-1 | 223 | CDRH2-4 | 237 | CDRH3-6 | 247 |
| 16B | HC-19 | 114 | HV-07 | 176 | CDRH1-1 | 223 | CDRH2-4 | 237 | CDRH3-6 | 247 |
| 16C | HC-20 | 115 | HV-07 | 176 | CDRH1-1 | 223 | CDRH2-4 | 237 | CDRH3-6 | 247 |
| 17A | HC-21 | 116 | HV-08 | 177 | CDRH1-1 | 223 | CDRH2-4 | 237 | CDRH3-6 | 247 |
| 17B | HC-22 | 117 | HV-08 | 177 | CDRH1-1 | 223 | CDRH2-4 | 237 | CDRH3-6 | 247 |
| 17C | HC-23 | 118 | HV-08 | 177 | CDRH1-1 | 223 | CDRH2-4 | 237 | CDRH3-6 | 247 |
| 18A | HC-18 | 113 | HV-07 | 176 | CDRH1-1 | 223 | CDRH2-4 | 237 | CDRH3-6 | 247 |
| 18B | HC-19 | 114 | HV-07 | 176 | CDRH1-1 | 223 | CDRH2-4 | 237 | CDRH3-6 | 247 |
| 18C | HC-20 | 115 | HV-07 | 176 | CDRH1-1 | 223 | CDRH2-4 | 237 | CDRH3-6 | 247 |
| 19A | HC-21 | 116 | HV-08 | 177 | CDRH1-1 | 223 | CDRH2-4 | 237 | CDRH3-6 | 247 |
| 19B | HC-22 | 117 | HV-08 | 177 | CDRH1-1 | 223 | CDRH2-4 | 237 | CDRH3-6 | 247 |
| 19C | HC-23 | 118 | HV-08 | 177 | CDRH1-1 | 223 | CDRH2-4 | 237 | CDRH3-6 | 247 |
| 20A | HC-24 | 119 | HV-09 | 178 | CDRH1-1 | 223 | CDRH2-4 | 237 | CDRH3-6 | 247 |
| 20B | HC-25 | 120 | HV-09 | 178 | CDRH1-1 | 223 | CDRH2-4 | 237 | CDRH3-6 | 247 |
| 20C | HC-26 | 121 | HV-09 | 178 | CDRH1-1 | 223 | CDRH2-4 | 237 | CDRH3-6 | 247 |
| 21A | HC-24 | 119 | HV-09 | 178 | CDRH1-1 | 223 | CDRH2-4 | 237 | CDRH3-6 | 247 |
| 21B | HC-25 | 120 | HV-09 | 178 | CDRH1-1 | 223 | CDRH2-4 | 237 | CDRH3-6 | 247 |
| 21C | HC-26 | 121 | HV-09 | 178 | CDRH1-1 | 223 | CDRH2-4 | 237 | CDRH3-6 | 247 |
| 22A | HC-27 | 122 | HV-10 | 179 | CDRH1-1 | 223 | CDRH2-4 | 237 | CDRH3-6 | 247 |
| 22B | HC-28 | 123 | HV-10 | 179 | CDRH1-1 | 223 | CDRH2-4 | 237 | CDRH3-6 | 247 |
| 22C | HC-29 | 124 | HV-10 | 179 | CDRH1-1 | 223 | CDRH2-4 | 237 | CDRH3-6 | 247 |
| 23A | HC-27 | 122 | HV-10 | 179 | CDRH1-1 | 223 | CDRH2-4 | 237 | CDRH3-6 | 247 |
| 23B | HC-28 | 123 | HV-10 | 179 | CDRH1-1 | 223 | CDRH2-4 | 237 | CDRH3-6 | 247 |
| 23C | HC-29 | 124 | HV-10 | 179 | CDRH1-1 | 223 | CDRH2-4 | 237 | CDRH3-6 | 247 |
| 24A | HC-30 | 125 | HV-11 | 180 | CDRH1-1 | 223 | CDRH2-4 | 237 | CDRH3-6 | 247 |
| 24B | HC-31 | 126 | HV-11 | 180 | CDRH1-1 | 223 | CDRH2-4 | 237 | CDRH3-6 | 247 |
| 24C | HC-32 | 127 | HV-11 | 180 | CDRH1-1 | 223 | CDRH2-4 | 237 | CDRH3-6 | 247 |
| 25A | HC-33 | 128 | HV-12 | 181 | CDRH1-1 | 223 | CDRH2-4 | 237 | CDRH3-6 | 247 |
| 25B | HC-34 | 129 | HV-12 | 181 | CDRH1-1 | 223 | CDRH2-4 | 237 | CDRH3-6 | 247 |
| 25C | HC-35 | 130 | HV-12 | 181 | CDRH1-1 | 223 | CDRH2-4 | 237 | CDRH3-6 | 247 |
| 26A | HC-36 | 131 | HV-13 | 182 | CDRH1-1 | 223 | CDRH2-4 | 237 | CDRH3-6 | 247 |
| 26B | HC-37 | 132 | HV-13 | 182 | CDRH1-1 | 223 | CDRH2-4 | 237 | CDRH3-6 | 247 |
| 26C | HC-38 | 133 | HV-13 | 182 | CDRH1-1 | 223 | CDRH2-4 | 237 | CDRH3-6 | 247 |
| 27A | HC-36 | 131 | HV-13 | 182 | CDRH1-1 | 223 | CDRH2-4 | 237 | CDRH3-6 | 247 |
| 27B | HC-37 | 132 | HV-13 | 182 | CDRH1-1 | 223 | CDRH2-4 | 237 | CDRH3-6 | 247 |
| 27C | HC-38 | 133 | HV-13 | 182 | CDRH1-1 | 223 | CDRH2-4 | 237 | CDRH3-6 | 247 |
| 28A | HC-39 | 134 | HV-14 | 183 | CDRH1-3 | 225 | CDRH2-5 | 238 | CDRH3-5 | 246 |
| 28B | HC-40 | 135 | HV-14 | 183 | CDRH1-3 | 225 | CDRH2-5 | 238 | CDRH3-5 | 246 |
| 28C | HC-41 | 136 | HV-14 | 183 | CDRH1-3 | 225 | CDRH2-5 | 238 | CDRH3-5 | 246 |
| 29A | HC-39 | 134 | HV-14 | 183 | CDRH1-3 | 225 | CDRH2-5 | 238 | CDRH3-5 | 246 |
| 29B | HC-40 | 135 | HV-14 | 183 | CDRH1-3 | 225 | CDRH2-5 | 238 | CDRH3-5 | 246 |
| 29C | HC-41 | 136 | HV-14 | 183 | CDRH1-3 | 225 | CDRH2-5 | 238 | CDRH3-5 | 246 |
| 30A | HC-42 | 137 | HV-15 | 184 | CDRH1-9 | 231 | CDRH2-6 | 239 | CDRH3-1 | 242 |
| 31A | HC-43 | 138 | HV-16 | 185 | CDRH1-9 | 231 | CDRH2-6 | 239 | CDRH3-1 | 242 |
| 32A | HC-44 | 139 | HV-17 | 186 | CDRH1-4 | 226 | CDRH2-7 | 240 | CDRH3-8 | 249 |
| 33A | HC-45 | 140 | HV-18 | 187 | CDRH1-4 | 226 | CDRH2-7 | 240 | CDRH3-8 | 249 |
| 34A | HC-46 | 141 | HV-19 | 188 | CDRH1-4 | 226 | CDRH2-7 | 240 | CDRH3-8 | 249 |
| 35A | HC-47 | 142 | HV-20 | 189 | CDRH1-10 | 232 | CDRH2-1 | 234 | CDRH3-7 | 248 |
| 36A | HC-48 | 143 | HV-21 | 190 | CDRH1-6 | 228 | CDRH2-8 | 241 | CDRH3-2 | 243 |
| 37A | HC-49 | 144 | HV-22 | 191 | CDRH1-7 | 229 | CDRH2-3 | 236 | CDRH3-4 | 245 |
| 38A | HC-50 | 145 | HV-23 | 192 | CDRH1-2 | 224 | CDRH2-8 | 241 | CDRH3-2 | 243 |

TABLE 5B-continued

Exemplary Anti-hPAC1 Antibody HC Sequence Organization

| Ab ID | HC ID | SEQ ID NO: | V$_H$ ID | SEQ ID NO: | HC CDR1 | SEQ ID NO: | HC CDR2 | SEQ ID NO: | HC CDR3 | SEQ ID NO: |
|---|---|---|---|---|---|---|---|---|---|---|
| 39A | HC-51 | 146 | HV-24 | 193 | CDRH1-6 | 228 | CDRH2-8 | 241 | CDRH3-2 | 243 |
| 39B | HC-52 | 147 | HV-25 | 194 | CDRH1-6 | 228 | CDRH2-8 | 241 | CDRH3-2 | 243 |
| 40A | HC-48 | 143 | HV-21 | 190 | CDRH1-6 | 228 | CDRH2-8 | 241 | CDRH3-2 | 243 |
| 41A | HC-53 | 148 | HV-26 | 195 | CDRH1-5 | 227 | CDRH2-8 | 241 | CDRH3-2 | 243 |

The structure and properties of CDRs within a naturally occurring antibody has been described, supra. Briefly, in a traditional antibody, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, may not only be used to define the antigen binding domain of a traditional antibody structure, but may be embedded in a variety of other polypeptide structures, as described herein.

Some of the antibodies disclosed herein share certain regions or sequences with other antibodies disclosed herein. These relationships are summarized in the tables above.

In one aspect, the isolated antibodies provided herein can be a monoclonal antibody, a polyclonal antibody, a recombinant antibody, a human antibody, a humanized antibody, a chimeric antibody, a multispecific antibody, or an antibody antigen binding fragment thereof.

In another embodiment, the antibody fragment of the isolated antibodies provided herein can be a Fab fragment, a Fab' fragment, an F(ab')$_2$ fragment, an Fv fragment, a diabody, or a single chain antibody molecule.

In a further embodiment, the isolated antibody provided herein is a human antibody and can be of the IgG1-, IgG2-IgG3- or IgG4-type. In a further embodiment, the isolated antibody is an IgG1- or IgG2-type. In a further embodiment, the isolated antibody is an IgG2-type. In a further embodiment, the isolated antibody is an IgG1-type. In a further embodiment, the IgG1-type antibody is an aglycosylated IgG1 antibody. In a further embodiment, the aglycosylated IgG1 antibody has an N297G mutation.

In another embodiment, the antibody consists of a just a light or a heavy chain polypeptide as set forth in Tables 2A-2B. In some embodiments, the antibody consists just of a light chain variable or heavy chain variable domain such as those listed in Tables 3A and 3B. Such antibodies can be pegylated with one or more PEG molecules.

In yet another aspect, the isolated antibody provided herein can be coupled to a labeling group and can compete for binding to the extracellular portion of human PAC1 with an antibody of one of the isolated antibodies provided herein. In one embodiment, the isolated antibody provided herein can reduce monocyte chemotaxis, inhibit monocyte migration into tumors or inhibit accumulation and function of tumor associated macrophage in a tumor when administered to a patient.

As will be appreciated by those in the art, for any antibody with more than one CDR from the depicted sequences, any combination of CDRs independently selected from the depicted sequences is useful. Thus, antibodies with one, two, three, four, five or six of independently selected CDRs can be generated. However, as will be appreciated by those in the art, specific embodiments generally utilize combinations of CDRs that are non-repetitive, e.g., antibodies are generally not made with two CDRH2 regions, etc.

Monoclonal Antibodies

The antibodies that are provided include monoclonal antibodies that bind to PAC1. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a PAC1 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds PAC1 (e.g., as described in Examples 1-3, below). Such hybridoma cell lines, and anti-PAC1 monoclonal antibodies produced by them, are aspects of the present application.

Monoclonal antibodies secreted by a hybridoma cell line can be purified using any technique known in the art.

Chimeric and Humanized Antibodies

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, *Proc. Natl. Acad. Sci. USA* 81:6851-6855, which are hereby incorporated by reference. CDR grafting is described, for example, in U.S. Pat. No. 6,180,370, No. 5,693,762, No. 5,693,761, No. 5,585,089, and No. 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and No. 5,693,762; Jones et al., 1986, *Nature* 321:522-525; Riechmann et al., 1988, *Nature* 332:323-27; Verhoeyen et al., 1988, *Science* 239: 1534-1536), In one aspect, the CDRs of the light and heavy chain variable regions of the antibodies provided herein are grafted to framework regions (FRs) from antibodies from the same, or a different, phylogenetic species. For example, the CDRs of the heavy and light chain variable regions described herein can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of anti-PAC1 antibody are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

Fully Human Antibodies

Fully human antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. No. 5,545,807; No. 6,713,610; No. 6,673,986; No. 6,162,963; No. 5,545,807; No. 6,300,129; No. 6,255,458; No. 5,877,397; No. 5,874,299 and No. 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. NY Acad. Sci.* 764:536-546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et al., 1994, *Nature* 368:856-859; Lonberg, 1994, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N.Y. Acad. Sci.* 764:536-546; Fishwild et al., 1996, *Nature Biotechnology* 14:845-851; the foregoing references are hereby incorporated by reference in their entirety for all purposes. See, further U.S. Pat. No. 5,545,806; No. 5,569,825; No. 5,625,126; No. 5,633,425; No. 5,789,650; No. 5,877,397; No. 5,661,016; No. 5,814,318;

No. 5,874,299; and No. 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, *Nature Genetics* 15:146-156, which are hereby incorporated by reference. For example, the HCo7 and HCo12 transgenic mice strains can be used to generate anti-PAC1 antibodies. Further details regarding the production of human antibodies using transgenic mice are provided in the examples below.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494 (hereby incorporated by reference), which describes the isolation of high affinity and functional agonistic antibodies for MPL- and msk-receptors using such an approach.

Bispecific or Bifunctional Antibodies

The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J Immunol.* 148:1547-1553.

Various Other Forms

Some of the antibodies that are provided are variant forms of the antibodies disclosed above. For instance, some of the antibodies have one or more conservative amino acid substitutions in one or more of the heavy or light chains, variable regions or CDRs listed above.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in Table 6.

TABLE 6

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |

TABLE 6-continued

Conservative Amino Acid Substitutions

| Original Residue | Exemplary Substitutions |
| --- | --- |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for PAC1 neutralizing activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% can have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105, which are each incorporated herein by reference.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to PAC1. For example, one or more of the CDRs listed in Tables 4A and 4B can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., PAC1 or epitope thereof).

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, 1986, *Adv. Drug Res.* 15:29; Veber and Freidinger, 1985, *TINS* p. 392; and Evans et al., 1987, *J. Med. Chem.* 30:1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as here the ability to specifically bind PAC1, but have one or more peptide linkages optionally replaced by a linkage selected from: —CH₂NH—, —CH₂S—, —CH₂—CH₂—, —CH═CH-(cis and trans), —COCH₂—, —CH(OH)CH₂—, and —CH₂SO—, by methods well known in the art. Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), incorporated herein by reference), for example, by adding internal cysteine residues capable of forming intramolecular disulfide bridges which cyclize the peptide.

Derivatives of the antibodies that are described herein are also provided. The derivatized antibodies can comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. Certain antibodies include a pegylated single chain polypeptide as described herein. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of PAC1 binding proteins with other proteins or polypeptides, such as by expression of recombinant fusion proteins comprising heterologous polypeptides fused to the N-terminus or C-terminus of a PAC1 binding protein. For example, the conjugated peptide may be a heterologous signal (or leader) polypeptide, e.g., the yeast alpha-factor leader, or a peptide such as an epitope tag. PAC1 antibody-containing fusion proteins can comprise peptides added to facilitate purification or identification of the PAC1 binding protein (e.g., poly-His). A PAC1 binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more PAC1 binding proteins may be employed as PAC1 antagonists. Oligomers may be in the form of covalently-linked or non-covalently-linked dimers, trimers, or higher oligomers. Oligomers comprising two or more PAC1 binding proteins are contemplated for use, with one example being a homodimer. Other oligomers include heterodimers, homotrimers, heterotrimers, homotetramers, heterotetramers, etc.

One embodiment is directed to oligomers comprising multiple PAC1-binding polypeptides joined via covalent or non-covalent interactions between peptide moieties fused to the PAC1 binding proteins. Such peptides may be peptide linkers (spacers), or peptides that have the property of promoting oligomerization. Leucine zippers and certain polypeptides derived from antibodies are among the peptides that can promote oligomerization of PAC1 binding proteins attached thereto, as described in more detail below.

In particular embodiments, the oligomers comprise from two to four PAC1 binding proteins. The PAC1 binding protein moieties of the oligomer may be in any of the forms described above, e.g., variants or fragments. Preferably, the oligomers comprise PAC1 binding proteins that have PAC1 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

One embodiment is directed to a dimer comprising two fusion proteins created by fusing a PAC1 binding protein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. No. 5,426,048 and No. 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457, 035, and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a PAC1 binding protein such as disclosed herein may be substituted for the variable portion of an antibody heavy and/or light chain.

Alternatively, the oligomer is a fusion protein comprising multiple PAC1 binding proteins, with or without peptide linkers (spacer peptides). Among the suitable peptide linkers are those described in U.S. Pat. Nos. 4,751,180 and 4,935,233.

Another method for preparing oligomeric PAC1 binding protein derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-278. In one approach, recombinant fusion proteins comprising a PAC1 binding protein fragment or derivative fused to a leucine zipper peptide are expressed in suitable host cells, and the soluble oligomeric PAC1 binding protein fragments or derivatives that form are recovered from the culture supernatant.

In certain embodiments, the antibody has a $K_D$ (equilibrium binding affinity) of less than 1 pM, 10 pM, 100 pM, 1 nM, 2 nM, 5 nM, 10 nM, 25 nM or 50 nM.

Another aspect provides an antibody having a half-life of at least one day in vitro or in vivo (e.g., when administered to a human subject). In one embodiment, the antibody has a half-life of at least three days. In another embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life as compared to the underivatized or unmodified antibody. In another embodiment, the antibody contains point mutations to increase serum half life, such as described in WO 00/09560, published Feb. 24, 2000, incorporated by reference.

Glycosylation

The antibody may have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence may be altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N— and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev, Biochem.*, pp. 259-306.

Removal of carbohydrate moieties present on the starting antibody may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Hence, aspects include glycosylation variants of the antibodies wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

It is known that human IgG1 has a glycosylation site at N297 (EU numbering system) and glycosylation contributes to the effector function of IgG1 antibodies. Groups have mutated N297 in an effort to make aglycosylated antibodies. The mutations have focuses on substituting N297 with amino acids that resemble asparagine in physiochemical nature such as glutamine (N297Q) or with alanine (N297A) which mimics asparagines without polar groups.

As used herein, "aglycosylated antibody" or "aglycosylated fc" refers to the glycosylation status of the residue at position 297 of the Fc. An antibody or other molecule may contain glycosylation at one or more other locations but may still be considered an aglycosylated antibody or aglcosylated Fc-fusion protein.

In an effort to make effector functionless IgG1 Fc molecules, it was discovered that mutation of amino acid N297 of human IgG1 to glycine, i.e., N297G, provides superior purification efficiency and biophysical properties over other amino acid substitutions at that residue. It was further discovered that antiPAC1 antibodies in an aglycosylated IgG1 framework prevented Fc gamma receptor induced platelet depletion as assessed using a phagocytosis assay (see Example 5) Thus, in preferred embodiments, the anti-PAC1 antibodies comprise antibodies with a "B" or "C" suffix, designating IgG1 aglycosylated variants. In certain embodiments, an antibody comprises the Fc having a N297G substitution.

An Fc comprising a human IgG1 Fc having the N297G mutation may also comprise further insertions, deletions, and substitutions. In certain embodiments the human IgG1 Fc comprises the N297G substitution and is at least 90% identical, at least 91% identical, at least 92% identical, at least 93% identical, at least 94% identical, at least 95% identical, at least 96% identical, at least 97% identical, at least 98% identical, or at least 99% identical to one or more of the amino acid sequences set forth in Table 2B (exemplary anti-hPAC1 Ab heavy chain amino acid sequences).

A glycosylated IgG1 Fc-containing molecules may be less stable than glycosylated IgG1 Fc-containing molecules. The Fc region may thus be further engineered to increase the stability of the aglycosylated molecule. In some embodiments, one or more amino acids are substituted to cysteine so to form di-sulfide bonds in the dimeric state. Residues corresponding to V259, A287, R292, V302, L306, V323, or I332 of an IgG1 amino acid heavy chain sequence may thus be substituted with cysteine. In preferred embodiments, specific pairs of residues are substitution such that they preferentially form a di-sulfide bond with each other, thus limiting or preventing di-sulfide bond scrambling. Preferred pairs include, but are not limited to, A287C and L306C, V259C and L306C, R292C and V302C, and V323C and I332C.

Specifically exemplified herein are aglycosylated (N297G) IgG1 Fc-containing heavy chains wherein one or both residues R292 and V302 are substituted with cysteine. The aglycosylated (N297G) IgG1 antibodies with a "C" suffix contain both R292C and V302C substitutions in their heavy chains.

Labels and Effector Groups

In some embodiments, the antigen-binding comprises one or more labels. The term "labeling group" or "label" means any detectable label. Examples of suitable labeling groups include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I)) fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antibody via spacer arms of various lengths to reduce potential steric hindrance. Various methods for labeling proteins are known in the art and may be used as is seen fit.

The term "effector group" means any group coupled to an antibody that acts as a cytotoxic agent. Examples for suitable effector groups are radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I). Other suitable groups include toxins, therapeutic groups, or chemotherapeutic groups. Examples of suitable groups include calicheamicin, auristatins, geldanamycin and maytansine. In some embodiments, the effector group is coupled to the antibody via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in MOLECULAR PROBES HANDBOOK by Richard P. Haugland, hereby expressly incorporated by reference.

Suitable proteinaceous fluorescent labels also include, but are not limited to, green fluorescent protein, including a *Renilla*, Ptilosarcus, or *Aequorea* species of GFP (Chalfie et al., 1994, *Science* 263:802-805), EGFP (Clontech Labs., Inc., Genbank Accession Number U55762), blue fluorescent protein (BFP, Quantum Biotechnologies, Inc., Quebec, Canada; Stauber, 1998, *Biotechniques* 24:462-471; Heim et al., 1996, *Curr. Biol.* 6:178-182), enhanced yellow fluorescent protein (EYFP, Clontech Labs., Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. No. 5,292,658, No. 5,418,155, No. 5,683,888, No. 5,741,668, No. 5,777,079, No. 5,804,387, No. 5,874,304, No. 5,876,995, No. 5,925,558).

Nucleic Acids

An aspect further provides nucleic acids that hybridize to other nucleic acids (e.g., nucleic acids comprising a nucleotide sequence listed in Tables 1A and 1B under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The basic parameters affecting the choice of hybridization conditions and guidance for devising suitable conditions are set forth by, for example, Sambrook, Fritsch, and Maniatis (2001, Molecular Cloning: A Laboratory Manual, Cold Spring Harbor Laboratory Press, Cold Spring Harbor, N.Y., supra; and Current Protocols in Molecular Biology, 1995, Ausubel et al., eds., John Wiley & Sons, Inc., sections 2.10 and 6.3-6.4), and can be readily determined by those having ordinary skill in the art based on, e.g., the length and/or base composition of the nucleic acid.

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody. In one embodiment, a nucleic acid encoding any antibody described herein can be mutated to alter the amino acid sequence using molecular biology techniques that are well-established in the art.

Another aspect provides nucleic acid molecules that are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion (e.g., a 1 binding portion) of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Another aspect provides vectors comprising a nucleic acid encoding a polypeptide or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors can comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see, Voss et al., 1986, *Trends Biochem. Sci.* 11:287, Maniatis et al., 1987, *Science* 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see, id.). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein.

Another aspect provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Preparing Antibodies

Non-human antibodies that are provided can be, for example, derived from any antibody-producing animal, such as mouse, rat, rabbit, goat, donkey, or non-human primate (such as monkey (e.g., cynomolgus or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments, the antibodies may be produced by immunizing animals using methods known in the art, as described above. The antibodies may be polyclonal, monoclonal, or may be synthesized in host cells by expressing recombinant DNA. Fully human antibodies may be prepared as described above by immunizing transgenic animals containing human immunoglobulin loci or by selecting a phage display library that is expressing a repertoire of human antibodies.

The monoclonal antibodies (mAbs) can be produced by a variety of techniques, including conventional monoclonal antibody methodology, e.g., the standard somatic cell hybridization technique of Kohler and Milstein, 1975, *Nature* 256:495. Alternatively, other techniques for producing monoclonal antibodies can be employed, for example, the viral or oncogenic transformation of B-lymphocytes. One suitable animal system for preparing hybridomas is the murine system, which is a very well established procedure. Immunization protocols and techniques for isolation of immunized splenocytes for fusion are known in the art and illustrative approaches are described in the Examples, below. For such procedures, B cells from immunized mice are typically fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$—comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. U.S.A.* 85:5879; Ward et al., 1989, *Nature* 334:544, de Graaf et al., 2002, *Methods Mol Biol.* 178:379-387. Single chain antibodies derived from antibodies provided herein include, but are not limited to scFvs comprising the variable domain combinations of the heavy and light chain variable regions depicted in Tables 3A and 3B, or combinations of light and heavy chain variable domains which include CDRs depicted in Tables 4A and 4B.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, *Methods Mol. Biol.* 178:303-316.

Accordingly, the antibodies that are provided include those comprising, for example, the variable domain combinations described, supra., having a desired isotype (for example, IgA, IgG1, IgG2, IgG3, IgG4, IgE, and IgD) as well as Fab or F(ab')2 fragments thereof. Moreover, if an IgG4 is desired, it may also be desired to introduce a point mutation (CPSCP->CPPCP) in the hinge region as described in Bloom et al., 1997, *Protein Science* 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, *BioTechnology* 10:779.

Conservative modifications may be made to the heavy and light chain variable regions described in Tables 3A and 3B, or the CDRs described in Tables 4A and 4B (and corresponding modifications to the encoding nucleic acids) to produce a PAC1 binding protein having certain desirable functional and biochemical characteristics. Methods for achieving such modifications are described above.

PAC1 antibodies may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or antigen binding fragment thereof. Another useful fusion partner for the antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a nonnative residue that has little or no effect on the polarity or charge of the amino acid residue at that position. See, Table 6, supra. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human PAC1 or for modifying the binding affinity of other antibodies described herein.

Methods of Expressing Antibodies

Expression systems and constructs in the form of plasmids, expression vectors, transcription or expression cassettes that comprise at least one polynucleotide as described above are also provided herein, as well host cells comprising such expression systems or constructs.

The antibodies provided herein may be prepared by any of a number of conventional techniques. For example, PAC1 antibodies may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Antibodies can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. No. 4,399,216; No. 4,912,040; No. 4,740,461; No. 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of a PAC1 antibody. These nucleic acid sequences are inserted into an appropriate expression vector using standard ligation techniques. In one embodiment, the heavy or light chain constant region is appended to the C-terminus of the anti-PAC1-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, 2003, *Biotech. Biotechnol. Bioeng.* 84:439-44, which is hereby incorporated by reference. Additional suitable expression vectors are discussed, for example, in *Methods Enzymol.*, vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the PAC1 binding protein coding sequence; the oligonucleotide sequence encodes polyHis (such as hexa-His), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the PAC1 binding protein from the host cell. Affinity purification can be accomplished, for example, by column chromatography using antibodies against the tag as an affinity matrix. Optionally, the tag can subsequently be removed from the purified PAC1 binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to PAC1. As a result, increased quantities of a polypeptide such as an antibody are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding a PAC1 binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising a PAC1 binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thomsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene (Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-fetoprotein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising a human PAC1 binding protein by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising a PAC1 antigen binding sequence has been inserted into the proper site of the vector, the completed vector may be inserted into a suitable host cell for amplification and/or polypeptide expression. The transformation of an expression vector for an antibody into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antibodies with PAC1 binding properties. In another embodiment, a cell line from the B cell lineage that does not make its own antibody but has a capacity to make and secrete a heterologous antibody can be selected.

Use of Human PAC1 Antibodies for Diagnostic and Therapeutic Purposes

Antibodies are useful for detecting PAC1 in biological samples and identification of cells or tissues that produce PAC1. For instance, the PAC1 antibodies can be used in diagnostic assays, e.g., binding assays to detect and/or quantify PAC1 expressed in a tissue or cell. Antibodies that specifically bind to PAC1 can also be used in treatment of diseases related to PAC1 in a patient in need thereof. In addition, PAC1 antibodies can be used to inhibit PAC1 from forming a complex with its ligand PACAP (e.g., PACAP-38), thereby modulating the biological activity of PAC1 in a cell or tissue. Examples of activities that can be modulated include, but are not limited to, inhibiting vasodialation and/or decrease neurogenic inflammation. Antibodies that bind to PAC1 thus can modulate and/or block interaction with other binding compounds and as such may have therapeutic use in ameliorating diseases related to PAC1.

Indications

A disease or condition associated with human PAC1 includes any disease or condition whose onset in a patient is caused by, at least in part, the interaction of PAC1 with its ligand, PACAP (e.g., PACAP-38). The severity of the disease or condition can also be increased or decreased by the interaction of PAC1 with PACAP (e.g., PACAP-38). Examples of diseases and conditions that can be treated with the antibodies described herein include headaches, such as cluster headaches, migraine, including migraine headaches, chronic pain, type II diabetes mellitus, inflammation, e.g., neurogenic inflammation, cardiovascular disorders, and hemodynamic derangement associated with endotoxemia and sepsis.

In particular, antibodies described herein can be used to treat migraine, either as an acute treatment commencing after a migraine attack has commenced, and/or as a prophylactic treatment administered, e.g., daily, weekly, biweekly, monthly, bimonthly, biannually, etc.) to prevent or reduce the frequency and/or severity of symptoms, e.g., pain symptoms, associated with migraine attacks.

Infusion of the PAC1 receptor agonist PACAP causes migraine-like headache in migraine patients, suggesting that blocking PAC1 may be useful for treating migraine. Immunohistochemistry studies in cynomolgus monkey performed in support of the present invention mapped PACAP and PAC1 localization to the parasympathetic pathway through the sphenopalatine ganglion (SPG; also known as pterygopalatine ganglion), which also innervates the dura vasculature. The parasympathetic pathway is independent and parallel to the sensory pathway that also controls the dura vasculature tone, hence likely plays a role in migraine pathophysiology. Additional experiments performed in support of the present invention showed that a selective PAC1 Ab blocked electrically stimulated trigeminal cervical complex (TCC) activation, an electrophysiology model that has been reported to correlate with clinical migraine efficacy. Taken together, the evidence supports the targeting of PAC1 with a selective antagonist such as an anti-PAC1 antibody as described herein to treat migraine. The expected efficacy of an anti-PAC1 therapeutic for the treatment of migraine in human patients is further supported by published papers, including, for example Schytz, H. W., et al., "The PACAP receptor: a novel target for migraine treatment.", Neurotherapeutics. 2010 April; 7(2):191-6; Olesen J., et al., "Emerging migraine treatments and drug targets", Trends Pharmacol Sci. 2011 June; 32(6):352-9; and Schytz, H. W., et al., "PACAP38 induces migraine-like attacks in patients with migraine without aura", Brain (2009) 132 (1): 16-25.

Cluster headache is a condition that involves, as its most prominent feature, an one-sided, immense degree of pain. Some doctors and scientists have described the pain resulting from cluster headaches as the most intense pain a human can endure—worse than giving birth, burns or broken bones. Cluster headaches often occur periodically: spontaneous remissions interrupt active periods of pain. The average age of onset of cluster headache is ~30-50 years. It is more prevalent in males with a male to female ratio varies 2.5:1 or 3.5:1. SPG stimulation has been used for the treatment of cluster headache. Most recently, Autonomic Technologies has developed the ATI™ Neurostimulation System to deliver low-level (but high frequency, physiologic-blocking) electrical stimulation to provide acute SPG stimulation therapy with the intention to relieve the acute debilitating pain of cluster headache. A robust efficacy has been demonstrated in their recent clinical trial (NCT01616511; Schoenen J, et al., "Stimulation of the sphenopalatine ganglion (SPG) for cluster headache treatment. Pathway CH-1: A randomized, sham-controlled study.", Cephalalgia. 2013; 33(10):816-30. In view of the above and because PACAP is one of the major neurotransmitters in SPG, a PAC1 receptor antagonist such as an anti-PAC1 antibody described herein is expected to have efficacy to treat cluster headache in humans.

Diagnostic Methods

The antibodies described herein can be used for diagnostic purposes to detect, diagnose, or monitor diseases and/or conditions associated with PAC1. Also provided are methods for the detection of the presence of PAC1 in a sample using classical immunohistological methods known to those of skill in the art (e.g., Tijssen, 1993, *Practice and Theory of Enzyme Immunoassays, Vol* 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of PAC1 can be performed in vivo or in vitro.

Diagnostic applications provided herein include use of the antibodies to detect expression of PAC1 and binding of the ligands to PAC1. Examples of methods useful in the detection of the presence of PAC1 include immunoassays, such as the enzyme linked immunosorbent assay (ELISA) and the radioimmunoassay (RIA).

For diagnostic applications, the antibody typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antibody via spacer arms of various lengths to reduce potential steric hindrance. Various methods for labeling proteins are known in the art and may be used.

In another aspect, an antibody can be used to identify a cell or cells that express PAC1. In a specific embodiment, the antibody is labeled with a labeling group and the binding of the labeled antibody to PAC1 is detected. In a further specific embodiment, the binding of the antibody to PAC1 detected in vivo. In a further specific embodiment, the PAC1 antibody is isolated and measured using techniques known in the art. See, for example, *Harlow and Lane,* 1988, *Antibodies: A Laboratory Manual*, New York: Cold Spring Harbor (ed. 1991 and periodic supplements); *John E. Coligan, ed.,* 1993, *Current Protocols In Immunology* New York: John Wiley & Sons.

Another aspect provides for detecting the presence of a test molecule that competes for binding to PAC1 with the antibodies provided. An example of one such assay would involve detecting the amount of free antibody in a solution containing an amount of PAC1 in the presence or absence of the test molecule. An increase in the amount of free antibody (i.e., the antibody not bound to PAC1) would indicate that the test molecule is capable of competing for PAC1 binding with the antibody. In one embodiment, the antibody is labeled with a labeling group. Alternatively, the test molecule is labeled and the amount of free test molecule is monitored in the presence and absence of an antibody.

Methods of Treatment: Pharmaceutical Formulations, Routes of Administration

Methods of using the antibodies are also provided. In some methods, an antibody is provided to a patient. The antibody inhibits binding of PACAP to human PAC1.

Pharmaceutical compositions that comprise a therapeutically effective amount of one or a plurality of the antibodies and a pharmaceutically acceptable diluent, carrier, solubilizer, emulsifier, preservative, and/or adjuvant are also provided. In addition, methods of treating a patient, e.g., for migraine, by administering such pharmaceutical composition are included. The term "patient" includes human patients.

Acceptable formulation materials are nontoxic to recipients at the dosages and concentrations employed. In specific embodiments, pharmaceutical compositions comprising a therapeutically effective amount of human PAC1 antibodies are provided.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies disclosed. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute. In certain embodiments, human PAC1 antibody compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the human PAC1 antibody may be formulated as a lyophilizate using appropriate excipients such as sucrose.

The pharmaceutical compositions can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions may be provided in the form of a pyrogen-free, parenterally acceptable aqueous solution comprising the desired human PAC1 binding protein in a pharmaceutically acceptable vehicle. A particularly suitable vehicle for parenteral injection is sterile distilled water in which the human PAC1 antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody.

Certain pharmaceutical compositions are formulated for inhalation. In some embodiments, human PAC1 antibodies are formulated as a dry, inhalable powder. In specific embodiments, human PAC1 antibody inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. Some formulations can be administered orally. Human PAC1 antibodies that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the human PAC1 antibody. Diluents, flavorings, low melting point waxes, vegetable oils, lubricants, suspending agents, tablet disintegrating agents, and binders may also be employed.

Some pharmaceutical compositions comprise an effective quantity of one or a plurality of human PAC1 antibodies in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving human PAC1 antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J Biomed. Mater. Res.* 15:167-277 and Langer, 1982, *Chem. Tech.* 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

In certain embodiments, cells expressing a recombinant antibody as disclosed herein is encapsulated for delivery (see, Invest. Ophthalmol Vis Sci 43:3292-3298, 2002 and Proc. Natl. Acad. Sciences 103:3896-3901, 2006).

In certain formulations, an antibody has a concentration of at least 10 mg/ml, 20 mg/ml, 30 mg/ml, 40 mg/ml, 50 mg/ml, 60 mg/ml, 70 mg/ml, 80 mg/ml, 90 mg/ml, 100 mg/ml or 150 mg/ml. Some formulations contain a buffer, sucrose and polysorbate. An example of a formulation is one containing 50-100 mg/ml of antibody, 5-20 mM sodium acetate, 5-10% w/v sucrose, and 0.002-0.008% w/v polysorbate. Certain, formulations, for instance, contain 65-75 mg/ml of an antibody in 9-11 mM sodium acetate buffer, 8-10% w/v sucrose, and 0.005-0.006% w/v polysorbate. The pH of certain such formulations is in the range of 4.5-6. Other formulations have a pH of 5.0-5.5 (e.g., pH of 5.0, 5.2 or 5.4).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. Kits for producing a single-dose administration unit are also provided. Certain kits contain a first container having a dried protein and a second container having an aqueous formulation. In certain embodiments, kits containing single and multi-chambered pre-filled syringes (e.g., liquid syringes and lyosyringes) are provided. The therapeutically effective amount of a human PAC1 antibody-containing pharmaceutical composition to be employed will depend, for example, upon the therapeutic context and objectives. One skilled in the art will appreciate that the appropriate dosage levels for treatment will vary depending, in part, upon the molecule delivered, the indication for which the human PAC1 antibody is being used, the route of administration, and the size (body weight, body surface or organ size) and/or condition (the age and general health) of the patient. In certain embodiments, the clinician may titer the dosage and modify the route of administration to obtain the optimal therapeutic effect.

A typical dosage may range from about 1 µg/kg to up to about 30 mg/kg or more, depending on the factors mentioned above. In specific embodiments, the dosage may range from 10 µg/kg up to about 30 mg/kg, optionally from 0.1 mg/kg up to about 30 mg/kg, alternatively from 0.3 mg/kg up to about 20 mg/kg. In some applications, the dosage is from 0.5 mg/kg to 20 mg/kg. In some instances, an antibody is dosed at 0.3 mg/kg, 0.5 mg/kg, 1 mg/kg, 3 mg/kg, 10 mg/kg, or 20 mg/kg. The dosage schedule in some treatment regimes is at a dose of 0.3 mg/kg qW, 0.5 mg/kg qW, 1 mg/kg qW, 3 mg/kg qW, 10 mg/kg qW, or 20 mg/kg qW.

Dosing frequency will depend upon the pharmacokinetic parameters of the particular human PAC1 antibody in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. In certain embodiments, the antibodies can be administered to patients throughout an extended time period. Chronic administration of an antibody minimizes the adverse immune or allergic response commonly associated with antibodies that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use human PAC1 antibody pharmaceutical compositions ex vivo. In such instances, cells, tissues or organs that have been removed from the patient are exposed to human PAC1 antibody pharmaceutical compositions after which the cells, tissues and/or organs are subsequently implanted back into the patient.

In particular, human PAC1 antibodies can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

The following examples, including the experiments conducted and the results achieved, are provided for illustrative purposes only and are not to be construed as limiting the scope of the appended claims.

EXAMPLE 1

PAC1 Antibodies

A. Generation of Anti-PAC1 Antibodies

Fully human antibodies were generated through immunization of XENOMOUSE animals with the PAC1 extracellular domain protein, DNA tagged with a T-cell epitope tag, L1.2 cells expressing full-length human PAC1, and other hPAC1 antigens using standard methods, e.g., substantially as detailed in US patent publication US 2010-0172895 A1.

B. Screening of anti-PAC1 Antibodies

Hybridoma supernatants were screened for binding to PAC1 and also for functional antagonist activity in an assay detecting their ability to block generation of cAMP by activation of PAC1 with either PACAP (e.g., PACAP-27 or PACAP-38) or a selective, exogenous peptide ligand (Maxadilan), and then counter-screened against the related receptors VPAC1 and VPAC2. Those supernatants with desirable function and selectivity were sequenced and cloned, expressed recombinantly, purified, and tested again for function and selectivity using standard methods, e.g., substantially as detailed in US patent publication US 2010-0172895 A1, incorporated herein by reference.

C. Selectivity of PAC1 Agonists

Experiments were performed to assess the activity and selectivity of three PAC1 agonists (PACAP, VIP and Maxadilan) against the related receptors PAC1, VPAC1 and VPAC2. Data from these experiments are shown in Table 7 below, and demonstrate that PACAP has similar agonist activity on all three receptors, VIP has some activity on PAC1 but (~10-100×) higher activity on VPAC1 and VPAC2, and Maxadilan is highly-selective for PAC1 versus VPAC1 and VPAC2.

TABLE 7

PACAP Receptors & agonists

| Receptor agonist | PAC1 EC50 (nM) | VPAC1 EC50 (nM) | VPAC2 EC50 (nM) |
|---|---|---|---|
| PACAP | 0.03 | 0.03 | 0.06 |
| VIP | 2.3 | 0.02 | 0.08 |
| Maxadilan | 0.06 | >1000 | >1000 |

EXAMPLE 2

Activity of PAC1 Specific Blocking Monoclonal Antibodies in cAMP Functional Assay A. Activity of anti-PAC1 Antibodies Selected hPAC1 antibodies as described herein were screened in an in vitro PAC1 mediated cAMP assay to determine intrinsic potency. The assay employed SH-SY-5Y, a human neuroblastoma cell line endogenously expressing hPAC1 (Biedler, J. L., et al., 1978, "Multiple neurotransmitter synthesis by human neuroblastoma cell lines and clones". Cancer Res. 38 (11 Pt 1): 3751-7; Lutz, E. M., et al., "Characterization of novel splice variants of the PAC1 receptor in human neuroblastoma cells: consequences for signaling by VIP and PACAP." Mol Cell Neurosci 2006; 31:193-209), and several cells lines expressing recombinant PAC1, VPAC1 & VPAC2 constructs having the following accession numbers: human PAC1 (hPAC1): NM_001118.4; hPAC1 short (hPAC1 with amino acid residues 89-109 deleted (range used: 1-88, 110-468)): NM_001199637.1; cyno PAC1: XM_005549858.1; rat PAC1: NM_133511.2; mouse PAC1: NM_001025372.2; human VPAC1 (hVPAC1): NM_004624.3; human VPAC2 (hVPAC2): NM_003382.4; rat VPAC2: NM_017238.1; mouse VPAC2: NM_009511.2.

SHSY-5Y cells were grown in a 1:1 mixture of Minimum Essential Media (MEM) (Invitrogen 11095-072) and Ham's F12 nutrient mixture (Invitrogen 11765-047), 10% Fetal Bovine Serum (Invitrogen 10099-141), 1× Penicillin-Streptomycin-Glutamine (Invitrogen 10378016), and 1×MEM Non-Essential Amino Acids (Invitrogen 11140-050). PAC1-CHO, Rat PAC1, and Cyno PAC1 cells were grown in Dulbecco's modified Eagle's medium (DMEM) (Gibco Cat#11965), 10% dialyzed FBS (Invitrogen 26400044), 1% MEM non-essential amino acids (Invitrogen 11140-050), 1% sodium pyruvate (Invitrogen 11360070), 1% glutamine/pen/strep (Invitrogen 10378016). CHO-Trex-rat and mouse VPAC2R stable cell lines were grown in Basal Media: F12 (Invitrogen 11765-047), P/S/G: 1× (Invitrogen 10378016), Heat inactivated FBS: 10% (Invitrogen 10100147), Blasticidin: 5 ug/ml (Invitrogen R21001) and Hygromycin: 400 ug/ml (Invitrogen 10687010). The cells were induced with Tetracyclin (Sigma 87128): 3.5 ug/ml, add 24 hours before assay. hPAC1-CHO-K1 cells (Perkin Elmer; ES-272-A) were grown in Ham's F12 (Invitrogen 11765-047), 10% FBS (Invitrogen 10099-141), Pen-strep: 1× (Invitrogen 15140122), 400 ug/ml G418 (Stock: 50 mg/ml=>8 ml/L media) (Invitrogen 10131027), 250 ug/ml Zeocin (Stock: 100 mg/ml=>2.5 ml/L media) (Invitrogen R25005). VPAC1/CHO-CRE-BLA (Invitrogen; Agonist:VIP) cells were grown in Dulbecco's modified Eagle's medium (DMEM)

(Gibco Cat#11965), Dialyzed FBS: 10% (Invitrogen 26400044), NEAA: 1× (Invitrogen 11140-050), Pen/Strep: 1× (Invitrogen 15140122), HEPES (pH 7.3): 25 mM (Invitrogen 15630130). VPAC2/CHO-CRE-BLA (Invitrogen; Agonist:VIP) cells were grown as described above for the VPAC1 cells, with the addition of Blasticidin: 5 ug/ml (Invitrogen R21001) and Geneticin: 500 ug/ml (G418) (Invitrogen 10131027). SK-N-MC cells were grown in MEM (Invitrogen 11095-072), 10% FBS (Invitrogen 10099-141), 1× NEAA (Invitrogen 11140-050), 1× Sodium pyruvate (Invitrogen 11360070), 1× glutamine/pen/strep (Invitrogen 10378016). L6 cells were grown in Dulbecco's modified Eagle's medium (DMEM) (Gibco Cat#11965), 10% Fetal Bovine Serum (Gibco Cat#10099-141), 1× Glutamine/Pen/Strep (Gibco Cat#10378-016).

The cells were grown under the conditions described above and harvested at 80-90% confluence. The cells were dissociated with VERSENE (1:5000, Invitrogen, 15040-060) for SHSY5Y cells; with 0.05% Trypsin-EDTA (1×), Phenol Red (Invitrogen, 25300054), and were then centrifuged in a Beckman GS-6R unit at 1000 rpm for 5 minutes at 4° C. The pellets were resuspended with cell freezing medium (Invitrogen, 12648010). The cells were then counted using a Z1 Coulter Particle Counter and adjusted to desired concentration (5E6/ml or 2E6/ml) and aliquots were stored at −80° C. or in liquid nitrogen until use. Concentrations for PAC1 cells, hVPAC1/2 CHO were 4K/10 µl; the others at 2K/10 µl; for SKNMC and L6, the concentration was 1K/10 µl.

The LANCE Ultra cAMP assay kit (PerkinElmer, Boston, Mass.) was used in the screening. The assays were performed in triplicate in white Optiplates half-area 96-well plates (Costar 3642) in a total volume of 40 µL. Briefly, vials of frozen cells were thawed by incubating at 37° C. in a water bath. The thawed cells were washed once with assay buffer (F12, 0.1% BSA, 1 mM IBMX) and the cell concentration was adjusted to 2K/10 µl. The cell suspension was distributed in 10 µl aliquots into the 96 half area white plates. Five microliters of antagonist (e.g., an anti-PAC1 antibody as described herein) were then added, and the samples were incubated for 30 minutes at room temperature with gentle shaking. Five microliters of agonist (e.g., PACAP38) was then added, and the samples were incubated for an additional 15 minutes, again at room temperature, with gentle shaking. Ten microliters of 4× Eu-cAMP tracer working solution and ten microliters of 4× ULight-anti-cAMP working solution were then added and the samples were incubated an additional 45 minutes at room temperature.

The samples were analyzed on EnVision instrument at Em665/615 nM. The data were processed by GraphPad Prism software version 5/6 (GraphPad Inc., La Jolla, Calif.) to show POC (percent of control) as a function of the tested antagonist anti-PAC1 antibody concentration, and were fitted with standard nonlinear regression curves to yield IC50 values. POC was calculated as follows:

$$POC = 100 \times Em665 \text{ of } \frac{\text{Agonist response with antagonist} - \text{cell response without agonist and antagonist}}{\text{Agonist response without antagonist} - \text{cell response without agonist and antagonist}}$$

All antibodies described herein and tested in the assay had IC50 activity between about 0.1 nM and about 200 nM; most had activity between 0.1 nM and 100 nM. Similar experiments were performed using recombinant cells expressing cynomolgus PAC1 and rat cells expressing rat PAC1 as described above. IC50 obtained using human and cynomolgus PAC1s were similar, whereas the tested antibodies did not appear to uniformly cross-react well with rat PAC1. In addition, cells expressing related receptors hVPAC1 (CRE-Bla-CHO-K1/Invitrogen) and hVPAC2 (-Bla-CHO-K1/Invitrogen) were used to further assess the selectivity of the tested antibodies. None of the tested antibodies had significant inhibitory activity against hVPAC1 or hVPAC2 over the range tested (IC50 was >10,000 nM in all cases). Exemplary data are shown in Table 8, below.

TABLE 8

IC50 activity of exemplary anti-PAC1 antibodies in cells expressing PAC1, VPAC1 or VPAC2 receptors

| Ab ID | Agonist activity | hPAC1 IC50 (nM) | short hPAC1 IC50 (nM) | cyno PAC1 IC50 (nM) | rat PAC1 IC50 (nM) | hVPAC1 IC50 | hVPAC2 IC50 |
|---|---|---|---|---|---|---|---|
| 01B | >10 µM | 0.4 ± 0.2 | 4.6 ± 5.0 | 0.4 ± 0.1 | 21.6 ± 8.3 | >10 µM | >10 µM |
| 14B | >10 µM | 1.1 ± 0.3 | 4.1 ± 2.4 | 0.6 ± 0.2 | 16.9 ± 10.3 | >10 µM | >10 µM |
| 26B | >10 µM | 2.7 ± 1.8 | 8.8 ± 7.7 | 1.3 ± 0.3 | >1000 | >10 µM | >10 µM |
| 29B | >10 µM | 0.9 ± 0.2 | 4.7 ± 2.4 | 0.5 ± 0.0 | 50.7 ± 2.8 | >10 µM | >10 µM |
| 39B | >10 µM | 4.6 ± 2.8 | 16.7 ± 11.5 | 3.9 ± 1.9 | 22.5 ± 9.0 | >10 µM | >10 µM |

The differences in IC50 between human PAC1 and human VPAC1 and VPAC2 receptors illustrates the high selectivity of these antibodies for the PAC1 over related receptors.

EXAMPLE 3

Radioligand Binding Assays for Ki Determination of Receptor Blocking Antibodies $^{125}$I-labeled PAC-1 antibodies (for PAC1 binding assay) or $^{125}$I-labeled PEG-PACAP38 (for PACAP38 binding assay), both obtained from Perkin Elmer (Billerica, Mass.), and cell membranes prepared from hPAC-1 AequoScreen CHO (PerkinElmer Life and Analytical Sciences, Boston, Mass.) were used for radioligand binding experiments in the presence of various concentrations of the test antibodies to determine the corresponding Ki values.

Cell Membrane Preparation

Cells were grown to confluency in 40×T225 flasks in Ham's F12, 10% FBS, 100 µg/ml streptomycin, 400 µ/ml G418 (receptor expression selection) and Zeocin (Aequorin expression selection). Flasks were washed 1× with Ca/Mg free PBS. PBS was removed completely. 5 ml VERSENE was added to each flask and waited about 5 min. The flasks were tapped on the side and all the cells were dislodged. VERSENE/cell suspension from all flasks were transferred to 50 ml conical tubes and placed on ice. To collect any remaining cells, flasks were rinsed with ice cold PBS, without Ca/Mg, with protease inhibitors and solution was added to the cells in tubes. Tubes were spun down at 1000 rpm for 10 min. Pellets were stored at −80° C.

The day of the membrane preparation, the cell pellets were weighed and dissolved on ice. Pellets were resuspended in (10 ml/gram of pellet) 10 mM TrisHCl, pH7.4, 1 mM EDTA, Roche protease inhibitors (1 tablet/50 ml) and homogenized by 30 strokes with the motorized dounce homogenizer. Cell homogenates were centrifuged at 2500 rpm (~1000 g) for 10 min at 4° C. Supernatants were transferred to a Beckman centrifuge tube and keep on ice. Pellets were rehomogenized with 15 ml of the buffer and the spin step was repeated. Both supernatants were combined and centrifuged at 48,400 g for 30 min. Pellets were resuspended in 15 ml buffer and sheared through an 18G syringe to break up the pellet. Pellets were Homogenized by 20 strokes and centrifuged 48,400 g for 30 min. Pellets were resuspended in ~6 ml of PACAP Binding buffer without BSA (20 mM Tris HCl, 5 mM MgSO4+ Protease Inhibitors). Pellets were resuspended using an 18G syringe, dounce homogenized, aliquoted and stored at −70° C. Total membrane protein concentration was determined with a Microplate BCA Protein Assay (Pierce).

Binding Assay

The PAC1 binding assay was set up at room temperature in 96-well plates containing: 120 μl binding buffer (20 mM Tris-HCl, pH 7.5, 5.0 mM MgSO4, 150 mM NaCl, 0.1% BSA (Sigma), 1 tablet of Complete™/50 ml buffer (a protease inhibitor)); 10 μl test compound (20x); 50 μl human PAC1 CHO membrane suspension (0.2 μg per well); and 20 μl of either $^{125}$I-PAC-1 antibody (10x; for the PAC1 binding assay) or $^{125}$I-PEG-PACAP 38 (10x; for PACAP38 binding assay).

Non-specific binding was determined by adding 10 μl of (20x) 20 μM PACAP 6-38 into designated plates. The plates were incubated at room temperature for 2 hours with shaking at 60 rpm, and then the contents of each well were filtered over 0.5% polyethyleneimine (PEI)-treated (for at least two hours) GF/C 96-well filter plates. The GF/C filter plates were washed five times with ice-cold 50 mM Tris, pH 7.5 and dried in an oven at 55° C. for 1 hour. The bottoms of the GF/C plates were then sealed. 40 μl Microscint™ 20 was added to each well, the tops of the GF/C plates were sealed with TopSeal™-A (a press-on adhesive sealing film), and the GF/C plates were counted with TopCount NXT (Packard). The data were analyzed using Prizm (GraphPad Software Inc.)

Exemplary data showing the Ki values obtained as described above are shown in Table 9, below. Data from the PAC1 binding assay are shown with the indicated $^{125}$I-labeled PAC-1 antibodies in different columns, and test antibodies as shown in different rows. Samples from different production lots were run with some of the test antibodies, as shown (01A, 26A, 39A). The results indicate that the tested anti-PAC1 antibodies which have biological activity in the cAMP assay described in Example 2 compete with binding of an agonist of PAC1 ($^{125}$I-labeled PEG-PACAP38), and also cross-compete with one another for the same or similar epitope on hPAC1.

TABLE 9

| | Ki [nM] | | | | | | | | | |
|---|---|---|---|---|---|---|---|---|---|---|
| PACAP 38 | | | 0.51 | | 0.25 | | 0.46 | | | |
| PACAP 6-38 | 4.98 | 4.08 | 7.74 | 2.51 | 6.26 | 2.06 | 4.05 | 2.39 | 2.78 | 4.91 |
| | 125I Ab | | | | | | | | | |
| Antibody ID | 01B | 14A | 14B | 26A | 26B | 28A | 29A | 29B | 39A | 39B |
| 01B | 0.08 | | 0.04 | | 0.06 | | | 0.07 | | 0.05 |
| 14A | 0.16 | 0.05 | 0.12 | 0.05 | 0.11 | | | 0.07 | 0.04 | 0.08 |
| 14B | 0.18 | | 0.08 | | 0.05 | | | 0.10 | | 0.06 |
| 26A | | 0.08 | | 0.06 | | | | | 0.07 | |
| 26B | 0.22 | | 0.21 | | 0.10 | | | 0.06 | | 0.09 |
| 28A | | | | | | <0.01 | 0.04 | | | |
| 29A | 0.13 | 0.07 | 0.10 | 0.03 | 0.11 | | 0.04 | 0.09 | 0.06 | 0.08 |
| 29B | 0.14 | | 0.08 | | 0.07 | | | 0.08 | | 0.05 |
| 39A | | 0.20 | | 0.13 | | | | | 0.16 | |
| 39B | 0.18 | | 0.17 | | 0.25 | | | 0.11 | | 0.16 |
| 01A lot1 | | 0.03 | | 0.02 | | | | | 0.03 | |
| 01A lot2 | 0.13 | | 0.11 | | 0.07 | | | 0.09 | | 0.07 |
| 03A | | | | | | 0.01 | 0.14 | | | |
| 05A | | | | | | 0.02 | 0.03 | | | |
| 13A | | 0.07 | | 0.05 | | 0.02 | 0.04 | | 0.07 | |
| 26A lot1 | 0.13 | | 0.07 | | 0.05 | | | 0.08 | | 0.05 |
| 26A lot2 | 0.09 | | 0.09 | | 0.09 | | | 0.06 | | 0.06 |
| 38A | | 0.07 | | 0.07 | | | | | 0.11 | |
| 39A lot1 | 0.30 | | 0.24 | | 0.17 | | | 0.08 | | 0.20 |
| 39A lot2 | 0.15 | | 0.43 | | 0.14 | | | 0.14 | | 0.18 |

EXAMPLE 4

Binding $K_D$ Measured by KinExA

A. Experiments Using Whole Cells Expressing hPAC1.

Binding of anti-Pac1 antibody with CHOK1/huPac1 cells were tested on KinExA. Briefly, UltraLink Biosupport (Pierce cat#53110) was pre-coated with goat-anti-huFc (Jackson Immuno Research cat#109-005-098) and blocked with BSA. 10 pM, 30 pM, 100 pM, and 300 pM of anti-Pac1 antibody was incubated with various density (1.7×101-9× 106 cells/mL) of CHOK1 cells expressing huPac1 in medium F12 containing 1% FBS and 0.05% sodium azide. Samples containing anti-Pac1 antibody and whole cells were incubated with rotation at room temperature for 4 hours before 5-minute 220-g centrifugation at 4° C. to separate the whole cells and anti-Pac1 antibody-cell complexes from unbound anti-Pac1 antibody. The supernatants containing free anti-Pac1 antibody were filtered through 0.22 μm filter before loading to the goat-anti-huFc-coated beads on KinExA. The amount of the bead-bound anti-Pac1 antibody was quantified by fluorescent (Alexa Fluor 647) labeled anti-huIgG (H+L) antibody (Jackson Immuno Research cat#109-605-088). The binding signal is proportional to the concentration of free anti-Pac1 antibody in solution at each cell density. Equilibrium dissociation constant ($K_D$) was estimated by n-curve analysis in KinExA™ Pro software (Sapidyne Instruments, Inc., Boise, Id.).

B. Experiments Using hPAC1 Extra-cellular Domain (ECD; hPAC1 1-135).

Binding of anti-Pac1 Abs with huPac1(1-135)::6×His was tested on KinExA. Briefly, UltraLink Biosupport (Thermo Fisher Scientific cat#53110) was pre-coated with huPac1 (1-135)::6×His and blocked with BSA as described above. 30, 100, and 300 pM of Ab were incubated with various concentrations of huPac1 (1-135)::6×His at room temperature for at least 8 hours before run through the huPac1 (1-135)::6×His-coated beads. The amount of the bead-bound Ab were quantified by fluorescent (DyLight 649) labeled goat anti-huIgG (H+L) antibody (Jackson Immuno Research cat#109-495-088). The binding signal is proportional to the concentration of free Ab at binding equilibrium. Equilibrium dissociation constant (KD) was obtained from nonlinear regression of the competition curves using a one-site homogeneous binding model (KinExA™ Pro software).

A summary of the equilibrium dissociation constants for the tested samples binding with CHOK1/huPac1 cell and huPac1 (1-135)::6×His are shown in Table 10, below (average followed by (range)).

TABLE 10

| Ab ID | KD (95% CI) to huPAC1 whole cell (pM) | KD (95% CI) to huPAC1 ECD (pM) |
| --- | --- | --- |
| 01B | 12 (7-21) | |
| 03A | 126 (84-206) | 21 (16-28) |
| 13A | 12 (7-20) | 26 (23-28) |
| 14A | 17 (7-43) | 16 (7-30) |
| 14B | 17 (7-40) | |
| 26A | 21 (12-37) | 83 (62-109) |
| 26B | 41 (25-72) | |
| 29A | 13 (7-28) | 28 (25-32) |
| 29B | 15 (8-30) | |
| 38A | 16 (9-29) | 17 (14-21) |
| 39A | 36 (19-77) | 39 (33-46) |
| 39B | 75 (42-147) | |

EXAMPLE 5

Platelet Phagocytosis Assay

To address any potential Fc gamma receptor induced platelet depletion, a subset of the antibodies described herein was tested in a Phagocytosis Assay.

A. Preparation of Peripheral Blood Leukocytes (PBL) and Platelets

Both human and cynomolgus platelets were prepared as previously described (Semple, J. W., et al., Blood (2007) 109: 4803-4805). In brief, whole blood samples from healthy cynomolgus donors were centrifuged at 170×g for 15 minutes with no braking. Platelet-rich plasma (PRP) was collected from the top layer. The bottom layers of the sample were centrifuged at 2000×g for 10 minutes to obtain the platelet-poor plasma (PPP) layer and buffy coat. Platelets in the PRP fraction were labeled with 20 µM Cell Tracker Green CMFDA for 30 minutes at room temperature. Labeled platelets were washed with PBS, resuspended in RPMI-1640 with 10% FBS, and adjusted to a concentration of $1 \times 10^8$ cells/mL. PBL were prepared from the buffy coat obtained from the same donor. Erythrocytes were lysed with BD Pharm-lyse following the protocol provided by the vendor. After lysing, PBL were washed twice with RPMI-1640 with 10% FBS and the final concentration was adjusted to $5 \times 10^6$ cells/ml.

B. Phagocytosis Assay

The phagocytosis reaction was initiated by incubating 100 µL each of CMFDA-labeled platelets and PBMC with test articles in the dark. After six hours of incubation, the reaction was stopped by placing the plates on ice. Extracellular fluorescence was quenched by incubating 2 minutes with 0.1% trypan blue. After washing twice with ice cold PBS, the cells were incubated with propidium iodide and anti-CD14 for 30 minutes at 4° C. After washing, the cells were analyzed by a BD LSRII Flow Cytometer (FIG. 2). Based on previous experiences, monocytes phagocytosing platelets have CMFDA median fluorescence intensity values at least 2-fold or higher than negative controls (either a-SA or a-DNP) (2).

Exemplary data are shown in Table 11, below. The results show that none of the assayed aglycosylated IgG1 variants (antibodies ending with "B" or "C", although only the "B" were tested in this study) activated platelets in human or cynomolgus whole blood when tested at antibody concentrations up to 14 mg/mL. Similarly no effect was seen on in vitro platelet phagocytosis up to and including the highest concentration tested (3 mg/ml). No in vitro neutrophil activation was noted at any concentration tested.

TABLE 11

| Ab ID | cyno platelet | human platelet |
| --- | --- | --- |
| 01A | Positive at 3 mg/ml | Positive at 0.3 mg/ml |
| 01B | Negative | Negative |
| 13A | Positive at 0.1 mg/ml | Positive at 0.3 mg/ml |
| 14A | Positive at 0.3 mg/ml | Positive at 0.3 mg/ml |
| 14B | Negative | Negative |
| 26A | Positive at 0.3 mg/ml | Positive at 1 mg/ml |
| 26B | Negative | Negative |
| 29B | Negative | Negative |
| 39A | Positive at 0.1 mg/ml | Positive at 1 mg/ml |
| 39B | Negative | Negative |

All patents and other publications identified are expressly incorporated herein by reference for the purpose of describing and disclosing, for example, the methodologies described in such publications that might be used in connection with the subject matter disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method for inhibiting vasodilation in a patient in need thereof comprising administering to the patient an effective amount of an isolated monoclonal antibody that specifically binds to human pituitary adenylate cyclase-activating polypeptide type 1 receptor (PAC1) with an equilibrium binding affinity ($K_D$) of $\leq 1 \times 10^{-9}$ M, wherein the monoclonal antibody comprises (i) a heavy chain variable region comprising complementarity determining regions CDRH1, CDRH2, and CDRH3, and (ii) a light chain variable region comprising complementarity determining regions CDRL1, CDRL2, and CDRL3, wherein CDRH1 comprises the sequence of SEQ ID NO: 257 or 258; CDRH2 comprises the sequence of SEQ ID NO: 259, 260, or 261; CDRH3 comprises the sequence of SEQ ID NO: 262; CDRL1 comprises the sequence of SEQ ID NO: 251 or 252; CDRL2 comprises the sequence of SEQ ID NO: 253, 254, or 255; and CDRL3 comprises the sequence of SEQ ID NO: 256, and wherein the monoclonal antibody comprises a human IgG1 heavy chain having a N297G mutation according to EU numbering.

2. The method of claim 1, wherein the heavy chain of the monoclonal antibody further comprises a pair of mutations according to EU numbering selected from (i) A287C and L306C, (ii) V259C and L306C, (iii) R292C and V302C, and (iv) V323C and I332C.

3. The method of claim 2, wherein the heavy chain of the monoclonal antibody comprises R292C and V302C mutations according to EU numbering.

4. The method of claim 1, wherein platelets are not depleted in the patient following administration of the monoclonal antibody.

5. The method of claim 1, wherein the monoclonal antibody selectively inhibits human PAC1 relative to human VPAC1 and VPAC2.

6. The method of claim 1, wherein the monoclonal antibody is a humanized antibody.

7. The method of claim 1, wherein the monoclonal antibody is a fully human antibody.

8. The method of claim 1, wherein the patient has migraine headaches.

9. The method of claim 1, wherein the patient has cluster headaches.

10. A method for treating a headache in a patient in need thereof comprising administering to the patient an effective amount of an isolated monoclonal antibody that specifically binds to human PAC1 with a ($K_D$) of $\leq 1 \times 10^{-9}$ M, wherein the monoclonal antibody comprises (i) a heavy chain variable region comprising complementarity determining regions CDRH1, CDRH2, and CDRH3, and (ii) a light chain variable region comprising complementarity determining regions CDRL1, CDRL2, and CDRL3, wherein CDRH1 comprises the sequence of SEQ ID NO: 257 or 258; CDRH2 comprises the sequence of SEQ ID NO: 259, 260, or 261; CDRH3 comprises the sequence of SEQ ID NO: 262; CDRL1 comprises the sequence of SEQ ID NO: 251 or 252; CDRL2 comprises the sequence of SEQ ID NO: 253, 254, or 255; and CDRL3 comprises the sequence of SEQ ID NO: 256, and wherein the monoclonal antibody comprises a human IgG1 heavy chain having a N297G mutation according to EU numbering.

11. The method of claim 10, wherein the heavy chain of the monoclonal antibody further comprises a pair of mutations according to EU numbering selected from (i) A287C and L306C, (ii) V259C and L306C, (iii) R292C and V302C, and (iv) V323C and I332C.

12. The method of claim 11, wherein the heavy chain of the monoclonal antibody comprises R292C and V302C mutations according to EU numbering.

13. The method of claim 10, wherein platelets are not depleted in the patient following administration of the monoclonal antibody.

14. The method of claim 10, wherein the monoclonal antibody selectively inhibits human PAC1 relative to human VPAC1 and VPAC2.

15. The method of claim 10, wherein the monoclonal antibody is a humanized antibody.

16. The method of claim 10, wherein the monoclonal antibody is a fully human antibody.

17. The method of claim 10, wherein the headache is a migraine.

18. The method of claim 17, wherein the migraine is an episodic migraine or a chronic migraine.

19. The method of claim 10, wherein the headache is a cluster headache.

* * * * *